(12) United States Patent
Gonzalez, III et al.

(10) Patent No.: US 8,153,642 B2
(45) Date of Patent: Apr. 10, 2012

(54) QUINAZOLINES USEFUL AS MODULATORS OF ION CHANNELS

(75) Inventors: Jesus Gonzalez, III, Carlsbad, CA (US);
Dean Wilson, Bedford, MA (US);
Andreas Termin, Encinitas, CA (US);
Peter Grootenhuis, San Diego, CA (US); Yulian Zhang, Yardley, PA (US);
Benjamin Petzoldt, San Diego, CA (US); Lev Fanning, San Marcos, CA (US); Timothy Neubert, San Diego, CA (US); Roger Tung, Lexington, MA (US);
Esther Martinborough, San Diego, CA (US); Nicole Hilgraf, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/714,871

(22) Filed: Mar. 1, 2010

(65) Prior Publication Data

US 2010/0160316 A1 Jun. 24, 2010

Related U.S. Application Data

(60) Division of application No. 10/935,008, filed on Sep. 2, 2004, now Pat. No. 7,713,983, which is a continuation-in-part of application No. 10/792,688, filed on Mar. 3, 2004, now Pat. No. 7,678,802.

(60) Provisional application No. 60/463,797, filed on Apr. 18, 2003, provisional application No. 60/451,458, filed on Mar. 3, 2003.

(51) Int. Cl.
*A61K 31/517* (2006.01)
*A61P 19/02* (2006.01)
*A61P 25/06* (2006.01)
*A61P 25/08* (2006.01)
*A61P 29/02* (2006.01)
*A61P 35/00* (2006.01)
*C07D 239/94* (2006.01)
*C07D 403/12* (2006.01)

(52) U.S. Cl. ............... 514/266.2; 514/266.22; 544/283; 544/284

(58) Field of Classification Search ............... 544/283, 544/284; 514/266.2, 26.226, 266.22
See application file for complete search history.

(56) References Cited

U.S. PATENT DOCUMENTS

| | | | |
|---|---|---|---|
| 7,678,802 B2 | 3/2010 | Gonzalez, III et al. | |
| 7,713,983 B2 * | 5/2010 | Gonzalez et al. | ......... 514/266.1 |
| 7,718,658 B2 | 5/2010 | Wilson et al. | |
| 2006/0166963 A1 | 7/2006 | Silva | |
| 2006/0173018 A1 | 8/2006 | Wilson et al. | |
| 2008/0167305 A1 | 7/2008 | Wilson et al. | |
| 2008/0221137 A1 | 9/2008 | Wilson et al. | |
| 2009/0312342 A1 | 12/2009 | Wilson et al. | |
| 2010/0249100 A1 | 9/2010 | Wilson et al. | |
| 2011/0021495 A1 | 1/2011 | Gonzalez, III et al. | |

OTHER PUBLICATIONS

Krafte et al., Current Opinion in Pharmacology 2008, 8:50-56.*
Rush et al., Molecular Interventions 2007, vol. 4, issue 7, 192-195.*
Dermer et al., Bio/Technology, 1994, 12:320.*
Freshney et al., Culture of Animal Cells, A Manual of Basic Technique, Alan R. Liss, Inc., 1983, New York, p. 4.*
Clare et al, Drug Discovery Today 2000, vol. 5, No. 11, 506-520.*

* cited by examiner

*Primary Examiner* — Venkataraman Balasubramanian
(74) *Attorney, Agent, or Firm* — Nancy K. Brennan

(57) ABSTRACT

The present invention relates to compounds useful as inhibitors of voltage-gated sodium channels and calcium channels. The invention also provides pharmaceutically acceptable compositions comprising the compounds of the invention and methods of using the compositions in the treatment of various disorders.

4 Claims, No Drawings

QUINAZOLINES USEFUL AS MODULATORS OF ION CHANNELS

CROSS REFERENCE TO RELATED APPLICATIONS

This application is a divisional application of co-pending U.S. continuation-in-part application Ser. No. 10/935,008 filed Sep. 2, 2004 entitled "Quinazolines Useful as Modulators of Ion Channels" which claims the benefit of, under 35 U.S.C. §120, U.S. patent application Ser. No. 10/792,688 filed Mar. 3, 2004, entitled "Quinazolines Useful as Modulators of Ion Channels" which claims the benefit of, under 35 U.S.C. §119, U.S. Provisional Patent Application Nos. 60/451,458, filed Mar. 3, 2003, entitled "Compositions Useful as Inhibitors of Voltage-Gated Sodium Channels", and 60/463,797, filed Apr. 18, 2003, entitled "Compositions Useful as Inhibitors of Voltage-Gated Sodium Channels" and the entire contents of each of these applications is hereby incorporated by reference.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents*, 12(1): 85-91)), pain (See, Waxman, S. G., S. Dib-Hajj, et al. (1999) "Sodium channels and pain" *Proc. Natl. Acad. Sci. USA*, 96(14): 7635-9 and Waxman, S. G., T. R. Cummins, et al. (2000) "Voltage-gated sodium channels and the molecular pathogenesis of pain: a review" *J Rehabil. Res. Dev.*, 37(5): 517-28), myotonia (See, Meola, G. and V. Sansone (2000) "Therapy in myotonic disorders and in muscle channelopathies" *Neurol. Sci.*, 21(5): S953-61 and Mankodi, A. and C. A. Thornton (2002) "Myotonic syndromes" *Curr. Opin. Neurol.*, 15(5): 545-52), ataxia (See Meisler, M. H., J. A. Kearney, et al. (2002) "Mutations of voltage-gated sodium channels in movement disorders and epilepsy" *Novartis Found. Symp.*, 241: 72-81), multiple sclerosis (See Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc. Natl. Acad. Sci. USA*, 97(21): 11598-602, and Renganathan, M., M. Gelderblom, et al. (2003) "Expression of Na(v)1.8 sodium channels perturbs the firing patterns of cerebellar purkinje cells" *Brain Res.*, 959(2): 235-42), irritable bowel (See Su, X., R. E. Wachtel, et al. (1999) "Capsaicin sensitivity and voltage-gated sodium currents in colon sensory neurons from rat dorsal root ganglia" *Am. J. Physiol.*, 277(6 Pt 1): G1180-8, and Laird, J. M., V. Souslova, et al. (2002) "Deficits in visceral pain and referred hyperalgesia in Nav1.8 (SNS/PN3)— null mice" *J. Neurosci.*, 22(19): 8352-6), urinary incontinence and visceral pain (See Yoshimura, N., S. Seki, et al. (2001) "The involvement of the tetrodotoxin-resistant sodium channel Na(v)1.8 (PN3/SNS) in a rat model of visceral pain" *J. Neurosci.*, 21(21): 8690-6), as well as an array of psychiatry dysfunctions such as anxiety and depression (See Hurley, S. C. (2002) "Lamotrigine update and its use in mood disorders" *Ann. Pharmacother.*, 36(5): 860-73).

Voltage gated Na channels comprise a gene family consisting of 9 different subtypes (NaV1.1-NaV1.9). As shown in Table 1, these subtypes show tissue specific localization and functional differences (See Goldin, A. L. (2001) "Resurgence of sodium channel research" *Annu. Rev. Physiol.*, 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See Noda, M., H. Suzuki, et al. (1989) "A single point mutation confers tetrodotoxin and saxitoxin insensitivity on the sodium channel II" *FEBS Lett.*, 259(1): 213-6).

Table 1 (Abbreviations: CNS=central nervous system, PNS=peripheral nervous system, DRG=dorsal root ganglion, TG=Trigeminal ganglion):

| Na isoform | Tissue | TTX IC50 | Indications |
|---|---|---|---|
| NaV1.1 | CNS, PNS soma of neurons | 10 nM | Pain, Epilepsy, neurodegeneration |
| NaV1.2 | CNS, high in axons | 10 nM | Neurodegeneration Epilepsy |
| NaV1.3 | CNS, embryonic, injured nerves | 15 nM | Pain |
| NaV1.4 | Skeletal muscle | 25 nM | Myotonia |
| NaV1.5 | Heart | 2 µM | Arrythmia, long QT |
| NaV1.6 | CNS widespread, most abuntant | 6 nM | Pain, movement disorders |
| NaV1.7 | PNS, DRG, terminals neuroendocrine | 25 nM | Pain, Neuroendocrine disorders |
| NaV1.8 | PNS, small neurons in DRG & TG | >50 µM | Pain |
| NaV1.9 | PNS, small neurons in DRG & TG | 1 µM | Pain |

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See Mao, J. and L. L. Chen (2000) "Systemic lidocaine for neuropathic pain relief" *Pain*, 87(1): 7-17) bupivacaine, phenyloin (See, Jensen, T. S. (2002) "Anticonvulsants in neuropathic pain: rationale and clinical evidence" *Eur. J. Pain*, 6 (Suppl A): 61-8), lamotrigine (See, Rozen, T. D. (2001) "Antiepileptic drugs in the management of cluster headache and trigeminal neuralgia" *Headache*, 41 Suppl 1: S25-32 and Jensen, T. S. (2002) "Anticonvulsants in neuropathic pain: rationale and clinical evidence" *Eur. J. Pain*, 6 (Suppl A): 61-8), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See Goldin, A. L. (2001) "Resurgence of sodium channel research" *Annu Rev. Physiol.*, 63: 871-94). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in $PGE_2$-induced hyperalgesia (See Khasar, S. G., M. S. Gold, et al. (1998) "A tetrodotoxin-resistant sodium current mediates inflammatory pain in the rat" *Neurosci. Lett.*, 256(1): 17-20). More recently, a knockout mouse line was generated by Wood and colleagues, which lacks functional NaV1.8. The mutation has an analgesic effect in tests assessing the animal's response to the inflammatory agent carrageenan (See, Akopian, A. N., V. Souslova, et al. (1999) "The tetrodotoxin-resistant sodium channel SNS has a specialized function in pain pathways" *Nat. Neurosci.*, 2(6): 541-8). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature*, 379(6562): 257-62). The primary role of these neurons is the detection and transmission of nociceptive stimuli. Antisense and immunohistochemical evidence also supports a role for NaV1.8 in neuropathic pain (See Lai, J., M. S. Gold, et al. (2002) "Inhibition of neuropathic pain by decreased expression of the tetrodotoxin-resistant sodium channel, NaV1.8" *Pain*, 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol.*, 314: 201-13). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

In neuropathic pain states there is a remodeling of Na channel distribution and subtype. In the injured nerve, expression of NaV1.8 and NaV1.9 are greatly reduced whereas expression of the TTX sensitive subunit NaV1.3 is 5-10 fold upregulated (See Dib-Hajj, S. D., J. Fjell, et al. (1999) "Plasticity of sodium channel expression in DRG neurons in the chronic constriction injury model of neuropathic pain." *Pain*, 83(3): 591-600.) The timecourse of the increase in NaV1.3 parallels the appearance of allodynia in animal models subsequent to nerve injury. The biophysics of the NaV1.3 channel is distinctive in that it shows very fast repriming after inactivation following an action potential. This allows for sustained rates of high firing as is often seen in the injured nerve (See Cummins, T. R., F. Aglieco, et al. (2001) "Nav1.3 sodium channels: rapid repriming and slow closed-state inactivation display quantitative differences after expression in a mammalian cell line and in spinal sensory neurons" *J. Neurosci.*, 21(16): 5952-61.). NaV1.3 is expressed in the central and peripheral systems of man. NaV1.9 is similar to NaV1.8 as it is selectively localized to small sensory neurons of the dorsal root ganglion and trigeminal ganglion (See, Fang, X., L. Djouhri, et al. (2002). "The presence and role of the tetrodotoxin-resistant sodium channel Na(v)1.9 (NaN) in nociceptive primary afferent neurons." *J. Neurosci.*, 22(17): 7425-33.). It has a slow rate of inactivation and left-shifted voltage dependence for activation (See Dib-Hajj, S., J. A. Black, et al. (2002) "NaN/Nav1.9: a sodium channel with unique properties" *Trends Neurosci.*, 25(5): 253-9.). These two biophysical properties allow NaV1.9 to play a role in establishing the resting membrane potential of nociceptive neurons. The resting membrane potential of NaV1.9 expressing cells is in the −55 to −50 mV range compared to −65 mV for most other peripheral and central neurons. This persistent depolarization is in large part due to the sustained low-level activation of NaV1.9 channels. This depolarization allows the neurons to more easily reach the threshold for firing action potentials in response to nociceptive stimuli. Compounds that block the NaV1.9 channel may play an important role in establishing the set point for detection of painful stimuli. In chronic pain states, nerve and nerve ending can become swollen and hypersensitive exhibiting high frequency action potential firing with mild or even no stimulation. These pathologic nerve swellings are termed neuromas and the primary Na channels expressed in them are NaV1.8 and NaV1.7 (See, Kretschmer, T., L. T. Happel, et al. (2002) "Accumulation of PN1 and PN3 sodium channels in painful human neuroma-evidence from immunocytochemistry" *Acta Neurochir.* (*Wien*), 144(8): 803-10; discussion 810.). NaV1.6 and NaV1.7 are also expressed in dorsal root ganglion neurons and contribute to the small TTX sensitive component seen in these cells. NaV1.7 in particular my therefore be a potential pain target in addition to it's role in neuroendocrine excitability (See Klugbauer, N., L. Lacinova, et al. (1995) "Structure and functional expression of a new member of the tetrodotoxin-sensitive voltage-activated sodium channel family from human neuroendocrine cells" *Embo J.*, 14(6): 1084-90).

NaV1.1 (See Sugawara, T., E. Mazaki-Miyazaki, et al. (2001) "Nav1.1 mutations cause febrile seizures associated with afebrile partial seizures." *Neurology*, 57(4): 703-5.) and NaV1.2 (See Sugawara, T., Y. Tsurubuchi, et al. (2001) "A missense mutation of the Na+ channel alpha II subunit gene Na(v)1.2 in a patient with febrile and afebrile seizures causes channel dysfunction" *Proc. Natl. Acad. Sci. USA*, 98(11): 6384-9) have been linked to epilepsy conditions including febrile seizures. There are over 9 genetic mutations in NaV1.1 associated with febrile seizures (See Meisler, M. H., J. A. Kearney, et al. (2002) "Mutations of voltage-gated sodium channels in movement disorders and epilepsy" *Novartis Found. Symp.*, 241: 72-81)

Antagonists for NaV1.5 have been developed and used to treat cardiac arrhythmias. A gene defect in NaV1.5 that produces a larger noninactivating component to the current has been linked to long QT in man and the orally available local anesthetic mexilitine has been used to treat this condition (See, Wang, D. W., K. Yazawa, et al. (1997) "Pharmacological targeting of long QT mutant sodium channels." *J. Clin. Invest.*, 99(7): 1714-20).

Several Na channel blockers are currently used or being tested in the clinic to treat epilepsy (See, Moulard, B. and D. Bertrand (2002) "Epilepsy and sodium channel blockers" *Expert Opin. Ther. Patents*, 12(1): 85-91); acute (See, Wiffen, P., S. Collins, et al. (2000) "Anticonvulsant drugs for acute and chronic pain" *Cochrane Database Syst, Rev,* 3, chronic (See Wiffen, P., S. Collins, et al. (2000) "Anticonvulsant drugs for acute and chronic pain" *Cochrane Database Syst. Rev.*, 3, and Guay, D. R. (2001) "Adjunctive agents in the management of chronic pain" *Pharmacotherapy,* 21(9): 1070-81), inflammatory (See, Gold, M. S. (1999) "Tetrodotoxin-resistant Na+ currents and inflammatory hyperalgesia." *Proc. Natl. Acad. Sci. USA*, 96(14): 7645-9), and neuropathic pain (See, Strichartz, G. R., Z. Zhou, et al. (2002) "Therapeutic concentrations of local anaesthetics unveil the potential role of sodium channels in neuropathic pain" *Novartis Found. Symp.*, 241: 189-201, and Sandner-Kiesling, A., G. Rumpold Seitlinger, et al. (2002) "Lamotrigine monotherapy for control of neuralgia after nerve section" *Acta Anaesthesiol. Scand.*, 46(10): 1261-4); cardiac arrhythmias (See An, R. H., R. Bangalore, et al. (1996) "Lidocaine block of LQT-3 mutant human Na+ channels" *Circ. Res.*, 79(1): 103-8, and Wang, D. W., K. Yazawa, et al. (1997) "Pharmacological targeting of long QT mutant sodium channels" *J. Clin. Invest.*, 99(7): 1714-20); neuroprotection (See Taylor, C. P. and L. S, Narasimhan (1997) "Sodium channels and therapy of central nervous system diseases" *Adv. Pharmacol.*, 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found. Symp.*, 241: 189-201).

Various animal models with clinical significance have been developed for the study of sodium channel modulators for numerous different pain indications. E.g., malignant chronic pain, see, Kohase, H., et al., *Acta Anaesthesiol Scand.*, 2004; 48(3):382-3; femur cancer pain (see, Kohase, H., et al., *Acta Anaesthesiol Scand.*, 2004; 48(3):382-3); non-malignant chronic bone pain (see, Ciocon, J. O. et al., *J. Am. Geriatr. Soc.*, 1994; 42(6):593-6); rheumatoid arthritis (see, Calvino, B. et al., *Behav. Brain Res.*, 1987; 24(1):11-29); osteoarthritis (see, Guzman, R. E., et al., *Toxicol. Pathol.*, 2003; 31(6):619-24); spinal stenosis (see, Takenobu, Y. et al., *J. Neurosci. Methods*, 2001; 104(2):191-8); neuropathic low back pain (see, Hines, R., et al., *Pain Med.*, 2002; 3(4):361-5; Massie, J. B., et al., *J. Neurosci. Methods*, 2004; 137(2):283-9); myofascial pain syndrome (see, Dalpiaz & Dodds, *J. Pain Palliat. Care Pharmacother.*, 2002; 16(1):99-104; Sluka, K. A. et al., *Muscle Nerve*, 2001; 24(1):37-46); fibromyalgia (see, Bennet & Tai, *Int. J. Clin. Pharmacol. Res.*, 1995; 15(3):115-9); temporomandibular joint pain (see, Ime H., Ren K., *Brain Res. Mol. Brain Res.*, 1999; 67(1):87-97); chronic visceral pain, including, abdominal (see, Al-Chaer, E. D., et al., *Gastroenterology*, 2000; 119(5):1276-85; pelvic/perineal (see, Wesselmann et al., *Neurosci. Lett.*, 1998; 246(2):73-6); pancreatic (see, Vera-Portocarrero, L. B., et al., *Anesthesiology*, 2003; 98(2):474-84); IBS pain (see, Verne, G. N., et al., *Pain*, 2003; 105(1-2):223-30; La J. H. et al., *World Gastroenterol.*, 2003; 9(12):2791-5); chronic headache pain (see, Willimas & Stark, *Cephalalgia*, 2003; 23(10):963-71); migraine (see, Yamamura, H., et al., *J. Neurophysiol.*, 1999; 81(2):479-93); tension headache, including, cluster headaches (see, Costa, A., et al., *Cephalalgia*, 2000; 20(2):85-91); chronic neuropathic pain, including, post-herpetic neuralgia (see, Attal, N., et al., *Neurology*, 2004; 62(2):218-25; Kim & Chung 1992, *Pain,* 50:355); diabetic neuropathy (see, Beidoun A et al., *Clin. J. Pain.*, 2004; 20(3):174-8; Courteix, C., et al., *Pain*, 1993; 53(1):81-8); HIV-associated neuropathy (see, Portegies & Rosenberg, *Ned. Tijdschr. Geneeskd.*, 2001; 145(15): 731-5; Joseph, E. K. et al., *Pain*, 2004; 107(1-2):147-58; Oh, S. B., et al., *J. Neurosci.*, 2001; 21(14):5027-35); trigeminal neuralgia (see, Sato, J., et al., *Oral Surg. Oral Med. Oral Pathol. Oral Radiol. Endod.*, 2004; 97(1):18-22; Imamura, Y. et al., *Exp. Brain Res.*, 1997; 116(1): 97-103); Charcot-Marie Tooth neuropathy (see, Sereda, M., et al., *Neuron,* 1996; 16(5):1049-60); hereditary sensory neuropathies (see, Lee, M. J., et al., *Hum. Mol. Genet.*, 2003; 12(15):1917-25); peripheral nerve injury (see, Attal, N., et al., *Neurology,* 2004; 62(2):218-25; Kim & Chung 1992, *Pain,* 50:355; Bennett & Xie, 1988, *Pain.,* 33:87; Decostered, I. & Woolf, C. J., 2000, *Pain,* 87:149; Shir, Y. & Seltzer, Z. 1990; *Neurosci. Lett.*, 115:62); painful neuromas (see, Nahabedian & Johnson, *Ann. Plast. Surg.*, 2001; 46(1):15-22; Devor & Raber, *Behav. Neural. Biol.,* 1983; 37(2):276-83); ectopic proximal and distal discharges (see, Liu, X. et al., *Brain Res.*, 2001; 900(1):119-27); radiculopathy (see, Devers & Galer, (see, *Clin. J. Pain.*, 2000; 16(3):205-8; Hayashi, N. et al., *Spine*, 1998; 23(8):877-85); chemotherapy induced neuropathic pain (see, Aley, K. O., et al., *Neuroscience,* 1996; 73(1):259-65); radiotherapy-induced neuropathic pain; post-mastectomy pain (see, Devers & Galer, *Clin. J. Pain,* 2000; 16(3):205-8); central pain (Cahana, A., et al., *Anesth. Analg.*, 2004; 98(6):1581-4), spinal cord injury pain (see, Hains, B. C., et al., *Exp. Neurol.*, 2000; 164(2):426-37); post-stroke pain; thalamic pain (see, LaBuda, C. J., et al., *Neurosci. Lett.*, 2000; 290(1):79-83); complex regional pain syndrome (see, Wallace, M. S., et al., *Anesthesiology,* 2000; 92(1):75-83; Xantos D et al., *J. Pain,* 2004; 5(3 Suppl 2):S1); phanton pain (see, Weber, W. E., *Ned. Tijdschr. Geneeskd.*, 2001; 145(17):813-7; Levitt & Heyback, *Pain,* 1981; 10(1):67-73); intractable pain (see, Yokoyama, M., et al., *Can. J. Anaesth.*, 2002; 49(8):810-3); acute pain, acute post-operative pain (see, Koppert, W., et al., *Anesth. Analg.* 2004; 98(4):1050-5; Brennan, T. J., et al., *Pain,* 1996; 64(3):493-501); acute musculoskeletal pain; joint pain (see, Gotoh, S., et al., *Ann. Rheum. Dis.*, 1993; 52(11):817-22); mechanical low back pain (see, Kehl, L. J., et al., *Pain.,* 2000; 85(3):333-43); neck pain; tendonitis; injury/exercise pain (see, Sesay, M., et al., *Can. J. Anaesth.*, 2002; 49(2):137-43); acute visceral pain, including, abdominal pain; pyelonephritis; appendicitis; cholecystitis; intestinal obstruction; hernias; etc (see, Giambernardino, M. A., et al., *Pain,* 1995; 61(3): 459-69); chest pain, including, cardiac pain (see, Vergona, R. A., et al., *Life Sci.,* 1984; 35(18):1877-84); pelvic pain, renal colic pain, acute obstetric pain, including, labor pain (see, Segal, S., et al., *Anesth. Analg.,* 1998; 87(4):864-9); cesarean section pain; acute inflammatory, burn and trauma pain; acute intermittent pain, including, endometriosis (see, Cason, A. M., et al., *Horm. Behav.,* 2003; 44(2):123-31); acute herpes zoster pain; sickle cell anemia; acute pancreatitis (see, Toma, H.; *Gastroenterology,* 2000; 119(5):1373-81); breakthrough pain; orofacial pain, including, sinusitis pain, dental pain (see, Nusstein, J., et al., *J. Endod.,* 1998; 24(7):487-91; Chidiac, J. J., et al., *Eur. J. Pain.,* 2002; 6(1):55-67); multiple sclerosis (MS) pain (see, Sakurai & Kanazawa, *J. Neurol. Sci.,* 1999; 162(2):162-8); pain in depression (see, Greene, B., *Curr. Med. Res. Opin.,* 2003; 19(4):272-7); leprosy pain; Behcet's disease pain; adiposis dolorosa (see, Devillers & Oranje, *Clin. Exp. Dermatol.,* 1999; 24(3):240-1); phlebitic pain; Guillain-Barre pain; painful legs and moving toes; Haglund syndrome; erythromelalgia pain (see, Legroux-Crespel, E., et al., *Ann. Dermatol. Venereol.,* 2003; 130(4):429-33); Fabry's disease pain (see, Germain, D. P., *J. Soc. Biol.,* 2002; 196(2):183-90); bladder and urogenital disease, including, urinary incontinence (see, Berggren, T., et al., *J. Urol.,* 1993; 150(5 Pt 1):1540-3); hyperactivity bladder (see, Chuang, Y. C., et al., *Urology,* 2003; 61(3):664-70); painful bladder syndrome (see, Yoshimura, N., et al., *J. Neurosci.,* 2001; 21(21):8690-6); interstitial cyctitis (IC) (see, Giannakopoulos& Campilomatos, *Arch. Ital. Urol. Nefrol. Androl.,* 1992; 64(4):337-9; Boucher, M., et al., *J. Urol.,* 2000; 164(1):203-8); and prostatitis (see, Mayersak, J. S., *Int. Surg.,* 1998; 83(4):347-9; Keith, I. M., et al., *J. Urol.,* 2001; 166(1):323-8).

Calcium channels are membrane-spanning, multi-subunit proteins that allow Ca entry from the external milieu and concurrent depolarization of the cell's membrane potential. Traditionally calcium channels have been classified based on their functional characteristics such as low voltage or high voltage activated and their kinetics (L,T,N,P,Q). The ability to clone and express the calcium channel subunits has lead to an increased understanding of the channel composition that produces these functional responses. There are three primary subunit types that make up calcium channels—$\alpha1$, $\alpha2\delta$, and $\beta$. The $\alpha1$ is the subunit containing the channel pore and voltage sensor, $\alpha2$ is primarily extracellular and is disulfide linked to the transmembrane $\delta$ subunit, $\beta$ is nonglycosylated subunit found bound to the cytoplasmic region of the $\alpha1$ subunit of the Ca channel. Currently the various calcium channel subtypes are believed to made up of the following specific subunits:

L-type, comprising subunits $\alpha_{1C}\alpha_{1D}\alpha_{1F}$, or $\alpha_{1S}$, $\alpha2\delta$ and $\beta_{3a}$ N-Type, comprising subunits $\alpha_{1B}$, $\alpha2\delta$, $\beta_{1b}$ P-Type, comprising subunits $\alpha_{1A}$, $\alpha2\delta$, $\beta_{4a}$ Q-Type, comprising subunits $\alpha_{1A}$ (splice variant) $\alpha2\delta$, $\beta_{4a}$ R-Type, comprising subunits $\alpha_{1E}$, $\alpha2\delta$, $\beta_{1b}$ T-Type, comprising subunits $\alpha_{1G}$, $\alpha_{1H}$, or $\alpha_{1I}$ Calcium channels play a central role in neurotransmitter release. Ca influx into the presynaptic terminal of a nerve process binds to and produces a cascade of protein-protein interactions (syntaxin 1A, SNAP-25 and synaptotagmin) that ultimately ends with the fusion of a synaptic vesical and release of the neurotransmitter packet. Blockade of the presynaptic calcium channels reduces the influx of Ca and produces a cubic $X^3$ decrease in neurotransmitter release.

The N type Ca channel (CaV2.2) is highly expressed at the presynaptic nerve terminals of the dorsal root ganglion as it forms a synapse with the dorsal horn neurons in lamina I and II. These neurons in turn have large numbers of N type Ca channels at their presynaptic terminals as they synapse onto second and third order neurons. This pathway is very important in relaying pain information to the brain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain on the other had may last for much longer periods of time and it's intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opiods until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

The N type Ca channel has been validated in man by intrathecal infusion of the toxin Ziconotide for the treatment of intractable pain, cancer pain, opioid resistant pain, and neuropathic and severe pain. The toxin has an 85% success rate for the treatment of pain in humans with a greater potency than morphine. An orally available N type Ca channel antagonist would garner a much larger share of the pain market. Ziconotide causes mast cell degranulation and produces dose-dependent central side effects. These include dizziness, nystagmus, agitation, and dysmetria. There is also orthostatic hypotension in some patients at high doses. The primary risk for this target involves the CNS side effects seen with Ziconotide at high dosing. These include dizziness, nystagmus, agitation, and dysmetria. There is also orthostatic hypotension in some patients at high doses. It is believed that this may be due to Ziconotide induced mast cell degranulation and/or its effects on the sympathetic ganglion that like the dorsal root ganglion also expresses the N type Ca channel. Use-dependent compounds that block preferentially in the higher frequency range>10 Hz should be helpful in minimizing these potential side-effect issues. The firing rate in man of the sympathetic efferents is in the 0.3 Hz range. CNS neurons can fire at high frequencies but generally only do so in short bursts of action potentials. Even with the selectivity imparted by use-dependence intrinsic selectivity against the L type calcium channel is still necessary as it is involved in cardiac and vascular smooth muscle contraction.

Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Accordingly, there remains a need to develop additional Na channel and Ca channel antagonists, preferably those with higher potency and fewer side effects.

SUMMARY OF THE INVENTION

It has now been found that compounds of this invention, and pharmaceutically acceptable compositions thereof, are useful as inhibitors of voltage-gated sodium channels and calcium channels. These compounds have the general formula I:

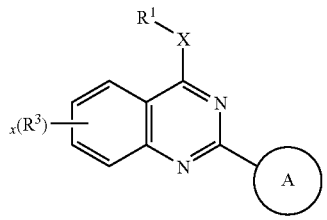

or a pharmaceutically acceptable derivative thereof, wherein $R^1$, X, $R^3$, x, and ring A are as defined below.

These compounds and pharmaceutically acceptable compositions are useful for treating or lessening the severity of a variety of diseases, disorders, or conditions, including, but not limited to, acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

DETAILED DESCRIPTION OF THE INVENTION

I. General Description of Compounds of the Invention

The present invention relates to compounds of formula I useful as inhibitors of voltage-gated sodium channels and calcium channels:

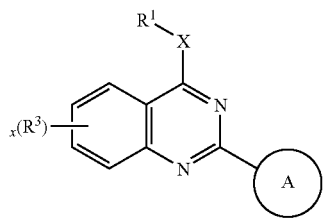

or a pharmaceutically acceptable salt thereof, wherein:
X is O or $NR^2$;
wherein $R^1$ and $R^2$ are each independently an optionally substituted group selected from hydrogen, $C_{1-6}$aliphatic, or $Cy^1$, wherein $Cy^1$ is a 5-7-membered monocyclic aryl ring or an 8-10-membered bicyclic aryl ring having 0-3 heteroatoms independently selected from nitrogen, oxygen, or sulfur, or is a 3-12-membered saturated, or partially unsaturated monocyclic or bicyclic ring having 0-3 heteroatoms independently selected from nitrogen, oxygen, or sulfur, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or $R^1$ and $R^2$, taken together with the nitrogen atom to which they are bound, form an optionally substituted 3-12-membered monocyclic or bicyclic saturated, partially unsaturated, or fully unsaturated ring having 0-3 additional heteroatoms independently selected from nitrogen, sulfur, or oxygen; wherein $R^1$ and $R^2$, or the ring formed by $R^1$ and $R^2$ taken together, are each optionally and independently substituted at one or more substitutable carbon, nitrogen, or sulfur atoms with z independent occurrences of —$R^4$, wherein z is 0-5;

Ring A is a 5-7-membered monocyclic aryl ring or an 8-10-membered bicyclic aryl ring having 0-3 heteroatoms independently selected from nitrogen, oxygen, or sulfur, or is a 3-12-membered monocyclic or bicyclic saturated or partially unsaturated monocyclic ring having 0-3 heteroatoms independently selected from nitrogen, oxygen, or sulfur, wherein ring A is optionally substituted with y independent occurrences of —$R^5$, wherein y is 0-5, and is additionally optionally substituted with q independent occurrences of $R^{5a}$, wherein q is 0-2;

x is 0-4;

each occurrence of $R^3$, $R^4$, and $R^5$ is independently Q-Rx; wherein Q is a bond or is a $C_1$-$C_6$ alkylidene chain wherein up to two non-adjacent methylene units of Q are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, —OP(O)(OR)—, or —POR—; and each occurrence of $R^x$ is independently selected from —R', =O, =NR', halogen, —NO$_2$, —CN, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$;

each occurrence of $R^{5a}$ is independently an optionally substituted $C_1$-$C_6$aliphatic group, halogen, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain embodiments for compounds described directly above:
i) when x is 1 and $R^3$ is optionally substituted 6-phenyl or 6-pyridyl, and $R^1$ is hydrogen, then $R^2$ is not $Cy^1$; and
ii) Piperazine, 1-(4-amino-6,7-dimethoxy-2-quinazolinyl)-4 (2-furanylcarbonyl)-monohydro chloride and Piperazine, 1-(4-amino-6,7-dimethoxy-2-quinazolinyl)-4[(2,3-dihydro-1,4-benzodioxin-2-yl)carbonyl]- are excluded.

2. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —R°; —OR°; —SR°; phenyl (Ph) optionally substituted with R°; —O(Ph) optionally substituted with R°; —(CH$_2$)$_{1-2}$(Ph), optionally substituted with R°; —CH═CH(Ph), optionally substituted with R°; —NO$_2$; —CN; —N(R°)$_2$; —NR°C(O)R°; —NR°C(S)R°; —NR°C(O)N(R°)$_2$; —NR°C(S)N(R°)$_2$; —NR°CO$_2$R°;

—NR°NR°C(O)R°; —NR°NR°C(O)N(R°)₂; —NR°NR°CO₂R°; —C(O)C(O)R°; —C(O)CH₂C(O)R°; —CO₂R°; —C(O)R°; —C(S)R°; —C(O)N(R°)₂; —C(S)N(R°)₂; —OC(O)N(R°)₂; —OC(O)R°; —C(O)N(OR°)R°; —C(NOR°)R°; —S(O)₂R°; —S(O)₃R°; —SO₂N(R°)₂; —S(O)R°; —NR°SO₂N(R°)₂; —NR°SO₂R°; —N(OR°)R°; —C(=NH)—N(R°)₂; —P(O)₂R°; —PO(R°)₂; —OPO(R°)₂; —(CH₂)₀₋₂NHC(O)R°; phenyl (Ph) optionally substituted with R°; —O(Ph) optionally substituted with R°; —(CH₂)₁₋₂(Ph), optionally substituted with R°; or —CH=CH(Ph), optionally substituted with R°; wherein each independent occurrence of R° is selected from hydrogen, optionally substituted C₁₋₆ aliphatic, an unsubstituted 5-6 membered heteroaryl or heterocyclic ring, phenyl, —O(Ph), or —CH₂(Ph), or, notwithstanding the definition above, two independent occurrences of R°, on the same substituent or different substituents, taken together with the atom(s) to which each R° group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R° are selected from NH₂, NH(C₁₋₄aliphatic), N(C₁₋₄aliphatic)₂, halogen, C₁₋₄aliphatic, OH, O(C₁₋₄aliphatic), NO₂, CN, CO₂H, CO₂(C₁₋₄aliphatic), O(halo C₁₋₄ aliphatic), or halo C₁₋₄aliphatic, wherein each of the foregoing C₁₋₄aliphatic groups of R° is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂(alkyl), =NNHSO₂(alkyl), or =NR*, where each R* is independently selected from hydrogen or an optionally substituted C₁₋₆ aliphatic group.

Unless otherwise defined above and herein, optional substituents on the nitrogen of a non-aromatic heterocyclic ring are generally selected from —R⁺, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺¹)₂, —C(=NH)—N(R⁺)₂, or —NR⁺SO₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R⁺ are selected from —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —CO₂H, —CO₂(C₁₋₄ aliphatic), —O(halo C₁₋₄ aliphatic), or halo(C₁₋₄ aliphatic), wherein each of the foregoing C₁₋₄aliphatic groups of R⁺ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R⁺, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R° (or R⁺, R, R' or any other variable similarly defined herein), are taken together with the atom(s) to which each variable is bound include, but are not limited to the following: a) two independent occurrences of R° (or R⁺, R, R' or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, R, R' or any other variable similarly defined herein) that are bound to different atoms and are taken together with both of those atoms to form a ring, for example where a phenyl group is substituted with two occurrences of OR°

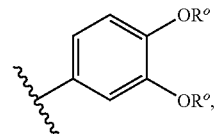

these two occurrences of R° are taken together with the oxygen atoms to which they are bound to form a fused 6-membered oxygen containing ring:

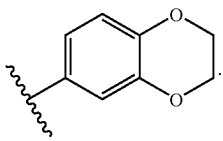

It will be appreciated that a variety of other rings can be formed when two independent occurrences of R° (or R⁺, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

3. Description of Exemplary Compounds

As described generally above, for compounds of the invention, X is O or NR$^2$. Accordingly, in certain embodiments, X is NR$^2$, and compounds have the structure of formula I-A:

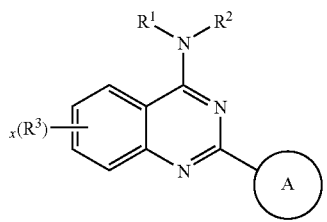

I-A

In other embodiments, X is O, and compounds have the structure of formula I-B:

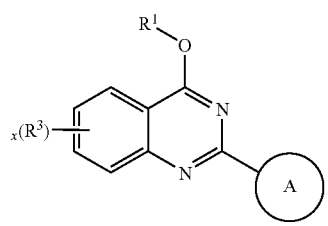

I-B

In one embodiment of the present invention:
(i) the following compounds: are excluded:
[4-(6-Bromo-4-piperidin-1-yl-quinazolin-2-yl)-benzyl]-phosphonic acid diethyl ester;
[4-(6-Bromo-4-pyrrolidin-1-yl-quinazolin-2-yl)-benzyl]-phosphonic acid diethyl ester;
[4-(6-Bromo-4-piperidin-1-yl-quinazolin-2-yl)-benzyl]-phosphonic acid monoethyl ester;
[4-(4-Methylamino-quinazolin-2-yl)-benzyl]-phosphonic acid diethyl ester;
[4-(4-Ethylamino-quinazolin-2-yl)-benzyl]-phosphonic acid diethyl ester;
[4-(6-Bromo-4-methylamino-quinazolin-2-yl)-benzyl]-phosphonic acid dimethyl ester;
[4-(6-Bromo-4-ethylamino-quinazolin-2-yl)-benzyl]-phosphonic acid dimethyl ester;
[4-(6-Bromo-4-methylamino-quinazolin-2-yl)-benzyl]-phosphonic acid diethyl ester;
[4-(6-Bromo-4-ethylamino-quinazolin-2-yl)-benzyl]-phosphonic acid diethyl ester;
[4-(6-Bromo-4-butylamino-quinazolin-2-yl)-benzyl]-phosphonic acid diethyl ester;
[4-(6-Bromo-4-cyclohexylamino-quinazolin-2-yl)-benzyl]-phosphonic acid diethyl ester;
[4-(6-Bromo-4-hydrazino-quinazolin-2-yl)-benzyl]-phosphonic acid diethyl ester;
[4-(6-Bromo-4-ethylamino-quinazolin-2-yl)-benzyl]-phosphonic acid diisopropyl ester;
[4-(6-Bromo-4-methylamino-quinazolin-2-yl)-benzyl]-phosphonic acid diisopropyl ester;
[4-(6-Chloro-4-methylamino-quinazolin-2-yl)-benzyl]-phosphonic acid diethyl ester;
[4-(6,7-Dimethoxy-4-methylamino-quinazolin-2-yl)-benzyl]-phosphonic acid diethyl ester;
[4-(6-Bromo-4-methylamino-quinazolin-2-yl)-benzyl]-phosphonic acid monoethyl ester;
[4-(6-Bromo-4-ethylamino-quinazolin-2-yl)-benzyl]-phosphonic acid monoethyl ester;
[4-(6-Bromo-4-dimethylamino-quinazolin-2-yl)-benzyl]-phosphonic acid monoethyl ester;
4-aziridin-1-yl-2-phenyl-quinazoline;
dimethyl-(2-phenyl-quinazolin-4-yl)-amine;
4-N-acetyl-N-[2-(4-morpholino)-ethyl]-amino-2-phenyl quinazoline;
N,N-Diethyl-N'-(2-phenyl-quinazolin-4-yl)-ethane-1,2-diamine;
(6-Methoxy-2-phenyl-quinazolin-4-yl)-(2-morpholin-4-yl-ethyl)-amine;
N,N-Dimethyl-N'-(2-phenyl-quinazolin-4-yl)-ethane-1,2-diamine;
(2-Phenyl-quinazolin-4-yl)-(2-piperidin-1-yl-ethyl)-amine;
4-(2-Morpholin-4-yl-ethylamino)-2-phenyl-quinazolin-6-ol;
7-fluoro-4-N-[2-(4-morpholino)-ethyl]-amino-2-phenyl-quinazoline;
4-N-(2-N,N-di-n-propyl-amino-ethyl)-amino-2-phenyl-quinazoline;
4-N-[2-(4-morpholino)-ethyl]-amino-2-(3,4,5-trimethoxyphenyl)-quinazoline;
2-phenyl-4-N-[2-(1-piperazino)-ethyl]-aminoquinazoline;
6-benzyloxy-4-N-[2-(4-morpholino)-ethyl]amino-2-phenylquinazoline;
2-phenyl-4-N-[2-(1-pyrrolidino)-ethyl]-aminoquinazoline;
2-(2-chloro-phenyl)-7-fluoro-4-N-[2-(4-morpholino)-ethyl]-aminoquinazoline;
4-N-[2-(4-morpholino)-ethyl]-amino-2-(2-thienyl)-quinazoline;
2-(4-chlorophenyl)-4-N-[2-(4-methyl-1-piperazino)-propyl]-aminoquinazoline;
7-methyl-2-phenyl-4-N-[2-(4-thiamorpholino)-ethyl]-aminoquinazoline;
6-fluoro-2-(4-methylphenyl)-4-N-methyl-N-[2-(1-pyrrolidino)-ethyl]-aminoquinazoline;
2-(2-chlorophenyl)-4-N-[2-(4-morpholino)-ethyl]-aminoquinazoline;
4-N-[2-(4-morpholino)-ethyl]-amino-2-phenyl-quinazoline;
2-(o-hydroxyphenyl)-4-bis(2-cyanoethyl)aminoquinazoline;
2-(o-hydroxyphenyl)-4-aminoquinazoline;
2-(o-hydroxyphenyl)-4-acetamidoquinazoline;
2-(o-hydroxyphenyl)-4-acrylamidoquinazoline;
2-(o-hydroxyphenyl)-4-[N-methyl-2-(N-methyl-methacrylamido)ethylamino]quinazoline;
2-(o-hydroxyphenyl)-4-dimethylamino-7-chloroquinazoline;
2-(o-hydroxyphenyl)-4-dimethylamino-7-nitroquinazoline;
2-(2-hydroxy-5-methylphenyl)-4-ethoxyquinazoline;
2-(2-hydroxy-5-methylphenyl)-4-butoxyquinazoline;
2-(o-hydroxyphenyl)-4-[2-hydroxyethoxy]quinazoline;
2-(o-hydroxyphenyl)-4-[2-dimethylaminoethoxy]quinazoline;
2-(o-hydroxyphenyl)-4-phenoxyquinazoline;
2-(o-hydroxyphenyl)-4-[p-cresyloxy]quinazoline;
2-(o-hydroxyphenyl)-4-[p-chlorophenoxy]quinazoline;
2-(o-hydroxyphenyl)-4-(2-beta-acryloxyethyl)quinazoline;

5-(4-{2-[methyl-(2-phenylquinazolin-4-yl)amino]-ethoxy}-benzyl)-thiazolidine-2,4-dione; and
methyl-phenyl-(2-phenyl-quinazolin-4-yl)-amine;
benzyl-methyl-(2-phenyl-quinazolin-4-yl)-amine;
phenethyl-(2-phenyl-quinazolin-4-yl)-amine;
4-(2-Phenyl-quinazolin-4-ylamino)-butyric acid ethyl ester;
(2-Phenyl-quinazolin-4-yl)-propyl-amine; and (ii) provided that when x, y, and q are 0, and $R^1$ is hydrogen, then $R^2$ is not phenyl, cyclohexyl, cyclopentyl, 2-ClPh, 3-ClPh, 4-ClPh, 3-$NO_2$Ph, 3-(OMe)Ph, 3-($CO_2$Me)Ph, 4-($CO_2$Me)Ph, 3-pyridyl, 1-pyyrolyl, or 3-(5-Me-isoxazolyl); and when x, y, and q are 0, $R^1$ is hydrogen, and $R^2$ is —$CH_2Cy^1$, then $Cy^1$ is not phenyl, 2-ClPh, 3-ClPh, 4-ClPh, 3-$NO_2$Ph, 2-thienyl, 2-furyl, 2-pyridyl, 3-pyridyl, or 2-THF.

In certain embodiments for compounds of general formula I-A, one of $R^1$ or $R^2$ is hydrogen, and the other of $R^1$ and $R^2$ is selected from an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2$NR—, or —$NRSO_2$—, or is $Cy^1$, wherein $Cy^1$ is a 5-7-membered monocyclic aryl ring or an 8-10-membered bicyclic aryl ring having 0-3 heteroatoms independently selected from nitrogen, oxygen, or sulfur, or is a 3-12-membered saturated, or partially unsaturated monocyclic or bicyclic ring having 0-3 heteroatoms independently selected from nitrogen, oxygen, or sulfur, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2$NR—, or —$NRSO_2$—.

In still other embodiments, $R^1$ and $R^2$ are each independently selected from $Cy^1$, wherein $Cy^1$ is a 5-7-membered monocyclic aryl ring or an 8-10-membered bicyclic aryl ring having 0-3 heteroatoms independently selected from nitrogen, oxygen, or sulfur, or is a 3-12-membered saturated, or partially unsaturated monocyclic or bicyclic ring having 0-3 heteroatoms independently selected from nitrogen, oxygen, or sulfur, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2$NR—, or —$NRSO_2$—; or from an optionally substituted $C_{1-4}$aliphatic group, wherein one or more methylene units in the $C_{1-4}$aliphatic group are optionally replaced with —NR—, —O—, —COO—, —OCO—, —NRCO—, —CONR—, —$SO_2$NR—, or —$NRSO_2$—.

In other embodiments, for compounds of formula I-A, one of $R^1$ or $R^2$ is hydrogen, and the other of $R^1$ or $R^2$ is an optionally substituted $C_{1-4}$aliphatic group, wherein one or more methylene units in the $C_{1-4}$aliphatic group are optionally replaced with —NR—, —O—, —COO—, —OCO—, —NRCO—, —CONR—, —$SO_2$NR—, or —$NRSO_2$—. In still other embodiments, the optionally substituted $C_{1-4}$aliphatic group is substituted with $Cy^1$, wherein $Cy^1$ is 5-7-membered monocyclic aryl ring or an 8-10-membered bicyclic aryl ring having 0-3 heteroatoms independently selected from nitrogen, oxygen, or sulfur, or is a 3-12 membered saturated or partially unsaturated monocyclic ring having 0-3 heteroatoms independently selected from nitrogen, oxygen, or sulfur, wherein $Cy^1$ is optionally substituted with 0-5 independent occurrences of —$R^5$. In yet other embodiments, one of $R^1$ or $R^2$ is hydrogen or $C_1$-$C_4$alkyl, and the other of $R^1$ or $R^2$ is —$CH_2$—$Cy^1$.

In yet other embodiments, for compounds of formula I-B, $R^1$ is an optionally substituted $C_{1-4}$aliphatic group, wherein one or more methylene units in the $C_{1-4}$aliphatic group are optionally replaced with —NR—, —O—, —COO—, —OCO, —NRCO—, —CONR—, —$SO_2$NR—, or —$NRSO_2$—.

In still other embodiments, for compounds of formula I-A, neither $R^1$ nor $R^2$ is hydrogen, and $R^1$ and $R^2$ are each independently selected from $Cy^1$, wherein $Cy^1$ is a 5-7-membered monocyclic aryl ring or an 8-10-membered bicyclic aryl ring having 0-3 heteroatoms independently selected from nitrogen, oxygen, or sulfur, or is a 3-12-membered saturated, or partially unsaturated monocyclic or bicyclic ring having 0-3 heteroatoms independently selected from nitrogen, oxygen, or sulfur, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2$NR—, or —$NRSO_2$—; or from an optionally substituted $C_{1-4}$aliphatic group, wherein one or more methylene units in the $C_{1-4}$aliphatic group are optionally replaced with —NR—, —O—, —COO—, —OCO—, —NRCO—, —CONR—, —$SO_2$NR—, or —$NRSO_2$—. In other embodiments, both $R^1$ and $R^2$ are an optionally substituted $C_{1-4}$aliphatic group, wherein one or more methylene units in the $C_{1-4}$aliphatic group are optionally replaced with —NR—, —O—, —COO—, —OCO—, —NRCO—, —CONR—, —$SO_2$NR—, or —$NRSO_2$—.

In some embodiments, for compounds of formula I, I-A or I-B, $Cy^1$ is selected from:

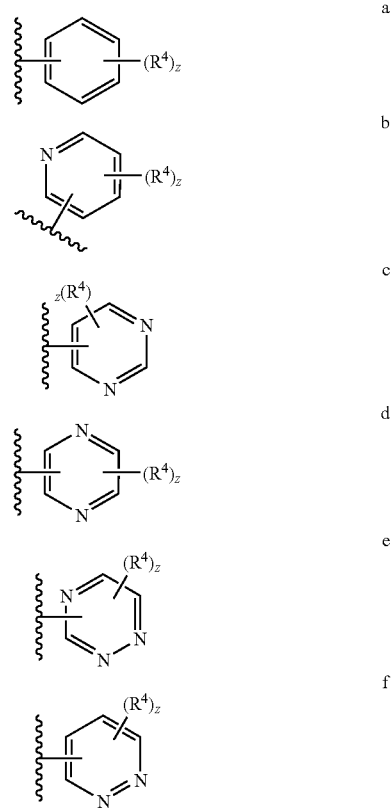

-continued
g
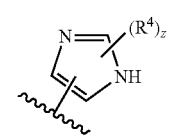
h
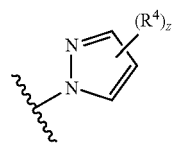
i
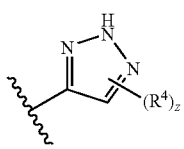
j
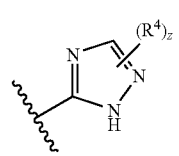
k
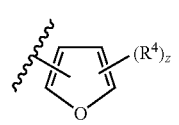
l
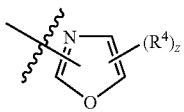
m
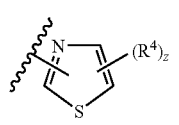
n
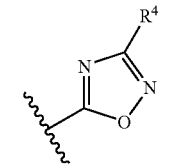
o
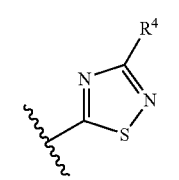
p
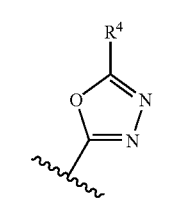
-continued
q
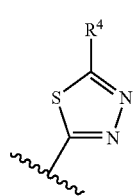
r
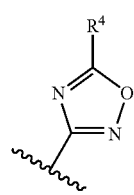
s
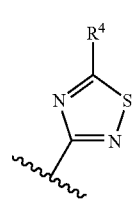
t
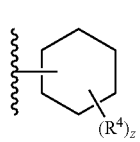
u
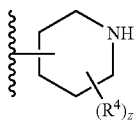
v
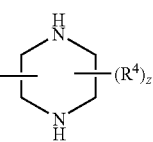
w
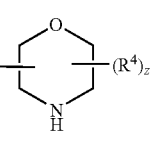
x
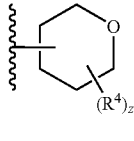
y
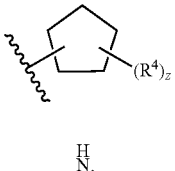
z
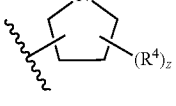

aa

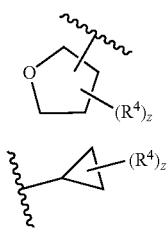

bb wherein $R^4$ is previously defined and z is 0-4. Other exemplary rings include those shown below in Table 2.

In yet other embodiments, for compounds of formula I, I-A, and I-B, exemplary $R^1$ and $R^2$ groups are optionally substituted methyl, ethyl, cyclopropyl, n-propyl, propenyl, cyclobutyl, (CO)OCH$_2$CH$_3$, (CH$_2$)$_2$OCH$_3$, CH$_2$(CO)OCH$_2$CH$_3$, CH$_2$(CO)OCH$_3$, CH(CH$_3$)CH$_2$CH$_3$, or n-butyl. Other exemplary $R^1$ and $R^2$ groups include those shown below in Table 2.

In still other embodiments, for compounds of formula I-A, $R^1$ and $R^2$, taken together with the nitrogen atom to which they are bound, form an optionally substituted 3-12 membered heterocyclyl ring having 1-3 heteroatoms independently selected from nitrogen, sulfur, or oxygen. In certain preferred embodiments, $R^1$ and $R^2$ are taken together with the nitrogen atom to which they are bound and form a group selected from:

cc

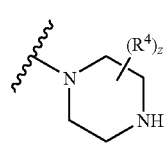

dd

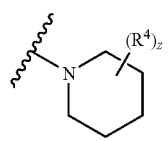

ee

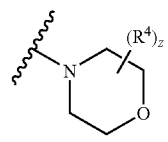

ff

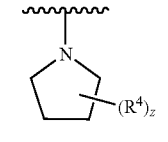

gg

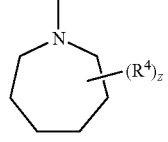

hh

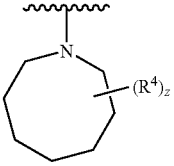

ii

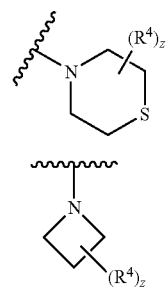

jj

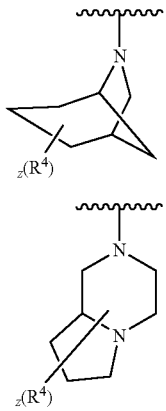

kk

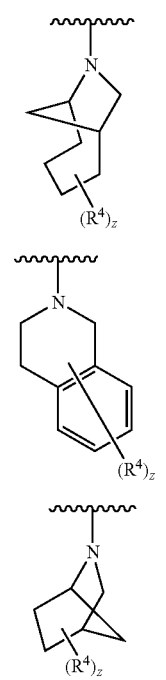

ll mm nn oo wherein the ring formed by $R^1$ and $R^2$ taken together, is optionally substituted at one or more substitutable carbon, nitrogen, or sulfur atoms with z independent occurrences of —$R^4$, and z is 0-5.

In other embodiments, for compounds of formula I-A, $R^1$ and $R^2$ taken together are optionally substituted azetidin-1-yl (jj), pyrrolidin-1-yl (ff), piperidin 1-yl (dd), piperazin-1-yl (cc), or morpholin-4-yl (ee). In other embodiments, for compounds of formula I-A, $R^1$ and $R^2$ taken together are optionally substituted azetidin-1-yl (jj), pyrrolidin-1-yl (ff), piperidin1-yl (dd), or piperazin-1-yl (cc). In yet other embodiments, for compounds of formula I-A, $R^1$ and $R^2$, taken together is optionally substituted azetidin-1-yl (jj). In yet other embodiments, for compounds of formula I-A, $R^1$ and $R^2$, taken together is optionally substituted pyrrolidin-1-yl (ff). In still other embodiments, for compounds of formula I-A, $R^1$ and $R^2$, taken together is optionally substituted piperidin1-yl (dd). In yet other embodiments, for compounds of formula I-A, $R^1$ and $R^2$, taken together is optionally substituted piperazin-1-yl (cc).

In certain embodiments, z is 0-2. In other embodiments, z is 0 and the ring is unsubstituted. Preferred $R^4$ groups, when present, are each independently halogen, CN, $NO_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl. Other exemplary $R^4$ groups are Cl, Br, F, $CF_3$, $CH_3$, —CH$_2$CH$_3$, CN, —COOH, N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, $C_{1-4}$alkoxy, phenyl, phenyloxy, benzyl, benzyloxy, —CH$_2$cyclohexyl, pyridyl, —CH$_2$pyridyl, or —CH$_2$thiazolyl. Still other exemplary $R^4$ groups include those shown below in Table 2.

In certain embodiments, for compounds of formula I-A, $R^1$ and $R^2$, taken together is optionally substituted azetidin-1-yl (jj), wherein z is 1 or 2 and at least one occurrence of $R^4$ is —NRSO$_2$R', —NRCOOR', or —NRCOR'. In certain other embodiments, for compounds of formula I-A, $R^1$ and $R^2$, taken together is optionally substituted azetidin-1-yl (jj), wherein z is 1 and $R^4$ is —NRSO$_2$R'. In other embodiments, for compounds of formula I-A, $R^1$ and $R^2$, taken together is optionally substituted azetidin-1-yl (jj), wherein z is 1 and $R^4$ is —NRCOOR'. In certain other embodiments, for compounds of formula I-A, $R^1$ and $R^2$, taken together is optionally substituted azetidin-1-yl (jj), wherein z is 1 and $R^4$ is —NRCOR'. In yet other embodiments, for compounds of formula I-A, $R^1$ and $R^2$, taken together is optionally substituted pyrrolidin-1-yl (ff), wherein z is 1 or 2 and $R^4$ is Cl, Br, F, $CF_3$, $CH_3$, —CH$_2$CH$_3$, —OR', or —CH$_2$OR'. In still other embodiments, for compounds of formula I-A, $R^1$ and $R^2$, taken together is optionally substituted piperidin-1-yl (dd), wherein z is 1 or 2 and at least one occurrence of $R^4$ is Cl, Br, F, $CF_3$, $CH_3$, —CH$_2$CH$_3$, —OR', or —CH$_2$OR', —NRSO$_2$R', —NRCOOR', or —OCON(R')$_2$. In certain other embodiments, for compounds of formula I-A, $R^1$ and $R^2$, taken together is optionally substituted piperidin-1-yl (dd), wherein z is 1 and $R^4$ is F, $CF_3$, $CH_3$, —CH$_2$CH$_3$, —OR', or —CH$_2$OR'. In other embodiments, for compounds of formula I-A, $R^1$ and $R^2$, taken together is optionally substituted piperidin-1-yl (dd), wherein z is 1 and $R^4$ is —NRSO$_2$R'. In certain other embodiments, for compounds of formula I-A, $R^1$ and $R^2$, taken together is optionally substituted piperidin-1-yl (dd), wherein z is 1 and $R^4$ is —NRCOOR'. In yet other embodiments, for compounds of formula I-A, $R^1$ and $R^2$, taken together is optionally substituted piperazin-1-yl (cc), wherein z is 1 or 2 and at least one occurrence of $R^4$ is —SOR', —CON(R')$_2$, —SO$_2$N(R')$_2$, —COR', or —COOR'. In certain other embodiments, for compounds of formula I-A, $R^1$ and $R^2$, taken together is optionally substituted piperazin-1-yl (cc), wherein z is 1 and $R^4$ is —SOR'. In certain other embodiments, for compounds of formula I-A, $R^1$ and $R^2$, taken together is optionally substituted piperazin-1-yl (cc), wherein z is 1 and $R^4$ is —COOR'. In certain other embodiments, for compounds of formula I-A, $R^1$ and $R^2$, taken together is optionally substituted piperazin-1-yl (cc), wherein z is 1 and $R^4$ is —CON(R')$_2$. In certain other embodiments, for compounds of formula I-A, $R^1$ and $R^2$, taken together is optionally substituted piperazin-1-yl (cc), wherein z is 1 and $R^4$ is —SO$_2$N(R')$_2$. In certain other embodiments, for compounds of formula I-A, $R^1$ and $R^2$, taken together is optionally substituted piperazin-1-yl (cc), wherein z is 1 and $R^4$ is —COR'.

As described generally above, for compounds of formulas I, I-A, or I-B, the quinazoline ring can be substituted with up to four independent occurrences of $R^3$. In certain embodiments, x is 0-2. In other embodiments, x is 1 or 2. In still other embodiments x is 1 and $R^3$ is substituted at the 6- or 7-position of the quinazoline ring. When the quinazoline ring is substituted (x is 1-4), $R^3$ groups are halogen, CN, $NO_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl. In still other embodiments, each occurrence of $R^3$ is independently Cl, Br, F, $CF_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy. In still other embodiments, x is 1 or 2 and each $R^3$ group is independently halogen, CN, optionally substituted $C_1$-$C_6$alkyl, OR', N(R')$_2$, CON(R')$_2$, or NRCOR'. In yet other embodiments, x is 1 or 2, and each $R^3$ group is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, x is 1 and $R^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. IN yet other embodiments, x is 1 and $R^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In other embodiments, x is 1 and $R^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, x is 1 and $R^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In other embodiments, x is 1 and $R^3$ is at the 6-position of the quinazoline ring and is —CON(R')$_2$, or NRCOR'. In yet other embodiments, x is 1 and $R^3$ is at the 7-position of the quinazoline ring and is —CON(R')$_2$, or NRCOR'. Other exemplary $R^3$ groups include those shown below in Table 2.

As described generally above, for compounds of formula I, I-A, or I-B, Ring A is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein ring A is optionally substituted with y independent occurrences of —R$^5$, wherein y is 0-5, and is additionally optionally substituted with q independent occurrences of R$^{5a}$, wherein q is 0-2.
In certain embodiments, ring A is selected from:
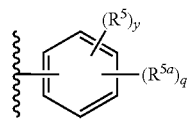
i
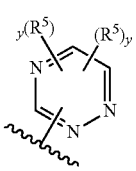
ii
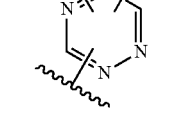
iii
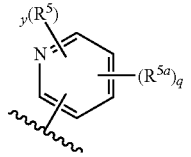
iv
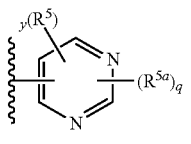
v
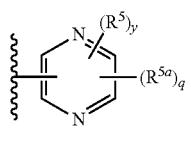
vi
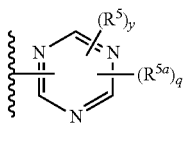
vii
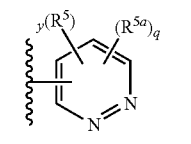
viii
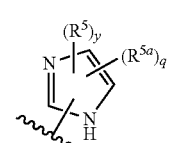
ix
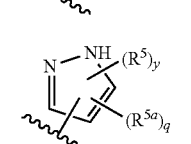
x
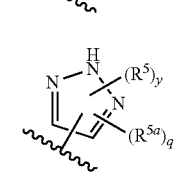
-continued
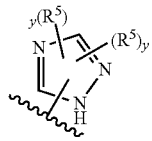
xi
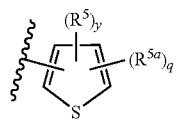
xii
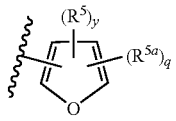
xiii
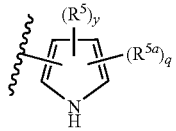
xiv
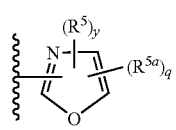
xv
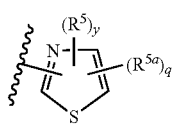
xvi
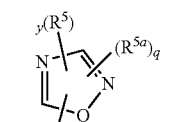
xvii
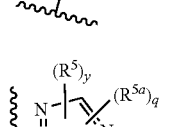
xviii
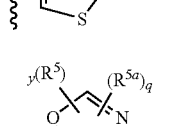
xix
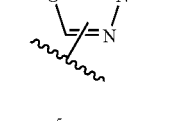
xx
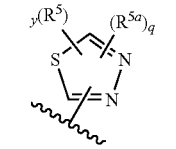
xxi
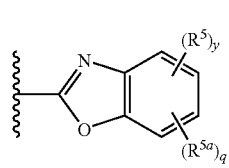

-continued xxii 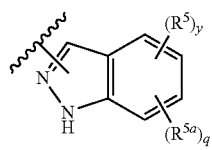

xxiii 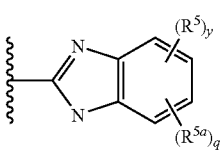

xxiv 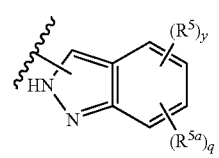

xxv 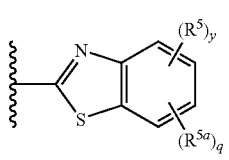

xxvi 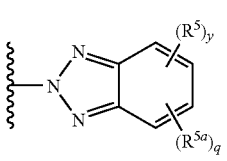

xxvii 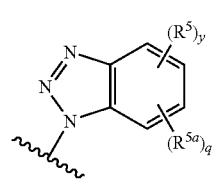

xxviii 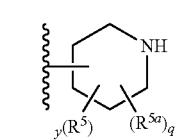

xxix 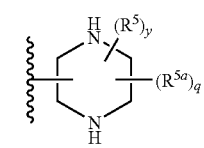

xxx 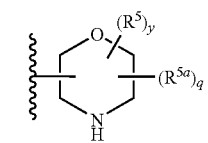

xxxi 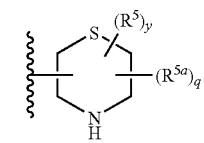

-continued xxxii 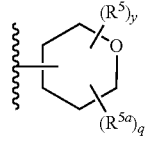

xxxiii 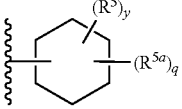

xxxiv 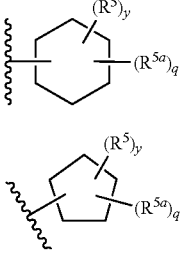

xxxv 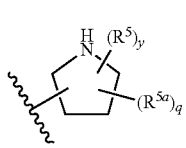

xxxvi 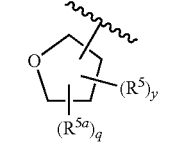

xxxvii 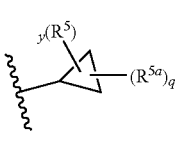

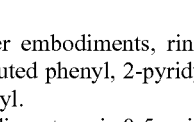

In certain other embodiments, ring A is selected from optionally substituted phenyl, 2-pyridyl, 3-pyridyl, or 4-pyridyl, or pyrrol-1-yl.

In some embodiments, y is 0-5, q is 0-2, and $R^5$ and $R^{5a}$ groups, when present, are each independently halogen, CN, $NO_2$, $-N(R')_2$, $-CH_2N(R')_2$, $-OR'$, $-CH_2OR'$, $-SR'$, $-CH_2SR'$, $-NRCOR'$, $-CON(R')_2$, $-S(O)_2N(R')_2$, $-OCOR'$, $-COR'$, $-CO_2R'$, $-OCON(R')_2$, $-NR'SO_2R'$, $-OP(O)(OR')_2$, $-P(O)(OR')_2$, $-OP(O)_2OR'$, $-P(O)_2OR'$, $-PO(R')_2$, $-OPO(R')_2$, or an optionally substituted group selected from $C_1$-$C_6$aliphatic, aryl, heteroaryl, cycloaliphatic, hetero cycloaliphatic, aryl $C_1$-$C_6$alkyl, hetero aryl $C_1$-$C_6$alkyl, cycloaliphatic $C_1$-$C_6$ alkyl, or heterocycloaliphatic $C_1$-$C_6$alkyl.

In yet other embodiments, y is 0-5, and q is 1 or 2, and each occurrence of $R^{5a}$ is independently Cl, Br, F, $CF_3$, Me, Et, CN, $-COOH$, $-NH_2$, $-N(CH_3)_2$, $-N(Et)_2$, $-N(iPr)_2$, $-O(CH_2)_2OCH_3$, $-CONH_2$, $-COOCH_3$, $-OH$, $-OCH_3$, $-OCH_2CH_3$, $-CH_2OH$, $-NHCOCH_3$, $-SO_2NH_2$, $-SO_2NHC(CH_3)_2$, $-OCOC(CH_3)_3$, $-OCOCH_2C(CH_3)_3$, $-O(CH_2)_2N(CH_3)_2$, 4-$CH_3$-piperazin-1-yl, OCOCH$(CH_3)_2$, OCO(cyclopentyl), $-COCH_3$, optionally substituted phenoxy, or optionally substituted benzyloxy.

In still other embodiments, y is 0, and q is 1 and $R^{5a}$ is F. In yet other embodiments, y is 0, q is 1, and $R^{5a}$ is OR'. In still other embodiments, y is 0, q is 1 and $R^{5a}$ is OH. In yet other embodiments, y is 0, q is 2 and one occurrence of $R^{5a}$ is OR' and the other occurrence of $R^{5a}$ is F. In yet other embodiments, y is 0, q is 2 and one occurrence of $R^{5a}$ is OH and the other occurrence of $R^{5a}$ is F.

In still other embodiments, ring A is phenyl, y is 0, and q is 1 and $R^{5a}$ is F substituted at the 2-position of the phenyl ring. In yet other embodiments, ring A is phenyl, y is 0, q is 1, and $R^{5a}$ is OR' substituted at the 2-position of the phenyl ring. In still other embodiments, ring A is phenyl, y is 0, q is 1 and $R^{5a}$ is OH substituted at the 2-position of the phenyl ring. In yet other embodiments, ring A is phenyl, y is 0, q is 2 and one occurrence of $R^{5a}$ is OR' and the other occurrence of $R^{5a}$ is F, wherein OR' is substituted at the 2-position of the phenyl ring and F is substituted at the 6-position of the phenyl ring. In yet other embodiments, ring A is phenyl, y is 0, q is 2 and one occurrence of $R^{5a}$ is OH and the other occurrence of $R^{5a}$ is F, wherein OH is substituted at the 2-position of the phenyl ring and F is substituted at the 6-position of the phenyl ring.

Other exemplary $R^5$ and $R^{5a}$ groups include those shown below in Table 2.

For compounds described in this section above, in general, compounds are useful as inhibitors of ion channels, preferably voltage gated sodium channels and N-type calcium channels. In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

Certain additional embodiments of compounds described generally above are described in more detail below. For example:

I. Compounds of Formula IA:

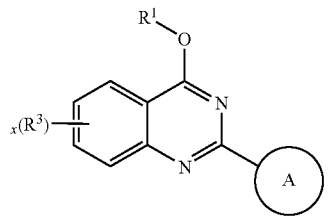

IA or a pharmaceutically acceptable salt thereof, wherein:

$R^1$ and $R^2$, taken together with the nitrogen atom to which they are bound, form an optionally substituted 3-12-membered monocyclic or bicyclic saturated, partially unsaturated, or fully unsaturated ring having 0-3 additional heteroatoms independently selected from nitrogen, sulfur, or oxygen; wherein the ring formed by $R^1$ and $R^2$ taken together, is optionally substituted at one or more substitutable carbon, nitrogen, or sulfur atoms with z independent occurrences of —$R^4$, wherein z is 0-5;

Ring A is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein ring A is optionally substituted with y independent occurrences of —$R^5$, wherein y is 0-5, and is additionally optionally substituted with q independent occurrences of $R^{5a}$, wherein q is 0-2;

x is 0-4;

each occurrence of $R^3$, $R^4$, and $R^5$ is independently Q-$R^x$; wherein Q is a bond or is a $C_1$-$C_6$ alkylidene chain wherein up to two non-adjacent methylene units of Q are optionally and independently replaced by —NR—, —S—, —O—, —CS—, —$CO_2$—, —OCO—, —CO—, —COCO—, —CONR—, —NRCO—, —$NRCO_2$—, —$SO_2NR$—, —$NRSO_2$—, —CONRNR—, —NRCONR—, —OCONR—, —NRNR—, —$NRSO_2NR$—, —SO—, —$SO_2$—, —PO—, —$PO_2$—, —OP(O)(OR)—, or —POR—; and each occurrence of $R^x$ is independently selected from —R', halogen, =O, =NR', —$NO_2$, —CN, —OR', —SR', —N(R')$_2$, —NR'COR', —NR'CON(R')$_2$, —NR'$CO_2$R', —COR', —$CO_2$R', —OCOR', —CON(R')$_2$, —OCON(R')$_2$, —SOR', —$SO_2$R', —$SO_2$N(R')$_2$, —NR'$SO_2$R', —NR'$SO_2$N(R')$_2$, —COCOR', —$COCH_2$COR', —OP(O)(OR')$_2$, —P(O)(OR')$_2$, —OP(O)$_2$OR', —P(O)$_2$OR', —PO(R')$_2$, or —OPO(R')$_2$;

each occurrence of $R^{5a}$ is independently an optionally substituted $C_1$-$C_6$ aliphatic group, halogen, —OR', —SR', —N(R')$_2$, —NR'COR', —NR'CON(R')$_2$, —NR'$CO_2$R', —COR', —$CO_2$R', —OCOR', —CON(R')$_2$, —OCON(R')$_2$, —SOR', —$SO_2$R', —$SO_2$N(R')$_2$, —NR'$SO_2$R', —NR'$SO_2$N(R')$_2$, —COCOR', —$COCH_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain embodiments, for compounds described directly above:

a. when $R^1$ and $R^2$, taken together with the nitrogen atom to which they are bound, form an optionally substituted 4-membered monocyclic saturated or partially unsaturated ring having 0-3 additional heteroatoms independently selected from nitrogen, sulfur, or oxygen; then 2-Oxazolidinone, 3-[(3R, 4R)-2-oxo-1-(2-phenyl-4-quinazolinyl)-4-[2-(3-pyridinyl) ethenyl]-3-azetidinyl]-4-phenyl-, (4S)- is excluded;

b. when $R^1$ and $R^2$, taken together with the nitrogen atom to which they are bound, form an optionally substituted 5-membered monocyclic saturated or partially unsaturated ring having 0-3 additional heteroatoms independently selected from nitrogen, sulfur, or oxygen; then:

i. ring A is not optionally substituted hexahydro-1H-1,4-diazepin-1-yl; and ii. Benzenesulfonamide, 2-methoxy-5-[2-[[1-(2-phenyl-4-quinazolinyl)-3-pyrrolidinyl]amino]ethyl]-, (R)—, bis (trifluoroacetate), and Benzenesulfonamide, 2-methoxy-5-[2-[[1-(2-phenyl-4-quinazolinyl)-3-pyrrolidinyl] amino]ethyl]-, (S)—, bis(trifluoroacetate) are excluded;

iii. 3-Pyrrolidinamine, 1-(2-phenyl-4-quinazolinyl)-, and (R)-3-Pyrrolidinamine, 1-(2-phenyl-4-quinazolinyl)-, (S)— are excluded;

iv. when $R^1$ and $R^2$, taken together are unsubstituted pyrrolidin-1-yl, ring A is unsubstituted phenyl, and x is 1, then $R^3$ is not 6-OMe or 6-OH;

v. when $R^1$ and $R^2$, taken together are unsubstituted pyrrolidin-1-yl, ring A is unsubstituted phenyl, and x is 2, then the two $R^3$ groups are not 6-OMe and 7-OMe;

vi. when R¹ and R², taken together are unsubstituted pyrrolidin-1-yl, then ring A is not unsubstituted pyrrolidin-1-yl, optionally substituted piperazin-1-yl, unsubstituted morpholin-1-yl; or unsubstituted piperidin-1-yl;

vii. when R¹ and R², taken together are pyrrolidin-1-yl, x is 0 and ring A is unsubstituted phenyl, then the pyrrolidin-1-yl group is not substituted at the 3-position with —OH or 2-methoxy-phenoxy;

viii. when R¹ and R², taken together are unsubstituted pyrrolidin-1-yl, and x is 0, then ring A is not 2,3-xylyl, 3-methylphenyl, unsubstituted phenyl, 4-bromo-phenyl, 4-chloro-phenyl, 3-nitro-phenyl, unsubstituted pyrid-3-yl, 2,4-dichlorophenyl, 3,4-dichlorophenyl, 4-propoxyphenyl, 3-methylphenyl, 3,4,5-trimethoxyphenyl, 2-chlorophenyl, unsubstituted pyrid-4-yl, 2-hydroxyphenyl, or 4-(1,1-dimethylethyl)phenyl;

c. when R¹ and R², taken together with the nitrogen atom to which they are bound, form an optionally substituted 6-membered monocyclic or bicyclic saturated or partially unsaturated ring having 0-3 additional heteroatoms independently selected from nitrogen, sulfur, or oxygen; then:

i. when R¹ and R², taken together form an unsubstituted morpholino ring, and ring A is unsubstituted phenyl, then x is not 0, or if x is 1 or 2, then R³ is not: 6-fluoro, 6,7-dimethoxy, 6-nitro, 6-AcHN—, 6-methox, 6-NH2, 6-OCHN—, 6-OH, 6-AcMeN—, 6-TsHN—, 6-Me2N—, 7-OH, 6-amino-thiazol-2-yl, 6-NHCO-COOEt, or 6-(4-phenyl-amino-thiazol-2-yl);

ii. when R¹ and R², taken together form an unsubstituted morpholino ring, and ring A is unsubstituted cyclohexyl, unsubstituted pyrid-3-yl, unsubstituted 2-furyl, 2-fluorophenyl, 3-thienyl, benzofuran, pyridazine, phenyl substituted in one or more of the 3, 4, or 5-position of the phenyl ring, and x is 1 or 2, then R³ is not 6-NH₂, 6-OHCHN—, 6-OH, 7-OH, 6-MsHN—, 6-AcHN—, 6-fluoro, or 6-OMe;

iii. when R¹ and R², taken together, form a piperid-4-one, piperid-4-ol, or thiomorpholino, or a dimethyl substituted morpholino ring, ring A is unsubstituted phenyl, and x is 1, then R³ is not 6-OH;

iv. when x is 0 and A is unsubstituted phenyl, 3,4,5-trimethoxyphenyl, or 3,4-dimethoxyphenyl, then R¹ and R², taken together is not optionally substituted piperidinyl or optionally substituted piperazinyl;

v. when x is 2 or 3, and R³ is 6,7-diOMe, or 6,7,8-triOMe, then R¹ and R², taken together is not optionally substituted piperidin-1-yl, piperazin-1-yl, or morpholin-1-yl;

vi. when x is 0 and ring A is unsubstituted phenyl, then R¹ and R₂, taken together is not optionally substituted or fused piperazinyl;

vii. when x is 0 and ring A is phenyl optionally substituted in one or more of the 3-, 4-, or 5-positions of the phenyl ring, then R¹ and R², taken together is not optionally substituted piperazin-1-yl, or morpholin-1-yl;

viii. when x is 0 and ring A is 2-F-phenyl, then R¹ and R², taken together is not 4-(2-Cl-phenyl)-piperazin-1-yl, 4-(3-Cl-phenyl)-piperazin-1-yl, or unsubstituted morpholin-1-yl;

ix. when x is 0 and ring A is 2-Cl-phenyl, then R¹ and R², taken together is not unsubstituted morpholin-1-yl, 4-Me-piperazin-1-yl, 4-Et-piperazin-1-yl, 4-phenyl-piperazin-1-yl, or 4-CH₂Ph₂-piperazin-1-yl;

x. when x is 0 and ring A is 2-OH-phenyl, then R1 and R2, taken together is not unsubstituted morpholin-1-yl, 4-(2-OMe-phenyl)-piperazin-1-yl, 4-CH2Ph-piperazin-1-yl, 4-Et-piperazin-1-yl, or 4-Me-piperazin-1-yl;

xi. when x is 0, x is 1 and R³ is 6-Br, or x is 2 and R³ is 6-7-diOMe, and ring A is optionally substituted 2- or 3-thienyl, then R¹ and R², taken together is not 4-Ph-piperazin-1-yl, 4-(3-CF₃-phenyl)-piperazin-1-yl, 4-(2-OEt-phenyl)-piperazin-1-yl, 4-Me-piperazinyl, or unsubstituted morpholin-1-yl;

xii when x is 0, and ring A is unsubstituted pyrid-3-yl or pyrid-4-yl, then R¹ and R², taken together is not optionally substituted morpholin-1-yl, or optionally substituted piperazin-1-yl;

xiii. when x is 0, and ring A is optionally substituted 1H-imidazol-2-yl or 1H-imidazol-1-yl, then R¹ and R² taken together is not unsubstituted morpholin-1-yl, 4-Me-piperazin-1-yl, or 4-CH₂CH₂OH-piperazin-1-yl;

xiv. when x is 0 and ring A is 5-NO₂-thiazol-2-yl, then R¹ and R², taken together is not 4-Me-piperazin-1-yl;

xv. when x is 0 and ring A is 5-NO₂-2-furanyl, then R¹ and R², taken together is not 4-CH₂CH₂OH-piperazin-1-yl, 4-Me-piperazin-1-yl, or unsubstituted morpholin-1-yl;

xvi. when x is 1, R³ is 6-OH and ring A is unsubstituted phenyl, then R¹ and R², taken together is not unsubstituted morpholin-1-yl, or 4-Me-piperazin-1-yl;

xvii. when x is 0 and R¹ and R², taken together is unsubstituted piperidinyl, then ring A is not 2-OH-phenyl, 4-OMe-phenyl, 4-F-phenyl, 4-NO₂-phenyl, pyrid-3-yl, pyrid-4-yl, 2-Cl-phenyl, 4-OₙPr-phenyl, 3,4-dichlorophenyl, 2-F-phenyl, 4-Br-phenyl, 4-Cl-phenyl, 3-NO₂-phenyl, or 2,4-dichlorophenyl;

xviii. when x is 0, ring A is 4-Br-phenyl, 2-F-phenyl, 2-Cl-phenyl, 4-Cl-phenyl, 4-OnPr-phenyl, 2,4-dichlorophenyl, 3,4-dichlorophenyl, 4-Me-phenyl, 3-Me-phenyl, pyrid-3-yl, pyrid-4-yl, 2-OH-phenyl, 4-NO₂-phenyl, 4-tBu-phenyl, then R¹ and R², taken together is not 2-Me-piperidin-1-yl, 4-CH₂-Ph-piperidin-1-yl, 4-Me-piperidin-1-yl, 3-COOEt-piperidin-1-yl, 4-COOEt-piperidin-1-yl, 2-Et-piperidin-1-yl, 3-Me-piperidin-1-yl, 3,5-diMe-piperidin-1-yl, 4-CONH₂-piperidin-1-yl, (4-piperidinyl, 4-carboxamide)-piperidin-1-yl, 1,4-dioxa-8-azaspiro[4.5]decane, 3,4-dihydro-2(1H)-isoquinolinyl, or piperidin-4-one;

xix. when x is 1, R³ is 6-Br, 6-Cl, 6-OH, 6-OMe, or 6-Me and ring A is 4-bromophenyl, 4-CH₂P(O)(OH)(OEt) phenyl, or unsubstituted phenyl, then R¹ and R², taken together, is not optionally substituted piperidinyl;

xx. when x is 2, and R³ is 6,7-dimethoxy, and A is unsubstituted phenyl, then R¹ and R², taken together is not 1,4-dioxa-8-azaspiro[4.5]decane or 3,4-dihydro-2(1H)-isoquinolinyl;

xxi. when x is 3, and the three occurrences of R³ are 5-OAc, 6-OAc, and 8-piperidinyl, and ring A is unsubstituted phenyl, then R¹ and R², taken together is not an unsubstituted piperidinyl ring;

xxii. when x is 3 and the three occurrences of R³ are 6-Me, 7-COOEt, and 8-Me, and ring A is 2-Cl-phenyl, then R¹ and R², taken together, is not 4-phenyl-piperidin-1-yl, 4-(4-Cl-phenyl)-piperazin-1-yl, unsubstituted piperazin-1-yl, 4-CH₂Ph-piperazin-1-yl, 4(2-Cl-phenyl)piperazin-1-yl, or 4-COOEt-piperazin-1-yl;

c. when R¹ and R², taken together with the nitrogen atom to which they are bound, form an optionally substituted 7-membered monocyclic or bicyclic saturated or partially unsaturated ring having 0-3 additional heteroatoms independently selected from nitrogen, sulfur, or oxygen; then:

i. Benzenesulfonamide, 2-methoxy-5-[2-[5-(2-phenyl-4-quinazolinyl)-2,5-diazabicyclo[2.2.1]hept-2-yl]ethyl]-, and bis(trifluoro acetate) 2,5-Diazabicyclo[2.2.1]heptane, 2-(2-phenyl-4-quinazolinyl)- are excluded;

ii. when x is 2 and both occurrences of $R^3$ are OMe, and ring A is 4-Cl-phenyl, then $R^1$ and $R^2$, taken together is not unsubstituted hexahydro-1H-azepin-1-yl;

iii. when x is 0 and $R^1$ and $R^2$, taken together is unsubstituted hexahydro-1H-azepin-1-yl, then ring A is not unsubstituted phenyl, 4-F-phenyl, 4-NO$_2$-phenyl, pyrid-4-yl, 3,4-diCl-phenyl, 2-Cl-phenyl, 2,4-diCl-phenyl, 2,4-diCl-phenyl, 3-NO$_2$-phenyl, 4-Cl-phenyl, 4-O$_n$Pr-phenyl, 3-Me-phenyl, 3,4-OMe-phenyl, 3,4,5-OMe-phenyl, pyrid-3-yl, or 2-OH-phenyl;

d. when $R^1$ and $R^2$, taken together with the nitrogen atom to which they are bound, form an optionally substituted 8-membered monocyclic or bicyclic saturated or partially unsaturated ring having 0-3 additional heteroatoms independently selected from nitrogen, sulfur, or oxygen; then:

i. Benzenesulfonamide, 2-methoxy-5-[2-[8-(2-phenyl-4-quinazolinyl)-3,8-diazabicyclo[3.2.1]oct-3-yl]ethyl]-, bis(trifluoroacetate) 3,8-Diazabicyclo[3.2.1]octane, 3-(phenylmethyl)-8-(2-phenyl-4-quinazolinyl)-3,8-Diazabicyclo[3.2.1]octane, 8-(2-phenyl-4-quinazolinyl)-; Quinazoline, 2-(3-methylphenyl)-4-(1,3,3-trimethyl-6-azabicyclo[3.2.1]oct-6-yl)-, monohydrochloride; Quinazoline, 2-(4-nitrophenyl)-4-(1,3,3-trimethyl-6-azabicyclo[3.2.1]oct-6-yl)-, monohydro chloride; Quinazoline, 2-(3-methylphenyl)-4-(1,3,3-trimethyl-6-azabicyclo[3.2.1]oct-6-yl)-; Quinazoline, 2-(4-methylphenyl)-4-(1,3,3-trimethyl-6-azabicyclo[3.2.1]oct-6-yl)-; and Quinazoline, 2-(4-nitrophenyl)-4-(1,3,3-trimethyl-6-azabicyclo[3.2.1]oct-6-yl)- are excluded; and e. when $R^1$ and $R^2$, taken together with the nitrogen atom to which they are bound, form an optionally substituted 9-membered monocyclic or bicyclic saturated or partially unsaturated ring having 0-3 additional heteroatoms independently selected from nitrogen, sulfur, or oxygen; then: piperazine, 1-[4-(1,3-dihydro-1,3-dioxo-2H-isoindol-2-yl)-6,7-dimethoxy-2-quinazolinyl]-4-(2-furanylcarbonyl)- is excluded.

In other embodiments, for compounds described directly above, the ring formed by $R^1$ and $R^2$ taken together is selected from:

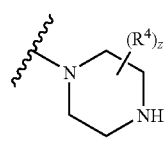

cc

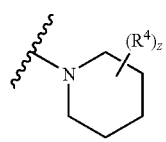

dd

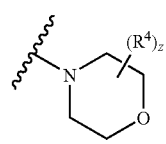

ee

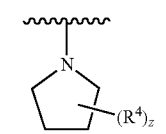

ff

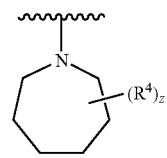

gg

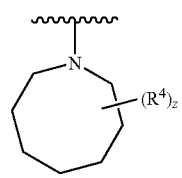

hh

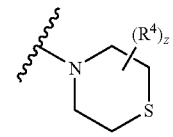

ii

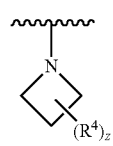

jj

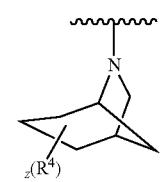

kk

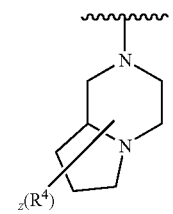

ll

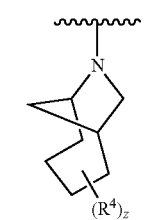

mm

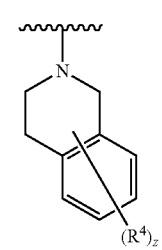

nn

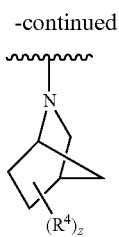

wherein the ring formed by $R^1$ and $R^2$ taken together, is optionally substituted at one or more substitutable carbon, nitrogen, or sulfur atoms with z independent occurrences of —$R^4$, and z is 0-5.

In other embodiments, for compounds of formula I-A, $R^1$ and $R^2$ taken together are optionally substituted azetidin-1-yl; (jj), pyrrolidin-1-yl (ff), piperidin 1-yl (dd), piperazin-1-yl (cc), or morpholin-4-yl (ee). In other embodiments, for compounds of formula I-A, $R^1$ and $R^2$ taken together are optionally substituted azetidin-1-yl (jj), pyrrolidin-1-yl (ff), piperidin-1-yl (dd), or piperazin-1-yl (cc). In yet other embodiments, for compounds of formula I-A, $R^1$ and $R^2$, taken together is optionally substituted azetidin-1-yl (jj). In yet other embodiments, for compounds of formula I-A, $R^1$ and $R^2$, taken together is optionally substituted pyrrolidin-1-yl (ff). In still other embodiments, for compounds of formula I-A, $R^1$ and $R^2$, taken together is optionally substituted piperidin-1-yl (dd). In yet other embodiments, for compounds of formula I-A, $R^1$ and $R^2$, taken together is optionally substituted piperazin-1-yl (cc).

For compounds described directly above, z is 0-5, and $R^4$ groups, when present, are each independently halogen, CN, $NO_2$, —$N(R')_2$, —$CH_2N(R')_2$, —OR', —$CH_2OR'$, —SR', —$CH_2SR'$, —COOR', —NRCOR', —$CON(R')_2$, —$OCON(R')_2$, COR', —NHCOOR', —$SO_2R'$, —$SO_2N(R')_2$, or an optionally substituted group selected from $C_1$-$C_6$aliphatic, aryl, heteroaryl, cycloaliphatic, hetero cycloaliphatic, aryl $C_1$-$C_6$alkyl, hetero aryl $C_1$-$C_6$alkyl, cycloaliphatic $C_1$-$C_6$ alkyl, or heterocycloaliphatic $C_1$-$C_6$alkyl.

In still other embodiments, z is 0-5 and $R^4$ groups are each independently Cl, Br, F, $CF_3$, $CH_3$, —$CH_2CH_3$, CN, —COOH, —$N(CH_3)_2$, —$N(Et)_2$, —$N(iPr)_2$, —$O(CH_2)_2$ $OCH_3$, —$CONH_2$, —$COOCH_3$, —OH, —$CH_2OH$, —NH-$COCH_3$, —$SO_2NH_2$, —$SO_2(CH_2)_3CH_3$, —$SO_2CH(CH_3)_2$, —$SO_2N(CH_3)_2$, —$SO_2CH_2CH_3$, —$C(O)OCH_2CH(CH_3)_2$, —$C(O)NHCH_2CH(CH_3)_2$, —$NHCOOCH_3$, —$C(O)C$ $(CH_3)_3$, —$COO(CH_2)_2CH_3$, —$C(O)NHCH(CH_3)_2$, —$C(O)$ $CH_2CH_3$, or an optionally substituted group selected from -piperidinyl, piperizinyl, morpholino, $C_{1-4}$alkoxy, phenyl, phenyloxy, benzyl, benzyloxy, —$CH_2$cyclohexyl, pyridyl, —$CH_2$pyridyl, or —$CH_2$thiazolyl.

In certain embodiments, for compounds of formula I-A, $R^1$ and $R^2$, taken together is optionally substituted azetidin-1-yl (jj), wherein z is 1 or 2 and at least one occurrence of $R^4$ is —$NRSO_2R'$, —NRCOOR', or —NRCOR'. In certain other embodiments, for compounds of formula I-A, $R^1$ and $R^2$, taken together is optionally substituted azetidin-1-yl (jj), wherein z is 1 and $R^4$ is —$NRSO_2R'$. In other embodiments, for compounds of formula I-A, $R^1$ and $R^2$ taken together is optionally substituted azetidin-1-yl (jj), wherein z is 1 and $R^4$ is —NRCOOR'. In certain other embodiments, for compounds of formula I-A, $R^1$ and $R^2$, taken together is optionally substituted azetidin-1-yl (jj), wherein z is 1 and $R^4$ is —NR-COR'. In yet other embodiments, for compounds of formula I-A, $R^1$ and $R^2$, taken together is optionally substituted pyrrolidin-1-yl (ff), wherein z is 1 or 2 and $R^4$ is Cl, Br, F, $CF_3$, $CH_3$, —$CH_2CH_3$, —OR', or —$CH_2OR'$. In still other embodiments, for compounds of formula I-A, $R^1$ and $R^2$, taken together is optionally substituted piperidin-1-yl (dd), wherein z is 1 or 2 and at least one occurrence of $R^4$ is Cl, Br, F, $CF_3$, $CH_3$, —$CH_2CH_3$, —OR', or —$CH_2OR'$, —$NRSO_2R'$, —NR-COOR', or —$OCON(R')_2$. In certain other embodiments, for compounds of formula I-A, $R^1$ and $R^2$, taken together is optionally substituted piperidin-1-yl (dd), wherein z is 1 and $R^4$ is F, $CF_3$, $CH_3$, —$CH_2CH_3$, —OR', or —$CH_2OR'$. In other embodiments, for compounds of formula I-A, $R^1$ and $R^2$, taken together is optionally substituted piperidin-1-yl (dd), wherein z is 1 and $R^4$ is —$NRSO_2R'$. In certain other embodiments, for compounds of formula I-A, $R^1$ and $R^2$, taken together is optionally substituted piperidin-1-yl (dd), wherein z is 1 and $R^4$ is —NRCOOR'. In yet other embodiments, for compounds of formula I-A, $R^1$ and $R^2$, taken together is optionally substituted piperazin-1-yl (cc), wherein z is 1 or 2 and at least one occurrence of $R^4$ is —SOR', —$CON(R')_2$, —$SO_2N(R')_2$, —COR', or —COOR'. In certain other embodiments, for compounds of formula I-A, $R^1$ and $R^2$, taken together is optionally substituted piperazin-1-yl (cc), wherein z is 1 and $R^4$ is —SOR'. In certain other embodiments, for compounds of formula I-A, $R^1$ and $R^2$, taken together is optionally substituted piperazin-1-yl (cc), wherein z is 1 and $R^4$ is —COOR'. In certain other embodiments, for compounds of formula I-A, $R^1$ and $R^2$, taken together is optionally substituted piperazin-1-yl (cc), wherein z is 1 and $R^4$ is —$CON(R')_2$. In certain other embodiments, for compounds of formula I-A, $R^1$ and $R^2$, taken together is optionally substituted piperazin-1-yl (cc), wherein z is 1 and $R^4$ is —$SO_2N(R')_2$. In certain other embodiments, for compounds of formula I-A, $R^1$ and $R^2$, taken together is optionally substituted piperazin-1-yl (cc), wherein z is 1 and $R^4$ is —COR'.

For compounds described directly above, in some embodiments, x is 0-4, and $R^3$ groups, when present, are each independently halogen, CN, $NO_2$, —$N(R')_2$, —$CH_2N(R')_2$, —OR', —$CH_2OR'$, —SR', —$CH_2SR'$, —COOR', —NR-COR', —$CON(R')_2$, —$OCON(R')_2$, COR', —NHCOOR', —$SO_2R'$, —$SO_2N(R')_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In yet other embodiments, x is 1 or 2, and each occurrence of $R^3$ is independently Cl, Br, F, $CF_3$, —$OCF_3$, Me, Et, CN, —COOH, —$NH_2$, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$CH_2OH$, —$NHCOCH_3$, —NHCOC$H(CH_3)_2$, —$SO_2NH_2$, —CONH(cyclopropyl), —CON-$HCH_3$, —$CONHCH_2CH_3$, or an optionally substituted group selected from -piperidinyl, piperizinyl, morpholino, phenyl, phenyloxy, benzyl, or benzyloxy.

In still other embodiments, x is 1 or 2 and each $R^3$ group is independently halogen, CN, optionally substituted $C_1$-$C_6$alkyl, OR', $N(R')_2$, $CON(R')_2$, or NRCOR'.

In yet other embodiments, x is 1 or 2, and each $R^3$ group is —Cl, —$CH_3$, —$CH_2CH_3$, —F, —$CF_3$, —$OCF_3$, —CON-$HCH_3$, —$CONHCH_2CH_3$, —CONH(cyclopropyl), —$OCH_3$, —$NH_2$, —$OCH_2CH_3$, or —CN.

In still other embodiments, x is 1 and $R^3$ is at the 6-position of the quinazoline ring and is —Cl, —$CH_3$, —$CH_2CH_3$, —F, —$CF_3$, —$OCF_3$, —$CONHCH_3$, —$CONHCH_2CH_3$, —CONH(cyclopropyl), —$OCH_3$, —$NH_2$, —$OCH_2CH_3$, or —CN.

In yet other embodiments, x is 1 and $R^3$ is at the 7-position of the quinazoline ring and is —Cl, —$CH_3$, —$CH_2CH_3$, —F, —CF₃, —OCF₃, —CONHCH₃, —CONHCH₂CH₃, —CONH(cyclopropyl), —OCH₃, —NH₂, —OCH₂CH₃, or —CN.

In still other embodiments, x is 1 and $R^3$ is at the 6-position of the quinazoline ring and is —Cl, —CH₃, —CH₂CH₃, —F, —CF₃, —OCF₃, —OCH₃, or —OCH₂CH₃.

In yet other embodiments, x is 1 and $R^3$ is at the 7-position of the quinazoline ring and is —Cl, —CH₃, —CH₂CH₃, —F, —CF₃, —OCF₃, —OCH₃, or —OCH₂CH₃.

In still other embodiments, x is 1 and $R^3$ is at the 6-position of the quinazoline ring and is —CON(R')₂, or NRCOR'.

In yet other embodiments, x is 1 and $R^3$ is at the 7-position of the quinazoline ring and is —Cl, —CH₃, —CH₂CH₃, —F, —CF₃, —OCF₃, —OCH₃, or —OCH₂CH₃.

For compounds described directly above, in certain embodiments, ring A is a group selected from:

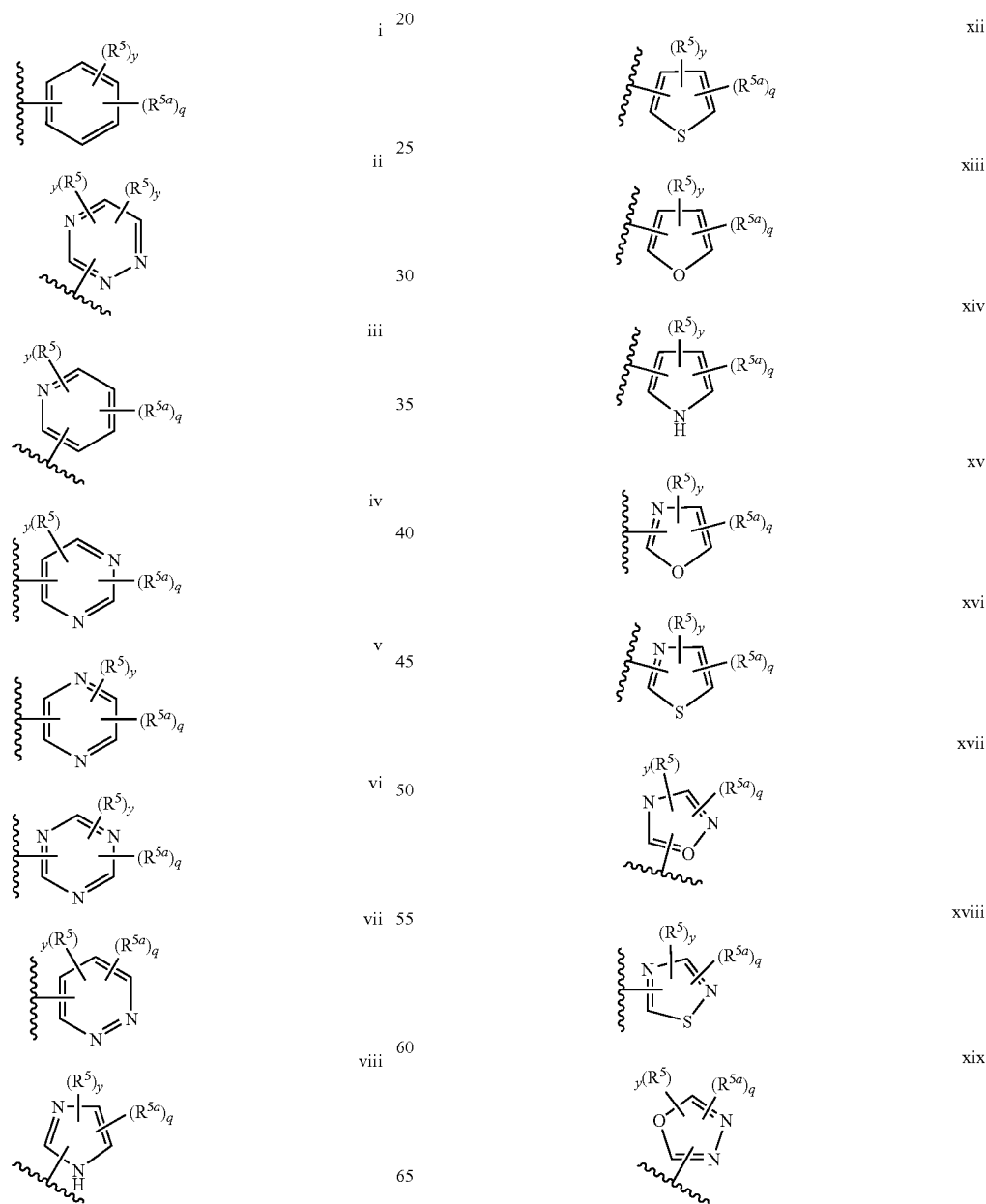

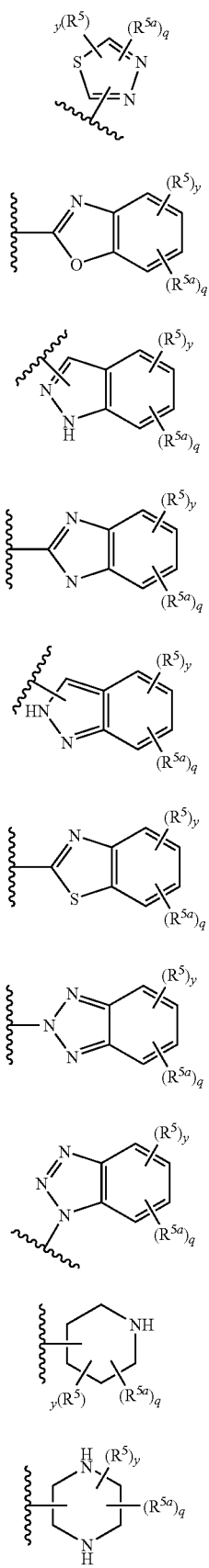
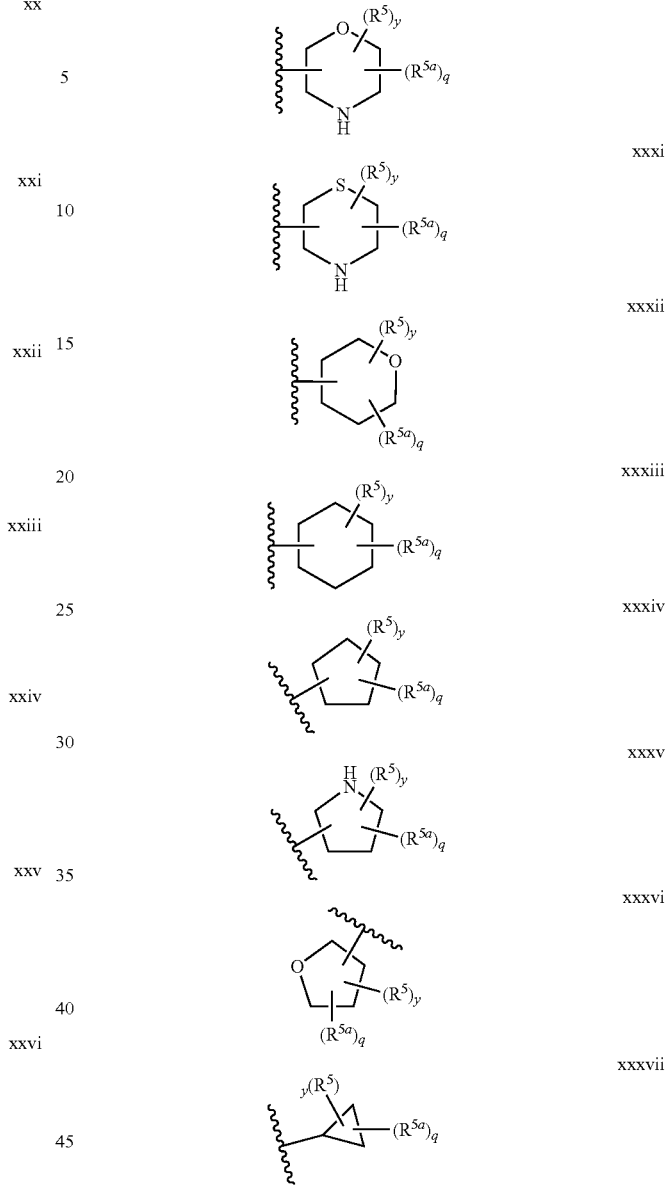

In other embodiments, ring A is optionally substituted phenyl, 2-pyridyl, 3-pyridyl, or 4-pyridyl, or pyrrol-1-yl.

For compounds described directly above, in some embodiments, y is 0-5, q is 0-2, and $R^5$ and $R^{5a}$ groups, when present, are each independently halogen, CN, $NO_2$, —N(R')$_2$, —CH$_2$N(R')$_2$, —OR', —CH$_2$OR', —SR', —CH$_2$SR', —NRCOR', —CON(R')$_2$, —S(O)$_2$N(R)$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In still other embodiments, y is 0-5, and q is 1 or 2, and each occurrence of $R^{5a}$ is independently Cl, Br, F, $CF_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In still other embodiments, y is 0, and q is 1 and R$^{5a}$ is F. In yet other embodiments, y is 0, q is 1, and R$^{5a}$ is OR'. In still other embodiments, y is 0, q is 1 and R$^{5a}$ is OH. In yet other embodiments, y is 0, q is 2 and one occurrence of R$^{5a}$ is OR' and the other occurrence of R$^{5a}$ is F. In yet other embodiments, y is 0, q is 2 and one occurrence of R$^{5a}$ is OH and the other occurrence of R$^{5a}$ is F.

In yet other embodiments, ring A is optionally substituted phenyl and compounds have the structure IA-i:

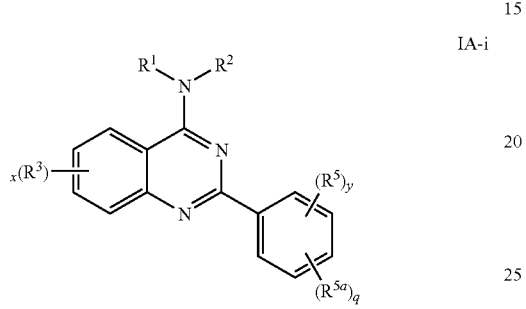

IA-i wherein:

y is 0-5;

q is 0-2; and each occurrence of R$^{5a}$ is independently an optionally substituted C$_1$-C$_6$aliphatic group, halogen, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$.

In certain exemplary embodiments, the ring formed by R$^1$ and R$^2$ taken together is selected from

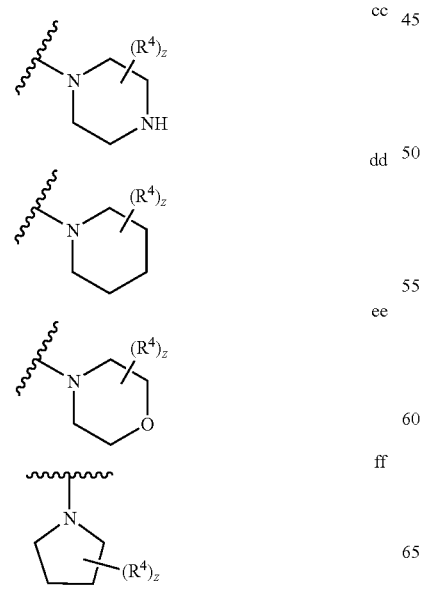

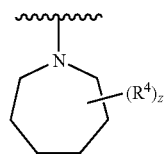  gg

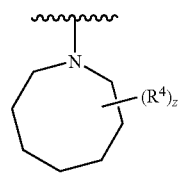  hh

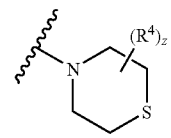  ii

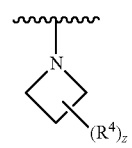  jj

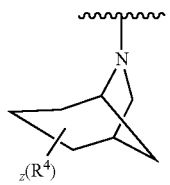  kk

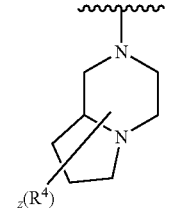  ll

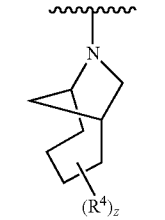  mm

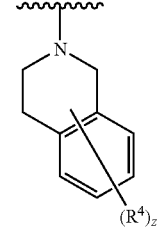  nn

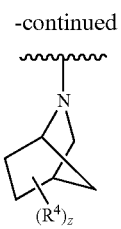

(oo)

wherein the ring formed by $R^1$ and $R^2$ taken together, is optionally substituted at one or more substitutable carbon, nitrogen, or sulfur atoms with z independent occurrences of —$R^4$, and z is 0-5.

In other embodiments, for compounds of formula IA-i, $R^1$ and $R^2$ taken together are optionally substituted azetidin-1-yl (jj), pyrrolidin-1-yl (ff), piperidin 1-yl (dd), piperazin-1-yl (cc), or morpholin-4-yl (ee). In other embodiments, for compounds of formula I-A, $R^1$ and $R^2$ taken together are optionally substituted azetidin-1-yl (jj), pyrrolidin-1-yl (ff), piperidin-1-yl (dd), or piperazin-1-yl (cc). In yet other embodiments, for compounds of formula IA-i, $R^1$ and $R^2$, taken together is optionally substituted azetidin-1-yl (jj). In yet other embodiments, for compounds of formula IA-i, $R^1$ and $R^2$, taken together is optionally substituted pyrrolidin-1-yl (ff). In still other embodiments, for compounds of formula IA-i, $R^1$ and $R^2$, taken together is optionally substituted piperidin1-yl (dd). In yet other embodiments, for compounds of formula IA-i, $R^1$ and $R^2$, taken together is optionally substituted piperazin-1-yl (cc).

For compounds of formula IA-i, z is 0-5, and $R^4$ groups, when present, are each independently halogen, CN, $NO_2$, —$N(R')_2$, —$CH_2N(R')_2$, —OR', —$CH_2OR'$, —SR', —$CH_2SR'$, —COOR', —NRCOR', —$CON(R')_2$, —$OCON(R')_2$, COR', —NHCOOR', —$SO_2R'$, —$SO_2N(R')_2$, or an optionally substituted group selected from $C_1$-$C_6$ aliphatic, aryl, heteroaryl, cycloaliphatic, hetero cycloaliphatic, aryl $C_1$-$C_6$alkyl, hetero aryl $C_1$-$C_6$alkyl, cycloaliphatic $C_1$-$C_6$ alkyl, or heterocycloaliphatic $C_1$-$C_6$alkyl. In other embodiments, z is 0-5 and $R^4$ groups are each independently Cl, Br, F, $CF_3$, $CH_3$, —$CH_2CH_3$, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, —$SO_2(CH_2)_3CH_3$, —$SO_2CH(CH_3)_2$, —$SO_2N(CH_3)_2$, —$SO_2CH_2CH_3$, —$C(O)OCH_2CH(CH_3)_2$, —$C(O)NHCH_2CH(CH_3)_2$, —$NHCOOCH_3$, —$C(O)C(CH_3)_3$, —$COO(CH_2)_2CH_3$, —$C(O)NHCH(CH_3)_2$, —$C(O)CH_2CH_3$, or an optionally substituted group selected from -piperidinyl, piperizinyl, morpholino, $C_{1-4}$alkoxy, phenyl, phenyloxy, benzyl, benzyloxy, —$CH_2$cyclohexyl, pyridyl, —$CH_2$pyridyl, or —$CH_2$thiazolyl.

In certain embodiments, for compounds of formula IA-i, $R^1$ and $R^2$, taken together is optionally substituted azetidin-1-yl (jj), wherein z is 1 or 2 and at least one occurrence of $R^4$ is —$NRSO_2R'$, —NRCOOR', or —NRCOR'. In certain other embodiments, for compounds of formula IA-i, $R^1$ and $R^2$, taken together is optionally substituted azetidin-1-yl (jj), wherein z is 1 and $R^4$ is —$NRSO_2R'$. In other embodiments, for compounds of formula IA-i, $R^1$ and $R^2$, taken together is optionally substituted azetidin-1-yl (jj), wherein z is 1 and $R^4$ is —NRCOOR'. In certain other embodiments, for compounds of formula IA-i, $R^1$ and $R^2$, taken together is optionally substituted azetidin-1-yl (jj), wherein z is 1 and $R^4$ is —NRCOR'. In yet other embodiments, for compounds of formula IA-i, $R^1$ and $R^2$, taken together is optionally substituted pyrrolidin-1-yl (ff), wherein z is 1 or 2 and $R^4$ is Cl, Br, F, $CF_3$, $CH_3$, —$CH_2CH_3$, —OR', or —$CH_2OR'$. In still other embodiments, for compounds of formula IA-i, $R^1$ and $R^2$, taken together is optionally substituted piperidin-1-yl (dd), wherein z is 1 or 2 and at least one occurrence of $R^4$ is Cl, Br, F, $CF_3$, $CH_3$, —$CH_2CH_3$, —OR', or —$CH_2OR'$, —$NRSO_2R'$, —NRCOOR', or —$OCON(R')_2$. In certain other embodiments, for compounds of formula IA-i, $R^1$ and $R^2$, taken together is optionally substituted piperidin-1-yl (dd), wherein z is 1 and $R^4$ is F, $CF_3$, $CH_3$, —$CH_2CH_3$, —OR', or —$CH_2OR'$. In other embodiments, for compounds of formula IA-i, $R^1$ and $R^2$, taken together is optionally substituted piperidin-1-yl (dd), wherein z is 1 and $R^4$ is —$NRSO_2R'$. In certain other embodiments, for compounds of formula IA-i, $R^1$ and $R^2$, taken together is optionally substituted piperidin-1-yl (dd), wherein z is 1 and $R^4$ is —NRCOOR'. In yet other embodiments, for compounds of formula IA-i, $R^1$ and $R^2$, taken together is optionally substituted piperazin-1-yl (cc), wherein z is 1 or 2 and at least one occurrence of $R^4$ is —SOR', —$CON(R')_2$, —$SO_2N(R')_2$, —COR', or —COOR'. In certain other embodiments, for compounds of formula IA-i, $R^1$ and $R^2$, taken together is optionally substituted piperazin-1-yl (cc), wherein z is 1 and $R^4$ is —SOR'. In certain other embodiments, for compounds of formula IA-i, $R^1$ and $R^2$, taken together is optionally substituted piperazin-1-yl (cc), wherein z is 1 and $R^4$ is —COOR'. In certain other embodiments, for compounds of formula IA-i, $R^1$ and $R^2$, taken together is optionally substituted piperazin-1-yl (cc), wherein z is 1 and $R^4$ is —$CON(R')_2$. In certain other embodiments, for compounds of formula IA-i, $R^1$ and $R^2$, taken together is optionally substituted piperazin-1-yl (cc), wherein z is 1 and $R^4$ is —$SO_2N(R')_2$. In certain other embodiments, for compounds of formula IA-i, $R^1$ and $R^2$, taken together is optionally substituted piperazin-1-yl (cc), wherein z is 1 and $R^4$ is —COR'.

In some embodiments for compounds of formula IA-i, x is 0-4, and $R^3$ groups, when present, are each independently halogen, CN, $NO_2$, —$N(R')_2$, —$CH_2N(R')_2$, —OR', —$CH_2OR'$, —SR', —$CH_2SR'$, —COOR', —NRCOR', —$CON(R')_2$, —$OCON(R')_2$, COR', —NHCOOR', —$SO_2R'$, —$SO_2N(R')_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In still other embodiments, x is 1 or 2, and each occurrence of $R^3$ is independently Cl, Br, F, $CF_3$, —$OCF_3$, Me, Et, CN, —COOH, —$NH_2$, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$CH_2OH$, —$NHCOCH_3$, —NHCOCH$(CH_3)_2$, —$SO_2NH_2$, —CONH(cyclopropyl), —$CONHCH_3$, —$CONHCH_2CH_3$, or an optionally substituted group selected from -piperidinyl, piperizinyl, morpholino, phenyl, phenyloxy, benzyl, or benzyloxy.

In yet other embodiments, x is 1 or 2 and each $R^3$ group is independently halogen, CN, optionally substituted $C_1$-$C_6$alkyl, OR', $N(R')_2$, $CON(R')_2$, or NRCOR'.

In still other embodiments, x is 1 or 2, and each $R^3$ group is —Cl, —$CH_3$, —$CH_2CH_3$, —F, —$CF_3$, —$OCF_3$, —CONHCH$_3$, —$CONHCH_2CH_3$, —CONH(cyclopropyl), —$OCH_3$, —$NH_2$, —$OCH_2CH_3$, or —CN.

In yet other embodiments x is 1 and $R^3$ is at the 6-position of the quinazoline ring and is —Cl, —$CH_3$, —$CH_2CH_3$, —F, —$CF_3$, —$OCF_3$, —$CONHCH_3$, —$CONHCH_2CH_3$, —CONH(cyclopropyl), —$OCH_3$, —$NH_2$, —$OCH_2CH_3$, or —CN.

In still other embodiments, x is 1 and $R^3$ is at the 7-position of the quinazoline ring and is —Cl, —$CH_3$, —$CH_2CH_3$, —F, —CF₃, —OCF₃, —CONHCH₃, —CONHCH₂CH₃, —CONH(cyclopropyl), —OCH₃, —NH₂, —OCH₂CH₃, or —CN.

In yet other embodiments, x is 1 and $R^3$ is at the 6-position of the quinazoline ring and is —Cl, —CH₃, —CH₂CH₃, —F, —CF₃, —OCF₃, —OCH₃, or —OCH₂CH₃.

In still other embodiments, x is 1 and $R^3$ is at the 7-position of the quinazoline ring and is —Cl, —CH₃, —CH₂CH₃, —F, —CF₃, —OCF₃, —OCH₃, or —OCH₂CH₃.

In yet other embodiments, x is 1 and $R^3$ is at the 6-position of the quinazoline ring and is —CON(R')₂, or NRCOR'.

In still other embodiments, x is 1 and $R^3$ is at the 7-position of the quinazoline ring and is —CON(R')₂, or NRCOR'.

In some embodiments for compounds of formula IA-i, y is 0-5, q is 0-2, and $R^5$ and $R^{5a}$ groups, when present, are each independently halogen, CN, NO₂, —N(R')₂, —CH₂N(R')₂, —OR', —CH₂OR', —SR', —CH₂SR', —NRCOR', —CON(R')₂, —S(O)₂N(R')₂, —OCOR', —COR', —CO₂R', —OCON(R')₂, —NR'SO₂R', —OP(O)(OR')₂, —P(O)(OR')₂, —OP(O)₂OR', —P(O)₂OR', —PO(R')₂, —OPO(R')₂, or an optionally substituted group selected from C₁-C₆aliphatic, aryl, heteroaryl, cycloaliphatic, heterocycloaliphatic, aryl C₁-C₆alkyl, heteroaryl C₁-C₆alkyl, cycloaliphatic C₁-C₆alkyl, or heterocycloaliphatic C₁-C₆alkyl.

In yet other embodiments, y is 0-5, and q is 1 or 2, and each occurrence of $R^{5a}$ is independently Cl, Br, F, CF₃, Me, Et, CN, —COOH, —NH₂, —N(CH₃)₂, —N(Et)₂, —N(iPr)₂, —O(CH₂)₂OCH₃, —CONH₂, —COOCH₃, —OH, —OCH₃, —OCH₂CH₃, —CH₂OH, —NHCOCH₃, —SO₂NH₂, —SO₂NHC(CH₃)₂, —OCOC(CH₃)₃, —OCOCH₂C(CH₃)₃, —O(CH₂)₂N(CH₃)₂, 4-CH₃-piperazin-1-yl, OCOCH(CH₃)₂, OCO(cyclopentyl), —COCH₃, optionally substituted phenoxy, or optionally substituted benzyloxy.

In still other embodiments, when ring A is phenyl, y is 0, and q is 1 and $R^{5a}$ is F substituted at the 2-position of the phenyl ring. In yet other embodiments, when ring A is phenyl, y is 0, q is 1, and $R^{5a}$ is OR' substituted at the 2-position of the phenyl ring. In still other embodiments, when ring A is phenyl, y is 0, q is 1 and $R^{5a}$ is OH substituted at the 2-position of the phenyl ring. In yet other embodiments, when ring A is phenyl, y is 0, q is 2 and one occurrence of $R^{5a}$ is OR' and the other occurrence of $R^{5a}$ is F, wherein OR' is substituted at the 2-position of the phenyl ring and F is substituted at the 6-position of the phenyl ring. In yet other embodiments, when ring A is phenyl, y is 0, q is 2 and one occurrence of $R^{5a}$ is OH and the other occurrence of $R^{5a}$ is F, wherein OH is substituted at the 2-position of the phenyl ring and F is substituted at the 6-position of the phenyl ring.

In still other embodiments, for compounds of formula IA-i, q is 1 and $R^{5a}$ is at the 2-position of the phenyl ring, and compounds have the structure IA-ii:

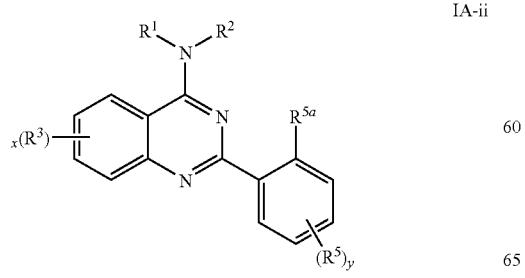

IA-ii wherein:

a) the ring formed by $R^1$ and $R^2$ taken together is selected from:

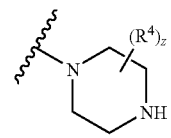
cc

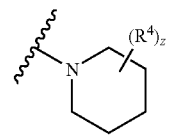
dd

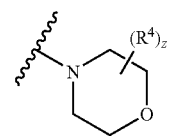
ee

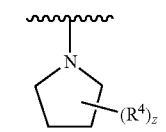
ff

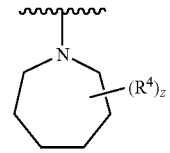
gg

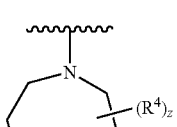
hh

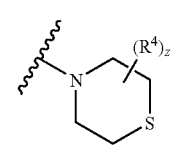
ii

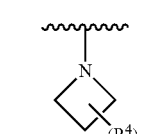
jj

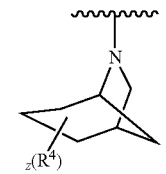
kk

-continued

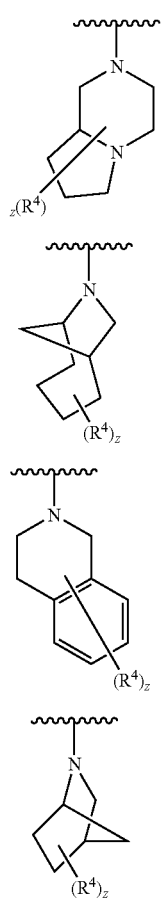

and the ring formed by $R^1$ and $R^2$ taken together, is optionally substituted at one or more substitutable carbon, nitrogen, or sulfur atoms with z independent occurrences of —$R^4$, and z is 0-5;

b) wherein z is 0-5, and $R^4$ groups, when present, are each independently halogen, CN, $NO_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or hetero cycloaliphatic $C_1$-$C_6$ alkyl.

c) wherein x is 0-4, and $R^3$ groups, when present, are each independently halogen, CN, $NO_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or hetero cycloaliphatic $C_1$-$C_6$ alkyl.

d) wherein y is 0-5, and $R^5$ groups, when present, are each independently halogen, CN, $NO_2$, —N(R')$_2$, —CH$_2$N(R')$_2$, —OR', —CH$_2$OR', —SR', —CH$_2$SR', —NRCOR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from $C_1$-$C_6$aliphatic, aryl, heteroaryl, cycloaliphatic, heterocycloaliphatic, aryl $C_1$-$C_6$alkyl, hetero aryl $C_1$-$C_6$ alkyl, cycloaliphatic $C_1$-$C_6$ alkyl, or heterocycloaliphatic $C_1$-$C_6$ alkyl; and e) $R^{5a}$ is Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In still other embodiments, for compounds of formula IA-ii: q is 1 and $R^{5a}$ is at the 2-position of the phenyl ring, and compounds have the structure IA-ii:

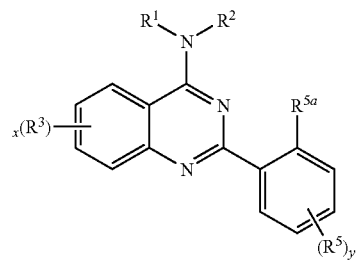

IA-ii wherein:

a) $R^1$ and $R^2$ taken together is an optionally substituted ring selected from azetidin-1-yl (jj), pyrrolidin-1-yl (ff), piperidin 1-yl (dd), or piperazin-1-yl (cc);

b) z is 0-5 and $R^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, $C_{1-4}$alkoxy, phenyl, phenyloxy, benzyl, benzyloxy, —CH$_2$cyclohexyl, pyridyl, —CH$_2$pyridyl, or —CH$_2$thiazolyl;

c) x is 1 or 2, and each occurrence of $R^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy;

d) wherein y is 0-4, and $R^5$ groups, when present, are each independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy; and e) $R^{5a}$ is Cl, F, CF$_3$, Me, Et, —OH, —OCH$_3$, —OCH$_2$CH$_3$, —CH$_2$OH, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), or —COCH$_3$.

In still other embodiments, for compounds of formula IA-ii x is 1 and R³ is at the 6-position of the quinazoline ring and is —Cl, —CH₃, —CH₂CH₃, —F, —CF₃, —OCF₃, —CON-HCH₃, —CONHCH₂CH₃, —CONH(cyclopropyl), —OCH₃, —NH₂, —OCH₂CH₃, or —CN. In yet other embodiments, x is 1 and R³ is at the 7-position of the quinazoline ring and is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In still other embodiments, x is 1 and R³ is at the 6-position of the quinazoline ring and is —Cl, —CH₃, —CH₂CH₃, —F, —CF₃, —OCF₃, —OCH₃, or —OCH₂CH₃. In yet other embodiments, x is 1 and R³ is at the 7-position of the quinazoline ring and is —Cl, —CH₃, —CH₂CH₃, —F, —CF₃, —OCF₃, —OCH₃, or —OCH₂CH₃. In still other embodiments, x is 1 and R³ is at the 6-position of the quinazoline ring and is —CON(R')₂, or NRCOR'.

In yet other embodiments, x is 1 and R³ is at the 7-position of the quinazoline ring and is —CON(R')₂, or NRCOR'.

In still other embodiments, R^{5a} is Cl, F, CF₃, Me, Et, OR', —OH, —OCH₃, —OCH₂CH₃.

In yet other embodiments, R^{5a} is OR'. In still other embodiments, R^{5a} is F.

In still other exemplary embodiments compounds have formula IA-ii:

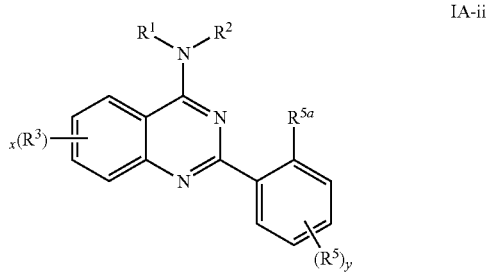

wherein:

a) R¹ and R² taken together is an optionally substituted ring selected from azetidin-1-yl (jj), pyrrolidin-1-yl (ff), piperidin 1-yl (dd), or piperazin-1-yl (cc);

b) z is 0-5 and R⁴ groups are each independently Cl, Br, F, CF₃, CH₃, —CH₂CH₃, CN, —COOH, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, —SO₂(CH₂)₃CH₃, —SO₂CH(CH₃)₂, —SO₂N(CH₃)₂, —SO₂CH₂CH₃, —C(O)OCH₂CH(CH₃)₂, —C(O)NHCH₂CH(CH₃)₂, —NHCOOCH₃, —C(O)C(CH₃)₃, —COO(CH₂)₂CH₃, —C(O)NHCH(CH₃)₂, —C(O)CH₂CH₃, or an optionally substituted group selected from -piperidinyl, piperizinyl, morpholino, C₁₋₄alkoxy, phenyl, phenyloxy, benzyl, benzyloxy, —CH₂cyclohexyl, pyridyl, —CH₂pyridyl, or —CH₂thiazolyl;

c) x is 1, and each occurrence of R³ is independently Cl, Br, F, CF₃, —OCF₃, Me, Et, CN, —COOH, —OH, or —OCH₃;

d) y is 0 or 1, and R⁵ groups, when present, are each independently Cl, Br, F, CF₃, Me, —OH, —OCH₃, —OCH₂CH₃, —CH₂OH, —NHCOCH₃, —SO₂NH₂, —SO₂NHC(CH₃)₂; and e) R^{5a} is F, —OR', or NHSO₂R'.

In some embodiments for compounds described directly above, x is 1 and R³ is at the 6-position of the quinazoline ring and is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In still other embodiments, x is 1 and R³ is at the 7-position of the quinazoline ring and is —Cl, —CH₃, —CH₂CH₃, —F, —CF₃, —CONHCH₃, —CONHCH₂CH₃, —CONH(cyclopropyl), —OCH₃, —NH₂, —OCH₂CH₃, or —CN. In yet other embodiments, x is 1 and R³ is at the 6-position of the quinazoline ring and is —Cl, —CH₃, —CH₂CH₃, —F, —CF₃, —OCF₃, —OCH₃, or —OCH₂CH₃. In still other embodiments, x is 1 and R³ is at the 7-position of the quinazoline ring and is —Cl, —CH₃, —CH₂CH₃, —F, —CF₃, —OCH₃, or —OCH₂CH₃. In yet other embodiments, x is 1 and R³ is at the 6-position of the quinazoline ring and is —CON(R')₂, or NRCOR'. In still other embodiments, x is 1 and R³ is at the 7-position of the quinazoline ring and is —CON(R')₂, or NRCOR'.

In yet other embodiments, R^{5a} is OR' and x is 1 and R³ is at the 6-position of the quinazoline ring and is —Cl, —CH₃, —CH₂CH₃, —F, —CF₃, —OCF₃, —OCH₃, or —OCH₂CH₃. In yet other embodiments, R^{5a} is OR' and x is 1 and R³ is at the 7-position of the quinazoline ring and is —Cl, —CH₃, —CH₂CH₃, —F, —CF₃, —OCH₃, or —OCH₂CH₃.

In yet other embodiments, R^{5a} is OH and x is 1 and R³ is at the 6-position of the quinazoline ring and is —Cl, —CH₃, —CH₂CH₃, —F, —CF₃, —OCF₃, —OCH₃, or —OCH₂CH₃. In yet other embodiments, R^{5a} is OH and x is 1 and R³ is at the 7-position of the quinazoline ring and is —Cl, —CH₃, —CH₂CH₃, —F, —CF₃, —OCH₃, or —OCH₂CH₃.

In yet other embodiments, R^{5a} is F and x is 1 and R³ is at the 6-position of the quinazoline ring and is —Cl, —CH₃, —CH₂CH₃, —F, —CF₃, —OCF₃, —OCH₃, or —OCH₂CH₃. In yet other embodiments, R^{5a} is F and x is 1 and R³ is at the 7-position of the quinazoline ring and is —Cl, —CH₃, —CH₂CH₃, —F, —CF₃, —OCH₃, or —OCH₂CH₃.

In still other embodiments, for compounds of formula IA-ii, R¹ and R² taken together is optionally substituted azetidin-1 (jj). In yet other embodiments, for compounds of formula IA-ii, R¹ and R² taken together is optionally substituted pyrrolidin-1-yl (ff). In still other embodiments, for compounds of formula IA-ii, R¹ and R² taken together is optionally substituted piperidin-1-yl (dd). In yet other embodiments, for compounds of formula IA-ii, R¹ and R², taken together is optionally substituted piperazin-1-yl (cc).

In certain embodiments, for compounds of formula IA-ii, R¹ and R², taken together is optionally substituted azetidin-1-yl (jj), wherein z is 1 or 2 and at least one occurrence of R⁴ is —NRSO₂R', —NRCOOR', or —NRCOR'. In certain other embodiments, for compounds of formula IA-ii, R¹ and R², taken together is optionally substituted azetidin-1-yl (jj), wherein z is 1 and R⁴ is —NRSO₂R'. In other embodiments, for compounds of formula IA-ii, R¹ and R², taken together is optionally substituted azetidin-1-yl (jj), wherein z is 1 and R⁴ is —NRCOOR'. In certain other embodiments, for compounds of formula IA-ii, R¹ and R², taken together is optionally substituted azetidin-1-yl (jj), wherein z is 1 and R⁴ is —NRCOR'. In yet other embodiments, for compounds of formula IA-ii, R¹ and R², taken together is optionally substituted pyrrolidin-1-yl (ff), wherein z is 1 or 2 and R⁴ is Cl, Br, F, CF₃, CH₃, —CH₂CH₃, —OR', or —CH₂OR'. In still other embodiments, for compounds of formula IA-ii, R¹ and R², taken together is optionally substituted piperidin-1-yl (dd), wherein z is 1 or 2 and at least one occurrence of R⁴ is Cl, Br, F, CF₃, CH₃, —CH₂CH₃, —OR', or —CH₂OR', —NRSO₂R', —NRCOOR', or —OCON(R')₂. In certain other embodiments, for compounds of formula IA-ii, R¹ and R², taken together is optionally substituted piperidin-1-yl (dd), wherein z is 1 and R⁴ is F, CF₃, CH₃, —CH₂CH₃, —OR', or —CH₂OR'. In other embodiments, for compounds of formula IA-ii, R¹ and R², taken together is optionally substituted piperidin-1-yl (dd), wherein z is 1 and R⁴ is —NRSO₂R'. In certain other embodiments, for compounds of formula IA-ii, R¹ and R², taken together is optionally substituted piperidin-1-yl (dd), wherein z is 1 and R⁴ is —NRCOOR'. In yet other embodiments, for compounds of formula IA-ii, R¹ and R², taken together is optionally substituted piperazin-1-yl (cc), wherein z is 1 or 2 and at least one occurrence of R⁴ is —SOR', —CON(R')₂, —SO₂N(R')₂, —COR', or —COOR'. In certain other embodiments, for compounds of formula IA-ii, R¹ and R², taken together is optionally substituted piperazin-1-yl (cc), wherein z is 1 and R⁴ is —SOR'. In certain other embodiments, for compounds of formula IA-ii, R¹ and R², taken together is optionally substituted piperazin-1-yl (cc), wherein z is 1 and R⁴ is —COOR'. In certain other embodiments, for compounds of formula IA-ii, R¹ and R², taken together is optionally substituted piperazin-1-yl (cc), wherein z is 1 and R⁴ is —CON(R')₂. In certain other embodiments, for compounds of formula IA-ii, R¹ and R², taken together is optionally substituted piperazin-1-yl (cc), wherein z is 1 and R⁴ is —SO₂N(R')₂. In certain other embodiments, for compounds of formula IA-ii, R¹ and R², taken together is optionally substituted piperazin-1-yl (cc), wherein z is 1 and R⁴ is —COR'.

For compounds described in this section above, in general, compounds are useful as inhibitors of ion channels, preferably voltage gated sodium channels and N-type calcium channels. In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

II. Compounds of Formula IA-ii:

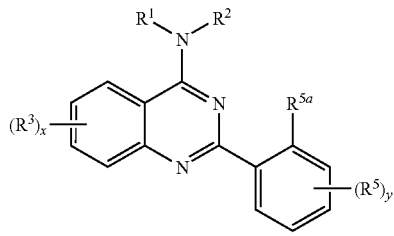

IA-ii wherein R¹ and R² are each independently hydrogen, or an optionally substituted group selected from C₁₋₆aliphatic, Cy¹, wherein Cy¹ is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein Cy¹ is bonded directly to the nitrogen atom or is bonded through an optionally substituted C₁₋₄aliphatic group, wherein one or more methylene units in the C₁₋₄aliphatic group are optionally replaced with —NR—, —O—, —COO, —OCO—, —NRCO—, —CONR—, —SO₂NR—, or —NRSO₂—; wherein R¹ and R² are each optionally and independently substituted at one or more substitutable carbon, nitrogen, or sulfur atoms with z independent occurrences of —R⁴, wherein z is 0-5;

x is 0-4;
y is 0-4;

each occurrence of R³, R⁴, and R⁵ is independently Q-Rˣ; wherein Q is a bond or is a C₁-C₆ alkylidene chain wherein up to two non-adjacent methylene units of Q are optionally and independently replaced by —NR—, —S—, —O—, —CS—, —CO₂—, —OCO—, —CO—, —COCO—, —CONR—, —NRCO—, —NRCO₂—, —SO₂NR—, —NRSO₂—, —CONRNR—, —NRCONR—, —OCONR—, —NRNR—, —NRSO₂NR—, —SO—, —SO₂—, —PO—, —PO₂—, —OP(O)(OR)—, or —POR—; and each occurrence of Rˣ is independently selected from —R', =O, =NR', halogen, —NO₂, —CN, —OR', —SR', —N(R')₂, —NR'COR', —NR'CON(R')₂, —NR'CO₂R', —COR', —CO₂R', —OCOR', —CON(R')₂, —OCON(R')₂, —SOR', —SO₂R', —SO₂N(R')₂, —NR'SO₂R', —NR'SO₂N(R')₂, —COCOR', —COCH₂COR', —OP(O)(OR')₂, —P(O)(OR')₂, —OP(O)₂OR', —P(O)₂OR', —PO(R')₂, or —OPO(R')₂;

R⁵ᵃ is an optionally substituted C₁-C₆aliphatic group, halogen, —OR', —SR', —N(R')₂, —NR'COR', —NR'CON(R')₂, —NR'CO₂R', —COR', —CO₂R', —OCOR', —CON(R')₂, —OCON(R')₂, —SOR', —SO₂R', —SO₂N(R)₂, —NR'SO₂R', —NR'SO₂N(R')₂, —COCOR', —COCH₂COR', —OP(O)(OR')₂, —P(O)(OR')₂, —OP(O)₂OR', —P(O)₂OR', —PO(R')₂, or —OPO(R')₂; and each occurrence of R is independently hydrogen or an optionally substituted C₁₋₆ aliphatic group; and each occurrence of R' is independently hydrogen or an optionally substituted C₁₋₆ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain embodiments, for compounds described directly above, a. when x is 0, R¹ is hydrogen, and R⁵ᵃ is Cl, Me, CF₃, Br, or F, then R² is not —(CH₂)₂-4-Cy¹, —SO₂CH₂Cy¹, or —CH₂SO₂Cy¹, wherein Cy¹ is a 5-7-membered monocyclic aryl ring or an 8-10-membered bicyclic aryl ring having 0-3 heteroatoms independently selected from nitrogen, oxygen, or sulfur, or is a 3-8-membered saturated or partially unsaturated monocyclic ring having 0-3 heteroatoms independently selected from nitrogen, oxygen, or sulfur;

b. when x is 0, and R⁵ᵃ is Cl, Me, NO₂, or OH, then:
 i. when R¹ is hydrogen, R² is not Me, iBu, nBu, —COCH₃, —CH₂COOEt, —CH₂COOMe, —CH₂CH₂OH, iPr, —CH₂-pyridyl, —CH₂Ph, —(CH₂)₃NH₂, —(CH₂)₂-morpholinyl, or —CH₂CH₂Ph;
 ii. R¹ and R² are not simultaneously Et or Me; and
 iii. when R¹ is Et, then R² is not 4-Me-phenyl, 4-OMe-phenyl, or 2-Me-phenyl;

c. when x is 1 and R³ is 6-Cl, or 7-F, or x is 0 and R⁵ᵃ is —OPrₙ or Cl, then when R¹ is hydrogen, R² is not —(CH₂)₂-morpholino, or —CH₂(benzofuran); and d. when x is 2 and one occurrence of R³ is 6-OMe and the other occurrence of R³ is 7-OMe, and R⁵ᵃ is F, then when R¹ is hydrogen, R² is not —(CH₂)₃N(CH₃)₂.

In certain other embodiments, for compounds of formula IA-ii described directly above, the following compounds are excluded:

2-(o-hydroxyphenyl)-4-bis(2-cyanoethyl)aminoquinazoline;
2-(o-hydroxyphenyl)-4-aminoquinazoline;
2-(o-hydroxyphenyl)-4-acetamidoquinazoline;
2-(o-hydroxyphenyl)-4-acrylamidoquinazoline;
2-(o-hydroxyphenyl)-4-[N-methyl-2-(N-methyl-methacrylamido)ethylamino]quinazoline;
2-(o-hydroxyphenyl)-4-dimethylamino-7-chloroquinazoline; and
2-(o-hydroxyphenyl)-4-dimethylamino-7-nitroquinazoline.

In certain other embodiments, for compounds described directly above, one of $R^1$ or $R^2$ is hydrogen and the other of $R^1$ or $R^2$ is not hydrogen.

In certain other embodiments, for compounds described directly above,
a) one of $R^1$ or $R^2$ is hydrogen, and the other of $R^1$ and $R^2$ is selected from:
  i) $Cy^1$ wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or
  ii) an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or
b) $R^1$ and $R^2$ are each independently selected from $Cy^1$, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or an optionally substituted $C_{1-4}$aliphatic group, wherein one or more methylene units in the $C_{1-4}$ aliphatic group are optionally replaced with —NR—, —O—, —COO—, —OCO—, —NRCO—, —CONR—, —SO$_2$NR—, or —NRSO$_2$—.

In other embodiments $Cy^1$ is:

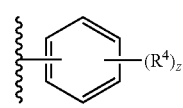

a

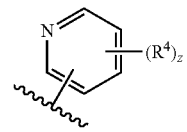

b

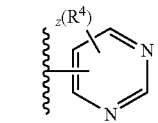

c

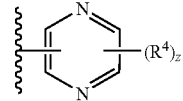

d

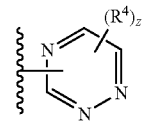

e

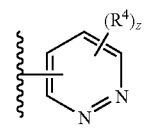

f

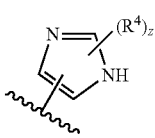

g

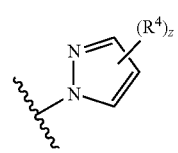

h

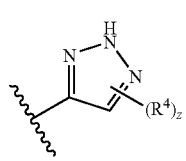

i

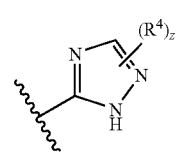

j

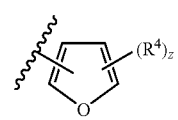

k

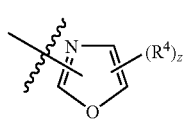

l

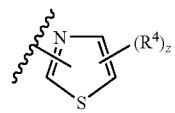

m

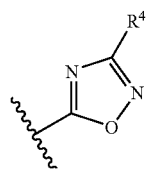

n

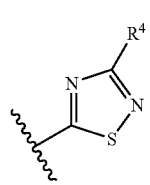

o p 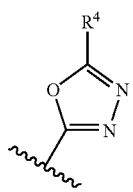
q 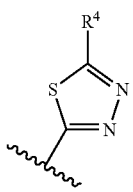
r 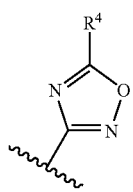
s 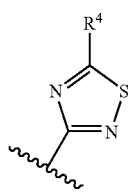
t 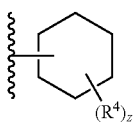
u 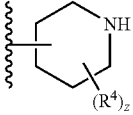
v 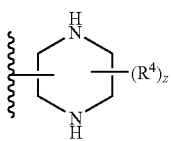
w 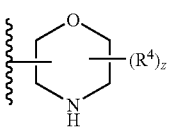
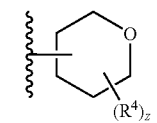
y 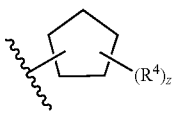
z 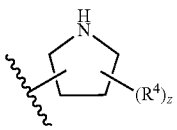
aa 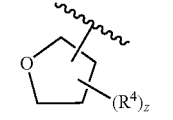
bb 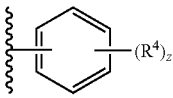
In still other embodiments, for compounds described directly above, $R^1$ is hydrogen or an optionally substituted $C_1$-$C_4$ aliphatic group and $R^2$ is —CHR-Cy$^1$, wherein R is hydrogen or $C_1$-$C_4$ alkyl, and Cy$^1$ is:
a 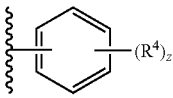
b 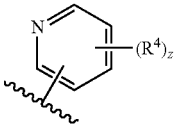
c 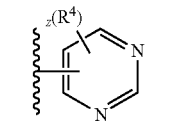
d 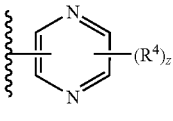
e 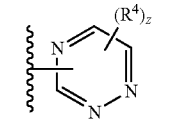
f 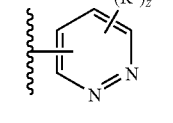
g 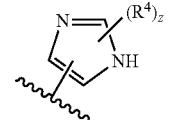
h 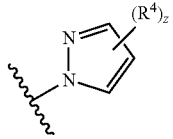

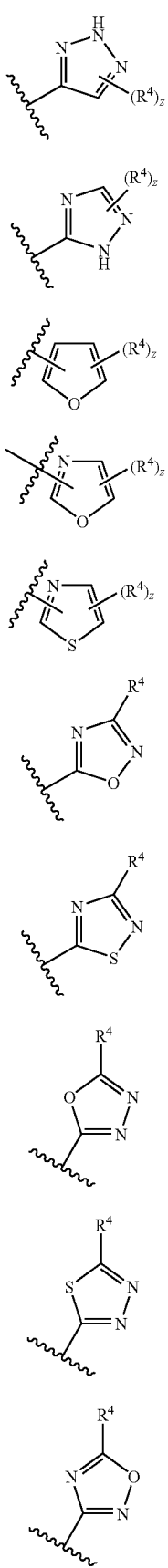
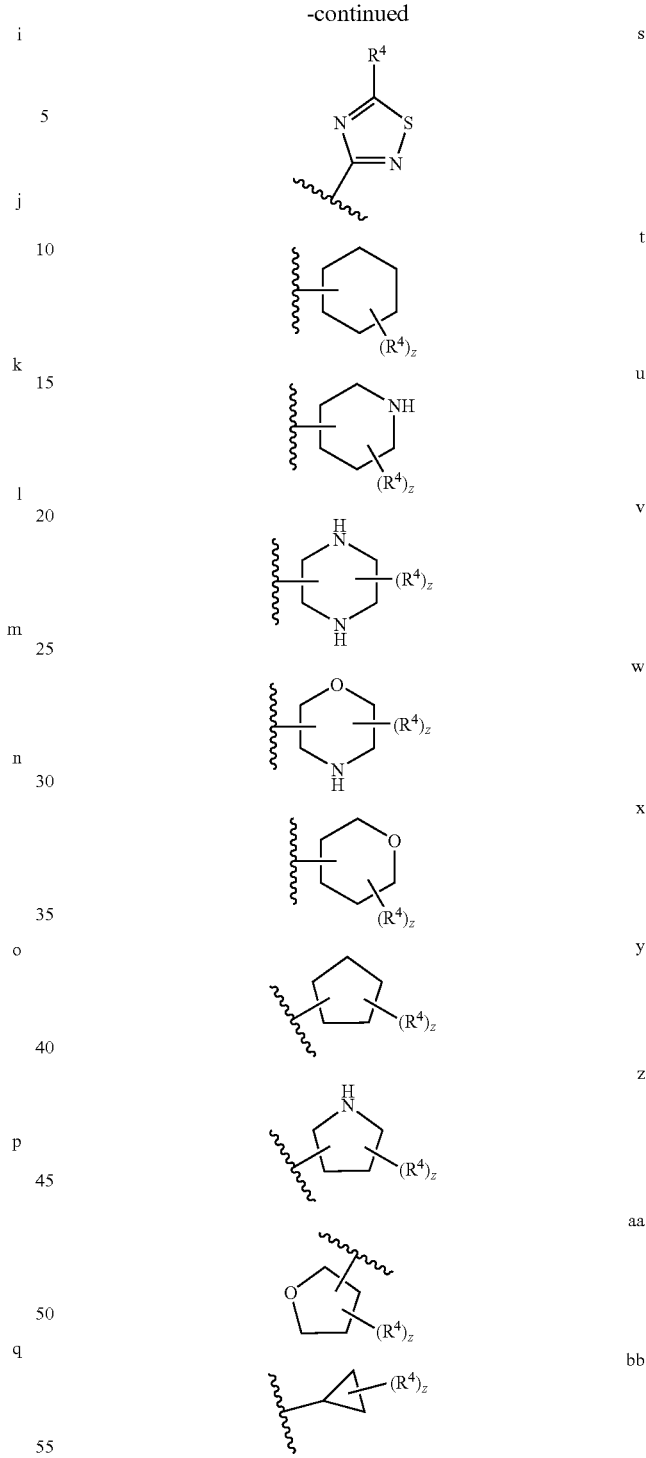

In yet other embodiments, $R^1$ and $R^2$ groups are each independently an optionally substituted $C_{1-4}$ aliphatic group and are each independently selected from optionally substituted methyl, ethyl, cyclopropyl, n-propyl, propenyl, cyclobutyl, (CO)OCH$_2$CH$_3$, (CH$_2$)$_2$OCH$_3$, CH$_2$CO)OCH$_2$CH$_3$, CH$_2$(CO)OCH$_3$, CH(CH$_3$)CH$_2$CH$_3$, or n-butyl.

For compounds described directly above, z is 0-5, and $R^4$ groups, when present, are each independently halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON (R')$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, hetero cycloaliphatic, aryl C$_1$-C$_6$alkyl, heteroaryl C$_1$-C$_6$alkyl, cycloaliphatic C$_1$-C$_6$alkyl, or heterocycloaliphatic C$_1$-C$_6$alkyl.

In other embodiments, z is 0-5 and R$^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, C$_{1-4}$alkoxy, phenyl, phenyloxy, benzyl, benzyloxy, —CH$_2$cyclohexyl, pyridyl, —CH$_2$pyridyl, or —CH$_2$thiazolyl.

In still other embodiments, for compounds described directly above, x is 0-4, and R$^3$ groups, when present, are each independently halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from C$_1$-C$_6$aliphatic, aryl, hetero aryl, cycloaliphatic, hetero cycloaliphatic, aryl C$_1$-C$_6$alkyl, heteroaryl C$_1$-C$_6$alkyl, cycloaliphatic C$_1$-C$_6$alkyl, or heterocycloaliphatic C$_1$-C$_6$alkyl.

In yet other embodiments, for compounds described directly above, x is 1 or 2, and each occurrence of R$^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy.

In still other embodiments, x is 1 or 2 and each R$^3$ group is independently halogen, CN, optionally substituted C$_1$-C$_6$alkyl, OR', N(R')$_2$, CON(R')$_2$, or NRCOR'.

In yet other embodiments, x is 1 or 2, and each R$^3$ group is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In still other embodiments, x is 1 and R$^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet other embodiments, x is 1 and R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In still other embodiments, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$.

In other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$.

In yet other embodiments, R$^3$ is at the 6-position of the quinazoline ring and is —CON(R')$_2$, or NRCOR'.

In still other embodiments, x is 1 and R$^3$ is at the 7-position of the quinazoline ring and is —CON(R')$_2$, or NRCOR'.

For compounds described directly above, y is 0-4, q is 0-2, and R$^5$ and R$^{5a}$ groups, when present, are each independently halogen, CN, NO$_2$, —N(R')$_2$, —CH$_2$N(R')$_2$, —OR', —CH$_2$OR', —SR', —CH$_2$SR', —NRCOR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from C$_1$-C$_6$aliphatic, aryl, heteroaryl, cycloaliphatic, hetero cycloaliphatic, aryl C$_1$-C$_6$alkyl, hetero aryl C$_1$-C$_6$alkyl, cycloaliphatic C$_1$-C$_6$alkyl, or heterocycloaliphatic C$_1$-C$_6$alkyl.

In other embodiments, y is 0-4, and q is 1 or 2, and each occurrence of R$^{5a}$ is independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In still other embodiments, y is 0, and R$^{5a}$ is F. In yet other embodiments y is 0, q is 1, and R$^{5a}$ is OR'. In still other embodiments, y is 0, q is 1 and R$^{5a}$ is OH. In yet other embodiments, y is 1, R$^{5a}$ is OR' and R$^5$ is F, wherein OR' is substituted at the 2-position of the phenyl ring and F is substituted at the 6-position of the phenyl ring. In yet other embodiments, y is 1, R$^{5a}$ is OH and R$^5$ is F, wherein OH is substituted at the 2-position of the phenyl ring and F is substituted at the 6-position of the phenyl ring.

In still other embodiments for compounds of formula IA-ii described directly above:

a) one of R$^1$ or R$^2$ is hydrogen, and the other of R$^1$ and R$^2$ is selected from Cy$^1$, wherein Cy$^1$ is bonded directly to the nitrogen atom or is bonded through an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—, or an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—; or R$^1$ and R$^2$ are each independently selected from an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—; or Cy$^1$ wherein Cy$^1$ is bonded to the nitrogen atom directly or is bonded through an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—;

b) z is 0-5 and R$^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, C$_{1-4}$alkoxy, phenyl, phenyloxy, benzyl, benzyloxy, —CH$_2$cyclohexyl, pyridyl, —CH$_2$pyridyl, or —CH$_2$thiazolyl;

c) x is 0, 1, or 2, and each occurrence of R$^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy;

d) wherein y is 0-4, and $R^5$ groups, when present, are each independently Cl, Br, F, $CF_3$, Me, Et, CN, —COOH, —$NH_2$, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$CH_2OH$, —$NHCOCH_3$, —$SO_2NH_2$, —$SO_2NHC(CH_3)_2$, —$OCOC(CH_3)_3$, —$OCOCH_2C(CH_3)_3$, —$O(CH_2)_2N(CH_3)_2$, 4-$CH_3$-piperazin-1-yl, $OCOCH(CH_3)_2$, OCO(cyclopentyl), —$COCH_3$, optionally substituted phenoxy, or optionally substituted benzyloxy; and e) $R^{5a}$ is Cl, F, $CF_3$, Me, Et, —OH, —$OCH_3$, —$OCH_2CH_3$, —$CH_2OH$, —$SO_2NH_2$, —$SO_2NHC(CH_3)_2$, —$OCOC(CH_3)_3$, —$OCOCH_2C(CH_3)_3$, —$O(CH_2)_2N(CH_3)_2$, 4-$CH_3$-piperazin-1-yl, $OCOCH(CH_3)_2$, OCO(cyclopentyl), or —$COCH_3$.

In other embodiments, for compounds described directly above, x is 1 and $R^3$ is at the 6-position of the quinazoline ring and is —Cl, —$CH_3$, —$CH_2CH_3$, —F, —$CF_3$, —$OCF_3$, —$CONHCH_3$, —$CONHCH_2CH_3$, —CONH(cyclopropyl), —$OCH_3$, —$NH_2$, —$OCH_2CH_3$, or —CN. In yet other embodiments, x is 1 and $R^3$ is at the 7-position of the quinazoline ring and is —Cl, —$CH_3$, —$CH_2CH_3$, —F, —$CF_3$, —$OCF_3$, —$CONHCH_3$, —$CONHCH_2CH_3$, —CONH(cyclopropyl), —$OCH_3$, —$NH_2$, —$OCH_2CH_3$, or —CN. In still other embodiments, x is 1 and $R^3$ is at the 6-position of the quinazoline ring and is —Cl, —$CH_3$, —$CH_2CH_3$, —F, —$CF_3$, —$OCF_3$, —$OCH_3$, or —$OCH_2CH_3$. In still other embodiments, x is 1 and $R^3$ is at the 7-position of the quinazoline ring and is —Cl, —$CH_3$, —$CH_2CH_3$, —F, —$CF_3$, —$OCF_3$, —$OCH_3$, or —$OCH_2CH_3$. In yet other embodiments, x is 1 and $R^3$ is at the 6-position of the quinazoline ring and is —$CON(R')_2$, or $NRCOR'$.

In still other embodiments, x is 1 and $R^3$ is at the 7-position of the quinazoline ring and is —$CON(R')_2$, or $NRCOR'$.

In yet other embodiments, $R^{5a}$ is Cl, F, $CF_3$, Me, Et, —OH, —$OCH_3$, —$OCH_2CH_3$.

In still other embodiments, y is 0, and $R^{5a}$ is F. In yet other embodiments y is 0, q is 1, and $R^{5a}$ is OR'. In still other embodiments, y is 0, q is 1 and $R^{5a}$ is OH. In yet other embodiments, y is 1, $R^{5a}$ is OR' and $R^5$ is F, wherein OR' is substituted at the 2-position of the phenyl ring and F is substituted at the 6-position of the phenyl ring. In yet other embodiments, y is 1, $R^{5a}$ is OH and $R^5$ is F, wherein OH is substituted at the 2-position of the phenyl ring and F is substituted at the 6-position of the phenyl ring.

In still other embodiments for compounds of formula IA-ii described above:

a): one of $R^1$ or $R^2$ is hydrogen, and the other of $R^1$ and $R^2$ is selected from $Cy^1$, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2NR$—, or —$NRSO_2$—, or an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2NR$—, or —$NRSO_2$—; or $R^1$ and $R^2$ are each independently selected from an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2NR$—, or —$NRSO_2$—; or $Cy^1$ wherein $Cy^1$ is bonded to the nitrogen atom directly or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —$SO_2NR$—, or —$NRSO_2$—; and $Cy^1$ is selected from:

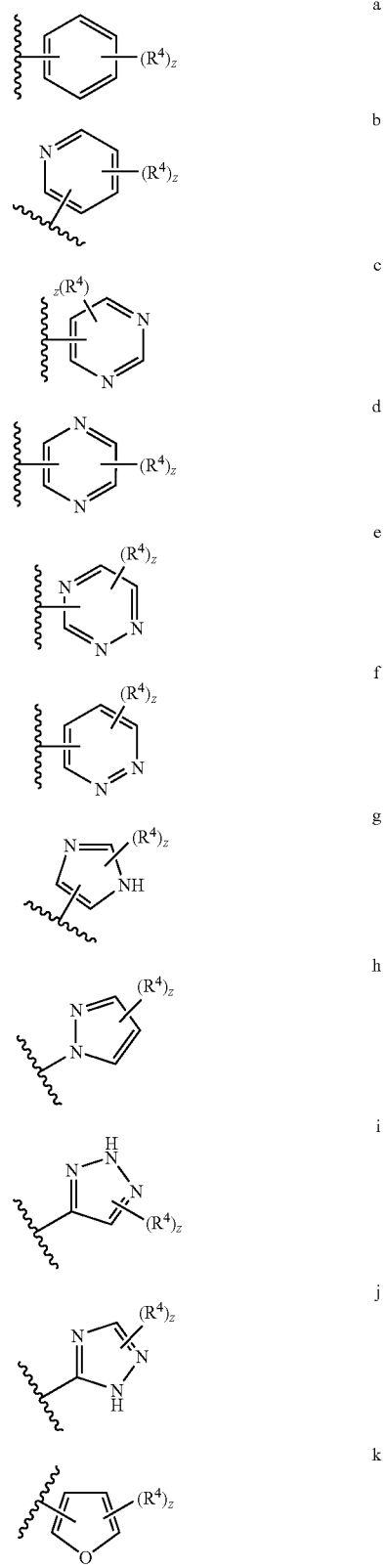

-continued

| | |
|---|---|
| 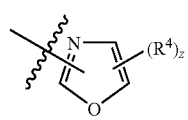 | l 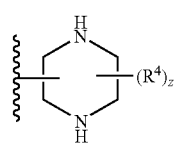 v |
| 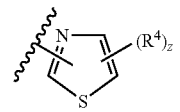 m | 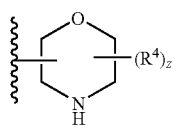 w |
| 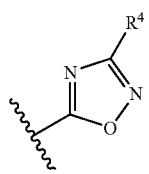 n | 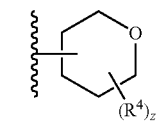 x |
| 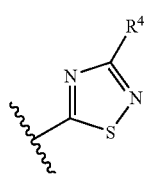 o | 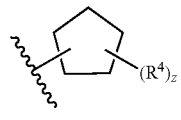 y |
| 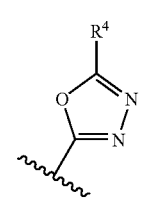 p | 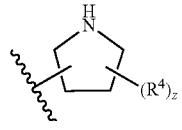 z |
| 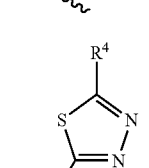 q | 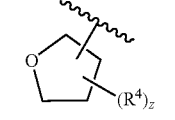 aa |
| 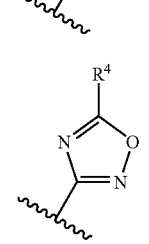 r |  bb |
| 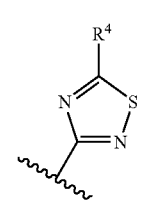 s | |
| 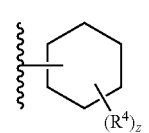 t | |
| 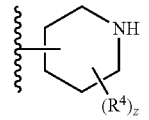 u | | or $R^1$ and $R^2$ are each independently an optionally substituted $C_{1-4}$ aliphatic group and are each independently selected from optionally substituted methyl, ethyl, cyclopropyl, n-propyl, propenyl, cyclobutyl, $(CO)OCH_2CH_3$, $(CH_2)_2OCH_3$, $CH_2CO)OCH_2CH_3$, $CH_2(CO)OCH_3$, $CH(CH_3)CH_2CH_3$, or n-butyl;

b) z is 0-5 and $R^4$ groups are each independently Cl, Br, F, $CF_3$, $CH_3$, —$CH_2CH_3$, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, —$SO_2(CH_2)_3CH_3$, —$SO_2CH(CH_3)_2$, —$SO_2N(CH_3)_2$, —$SO_2CH_2CH_3$, —$C(O)OCH_2CH(CH_3)_2$, —$C(O)NHCH_2CH(CH_3)_2$, —NHCOOCH$_3$, —$C(O)C(CH_3)_3$, —$COO(CH_2)_2CH_3$, —$C(O)NHCH(CH_3)_2$, —$C(O)CH_2CH_3$, or an optionally substituted group selected from -piperidinyl, piperizinyl, morpholino, $C_{1-4}$alkoxy, phenyl, phenyloxy, benzyl, benzyloxy, —$CH_2$cyclohexyl, pyridyl, —$CH_2$pyridyl, or —$CH_2$thiazolyl;

c) x is 0, 1, or 2, and each occurrence of $R^3$ is independently Cl, Br, F, $CF_3$, —$OCF_3$, Me, Et, CN, —COOH, —$NH_2$, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$CH_2OH$, —$NHCOCH_3$, —$NHCOCH(CH_3)_2$, —$SO_2NH_2$, —$CONH$(cyclopropyl), —$CONHCH_3$, —$CONHCH_2CH_3$, or an optionally substituted group selected from -piperidinyl, piperizinyl, morpholino, phenyl, phenyloxy, benzyl, or benzyloxy;

d) wherein y is 0-4, and $R^5$ groups, when present, are each independently Cl, Br, F, $CF_3$, Me, Et, CN, —COOH, —$NH_2$, —$N(CH_3)_2$, —$N(Et)_2$, —$N(iPr)_2$, —$O(CH_2)_2OCH_3$, —CONH₂, —COOCH₃, —OH, —OCH₃, —OCH₂CH₃, —CH₂OH, —NHCOCH₃, —SO₂NH₂, —SO₂NHC(CH₃)₂, —OCOC(CH₃)₃, —OCOCH₂C(CH₃)₃, —O(CH₂)₂N(CH₃)₂, 4-CH₃-piperazin-1-yl, OCOCH(CH₃)₂, OCO(cyclopentyl), —COCH₃, optionally substituted phenoxy, or optionally substituted benzyloxy; and e) $R^{5a}$ is Cl, F, CF₃, Me, Et, —OH, —OCH₃, —OCH₂CH₃, —CH₂OH, —SO₂NH₂, —SO₂NHC(CH₃)₂, —OCOC(CH₃)₃, —OCOCH₂C(CH₃)₃, —O(CH₂)₂N(CH₃)₂, 4-CH₃-piperazin-1-yl, OCOCH(CH₃)₂, OCO(cyclopentyl), or —COCH₃.

In yet other embodiments for compounds described directly above, x is 1 and $R^3$ is at the 6-position of the quinazoline ring and is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In still other embodiments, x is 1 and $R^3$ is at the 7-position of the quinazoline ring and is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In still other embodiments, x is 1 and $R^3$ is at the 6-position of the quinazoline ring and is —Cl, —CH₃, —CH₂CH₃, —F, —CF₃, —OCF₃, —OCH₃, or —OCH₂CH₃. In yet other embodiments, x is 1 and $R^3$ is at the 7-position of the quinazoline ring and is —Cl, —CH₃, —CH₂CH₃, —F, —CF₃, —OCF₃, —OCH₃, or —OCH₂CH₃. In still other embodiments, x is 1 and $R^3$ is at the 6-position of the quinazoline ring and is —CON(R')₂, or NRCOR'. In yet other embodiments, x is 1 and $R^3$ is at the 7-position of the quinazoline ring and is —CON(R')₂, or NRCOR'. In still other embodiments, $R^{5a}$ is Cl, F, CF₃, Me, Et, —OH, —OCH₃, —OCH₂CH₃.

In still other embodiments, y is 0, and $R^{5a}$ is F. In yet other embodiments y is 0, q is 1, and $R^{5a}$ is OR'. In still other embodiments, y is 0, q is 1 and $R^{5a}$ is OH. In yet other embodiments, y is 1, $R^{5a}$ is OR' and $R^5$ is F, wherein OR' is substituted at the 2-position of the phenyl ring and F is substituted at the 6-position of the phenyl ring. In yet other embodiments, y is 1, $R^{5a}$ is OH and $R^5$ is F, wherein OH is substituted at the 2-position of the phenyl ring and F is substituted at the 6-position of the phenyl ring.

For compounds described in this section above, in general, compounds are useful as inhibitors of ion channels, preferably voltage gated sodium channels and N-type calcium channels. In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

III. Compounds of Formula IA-i:

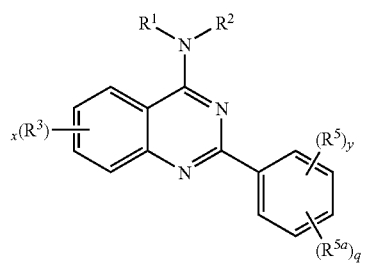

IA-i or a pharmaceutically acceptable salt thereof, wherein $R^1$ and $R^2$ are each independently hydrogen, or an optionally substituted group selected from $C_{1-6}$aliphatic, $Cy^1$, wherein $Cy^1$ is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO₂NR—, or —NRSO₂—; wherein $R^1$ and $R^2$, are each optionally and independently substituted at one or more substitutable carbon, nitrogen, or sulfur atoms with z independent occurrences of —$R^4$, wherein z is 0-5;

x is 1 and $R^3$ is substituted at either the 6- or 7-position of the quinazoline ring;

y is 0-4;

q is 0, 1 or 2;

each occurrence of $R^3$, $R^4$, and $R^5$ is independently Q-$R^X$; wherein Q is a bond or is a $C_1$-$C_6$ alkylidene chain wherein up to two non-adjacent methylene units of Q are optionally and independently replaced by —NR—, —S—, —O—, —CS—, —CO₂—, —OCO—, —CO—, —COCO—, —CONR—, —NRCO—, —NRCO₂—, —SO₂NR—, —NRSO₂—, —CONRNR—, —NRCONR—, —OCONR—, —NRNR—, —NRSO₂NR—, —SO—, —SO₂—, —PO—, —PO₂—, —OP(O)(OR)—, or —POR—; and each occurrence of $R^X$ is independently selected from —R', =O, =NR', halogen, —NO₂, —CN, —OR', —SR', —N(R')₂, —NR'COR', —NR'CON(R')₂, —NR'CO₂R', —COR', —CO₂R', —OCOR', —CON(R')₂, —OCON(R')₂, —SOR', —SO₂R', —SO₂N(R')₂, —NR'SO₂R', —NR'SO₂N(R')₂, —COCOR', —COCH₂COR', —OP(O)(OR')₂, —P(O)(OR')₂, —OP(O)₂OR', —P(O)₂OR', —PO(R')₂, or —OPO(R')₂;

each occurrence of $R^{5a}$ is independently an optionally substituted $C_1$-$C_6$aliphatic group, halogen, —OR', —SR', —N(R')₂, —NR'COR', —NR'CON(R')₂, —NR'CO₂R', —COR', —CO₂R', —OCOR', —CON(R')₂, —OCON(R')₂, —SOR', —SO₂R', —SO₂N(R')₂, —NR'SO₂R', —NR'SO₂N(R')₂, —COCOR', —COCH₂COR', —OP(O)(OR')₂, —P(O)(OR')₂, —OP(O)₂OR', —P(O)₂OR', —PO(R')₂, or —OPO(R')₂; and each occurrence of R is independently hydrogen or an optionally substituted $C_{1-6}$ aliphatic group; and each occurrence of R' is independently hydrogen or an optionally substituted $C_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain embodiments, for compounds described directly above:

a) when $R^3$ is at the 7-position of the quinazoline ring then:
  i) when $R^3$ is Cl or Me, ring A is unsubstituted naphthyl, and $R^1$ is hydrogen, then $R^2$ is not —(CH₂)₃NMe₂;

ii) when $R^3$ is Cl, the sum of q and y is 1 and the phenyl ring is substituted at the 4-position with Br, and $R^1$ is hydrogen, then $R^2$ is not $Cy^1$, wherein $Cy^1$ is bonded to the nitrogen atom through an optionally substituted $C_{1-4}$aliphatic group, wherein one or more methylene units in the $C_{1-4}$aliphatic group are optionally replaced with —NR—, —O—, —COO—, —OCO—, —NRCO—, —CONR—, —SO$_2$NR—, or —NRSO$_2$—;

iii) when $R^3$ is Cl or OMe, the sum of q and y is 1 and the phenyl ring is substituted at the 4-position with either OMe or Cl, and $R^1$ is hydrogen, then $R^2$ is not —CH(CH$_3$)(CH$_2$)$_3$N(Et)$_2$;

iv) when $R^3$ is Me, OMe, or NO$^2$, and q and y are 0, then $R^1$ and $R^2$ are not both methyl;

v) when $R^3$ is OMe, q and y are 0, and $R^1$ is hydrogen, then $R^2$ is not —SO$_2$(4-Me-phenyl);

vi) when $R^3$ is F, the sum of q and y is 1 and the phenyl ring is substituted at the 2-position with Cl, and $R^1$ is hydrogen, then $R^2$ is not —(CH$_2$)morpholino; and b) a) when $R^3$ is at the 6-position of the quinazoline ring then:
i) when $R^3$ is NH$_2$, Me, Cl, Br, —NHAc, the sum of q and y is 1 and the phenyl ring is substituted at the 4-position with F, or ring A is naphthyl, and $R^1$ is hydrogen, then $R^2$ is not —(CH$_3$)$_3$-4N(R')$_2$;

ii) when $R^3$ is —OCH$_2$Ph, or OH, and q and y are 0, then when $R^1$ is hydrogen, $R^2$ is not Me, nBu, or —(CH$_2$)$_2$morpholino, or $R^1$ and $R^2$ are not simultaneously Me or Et;

iii) when $R^3$ is Me or Cl, and the sum of q and y are 1, then the phenyl ring is not substituted in the 4-position with Br;

iv) when $R^3$ is Cl, q and y are 0, and $R^1$ is hydrogen, then $R^2$ is not —SO$_2$(4-Me-phenyl);

v) when $R^3$ is OMe, and q and y are 0, and $R^1$ is hydrogen, then $R^2$ is not —CH$_2$CH$_2$OH or —CH$_2$CH$_2$pyrrolidinyl;

vi) when $R^3$ is Cl or Br, the sum of q and y is 1, and the phenyl ring is substituted in the 4-position with —CH$_2$PO(OR')$_2$, then $R^1$ is not hydrogen when $R^2$ is -Me, or $R^1$ and $R^2$ are not simultaneously Me or Et;

vii) when $R^3$ is OH and q and y are 0, then $R^1$ and $R^2$ are not simultaneously —CH$_2$CH$_2$OMe;

viii) when $R_3$ is Cl, the sum of q and y is 1 and the phenyl ring is substituted in the 2-position with OnPr, and $R^1$ is hydrogen, then $R^2$ is not —CH$_2$(1,3-benzodioxol);

ix) when $R^3$ is OMe, OH, Br, C$_1$, NO$_2$, Me, and q and y are 0, then when $R^1$ is hydrogen, $R^2$ is not Me, —CH$_2$CH$_2$COOMe, —CH$_2$COOMe, or —(CH$_2$)$_3$CH$_3$, or $R^1$ and $R^2$ are not simultaneously Me; and x) when $R^3$ is Cl, the sum of q and y is 1 and the phenyl ring is substituted in the 4-position with Cl, then $R^1$ and $R^2$ are not simultaneously Me or iPr.

In certain other embodiments, for compounds of formula IA-i described directly above:

c) when x, y, and q are 0, and $R^1$ is hydrogen, then $R^2$ is not phenyl, cyclohexyl, cyclopentyl, 2-ClPh, 3-ClPh, 4-ClPh, 3-NO$_2$Ph, 3-(OMe)Ph, 3-(CO$_2$Me)Ph, 4-(CO$_2$Me)Ph, 3-pyridyl, 1-pyyrolyl, or 3-(5-Me-isoxazolyl);

d) when x, y, and q are 0, $R^1$ is hydrogen, and $R^2$ is —CH$_2$Cy$^1$, then Cy$^1$ is not phenyl, 2-ClPh, 3-ClPh, 4-ClPh, 3-NO$_2$Ph, 2-thienyl, 2-furyl, 2-pyridyl, 3-pyridyl, or 2-THF;

and the following additional compounds are excluded:
Dimethyl-(2-phenyl-quinazolin-4-yl)-amine;
Methyl-phenyl-(2-phenyl-quinazolin-4-yl)-amine;
Benzyl-methyl-(2-phenyl-quinazolin-4-yl)-amine;
Phenethyl-(2-phenyl-quinazolin-4-yl)-amine;
4-(2-Phenyl-quinazolin-4-ylamino)-butyric acid ethyl ester;
(2-Phenyl-quinazolin-4-yl)-propyl-amine;
5-(4-{2-[methyl-(2-phenylquinazolin-4-yl)amino]-ethoxy}-benzyl)-thiazolidine-2,4-dione;
4-N-acetyl-N-[2-(4-morpholino)-ethyl]-amino-2-phenyl quinazoline;
N,N-Diethyl-N'-(2-phenyl-quinazolin-4-yl)-ethane-1,2-diamine;
(6-Methoxy-2-phenyl-quinazolin-4-yl)-(2-morpholin-4-yl-ethyl)-amine;
N,N-Dimethyl-N'-(2-phenyl-quinazolin-4-yl)-ethane-1,2-diamine;
(2-Phenyl-quinazolin-4-yl)-(2-piperidin-1-yl-ethyl)-amine;
4-(2-Morpholin-4-yl-ethylamino)-2-phenyl-quinazolin-6-ol;
7-fluoro-4-N-[2-(4-morpholino)-ethyl]-amino-2-phenyl-quinazoline;
4-N-(2-N,N-di-n-propyl-amino-ethyl)-amino-2-phenyl-quinazoline;
4-N-[2-(4-morpholino)-ethyl]-amino-2-(3,4,5-trimethoxyphenyl)-quinazoline;
2-phenyl-4-N-[2-(1-piperazino)-ethyl]-aminoquinazoline;
6-benzyloxy-4-N-[2-(4-morpholino)-ethyl]amino-2-phenylquinazoline;
2-phenyl-4-N-[2-(1-pyrrolidino)-ethyl]-aminoquinazoline;
2-(2-chloro-phenyl)-7-fluoro-4-N-[2-(4-morpholino)-ethyl]-aminoquinazoline;
4-N-[2-(4-morpholino)-ethyl]-amino-2-(2-thienyl)-quinazoline;
2-(4-chlorophenyl)-4-N-[2-(4-methyl-1-piperazino)-propyl]-aminoquinazoline;
7-methyl-2-phenyl-4-N-[2-(4-thiamorpholino)-ethyl]-aminoquinazoline;
6-fluoro-2-(4-methylphenyl)-4-N-methyl-N-[2-(1-pyrrolidino)-ethyl]-aminoquinazoline;
2-(2-chlorophenyl)-4-N-[2-(4-morpholino)-ethyl]-aminoquinazoline;
4-N-[2-(4-morpholino)-ethyl]-amino-2-phenyl-quinazoline;
[4-(4-Methylamino-quinazolin-2-yl)-benzyl]-phosphonic acid diethyl ester;
[4-(4-Ethylamino-quinazolin-2-yl)-benzyl]-phosphonic acid diethyl ester;
[4-(6-Bromo-4-methylamino-quinazolin-2-yl)-benzyl]-phosphonic acid dimethyl ester;
[4-(6-Bromo-4-ethylamino-quinazolin-2-yl)-benzyl]-phosphonic acid dimethyl ester;
[4-(6-Bromo-4-methylamino-quinazolin-2-yl)-benzyl]-phosphonic acid diethyl ester;
[4-(6-Bromo-4-ethylamino-quinazolin-2-yl)-benzyl]-phosphonic acid diethyl ester;
[4-(6-Bromo-4-butylamino-quinazolin-2-yl)-benzyl]-phosphonic acid diethyl ester;
[4-(6-Bromo-4-cyclohexylamino-quinazolin-2-yl)-benzyl]-phosphonic acid diethyl ester;
[4-(6-Bromo-4-hydrazino-quinazolin-2-yl)-benzyl]-phosphonic acid diethyl ester;
[4-(6-Bromo-4-ethylamino-quinazolin-2-yl)-benzyl]-phosphonic acid diisopropyl ester;
[4-(6-Bromo-4-methylamino-quinazolin-2-yl)-benzyl]-phosphonic acid diisopropyl ester;
[4-(6-Chloro-4-methylamino-quinazolin-2-yl)-benzyl]-phosphonic acid diethyl ester;
[4-(6,7-Dimethoxy-4-methylamino-quinazolin-2-yl)-benzyl]-phosphonic acid diethyl ester;
[4-(6-Bromo-4-methylamino-quinazolin-2-yl)-benzyl]-phosphonic acid monoethyl ester;

[4-(6-Bromo-4-ethylamino-quinazolin-2-yl)-benzyl]-phosphonic acid monoethyl ester; and

[4-(6-Bromo-4-dimethylamino-quinazolin-2-yl)-benzyl]-phosphonic acid monoethyl ester.

In certain other embodiments, for compounds described directly above, one of $R^1$ or $R^2$ is hydrogen and the other of $R^1$ or $R^2$ is not hydrogen.

In certain other embodiments, for compounds described directly above:

a) one of $R^1$ or $R^2$ is hydrogen, and the other of $R^1$ and $R^2$ is selected from:

i) $Cy^1$ wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or ii) an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or b) $R^1$ and $R^2$ are each independently selected from $Cy^1$, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or an optionally substituted $C_{1-4}$aliphatic group, wherein one or more methylene units in the $C_{1-4}$aliphatic group are optionally replaced with —NR—, —O—, —OCO—, —OCO—, —NRCO—, —CONR—, —SO$_2$NR—, or —NRSO$_2$—.

In still other embodiments, $Cy^1$ is:

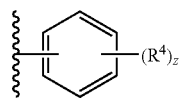

a

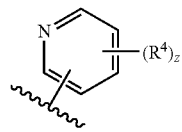

b

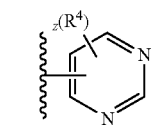

c

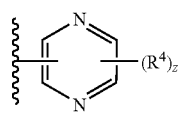

d

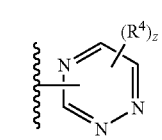

e

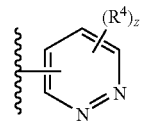

f

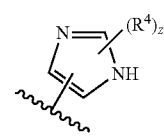

g

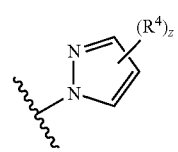

h

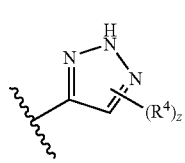

i

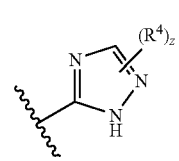

j

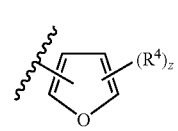

k

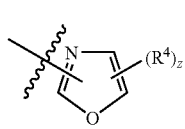

l

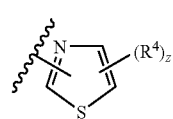

m

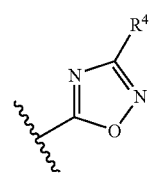

n

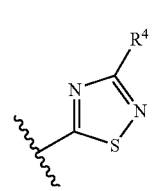

o

-continued
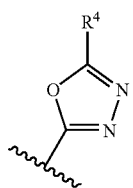 p
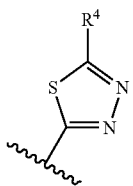 q
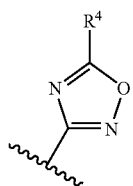 r
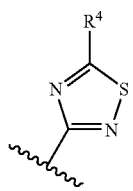 s
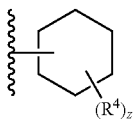 t
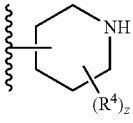 u
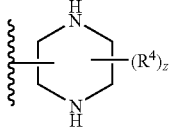 v
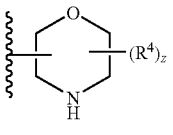 w
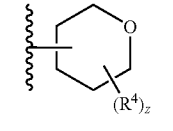 x
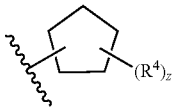 y
-continued
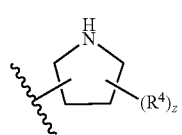 z
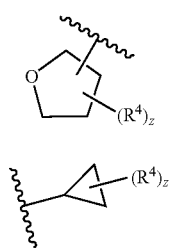 aa
bb
In yet other embodiments, $R^1$ is hydrogen or an optionally substituted $C_1$-$C_4$ aliphatic group and $R^2$ is —CHR-$Cy^1$, wherein R is hydrogen or $C_1$-$C_4$ alkyl, and $Cy^1$ is:
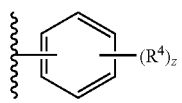 a
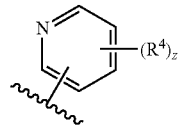 b
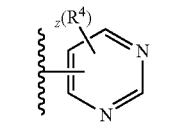 c
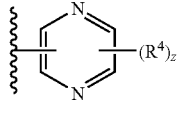 d
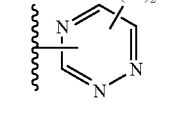 e
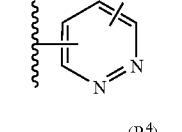 f
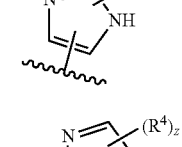 g
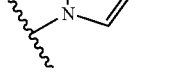 h

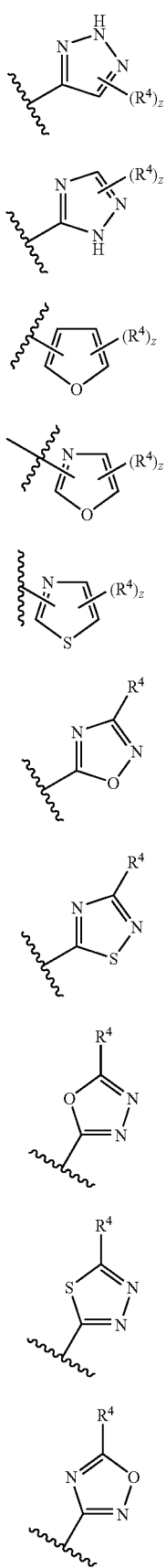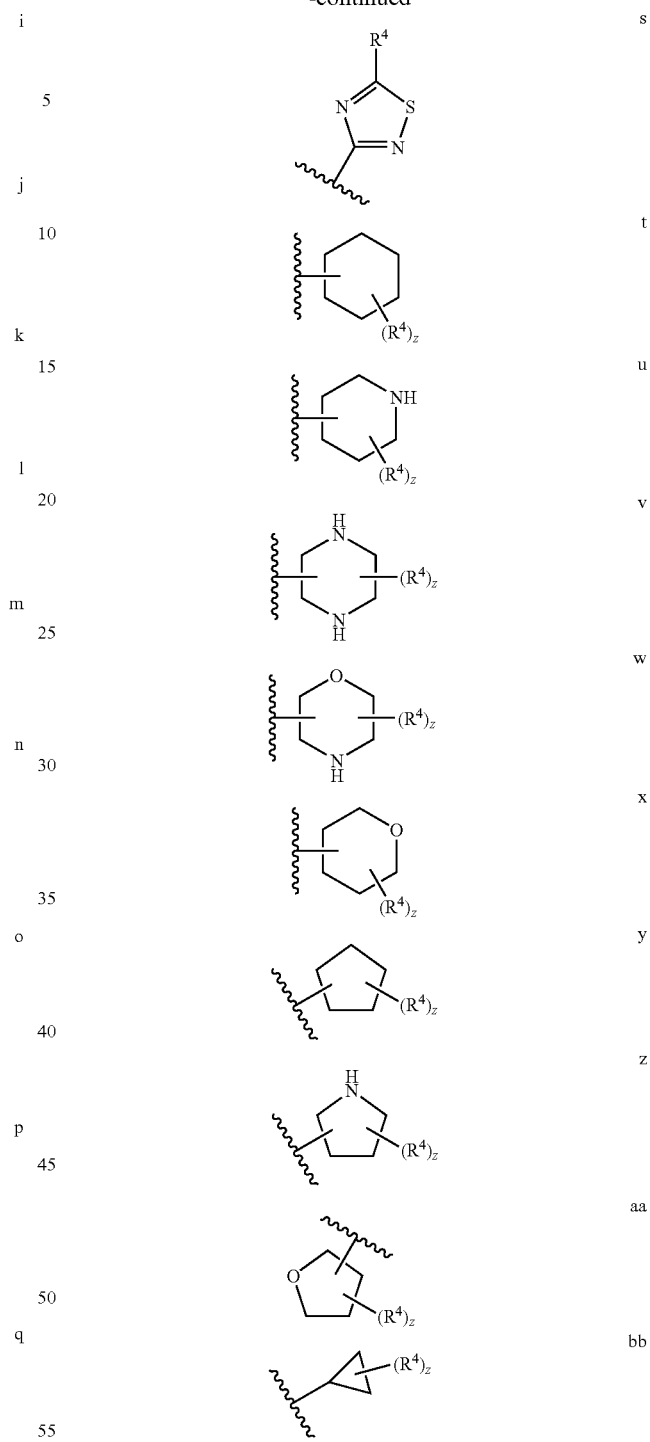

In yet other embodiments, $R^1$ and $R^2$ groups are each independently an optionally substituted $C_{1-4}$ aliphatic group and are each independently selected from optionally substituted methyl, ethyl, cyclopropyl, n-propyl, propenyl, cyclobutyl, $(CO)OCH_2CH_3$, $(CH_2)_2OCH_3$, $CH_2CO)OCH_2CH_3$, $CH_2(CO)OCH_3$, $CH(CH_3)CH_2CH_3$, or n-butyl.

In still other embodiments, for compounds described directly above, z is 0-5, and $R^4$ groups, when present, are each independently halogen, CN, $NO_2$, —$N(R')_2$, —$CH_2N(R')_2$, —OR', —$CH_2OR'$, —SR', —$CH_2SR'$, —COOR', —NR- COR', —CON(R')$_2$, —OCON(R')$_2$, COR', —NHCOOR', —SO$_2$R', —SO$_2$N(R)$_2$, or an optionally substituted group selected from C$_1$-C$_6$aliphatic, aryl, heteroaryl, cycloaliphatic, heterocycloaliphatic, arylC$_1$-C$_6$alkyl, heteroaryl C$_1$-C$_6$alkyl, cycloaliphatic C$_1$-C$_6$alkyl, or heterocycloaliphatic C$_1$-C$_6$alkyl.

In yet other embodiments, z is 0-5 and R$^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, C$_{1-4}$alkoxy, phenyl, phenyloxy, benzyl, benzyloxy, —CH$_2$cyclohexyl, pyridyl, —CH$_2$pyridyl, or —CH$_2$thiazolyl.

In still other embodiments, for compounds described directly above, R$^3$ is halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R)$_2$, COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, aryl C$_1$-C$_6$ alkyl, heteroaryl C$_1$-C$_6$alkyl, cycloaliphatic C$_1$-C$_6$alkyl, or heterocycloaliphatic C$_1$-C$_6$ alkyl.

In yet other embodiments, R$^3$ is Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy.

In still other embodiments, R$^3$ is halogen, CN, optionally substituted C$_1$-C$_6$alkyl, OR', N(R')$_2$, CON(R')$_2$, or NRCOR'. In yet other embodiments, R$^3$ is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, R$^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In yet other embodiments, R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In yet other embodiments, R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, R$^3$ is at the 6-position of the quinazoline ring and is —CON(R')$_2$, or NRCOR'. In still other embodiments, R$^3$ is at the 7-position of the quinazoline ring and is —CON(R')$_2$, or NRCOR'.

In still other embodiments for compounds described directly above, y is 0-5, q is 0-2, and R$^5$ and R$^{5a}$ groups, when present, are each independently halogen, CN, NO$_2$, —N(R')$_2$, —CH$_2$N(R')$_2$, —OR', —CH$_2$OR', —SR', —CH$_2$SR', —NRCOR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from C$_1$-C$_6$aliphatic, aryl, heteroaryl, cycloaliphatic, heterocycloaliphatic, aryl C$_1$-C$_6$alkyl, heteroaryl C$_1$-C$_6$alkyl, cycloaliphatic C$_1$-C$_6$alkyl, or heterocycloaliphatic C$_1$-C$_6$alkyl.

In yet other embodiments, y is 0-5, and q is 1 or 2, and each occurrence of R$^{5a}$ is independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In still other embodiments, y is 0, and R$^{5a}$ is F. In yet other embodiments y is 0, q is 1, and R$^{5a}$ is OR'. In still other embodiments, y is 0, q is 1 and R$^{5a}$ is OH. In yet other embodiments, y is 1, R$^{5a}$ is OR' and R$^5$ is F, wherein OR' is substituted at the 2-position of the phenyl ring and F is substituted at the 6-position of the phenyl ring. In yet other embodiments, y is 1, R$^{5a}$ is OH and R$^5$ is F, wherein OH is substituted at the 2-position of the phenyl ring and F is substituted at the 6-position of the phenyl ring.

In still other embodiments, R$^3$ is substituted at the 6-position of the quinazoline ring, q is 1, and y is 0, and compounds have formula III:

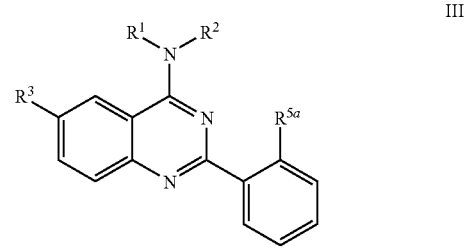

III

In certain embodiments, for compounds described above, a) R$^1$ and R$^2$ are each independently hydrogen, or an optionally substituted group selected from C$_{1-6}$aliphatic, Cy$^1$, wherein Cy$^1$ is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein Cy$^1$ is bonded directly to the nitrogen atom or is bonded through an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—; wherein R$^1$ and R$^2$, are each optionally and independently substituted at one or more substitutable carbon, nitrogen, or sulfur atoms with z independent occurrences of —R$^4$, wherein z is 0-5;

b) z is 0-5 and R$^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, C$_{1-4}$alkoxy, phenyl, phenyloxy, benzyl, benzyloxy, —CH$_2$cyclohexyl, pyridyl, —CH$_2$pyridyl, or —CH$_2$thiazolyl;

c) $R^3$ is Cl, Br, F, CF$_3$, —OCF$_3$, Me, Et, CN, —COON, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy; and d) $R^{5a}$ is Cl, F, CF$_3$, Me, Et, —OH, —OCH$_3$, —OCH$_2$CH$_3$, —CH$_2$OH, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), or —COCH$_3$.

In certain other embodiments, for compounds described directly above, one of $R^1$ or $R^2$ is hydrogen and the other of $R^1$ or $R^2$ is not hydrogen.

In certain other embodiments, for compounds described directly above $R^3$ is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, $R^3$ is —Cl, —CH$_3$, —CH$_2$CH$_3$, —F, —CF$_3$, —OCF$_3$, —OCH$_3$, or —OCH$_2$CH$_3$. In yet other embodiments, $R^3$ is —CON(R')$_2$, or NRCOR'. In still other embodiments, $R^{5a}$ is Cl, F, CF$_3$, Me, Et, —OH, —OCH$_3$, —OCH$_2$CH$_3$.

In still other embodiments, y is 0, and $R^{5a}$ is F. In yet other embodiments, y is 0, q is 1, and $R^{5a}$ is OR'. In still other embodiments, y is 0, q is 1 and $R^{5a}$ is OH.

In certain other embodiments, for compounds described directly above:

a) Cy$^1$ is:

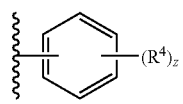

a

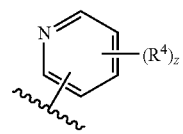

b

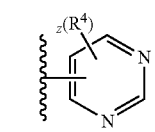

c

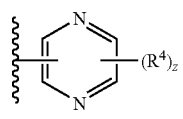

d

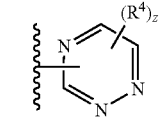

e

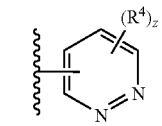

f

-continued

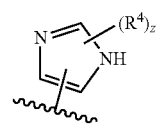

g

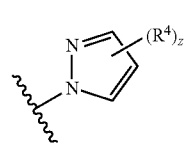

h

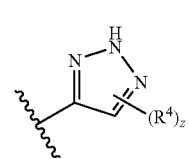

i

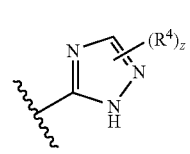

j

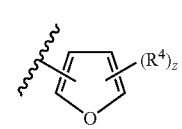

k

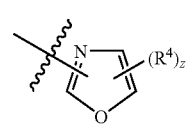

l

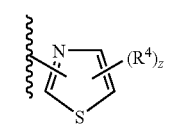

m

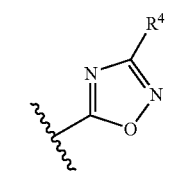

n

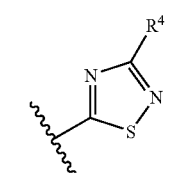

o

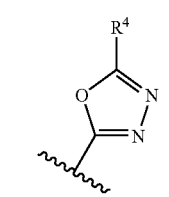

p

-continued q 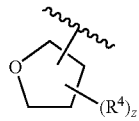

r 

s

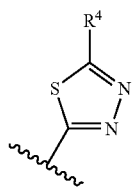

t 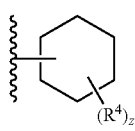

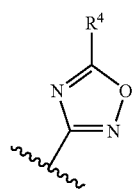

u 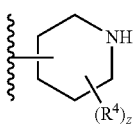

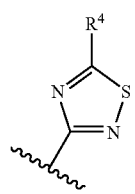

v 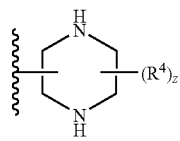

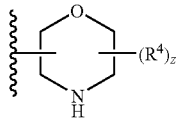

w 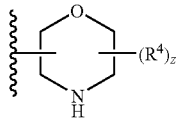

x 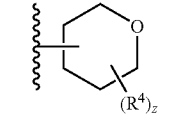

y 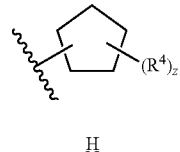

z 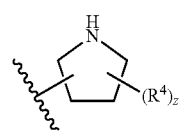

-continued aa 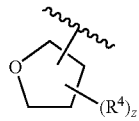

bb 

or $R^1$ and $R^2$ are each independently an optionally substituted $C_{1-4}$aliphatic group and are each independently selected from optionally substituted methyl, ethyl, cyclopropyl, n-propyl, propenyl, cyclobutyl, $(CO)OCH_2CH_3$, $(CH_2)_2OCH_3$, $CH_2CO)OCH_2CH_3$, $CH_2(CO)OCH_3$, $CH(CH_3)CH_2CH_3$, or n-butyl;

b) z is 0-5 and $R^4$ groups are each independently Cl, Br, F, $CF_3$, $CH_3$, —$CH_2CH_3$, CN, —COOH, —$N(CH_3)_2$, —$N(Et)_2$, —$N(iPr)_2$, —$O(CH_2)_2OCH_3$, —$CONH_2$, —$COOCH_3$, —OH, —$CH_2OH$, —$NHCOCH_3$, —$SO_2NH_2$, —$SO_2(CH_2)_3CH_3$, —$SO_2CH(CH_3)_2$, —$SO_2N(CH_3)_2$, —$SO_2CH_2CH_3$, —$C(O)OCH_2CH(CH_3)_2$, —$C(O)NHCH_2CH(CH_3)_2$, —NHCOOCH$_3$, —$C(O)C(CH_3)_3$, —$COO(CH_2)_2CH_3$, —$C(O)NHCH(CH_3)_2$, —$C(O)CH_2CH_3$, or an optionally substituted group selected from -piperidinyl, piperizinyl, morpholino, $C_{1-4}$alkoxy, phenyl, phenyloxy, benzyl, benzyloxy, —$CH_2$cyclohexyl, pyridyl, —$CH_2$pyridyl, or —$CH_2$thiazolyl;

c) $R^3$ is Cl, Br, F, $CF_3$, —$OCF_3$, Me, Et, CN, —COOH, —$NH_2$, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$CH_2OH$, —$NHCOCH_3$, —$NHCOCH(CH_3)_2$, —$SO_2NH_2$, —$CONH$(cyclopropyl), —$CONHCH_3$, —$CONHCH_2CH_3$, or an optionally substituted group selected from -piperidinyl, piperizinyl, morpholino, phenyl, phenyloxy, benzyl, or benzyloxy; and d) $R^{5a}$ is Cl, F, $CF_3$, Me, Et, —OH, —$OCH_3$, —$OCH_2CH_3$, —$CH_2OH$, —$SO_2NH_2$, —$SO_2NHC(CH_3)_2$, —OCOC$(CH_3)_3$, —$OCOCH_2C(CH_3)_3$, —$O(CH_2)_2N(CH_3)_2$, 4-$CH_3$-piperazin-1-yl, $OCOCH(CH_3)_2$, OCO(cyclopentyl), or —$COCH_3$.

In certain embodiments, for compounds described directly above $R^3$ is —Cl, —$CH_3$, —$CH_2CH_3$, —F, —$CF_3$, —$OCF_3$, —$CONHCH_3$, —$CONHCH_2CH_3$, —$CONH$(cyclopropyl), —$OCH_3$, —$NH_2$, —$OCH_2CH_3$, or —CN. In other embodiments, $R^3$ is —Cl, —$CH_3$, —$CH_2CH_3$, —F, —$CF_3$, —$OCF_3$, —$OCH_3$, or —$OCH_2CH_3$. In still other embodiments, $R^3$ is —$CON(R')_2$, or $NRCOR'$. In yet other embodiments, $R^{5a}$ is Cl, F, $CF_3$, Me, Et, —OH, —$OCH_3$, —$OCH_2CH_3$. In still other embodiments, y is 0, and $R^{5a}$ is F. In yet other embodiments y is 0, q is 1, and $R^{5a}$ is OR'. In still other embodiments, y is 0, q is 1 and $R^{5a}$ is OH.

In yet other embodiments, $R^3$ is substituted at the 7-position of the quinazoline ring, q is 1, and y is 0, and compounds have formula IV:

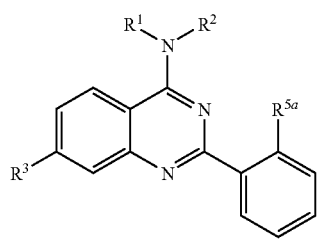

IV a) wherein $R^1$ and $R^2$ are each independently hydrogen, or an optionally substituted group selected from $C_{1-6}$aliphatic, $Cy^1$, wherein $Cy^1$ is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; wherein $R^1$ and $R^2$, are each optionally and independently substituted at one or more substitutable carbon, nitrogen, or sulfur atoms with z independent occurrences of —$R^4$, wherein z is 0-5;

b) z is 0-5 and $R^4$ groups are each independently Cl, Br, F, $CF_3$, $CH_3$, —$CH_2CH_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, $C_{1-4}$alkoxy, phenyl, phenyloxy, benzyl, benzyloxy, —CH$_2$cyclohexyl, pyridyl, —CH$_2$pyridyl, or —CH$_2$thiazolyl;

c) $R^3$ is Cl, Br, F, $CF_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy; and d) $R^{5a}$ is Cl, F, CF$_3$, Me, Et, —OH, —OCH$_3$, —OCH$_2$CH$_3$, —CH$_2$OH, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), or —COCH$_3$.

In certain other embodiments, for compounds described directly above, one of $R^1$ or $R^2$ is hydrogen and the other of $R^1$ or $R^2$ is not hydrogen.

In certain embodiments, for compounds described directly above, $R^3$ is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In other embodiments, $R^3$ is —Cl, —CH$_3$, —CH$_2$CH$_3$, —F, —CF$_3$, —OCF$_3$, —OCH$_3$, or —OCH$_2$CH$_3$. In still other embodiments, $R^3$ is —CON(R')$_2$, or NRCOR'. In yet other embodiments, $R^{5a}$ is Cl, F, CF$_3$, Me, Et, —OH, —OCH$_3$, —OCH$_2$CH$_3$. In still other embodiments, y is 0, and $R^{5a}$ is F. In yet other embodiments y is 0, q is 1, and $R^{5a}$ is OR'. In still other embodiments, y is 0, q is 1 and $R^{5a}$ is OH.

In certain other embodiments, for compounds described directly above:

a) $Cy^1$ is:

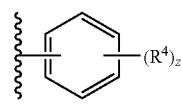 a

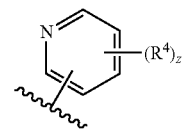 b

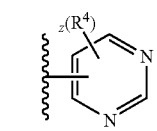 c

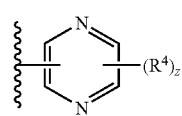 d

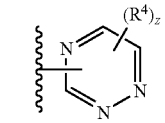 e

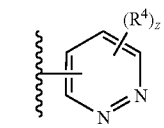 f

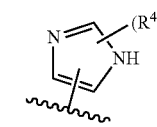 g

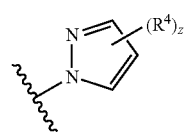 h

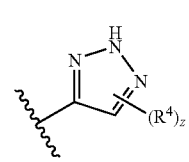 i

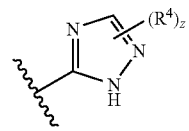 j

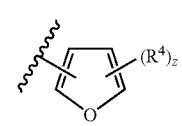 k l 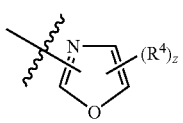

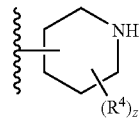 u m 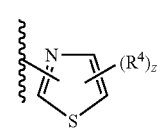

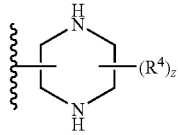 v n 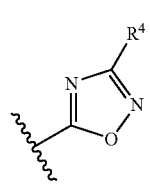

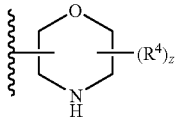 w

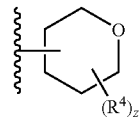 x o 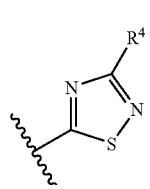

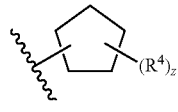 y p 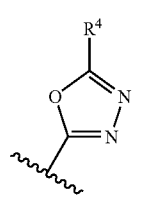

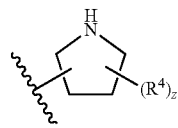 z

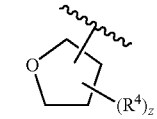 aa q 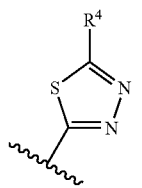

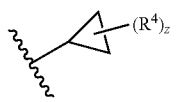 bb r 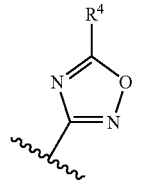

or $R^1$ and $R^2$ are each independently an optionally substituted $C_{1-4}$aliphatic group and are each independently selected from optionally substituted methyl, ethyl, cyclopropyl, n-propyl, propenyl, cyclobutyl, (CO)OCH$_2$CH$_3$, (CH$_2$)$_2$OCH$_3$, CH$_2$CO)OCH$_2$CH$_3$, CH$_2$(CO)OCH$_3$, CH(CH$_3$)CH$_2$CH$_3$, or n-butyl;

b) z is 0-5 and $R^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, $C_{1-4}$alkoxy, phenyl, phenyloxy, benzyl, benzyloxy, —CH$_2$cyclohexyl, pyridyl, —CH$_2$pyridyl, or —CH$_2$thiazolyl;

s 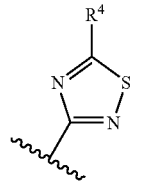

c) $R^3$ is Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, t 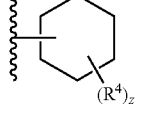

or an optionally substituted group selected from -piperidinyl, piperizinyl, morpholino, phenyl, phenyloxy, benzyl, or benzyloxy; and d) $R^{5a}$ is Cl, F, CF$_3$, Me, Et, —OH, —OCH$_3$, —OCH$_2$CH$_3$, —CH$_2$OH, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), or —COCH$_3$.

In certain other embodiments, for compounds described directly above $R^3$ is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In other embodiments, $R^3$ is —Cl, —CH$_3$, —CH$_2$CH$_3$, —F, —CF$_3$, —OCF$_3$, —OCH$_3$, or —OCH$_2$CH$_3$. In still other embodiments, $R^3$ is —CON(R')$_2$, or NRCOR'. In yet other embodiments, $R^{5a}$ is Cl, F, CF$_3$, Me, Et, —OH, —OCH$_3$, or —OCH$_2$CH$_3$. In still other embodiments, y is 0, and $R^{5a}$ is F. In yet other embodiments y is 0, q is 1, and $R^{5a}$ is OR'. In still other embodiments, y is 0, q is 1 and $R^{5a}$ is OH.

For compounds described in this section above, in general, compounds are useful as inhibitors of ion channels, preferably voltage gated sodium channels and N-type calcium channels. In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

IV. Compounds of Formula V:

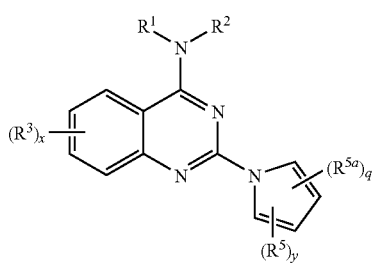

V wherein $R^1$ and $R^2$ are each independently hydrogen, or an optionally substituted group selected from C$_{1-6}$aliphatic, Cy$^1$, wherein Cy$^1$ is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein Cy$^1$ is bonded directly to the nitrogen atom or is bonded through an optionally substituted C$_{1-4}$aliphatic group, wherein one or more methylene units in the C$_{1-4}$aliphatic group are optionally replaced with —NR—, —O—, —COO—, —OCO—, —NRCO—, —CONR—, —SO$_2$NR—, or —NRSO$_2$—; or $R^1$ and $R^2$, taken together with the nitrogen atom to which they are bound, form an optionally substituted 3-12-membered monocyclic or bicyclic saturated or partially unsaturated ring having 0-3 additional heteroatoms independently selected from nitrogen, sulfur, or oxygen; wherein $R^1$ and $R^2$, or the ring formed by $R^1$ and $R^2$ taken together, are each optionally and independently substituted at one or more substitutable carbon, nitrogen, or sulfur atoms with z independent occurrences of —R$^4$, wherein z is 0-5;

x is 0-4;
y is 0-2;

each occurrence of $R^3$, $R^4$, and $R^5$ is independently Q-R$^X$; wherein Q is a bond or is a C$_1$-C$_6$ alkylidene chain wherein up to two non-adjacent methylene units of Q are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, —OP(O)(OR)—, or —POR—; and each occurrence of R$^X$ is independently selected from —R', =O, =NR', halogen, —NO$_2$, —CN, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R)$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$;

$R^{5a}$ is optionally substituted C$_1$-C$_6$aliphatic group, halogen, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R)$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or an optionally substituted C$_{1-6}$ aliphatic group; and each occurrence of R' is independently hydrogen or an optionally substituted C$_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In certain embodiments, for compounds described directly above, when x is 1 and $R^3$ is 6-OMe, $R^1$ is hydrogen, and y and q are both 0, then $R^2$ is not —CH$_2$CH$_2$OCH$_2$CH$_2$OH or the monomethanesulfonate salt.

In certain other embodiments, for compounds described directly above, one of $R^1$ or $R^2$ is hydrogen and the other of $R^1$ or $R^2$ is not hydrogen.

In certain other embodiments, for compounds described directly above, a) one of $R^1$ or $R^2$ is hydrogen, and the other of $R^1$ and $R^2$ is selected from:

i) Cy$^1$ wherein Cy$^1$ is bonded directly to the nitrogen atom or is bonded through an optionally substituted C$_{1-4}$aliphatic group, wherein one or more methylene units in the C$_{1-4}$aliphatic group are optionally replaced with —NR—, —O—, —COO—, —OCO—, —NRCO—, —CONR—, —SO$_2$NR—, or —NRSO$_2$—; or ii) an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—; or b) $R^1$ and $R^2$ are each independently selected from Cy$^1$, wherein Cy$^1$ is bonded directly to the nitrogen atom or is bonded through an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO₂NR—, or —NRSO₂—; or an optionally substituted $C_{1-4}$ aliphatic group, wherein one or more methylene units in the $C_{1-4}$ aliphatic group are optionally replaced with —NR—, —O—, —OCO—, —OCO—, —NRCO—, —CONR—, —SO₂NR—, or —NRSO₂—.
In other embodiments, $Cy^1$ is:
a
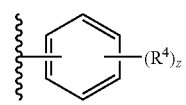
b
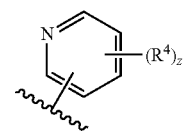
c
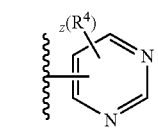
d
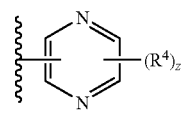
e
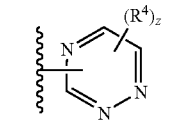
f
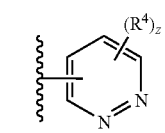
g
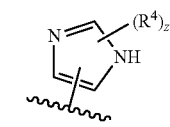
h
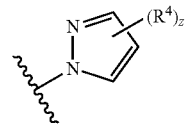
i
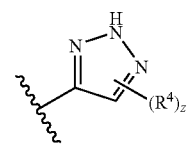
j
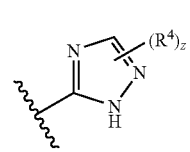
-continued
k
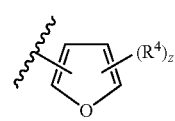
l
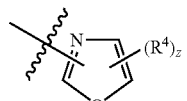
m
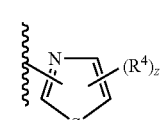
n
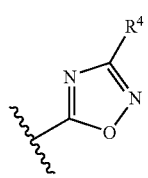
o
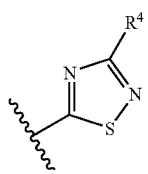
p
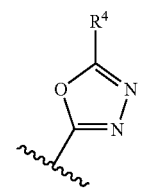
q
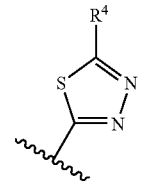
r
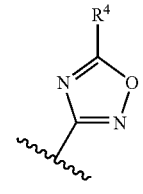
s
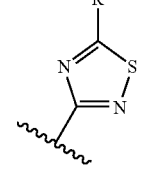
t
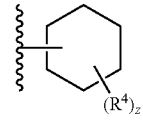

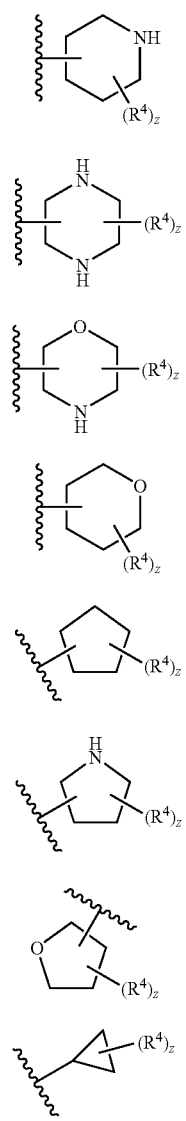
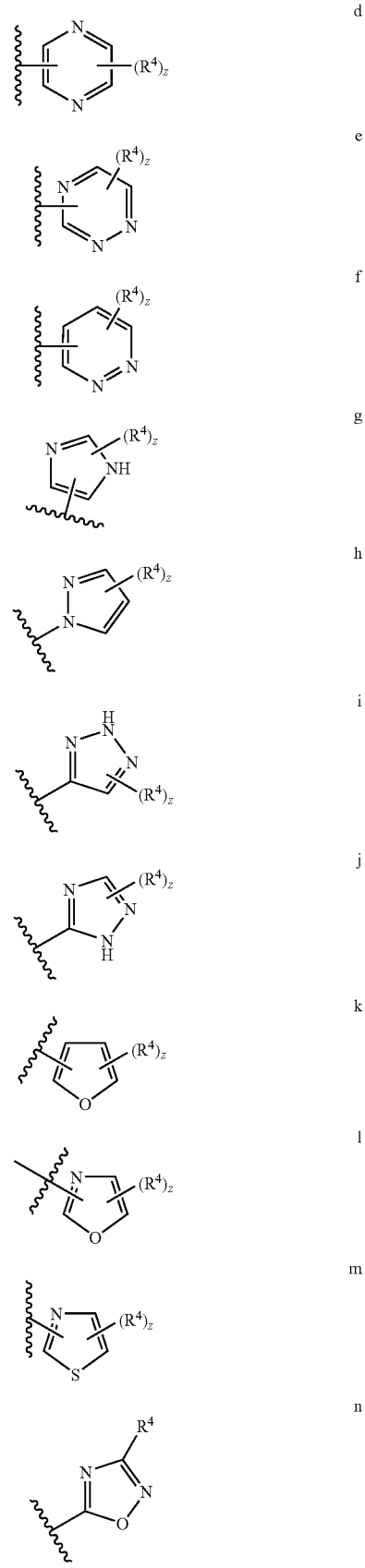
In still other embodiments, R¹ is hydrogen or an optionally substituted $C_1$-$C_4$ aliphatic group and R² is —CHR-Cy¹, wherein R is hydrogen or $C_1$-$C_4$ alkyl, and Cy¹ is:
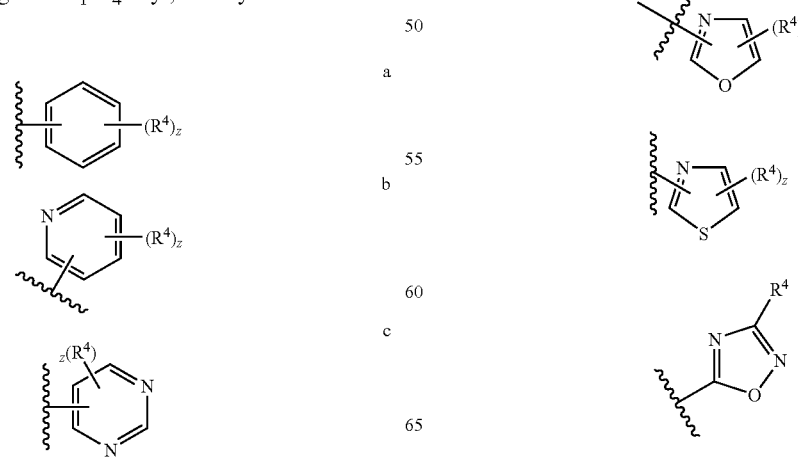

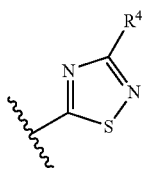 o

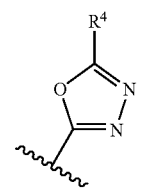 p

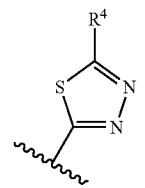 q

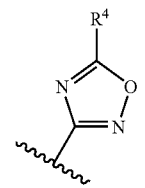 r

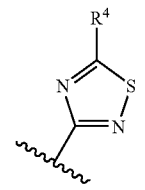 s

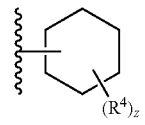 t

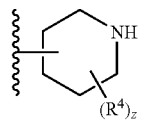 u

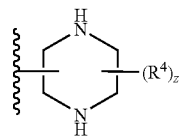 v

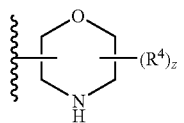 w

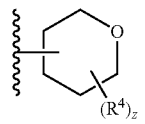 x

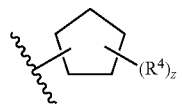 y

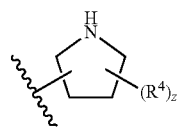 z

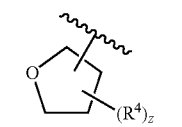 aa

 bb

In still other embodiments, $R^1$ and $R^2$ groups are each independently an optionally substituted $C_{1-4}$ aliphatic group and are each independently selected from optionally substituted methyl, ethyl, cyclopropyl, n-propyl, propenyl, cyclobutyl, $(CO)OCH_2CH_3$, $(CH_2)_2OCH_3$, $CH_2CO)OCH_2CH_3$, $CH_2(CO)OCH_3$, $CH(CH_3)CH_2CH_3$, or n-butyl.

In yet other embodiments for compounds described directly above, $R^1$ and $R^2$, taken together with the nitrogen atom to which they are bound, form an optionally substituted 3-12 membered heterocyclyl ring having 1-3 heteroatoms independently selected from nitrogen or oxygen and form a 3-12 membered heterocyclyl group selected from:

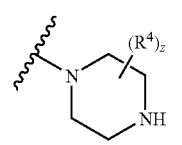 cc

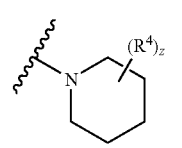 dd

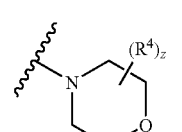 ee

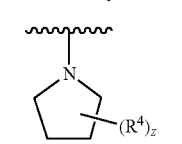 ff

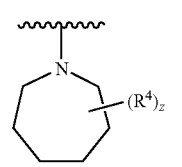 gg

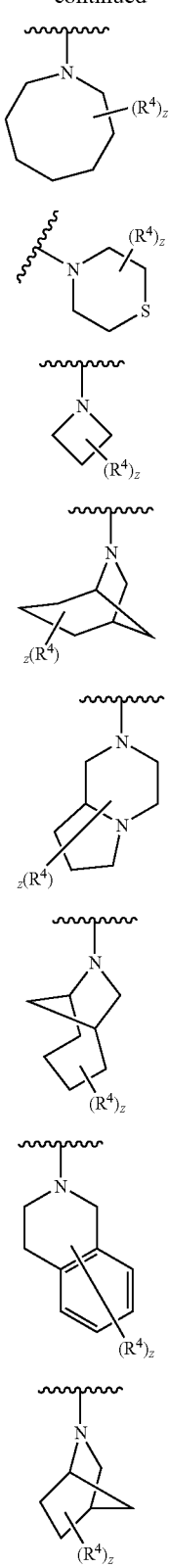

wherein the ring formed by $R^1$ and $R^2$ taken together, is optionally substituted at one or more substitutable carbon, nitrogen, or sulfur atoms with z independent occurrences of —$R^4$, and z is 0-5.

In other embodiments, for compounds of formula I-A, $R^1$ and $R^2$ taken together are optionally substituted azetidin-1-yl (jj), pyrrolidin-1-yl (ff), piperidin 1-yl (dd), piperazin-1-yl (cc), or morpholin-4-yl (ee). In other embodiments, for compounds of formula I-A, $R^1$ and $R^2$ taken together are optionally substituted azetidin-1-yl (jj), pyrrolidin-1-yl (ff), piperidin-1-yl (dd), or piperazin-1-yl (cc). In yet other embodiments, for compounds of formula I-A, $R^1$ and $R^2$, taken together is optionally substituted azetidin-1-yl (jj). In yet other embodiments, for compounds of formula I-A, $R^1$ and $R^2$, taken together is optionally substituted pyrrolidin-1-yl (ff). In still other embodiments, for compounds of formula I-A, $R^1$ and $R^2$, taken together is optionally substituted piperidin-1-yl (dd). In yet other embodiments, for compounds of formula I-A, $R^1$ and $R^2$, taken together is optionally substituted piperazin-1-yl (cc).

In still other embodiments, for compounds described directly above, z is 0-5, and $R^4$ groups, when present, are each independently halogen, CN, $NO_2$, —$N(R')_2$, —$CH_2N(R')_2$, —OR', —$CH_2OR'$, —SR', —$CH_2SR'$, —COOR', —NRCOR', —$CON(R')_2$, —$OCON(R')_2$, COR', —NHCOOR', —$SO_2R'$, —$SO_2N(R')_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In yet other embodiments, z is 0-5 and $R^4$ groups are each independently Cl, Br, F, $CF_3$, $CH_3$, —$CH_2CH_3$, CN, —COOH, —$N(CH_3)_2$, —$N(Et)_2$, —$N(iPr)_2$, —$O(CH_2)_2$ $OCH_3$, —$CONH_2$, —$COOCH_3$, —OH, —$CH_2OH$, —NHCOCH_3$, —$SO_2NH_2$, —$SO_2(CH_2)_3CH_3$, —$SO_2CH(CH_3)_2$, —$SO_2N(CH_3)_2$, —$SO_2CH_2CH_3$, —$C(O)OCH_2CH(CH_3)_2$, —$C(O)NHCH_2CH(CH_3)_2$, —$NHCOOCH_3$, —$C(O)C(CH_3)_3$, —$COO(CH_2)_2CH_3$, —$C(O)NHCH(CH_3)_2$, —$C(O)CH_2CH_3$, or an optionally substituted group selected from -piperidinyl, piperizinyl, morpholino, $C_{1-4}$alkoxy, phenyl, phenyloxy, benzyl, benzyloxy, —$CH_2$cyclohexyl, pyridyl, —$CH_2$pyridyl, or —$CH_2$thiazolyl.

In certain embodiments, for compounds of formula I-A, $R^1$ and $R^2$, taken together is optionally substituted azetidin-1-yl (jj), wherein z is 1 or 2 and at least one occurrence of $R^4$ is —$NRSO_2R'$, —NRCOOR', or —NRCOR'. In certain other embodiments, for compounds of formula I-A, $R^1$ and $R^2$, taken together is optionally substituted azetidin-1-yl (jj), wherein z is 1 and $R^4$ is —$NRSO_2R'$. In other embodiments, for compounds of formula I-A, $R^1$ and $R^2$, taken together is optionally substituted azetidin-1-yl (jj), wherein z is 1 and $R^4$ is —NRCOOR'. In certain other embodiments, for compounds of formula I-A, $R^1$ and $R^2$, taken together is optionally substituted azetidin-1-yl (jj), wherein z is 1 and $R^4$ is —NRCOR'. In yet other embodiments, for compounds of formula I-A, $R^1$ and $R^2$, taken together is optionally substituted pyrrolidin-1-yl (ff), wherein z is 1 or 2 and $R^4$ is Cl, Br, F, $CF_3$, $CH_3$, —$CH_2CH_3$, —OR', or —$CH_2OR'$. In still other embodiments, for compounds of formula I-A, $R^1$ and $R^2$, taken together is optionally substituted piperidin-1-yl (dd), wherein z is 1 or 2 and at least one occurrence of $R^4$ is Cl, Br, F, $CF_3$, $CH_3$, —$CH_2CH_3$, —OR', or —$CH_2OR'$, —$NRSO_2R'$, —NRCOOR', or —$OCON(R')_2$. In certain other embodiments, for compounds of formula I-A, $R^1$ and $R^2$, taken together is optionally substituted piperidin-1-yl (dd), wherein z is 1 and $R^4$ is F, $CF_3$, $CH_3$, —$CH_2CH_3$, —OR', or —$CH_2OR'$. In other embodiments, for compounds of formula I-A, $R^1$ and $R^2$, taken together is optionally substituted piperidin-1-yl (dd), wherein z is 1 and $R^4$ is —$NRSO_2R'$. In certain other embodiments, for compounds of formula I-A, $R^1$ and $R^2$, taken together is optionally substituted piperidin-1-yl (dd), wherein z is 1 and $R^4$ is —NRCOOR'. In yet other embodiments, for compounds of formula I-A, $R^1$ and $R^2$, taken together is optionally substituted piperazin-1-yl (cc), wherein z is 1 or 2 and at least one occurrence of $R^4$ is —SOR', —CON(R')$_2$, —SO$_2$N(R')$_2$, —COR', or —COOR'. In certain other embodiments, for compounds of formula I-A, $R^1$ and $R^2$, taken together is optionally substituted piperazin-1-yl (cc), wherein z is 1 and $R^4$ is —SOR'. In certain other embodiments, for compounds of formula I-A, $R^1$ and $R^2$, taken together is optionally substituted piperazin-1-yl (cc), wherein z is 1 and $R^4$ is —COOR'. In certain other embodiments, for compounds of formula I-A, $R^1$ and $R^2$, taken together is optionally substituted piperazin-1-yl (cc), wherein z is 1 and $R^4$ is —CON(R')$_2$. In certain other embodiments, for compounds of formula I-A, $R^1$ and $R^2$, taken together is optionally substituted piperazin-1-yl (cc), wherein z is 1 and $R^4$ is —SO$_2$N(R')$_2$. In certain other embodiments, for compounds of formula I-A, $R^1$ and $R^2$, taken together is optionally substituted piperazin-1-yl (cc), wherein z is 1 and $R^4$ is —COR'.

In still other embodiments, x is 0-4, and $R^3$ groups, when present, are each independently halogen, CN, NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, COR', —NHCOOR', —SO$_2$R', —SO$_2$N(R')$_2$, or an optionally substituted group selected from $C_1$-$C_6$aliphatic, aryl, heteroaryl, cycloaliphatic, hetero cycloaliphatic, aryl $C_1$-$C_6$alkyl, hetero aryl $C_1$-$C_6$alkyl, cycloaliphatic $C_1$-$C_6$ alkyl, or heterocycloaliphatic $C_1$-$C_6$alkyl. In yet other embodiments, x is 1 or 2, and each occurrence of $R^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy.

In still other embodiments, x is 1 or 2 and each $R^3$ group is independently halogen, CN, optionally substituted $C_1$-$C_6$alkyl, OR', N(R')$_2$, CON(R')$_2$, or NRCOR'. In yet other embodiments, x is 1 or 2, and each $R^3$ group is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, x is 1 and $R^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In yet other embodiments, x is 1 and $R^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, x is 1 and $R^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In yet other embodiments, x is 1 and $R^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, x is 1 and $R^3$ is at the 6-position of the quinazoline ring and is —CON(R')$_2$, or NRCOR'. In yet other embodiments, x is 1 and $R^3$ is at the 7-position of the quinazoline ring and is —CON(R')$_2$, or NRCOR'.

In still other embodiments for compounds described directly above, y is 0-2, q is 0-2, and $R^5$ and $R^{5a}$ groups, when present, are each independently halogen, CN, NO$_2$, —N(R')$_2$, —CH$_2$N(R')$_2$, —OR', —CH$_2$OR', —SR', —CH$_2$SR', —NR-COR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In yet other embodiments, y is 0-2, and q is 1 or 2, and each occurrence of $R^{5a}$ is independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy.

In still other embodiments, y is 0, and q is 1 and $R^{5a}$ is F. In yet other embodiments, y is 0, q is 1, and $R^{5a}$ is OR'. In still other embodiments, y is 0, q is 1 and $R^{5a}$ is OH. In yet other embodiments, y is 0, q is 2 and one occurrence of $R^{5a}$ is OR' and the other occurrence of $R^{5a}$ is F. In yet other embodiments, y is 0, q is 2 and one occurrence of $R^{5a}$ is OH and the other occurrence of $R^{5a}$ is F.

In still other embodiments:

a) $R^1$ and $R^2$ taken together is an optionally substituted ring selected from azetidin-1-yl (jj), pyrrolidin-1-yl (ff), piperidin-1-yl (dd), or piperazin-1-yl (cc); one of $R^1$ or $R^2$ is hydrogen, and the other of $R^1$ and $R^2$ is selected from $Cy^1$, wherein $Cy^1$ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—, or an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or $R^1$ and $R^2$ are each independently selected from an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; or $Cy^1$ wherein $Cy^1$ is bonded to the nitrogen atom directly or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—;

b) z is 0-5 and $R^4$ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, $C_{1-4}$alkoxy, phenyl, phenyloxy, benzyl, benzyloxy, —CH$_2$cyclohexyl, pyridyl, —CH$_2$pyridyl, or —CH$_2$thiazolyl;

c) x is 0, 1, or 2, and each occurrence of $R^3$ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy;

d) wherein y is 0-2, and $R^5$ groups, when present, are each independently Cl, Br, F, $CF_3$, Me, Et, CN, —COOH, —$NH_2$, —$N(CH_3)_2$, —$N(Et)_2$, —$N(iPr)_2$, —$O(CH_2)_2OCH_3$, —$CONH_2$, —$COOCH_3$, —OH, —$OCH_3$, —$OCH_2CH_3$, —$CH_2OH$, —$NHCOCH_3$, —$SO_2NH_2$, —$SO_2NHC(CH_3)_2$, —$OCOC(CH_3)_3$, —$OCOCH_2C(CH_3)_3$, —$O(CH_2)_2N(CH_3)_2$, 4-$CH_3$-piperazin-1-yl, $OCOCH(CH_3)_2$, OCO(cyclopentyl), —$COCH_3$, optionally substituted phenoxy, or optionally substituted benzyloxy; and e) $R^{5a}$ is Cl, F, $CF_3$, Me, Et, —OH, —$OCH_3$, —$OCH_2CH_3$, —$CH_2OH$, —$SO_2NH_2$, —$SO_2NHC(CH_3)_2$, —$OCOC(CH_3)_3$, —$OCOCH_2C(CH_3)_3$, —$O(CH_2)_2N(CH_3)_2$, 4-$CH_3$-piperazin-1-yl, $OCOCH(CH_3)_2$, OCO(cyclopentyl), or —$COCH_3$.

In yet other embodiments, for compounds of formula I-A, $R^1$ and $R^2$, taken together is optionally substituted azetidin-1-yl (jj). In yet other embodiments, for compounds of formula I-A, $R^1$ and $R^2$, taken together is optionally substituted pyrrolidin-1-yl (ff). In still other embodiments, for compounds of formula I-A, $R^1$ and $R^2$, taken together is optionally substituted piperidin1-yl (dd). In yet other embodiments, for compounds of formula I-A, $R^1$ and $R^2$, taken together is optionally substituted piperazin-1-yl (cc).

In certain embodiments, for compounds of formula I-A, $R^1$ and $R^2$, taken together is optionally substituted azetidin-1-yl (jj), wherein z is 1 or 2 and at least one occurrence of $R^4$ is —$NRSO_2R'$, —NRCOOR', or —NRCOR'. In certain other embodiments, for compounds of formula I-A, $R^1$ and $R^2$, taken together is optionally substituted azetidin-1-yl (jj), wherein z is 1 and $R^4$ is —$NRSO_2R'$. In other embodiments, for compounds of formula I-A, $R^1$ and $R^2$, taken together is optionally substituted azetidin-1-yl (jj), wherein z is 1 and $R^4$ is —NRCOOR'. In certain other embodiments, for compounds of formula I-A, $R^1$ and $R^2$, taken together is optionally substituted azetidin-1-yl (jj), wherein z is 1 and $R^4$ is —NRCOR'. In yet other embodiments, for compounds of formula I-A, $R^1$ and $R^2$, taken together is optionally substituted pyrrolidin-1-yl (ff), wherein z is 1 or 2 and $R^4$ is Cl, Br, F, $CF_3$, $CH_3$, —$CH_2CH_3$, —OR', or —$CH_2OR'$. In still other embodiments, for compounds of formula I-A, $R^1$ and $R^2$, taken together is optionally substituted piperidin-1-yl (dd), wherein z is 1 or 2 and at least one occurrence of $R^4$ is Cl, Br, F, $CF_3$, $CH_3$, —$CH_2CH_3$, —OR', or —$CH_2OR'$, —$NRSO_2R'$, —NRCOOR', or —$OCON(R')_2$. In certain other embodiments, for compounds of formula I-A, $R^1$ and $R^2$, taken together is optionally substituted piperidin-1-yl (dd), wherein z is 1 and $R^4$ is F, $CF_3$, $CH_3$, —$CH_2CH_3$, —OR', or —$CH_2OR'$. In other embodiments, for compounds of formula I-A, $R^1$ and $R^2$, taken together is optionally substituted piperidin-1-yl (dd), wherein z is 1 and $R^4$ is —$NRSO_2R'$. In certain other embodiments, for compounds of formula I-A, $R^1$ and $R^2$, taken together is optionally substituted piperidin-1-yl (dd), wherein z is 1 and $R^4$ is —NRCOOR'. In yet other embodiments, for compounds of formula I-A, $R^1$ and $R^2$, taken together is optionally substituted piperazin-1-yl (cc), wherein z is 1 or 2 and at least one occurrence of $R^4$ is —SOR', —$CON(R')_2$, —$SO_2N(R')_2$, —COR', or —COOR'. In certain other embodiments, for compounds of formula I-A, $R^1$ and $R^2$, taken together is optionally substituted piperazin-1-yl (cc), wherein z is 1 and $R^4$ is —SOR'. In certain other embodiments, for compounds of formula I-A, $R^1$ and $R^2$, taken together is optionally substituted piperazin-1-yl (cc), wherein z is 1 and $R^4$ is —COOR'. In certain other embodiments, for compounds of formula I-A, $R^1$ and $R^2$, taken together is optionally substituted piperazin-1-yl (cc), wherein z is 1 and $R^4$ is —$CON(R')_2$. In certain other embodiments, for compounds of formula I-A, $R^1$ and $R^2$, taken together is optionally substituted piperazin-1-yl (cc), wherein z is 1 and $R^4$ is —$SO_2N(R')_2$. In certain other embodiments, for compounds of formula I-A, $R^1$ and $R^2$, taken together is optionally substituted piperazin-1-yl (cc), wherein z is 1 and $R^4$ is —COR'.

In yet other embodiments for compounds described directly above, x is 1 and $R^3$ is at the 6-position of the quinazoline ring and is —Cl, —$CH_3$, —$CH_2CH_3$, —F, —$CF_3$, —$OCF_3$, —$CONHCH_3$, —$CONHCH_2CH_3$, —CONH(cyclopropyl), —$OCH_3$, —$NH_2$, —$OCH_2CH_3$, or —CN. In still other embodiments, x is 1 and $R^3$ is at the 7-position of the quinazoline ring and is —Cl, —$CH_3$, —$CH_2CH_3$, —F, —$CF_3$, —$OCF_3$, —$CONHCH_3$, —$CONHCH_2CH_3$, —CONH(cyclopropyl), —$OCH_3$, —$NH_2$, —$OCH_2CH_3$, or —CN. In yet other embodiments, x is 1 and $R^3$ is at the 6-position of the quinazoline ring and is —Cl, —$CH_3$, —$CH_2CH_3$, —F, —$CF_3$, —$OCF_3$, —$OCH_3$, or —$OCH_2CH_3$. In still other embodiments, x is 1 and $R^3$ is at the 7-position of the quinazoline ring and is —Cl, —$CH_3$, —$CH_2CH_3$, —F, —$CF_3$, —$OCF_3$, —$OCH_3$, or —$OCH_2CH_3$. In yet other embodiments, x is 1 and $R^3$ is at the 6-position of the quinazoline ring and is —$CON(R')_2$, or NRCOR'. In yet other embodiments, x is 1 and $R^3$ is at the 7-position of the quinazoline ring and is —$CON(R')_2$, or NRCOR'. In yet other embodiments, $R^{5a}$ is Cl, F, $CF_3$, Me, Et, —OH, —$OCH_3$, —$OCH_2CH_3$. In still other embodiments, y is 0, and q is 1 and $R^{5a}$ is F. In yet other embodiments, y is 0, q is 1, and $R^{5a}$ is OR'. In still other embodiments, y is 0, q is 1 and $R^{5a}$ is OH. In yet other embodiments, y is 0, q is 2 and one occurrence of $R^{5a}$ is OR' and the other occurrence of $R^{5a}$ is F. In yet other embodiments, y is 0, q is 2 and one occurrence of $R^{5a}$ is OH and the other occurrence of $R^{5a}$ is F.

In certain embodiments, for compounds described directly above, a) $Cy^1$ is:

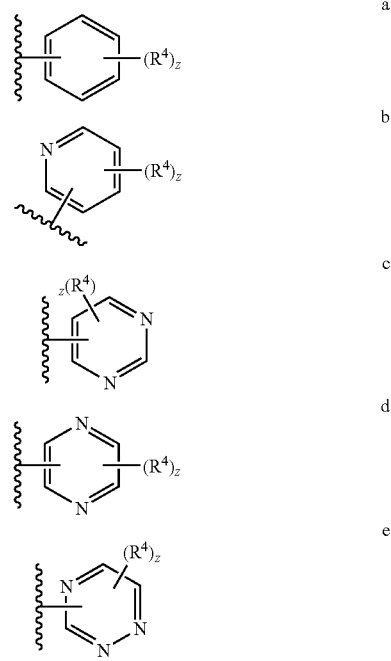

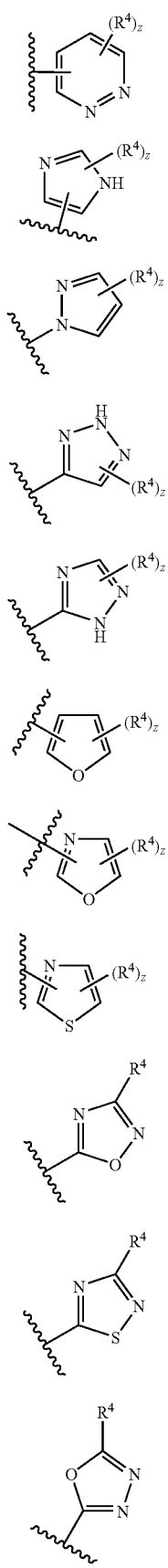
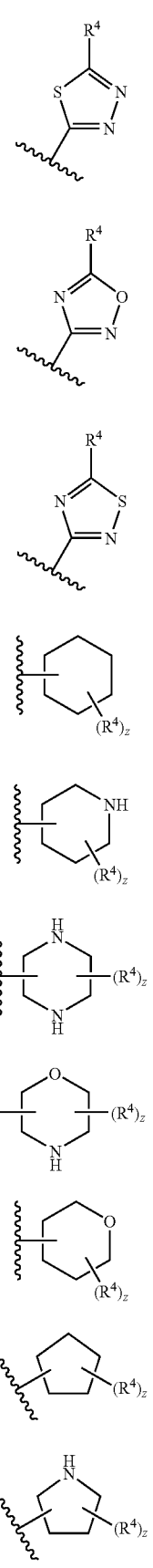

-continued

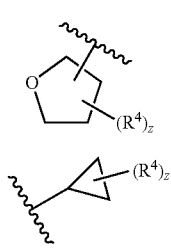

or R¹ and R² are each independently an optionally substituted $C_{1-4}$aliphatic group and are each independently selected from optionally substituted methyl, ethyl, cyclopropyl, n-propyl, propenyl, cyclobutyl, (CO)OCH$_2$CH$_3$, (CH$_2$)$_2$OCH$_3$, CH$_2$CO)OCH$_2$CH$_3$, CH$_2$(CO)OCH$_3$, CH(CH$_3$)CH$_2$CH$_3$, or n-butyl;

b) z is 0-5 and R⁴ groups are each independently Cl, Br, F, CF$_3$, CH$_3$, —CH$_2$CH$_3$, CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NH-COOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from -piperidinyl, piperizinyl, morpholino, $C_{1-4}$alkoxy, phenyl, phenyloxy, benzyl, benzyloxy, —CH$_2$cyclohexyl, pyridyl, —CH$_2$pyridyl, or —CH$_2$thiazolyl;

c) x is 0, 1, or 2, and each occurrence of R³ is independently Cl, Br, F, CF$_3$, —OCF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from -piperidinyl, piperizinyl, morpholino, phenyl, phenyloxy, benzyl, or benzyloxy;

d) wherein y is 0-5, and R⁵ groups, when present, are each independently Cl, Br, F, CF$_3$, Me, Et, CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), —COCH$_3$, optionally substituted phenoxy, or optionally substituted benzyloxy; and e) R$^{5a}$ is Cl, F, CF$_3$, Me, Et, —OH, —OCH$_3$, —OCH$_2$CH$_3$, —CH$_2$OH, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, OCOCH(CH$_3$)$_2$, OCO(cyclopentyl), or —COCH$_3$.

In yet other embodiments for compounds described directly above, x is 1 and R³ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, x is 1 and R³ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In yet other embodiments, x is 1 and R³ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, x is 1 and R³ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In yet other embodiments, x is 1 and R³ is at the 6-position of the quinazoline ring and is —CON(R')$_2$, or NRCOR'. In yet other embodiments, x is 1 and R³ is at the 7-position of the quinazoline ring and is —CON(R')$_2$, or NRCOR'. In yet other embodiments, R$^{5a}$ is Cl, F, CF$_3$, Me, Et, —OH, —OCH$_3$, —OCH$_2$CH$_3$. In still other embodiments, y is 0, and q is 1 and R$^{5a}$ is F. In yet other embodiments, y is 0, q is 1, and R$^{5a}$ is OR'. In still other embodiments, y is 0, q is 1 and R$^{5a}$ is OH. In yet other embodiments, y is 0, q is 2 and one occurrence of R$^{5a}$ is OR' and the other occurrence of R$^{5a}$ is F. In yet other embodiments, y is 0, q is 2 and one occurrence of R$^{5a}$ is OH and the other occurrence of R$^{5a}$ is F.

For compounds described in this section above, in general, compounds are useful as inhibitors of ion channels, preferably voltage gated sodium channels and N-type calcium channels. In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

V. Compounds of Formula I-B-i:

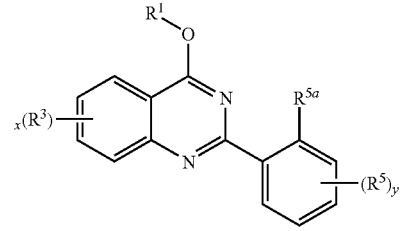

I-B-i or a pharmaceutically acceptable salt thereof, wherein R¹ is selected from $C_{1-6}$aliphatic, Cy¹, wherein Cy¹ is a 5-7-membered monocyclic aryl ring or an 8-10-membered bicyclic aryl ring having 0-3 heteroatoms independently selected from nitrogen, oxygen, or sulfur, or is a 3-12-membered saturated or partially unsaturated monocyclic ring having 0-3 heteroatoms independently selected from nitrogen, oxygen, or sulfur, wherein Cy¹ is bonded directly to the nitrogen atom or is bonded through an optionally substituted $C_{1-4}$aliphatic group, wherein one or more methylene units in the $C_{1-4}$aliphatic group are optionally replaced with —NR—, —O—, —COO, —OCO—, —NRCO—, —CONR—, —SO$_2$NR—, or —NRSO$_2$—; wherein R¹ is optionally substituted at one or more substitutable carbon, nitrogen, or sulfur atoms with z independent occurrences of —R⁴, wherein z is 0-5;

x is 0-4;

y is 0-4;

each occurrence of R³, R⁴, and R⁵ is independently Q-R$^X$; wherein Q is a bond or is a $C_1$-$C_6$ alkylidene chain wherein up to two non-adjacent methylene units of Q are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, —OP(O)(OR)—, or —POR—; and each occurrence of R$^X$ is independently selected from —R', =O, =NR', halogen, —NO$_2$, —CN, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$;

each occurrence of R$^{5a}$ is independently an optionally substituted C$_1$-C$_6$aliphatic group, halogen, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or an optionally substituted C$_{1-6}$ aliphatic group; and each occurrence of R' is independently hydrogen or an optionally substituted C$_{1-6}$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

For compounds described directly above, in certain embodiments, a) when R$^{5a}$ is Me, Cl, or OMe, and x is 0, then R$^1$ is not Et or Me;

b) when R$^{5a}$ is Cl, x is 3, and the three occurrences of R$^3$ are 6-Me, 7-COOEt, and 8-Me, then R$^1$ is not —(CH$_2$)$_2$piperidin-1-yl;

c) when R$^{5a}$ is Me, x is 1 and R$^3$ is NO$_2$ or NH$_2$, then R$^1$ is not Et;

d) when R$^{5a}$ is OH, NHMe, or N(NO)Me, and x is 0, then R$^1$ is not Et, Me or —CH$_2$CH=CH$_2$;

e) when R$^{5a}$ is NH$_2$, and x is 0, then R$^1$ is not —COCH$_3$;

f) when R$^{5a}$ is Cl or Me, and y is 0 or 1 and when y is 1, R$^5$ is 4-Cl, and x is 0, then R$^1$ is not 4-CN-phenyl, 4-Me-phenyl, 4-OMe-phenyl, 4-Cl-phenyl, 4-NO$_2$-phenyl, —CH$_2$CH$_2$NHMe, Et, Me, 4-COOMe-phenyl, —CH$_2$Ph, iPr, 2-Me-phenyl, 4-phenyl-phenyl, or —CH$_2$CH=CH$_2$.

For compounds of formula I-B-i described directly above, in certain other embodiments, the following compounds are excluded:
2-(2-hydroxy-5-methylphenyl)-4-ethoxyquinazoline;
2-(2-hydroxy-5-methylphenyl)-4-butoxyquinazoline;
2-(o-hydroxyphenyl)-4-[2-hydroxyethoxy]quinazoline;
2-(o-hydroxyphenyl)-4-[2-dimethylaminoethoxy]quinazoline;
2-(o-hydroxyphenyl)-4-phenoxyquinazoline;
2-(o-hydroxyphenyl)-4-[p-cresyloxy]quinazoline;
2-(o-hydroxyphenyl)-4-[p-chlorophenoxy]quinazoline; and
2-(o-hydroxyphenyl)-4-(2-beta-acryloxyethyl)quinazoline.

For compounds described directly above, in certain other embodiments, a) R$^1$ is selected from:
i) Cy$^1$ wherein Cy$^1$ is bonded directly to the nitrogen atom or is bonded through an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—; or ii) an optionally substituted C$_{1-4}$aliphatic group, wherein one or more methylene units in the C$_{1-4}$aliphatic group are optionally replaced with —NR—, —O—, —COO, —OCO—, —NRCO—, —CONR—, —SO$_2$NR—, or —NRSO$_2$—.

For compounds described directly above, in certain embodiments Cy$^1$ is,

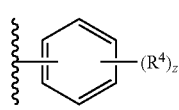

a

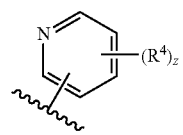

b

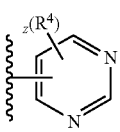

c

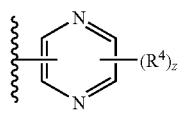

d

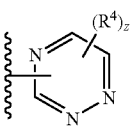

e

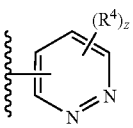

f

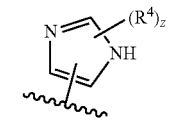

g

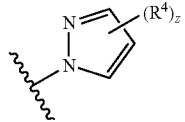

h

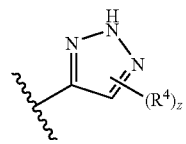

i

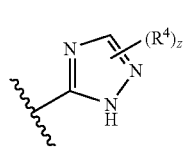

j k 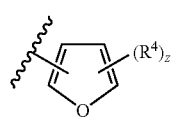
l 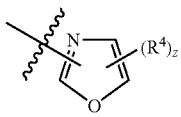
m 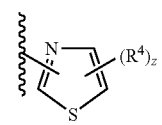
n 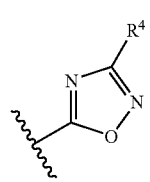
o 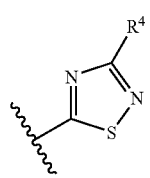
p 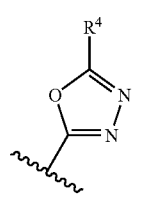
q 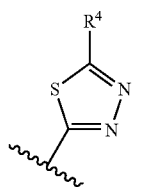
r 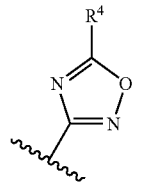
s 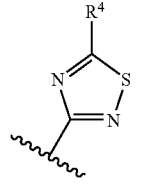
t 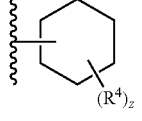
u 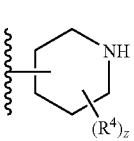
v 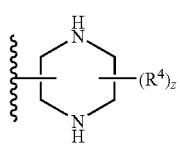
w 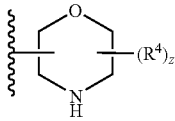
x 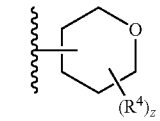
y 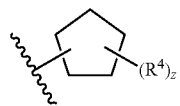
z 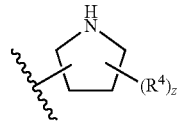
aa 
bb 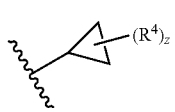
In other embodiments, $R^1$ is —CHR-Cy$^1$, wherein R is hydrogen or $C_1$-$C_4$alkyl, and Cy$^1$ is:
a 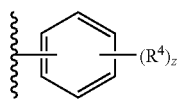
b 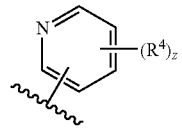
c 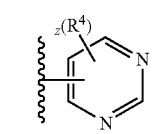

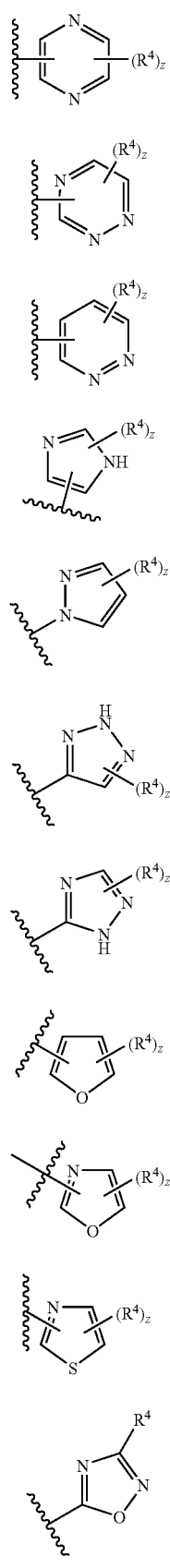
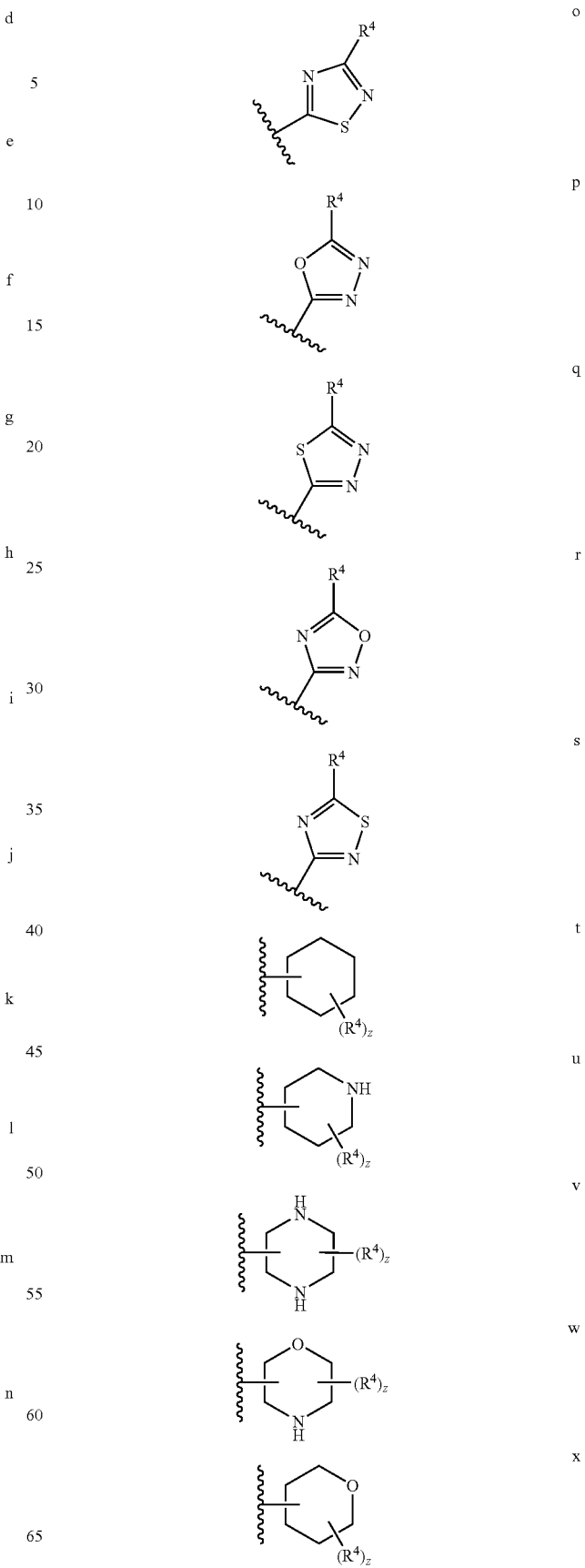

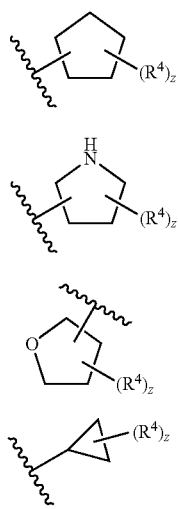

In still other embodiments, R¹ is an optionally substituted $C_{1-4}$aliphatic group and are each independently selected from optionally substituted methyl, ethyl, cyclopropyl, n-propyl, propenyl, cyclobutyl, (CO)OCH₂CH₃, (CH₂)₂OCH₃, CH₂CO)OCH₂CH₃, CH₂(CO)OCH₃, CH(CH₃)CH₂CH₃, or n-butyl.

In yet other embodiments, z is 0-5, and R⁴ groups, when present, are each independently halogen, CN, NO₂, —N(R')₂, —CH₂N(R)₂, —OR', —CH₂OR', —SR', —CH₂SR', —COOR', —NRCOR', —CON(R')₂, —OCON(R')₂, COR', —NHCOOR', —SO₂R', —SO₂N(R)₂, or an optionally substituted group selected from $C_1$-$C_6$aliphatic, aryl, heteroaryl, cycloaliphatic, hetero cycloaliphatic, aryl $C_1$-$C_6$alkyl, heteroaryl $C_1$-$C_6$alkyl, cycloaliphatic $C_1$-$C_6$ alkyl, or heterocycloaliphatic $C_1$-$C_6$alkyl.

In still other embodiments, z is 0-5 and R⁴ groups are each independently Cl, Br, F, CF₃, CH₃, —CH₂CH₃, CN, —COOH, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, —SO₂(CH₂)₃CH₃, —SO₂CH(CH₃)₂, —SO₂N(CH₃)₂, —SO₂CH₂CH₃, —C(O)OCH₂CH(CH₃)₂, —C(O)NHCH₂CH(CH₃)₂, —NHCOOCH₃, —C(O)C(CH₃)₃, —COO(CH₂)₂CH₃, —C(O)NHCH(CH₃)₂, —C(O)CH₂CH₃, or an optionally substituted group selected from -piperidinyl, piperizinyl, morpholino, $C_{1-4}$alkoxy, phenyl, phenyloxy, benzyl, benzyloxy, —CH₂cyclohexyl, pyridyl, —CH₂pyridyl, or —CH₂thiazolyl.

In yet other embodiments, R³ is halogen, CN, NO₂, —N(R')₂, —CH₂N(R')₂, —OR', —CH₂OR', —SR', —CH₂SR', —COOR', —NRCOR', —CON(R')₂, —OCON(R')₂, COR', —NHCOOR', —SO₂R', —SO₂N(R')₂, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In still other embodiments, R³ is Cl, Br, F, CF₃, —OCF₃, Me, Et, CN, —COOH, —NH₂, —N(CH₃)₂, —N(Et)₂, —N(iPr)₂, —O(CH₂)₂OCH₃, —CONH₂, —COOCH₃, —OH, —OCH₃, —OCH₂CH₃, —CH₂OH, —NHCOCH₃, —NHCOCH(CH₃)₂, —SO₂NH₂, —CONH(cyclopropyl), —CONHCH₃, —CONHCH₂CH₃, or an optionally substituted group selected from -piperidinyl, piperizinyl, morpholino, phenyl, phenyloxy, benzyl, or benzyloxy.

In yet other embodiments, R³ is halogen, CN, optionally substituted $C_1$-$C_6$alkyl, OR', N(R')₂, CON(R')₂, or NRCOR'. In still other embodiments, R³ is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In yet other embodiments, R³ is at the 6-position of the quinazoline ring and is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In still other embodiments, R³ is at the 7-position of the quinazoline ring and is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In yet other embodiments, R³ is at the 6-position of the quinazoline ring and is —Cl, —CH₃, —CH₂CH₃, —F, —CF₃, —OCF₃, —OCH₃, or —OCH₂CH₃. In still other embodiments, R³ is at the 7-position of the quinazoline ring and is —Cl, —CH₃, —CH₂CH₃, —F, —CF₃, —OCF₃, —OCH₃, or —OCH₂CH₃. In other embodiments, R³ is at the 6-position of the quinazoline ring and is —CON(R')₂, or NRCOR'. In yet other embodiments, R³ is at the 7-position of the quinazoline ring and is —CON(R')₂, or NRCOR'.

In yet other embodiments, for compounds described directly above, y is 0-5, q is 0-2, and R⁵ and $R^{5a}$ groups, when present, are each independently halogen, CN, NO₂, —N(R')₂, —CH₂N(R')₂, —OR', —CH₂OR', —SR', —CH₂SR', —NRCOR', —CON(R')₂, —S(O)₂N(R)₂, —OCOR', —COR', —CO₂R', —OCON(R')₂, —NR'SO₂R', —OP(O)(OR')₂, —P(O)(OR')₂, —OP(O)₂OR', —P(O)₂OR', —PO(R')₂, —OPO(R')₂, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In still other embodiments, y is 0-5, and q is 1 or 2, and each occurrence of $R^{5a}$ is independently Cl, Br, F, CF₃, Me, Et, CN, —COOH, —NH₂, —N(CH₃)₂, —N(Et)₂, —N(iPr)₂, —O(CH₂)₂OCH₃, —CONH₂, —COOCH₃, —OH, —OCH₃, —OCH₂CH₃, —CH₂OH, —NHCOCH₃, —SO₂NH₂, —SO₂NHC(CH₃)₂, —OCOC(CH₃)₃, —OCOCH₂C(CH₃)₃, —O(CH₂)₂N(CH₃)₂, 4-CH₃-piperazin-1-yl, OCOCH(CH₃)₂, OCO(cyclopentyl), —COCH₃, optionally substituted phenoxy, or optionally substituted benzyloxy.

In still other embodiments, y is 0, and $R^{5a}$ is F. In yet other embodiments y is 0, q is 1, and $R^{5a}$ is OR'. In still other embodiments, y is 0, q is 1 and $R^{5a}$ is OH. In yet other embodiments, y is 1, $R^{5a}$ is OR' and R⁵ is F, wherein OR' is substituted at the 2-position of the phenyl ring and F is substituted at the 6-position of the phenyl ring. In yet other embodiments, y is 1, $R^{5a}$ is OH and R⁵ is F, wherein OH is substituted at the 2-position of the phenyl ring and F is substituted at the 6-position of the phenyl ring.

For compounds described in this section above, in general, compounds are useful as inhibitors of ion channels, preferably voltage gated sodium channels and N-type calcium channels. In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

Representative examples of compounds as described above and herein are set forth below in Table 2.

TABLE 2
Examples of Compounds of Formula I:
| Compound | Cmpd # |
|---|---|
| 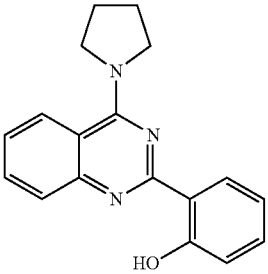 | 1 |
| 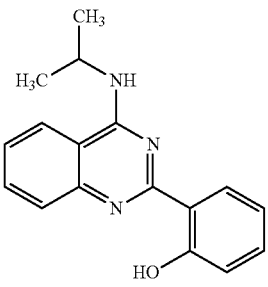 | 2 |
| 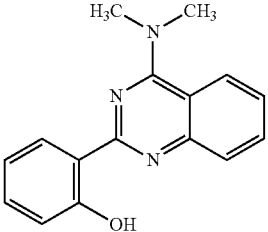 | 3 |
| 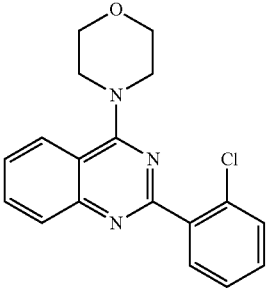 | 4 |
| 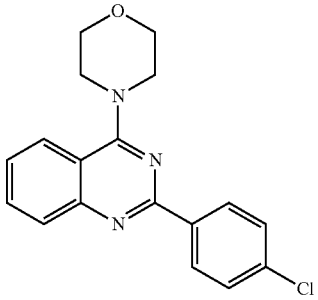 | 5 |

TABLE 2-continued

Examples of Compounds of Formula I:

| Compound | Cmpd # |
|---|---|
| 4-(3-fluorophenylamino)-2-(pyridin-4-yl)quinazoline | 6 |
| 2-(4-bromophenyl)-4-morpholinoquinazoline | 7 |
| 2-(4-bromophenyl)-4-(4-methylpiperazin-1-yl)quinazoline | 8 |
| 2-(2-chlorophenyl)-4-methoxyquinazoline | 9 |

TABLE 2-continued

Examples of Compounds of Formula I:

| Compound | Cmpd # |
|---|---|
| 4-(4-methylpiperazin-1-yl)-2-(4-chlorophenyl)quinazoline | 10 |
| 4-methoxy-2-(pyridin-4-yl)quinazoline | 11 |
| 4-amino-2-(4-(pyridin-2-yl)piperazin-1-yl)quinazoline | 12 |
| 4-amino-2-(4-(pyrimidin-2-yl)piperazin-1-yl)quinazoline | 13 |
| 4-amino-2-(4-benzylpiperazin-1-yl)quinazoline | 14 |

TABLE 2-continued

Examples of Compounds of Formula I:

| Compound | Cmpd # |
|---|---|
| 2-(4-morpholinyl)quinazolin-2-yl)phenol | 15 |
| 2-(4-(piperidin-1-yl)quinazolin-2-yl)phenol | 16 |
| 2-(4-(4-methylpiperazin-1-yl)quinazolin-2-yl)phenol | 17 |
| N-(3,4-difluorophenyl)-2-(pyridin-3-yl)quinazolin-4-amine | 18 |
| 2-(4-bromophenyl)-4-(piperazin-1-yl)quinazoline | 19 |

TABLE 2-continued

Examples of Compounds of Formula I:

| Compound | Cmpd # |
|---|---|
| 4-(4-hydroxypiperidin-1-yl)-2-phenylquinazoline | 20 |
| N-phenyl-N'-(2-phenylquinazolin-4-yl)urea | 21 |
| N-propyl-N'-(2-phenylquinazolin-4-yl)urea | 22 |
| 2-(3,5-dichlorophenyl)-N-(3-methyl-1H-pyrazol-5-yl)quinazolin-4-amine | 23 |

TABLE 2-continued

Examples of Compounds of Formula I:

| Compound | Cmpd # |
|---|---|
| (structure) | 24 |
| (structure) | 25 |
| (structure) | 26 |
| (structure) | 27 |

TABLE 2-continued

Examples of Compounds of Formula I:

| Compound | Cmpd # |
|---|---|
| *N-(3-methyl-1H-pyrazol-5-yl)-2-(4-methylpiperazin-1-yl)quinazolin-4-amine* | 28 |
| *N-(3-methyl-1H-pyrazol-5-yl)-2-(piperidin-1-yl)quinazolin-4-amine* | 29 |
| *2-(azepan-1-yl)-N-(3-methyl-1H-pyrazol-5-yl)quinazolin-4-amine* | 30 |
| *2-[4-(2-hydroxyethyl)piperidin-1-yl]-N-(3-methyl-1H-pyrazol-5-yl)quinazolin-4-amine* | 31 |

TABLE 2-continued

Examples of Compounds of Formula I:

| Compound | Cmpd # |
|---|---|
| 4-(4-methylpiperidin-1-yl)-2-(pyridin-3-yl)quinazoline | 32 |
| 4-(4-methylphenoxy)-2-(pyridin-4-yl)quinazoline | 33 |
| 4-methoxy-2-phenylquinazoline | 34 |
| methyl 3-((2-(4-chlorophenyl)quinazolin-4-yl)amino)propanoate | 35 |

TABLE 2-continued
Examples of Compounds of Formula I:
| Compound | Cmpd # |
|---|---|
| 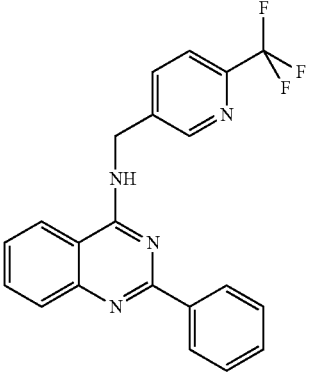 | 36 |
| 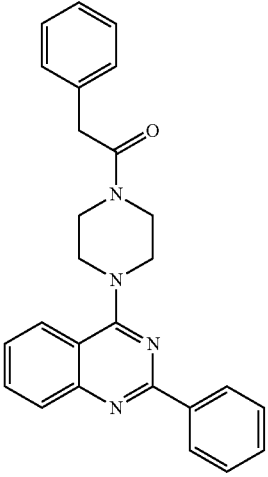 | 37 |
| 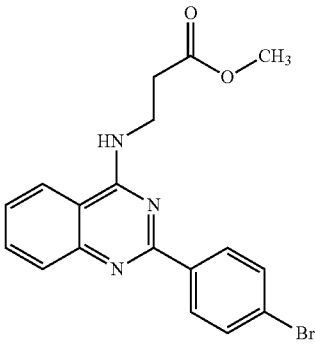 | 38 |

TABLE 2-continued

Examples of Compounds of Formula I:

| Compound | Cmpd # |
|---|---|
| | 39 |
| | 40 |
| | 41 |
| | 42 |

TABLE 2-continued

Examples of Compounds of Formula I:

| Compound | Cmpd # |
|---|---|
| (structure) | 43 |
| (structure) | 44 |
| (structure) | 45 |
| (structure) | 46 |
| (structure) | 47 |

TABLE 2-continued

Examples of Compounds of Formula I:

| Compound | Cmpd # |
|---|---|
| N-(3,4-dimethoxybenzyl)-2-phenylquinazolin-4-amine | 48 |
| N-cyclopentyl-2-phenylquinazolin-4-amine | 49 |
| N-(2,4-dimethoxyphenyl)-2-(pyridin-4-yl)quinazolin-4-amine | 50 |
| 4-(4-methylpiperazin-1-yl)-2-(pyridin-4-yl)quinazoline | 51 |
| N-(4-methoxyphenyl)-2-(pyridin-4-yl)quinazolin-4-amine | 52 |

TABLE 2-continued

Examples of Compounds of Formula I:

| Compound | Cmpd # |
|---|---|
| | 53 |
| | 54 |
| | 55 |
| | 56 |
| | 57 |

TABLE 2-continued

Examples of Compounds of Formula I:

| Compound | Cmpd # |
|---|---|
| (structure) | 58 |
| (structure) | 59 |
| (structure) | 60 |
| (structure) | 61 |
| (structure) | 62 |

TABLE 2-continued

Examples of Compounds of Formula I:

| Compound | Cmpd # |
|---|---|
| *N-(3-chlorophenyl)-2-(pyridin-4-yl)quinazolin-4-amine* | 63 |
| *N-(4-methylphenyl)-2-(pyridin-4-yl)quinazolin-4-amine* | 64 |
| *N-(3-(trifluoromethyl)phenyl)-2-(pyridin-4-yl)quinazolin-4-amine* | 65 |
| *N-(2-methoxyphenyl)-2-(pyridin-4-yl)quinazolin-4-amine* | 66 |
| *4-isopropoxy-2-(pyridin-4-yl)quinazoline* | 67 |

TABLE 2-continued

Examples of Compounds of Formula I:

| Compound | Cmpd # |
|---|---|
| (structure) | 68 |
| (structure) | 69 |
| (structure) | 70 |
| (structure) | 71 |

TABLE 2-continued
Examples of Compounds of Formula I:
| Compound | Cmpd # |
|---|---|
| 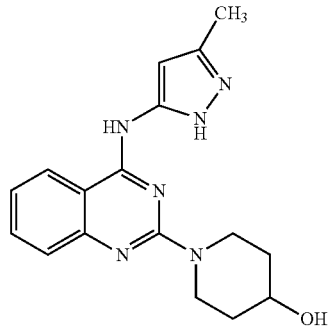 | 72 |
| 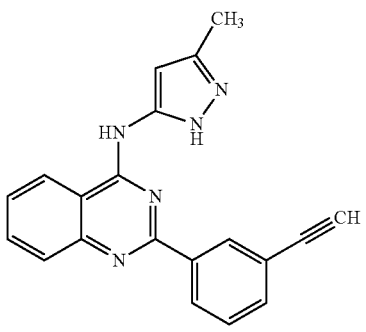 | 73 |
| 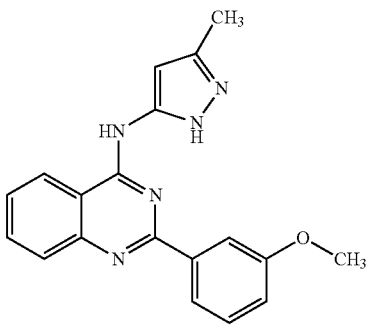 | 74 |
| 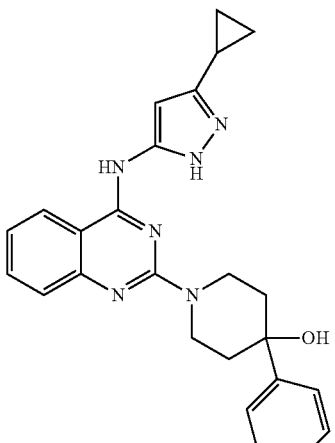 | 75 |

TABLE 2-continued

| Examples of Compounds of Formula I: | |
|---|---|
| Compound | Cmpd # |
| (structure) | 76 |
| (structure) | 77 |
| (structure) | 78 |
| (structure) | 79 |

TABLE 2-continued

Examples of Compounds of Formula I:

| Compound | Cmpd # |
|---|---|
| | 80 |
| | 81 |
| | 82 |
| | 83 |

TABLE 2-continued
Examples of Compounds of Formula I:
| Compound | Cmpd # |
|---|---|
| 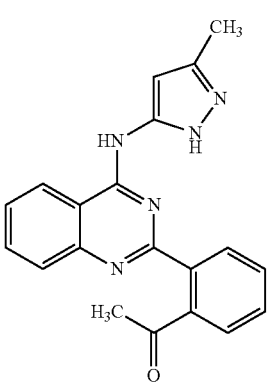 | 84 |
| 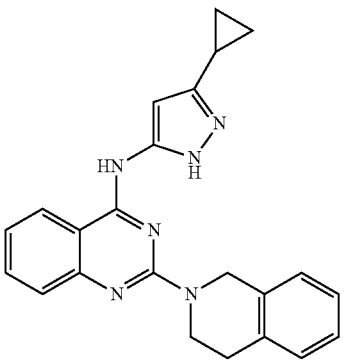 | 85 |
| 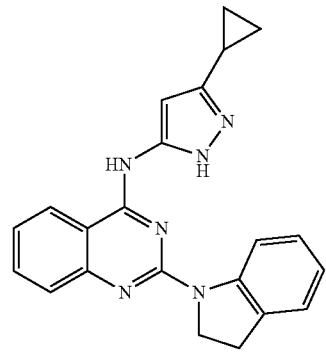 | 86 |
| 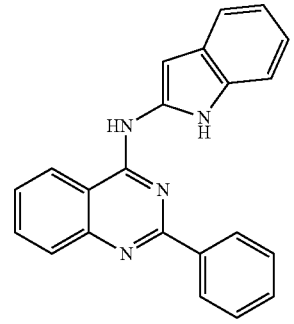 | 87 |

TABLE 2-continued

Examples of Compounds of Formula I:

| Compound | Cmpd # |
|---|---|
| | 88 |
| | 89 |
| | 90 |
| | 91 |

TABLE 2-continued

Examples of Compounds of Formula I:

| Compound | Cmpd # |
|---|---|
| | 92 |
| | 93 |
| | 94 |
| | 95 |

TABLE 2-continued

Examples of Compounds of Formula I:

| Compound | Cmpd # |
|---|---|
| | 96 |
| | 97 |
| | 98 |
| | 99 |

TABLE 2-continued
Examples of Compounds of Formula I:
| Compound | Cmpd # |
|---|---|
| 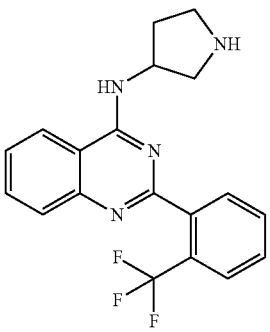 | 100 |
| 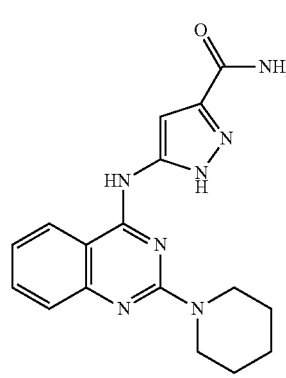 | 101 |
| 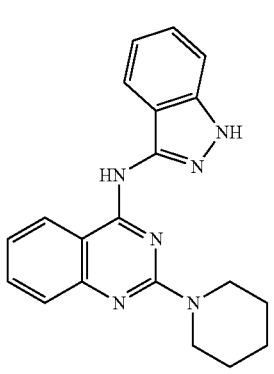 | 102 |
| 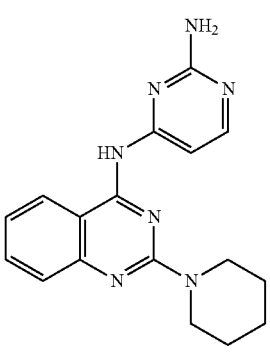 | 103 |

TABLE 2-continued

Examples of Compounds of Formula I:

| Compound | Cmpd # |
|---|---|
| (5-fluoro-1H-indazol-3-yl)-[2-(2-chlorophenyl)quinazolin-4-yl]amine | 104 |
| (1H-indazol-3-yl)-[2-(2-methylpiperidin-1-yl)quinazolin-4-yl]amine | 105 |
| (1H-indazol-3-yl)-[2-(decahydroquinolin-1-yl)quinazolin-4-yl]amine | 106 |
| (1H-indazol-3-yl)-[2-(2,6-dimethylmorpholin-4-yl)quinazolin-4-yl]amine | 107 |

161
162
TABLE 2-continued
Examples of Compounds of Formula I:
| Compound | Cmpd # |
|---|---|
| 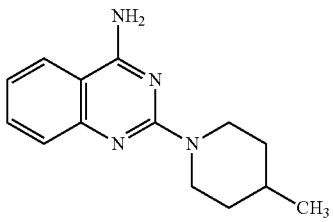 | 108 |
| 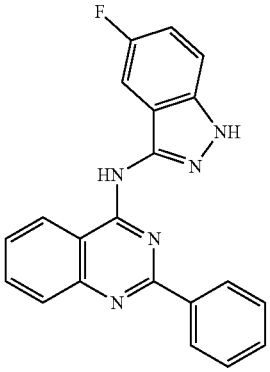 | 109 |
| 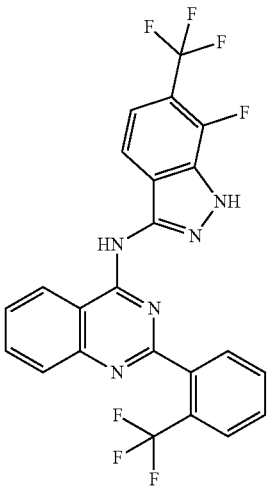 | 110 |
| 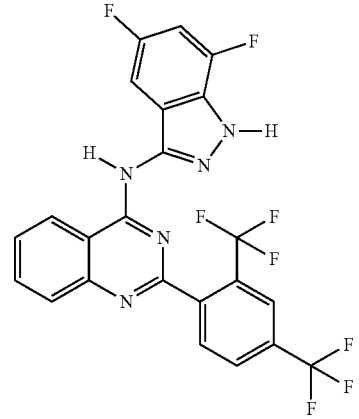 | 111 |

TABLE 2-continued

Examples of Compounds of Formula I:

| Compound | Cmpd # |
|---|---|
| | 112 |
| | 113 |
| | 114 |
| | 115 |

TABLE 2-continued

| Examples of Compounds of Formula I: | |
|---|---|
| Compound | Cmpd # |
| (structure) | 116 |
| (structure) | 117 |
| (structure) | 118 |

TABLE 2-continued
Examples of Compounds of Formula I:
| Compound | Cmpd # |
|---|---|
| 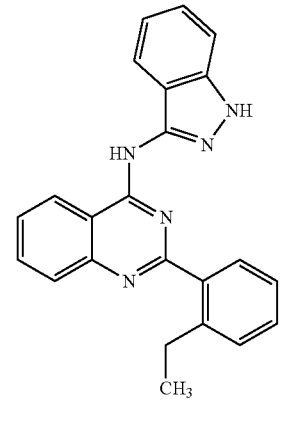 | 119 |
| 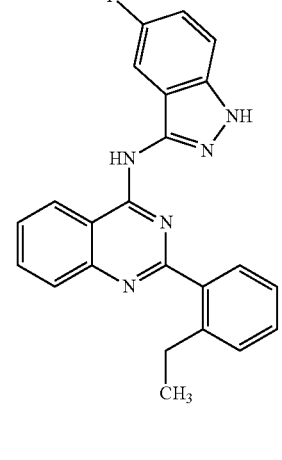 | 120 |
| 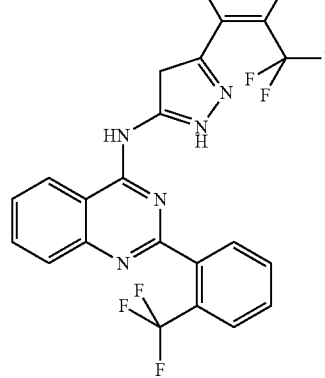 | 121 |

TABLE 2-continued

Examples of Compounds of Formula I:

| Compound | Cmpd # |
|---|---|
| | 122 |
| | 123 |
| | 124 |

TABLE 2-continued
Examples of Compounds of Formula I:
| Compound | Cmpd # |
|---|---|
| 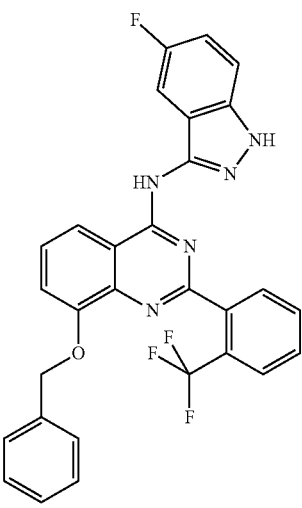 | 125 |
| 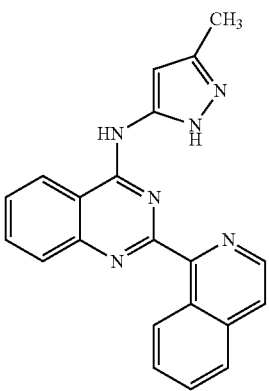 | 126 |
| 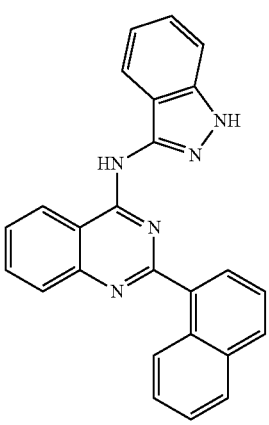 | 127 |

TABLE 2-continued

Examples of Compounds of Formula I:

| Compound | Cmpd # |
|---|---|
| (5-fluoro-1H-indazol-3-yl)-(2-naphthalen-1-yl-quinazolin-4-yl)-amine structure | 128 |
| (1H-indazol-5-yl)-[2-(2-trifluoromethyl-phenyl)-quinazolin-4-yl]-amine structure | 129 |
| 6-{2-[(2-phenyl-quinazolin-4-yl)amino]ethylamino}-nicotinonitrile structure | 130 |

TABLE 2-continued
Examples of Compounds of Formula I:
| Compound | Cmpd # |
|---|---|
| 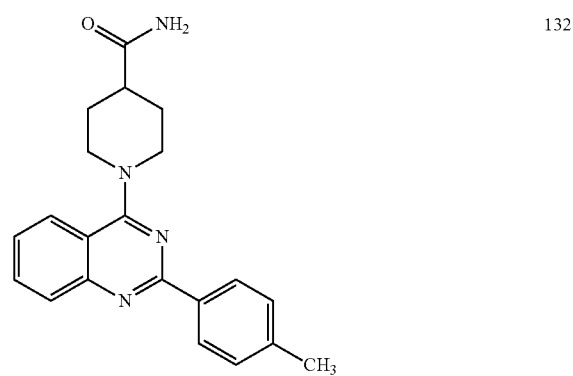 | 131 |
| 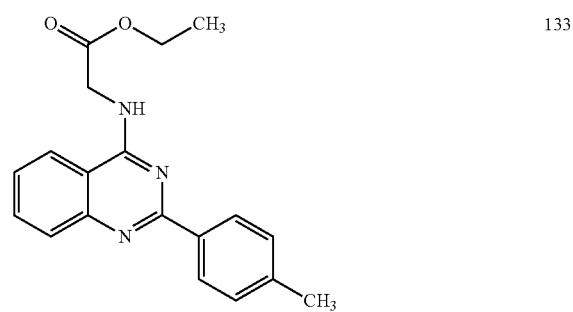 | 132 |
| | 133 |

TABLE 2-continued

Examples of Compounds of Formula I:

| Compound | Cmpd # |
|---|---|
| | 134 |
| | 135 |
| | 136 |
| | 137 |

TABLE 2-continued

Examples of Compounds of Formula I:

| Compound | Cmpd # |
|---|---|
| *structure* | 138 |
| *structure* | 139 |
| *structure* | 140 |
| *structure* | 141 |

TABLE 2-continued

Examples of Compounds of Formula I:

| Compound | Cmpd # |
|---|---|
| | 142 |
| | 143 |
| | 144 |
| | 145 |

TABLE 2-continued

Examples of Compounds of Formula I:

| Compound | Cmpd # |
|---|---|
| | 146 |
| | 147 |
| | 148 |
| | 149 |

TABLE 2-continued

Examples of Compounds of Formula I:

| Compound | Cmpd # |
|---|---|
| | 150 |
| | 151 |
| | 152 |
| | 153 |
| | 154 |

TABLE 2-continued
Examples of Compounds of Formula I:
| Compound | Cmpd # |
|---|---|
| 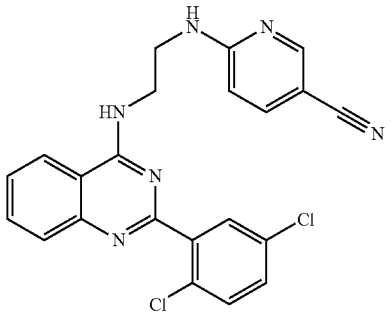 | 155 |
| 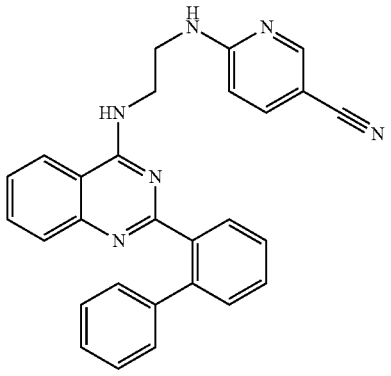 | 156 |
|  | 157 |
| 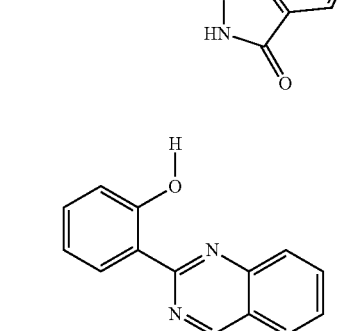 | 158 |

TABLE 2-continued
Examples of Compounds of Formula I:
| Compound | Cmpd # |
|---|---|
| 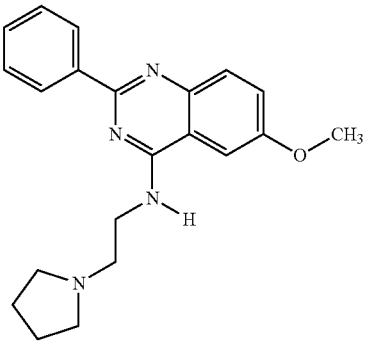 | 159 |
| 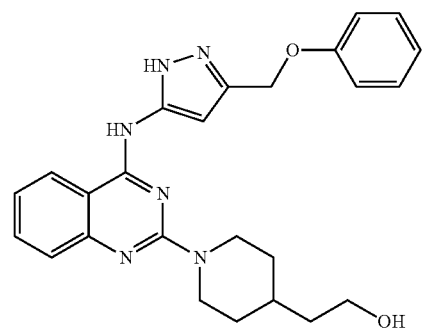 | 160 |
| 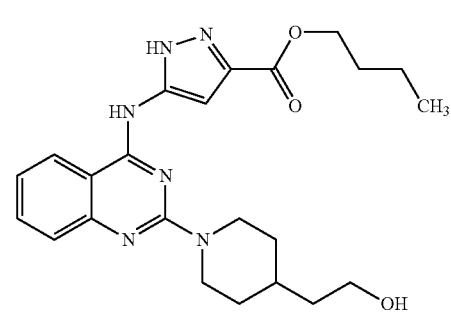 | 161 |
| 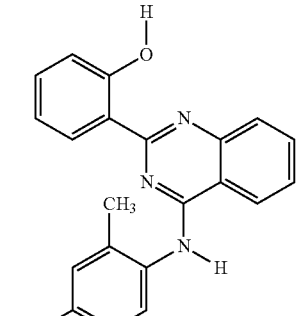 | 162 |

TABLE 2-continued

Examples of Compounds of Formula I:

| Compound | Cmpd # |
|---|---|
| | 163 |
| | 164 |
| | 165 |
| | 166 |

TABLE 2-continued
Examples of Compounds of Formula I:
| Compound | Cmpd # |
|---|---|
| 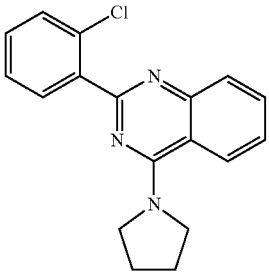 | 167 |
| 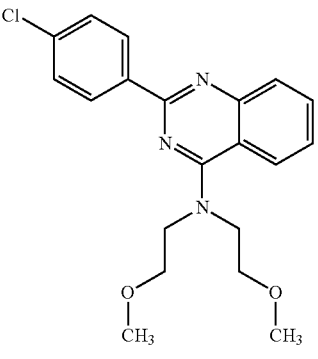 | 168 |
| 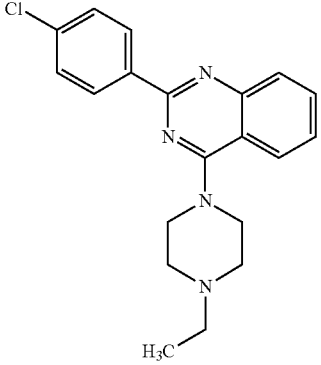 | 169 |
| 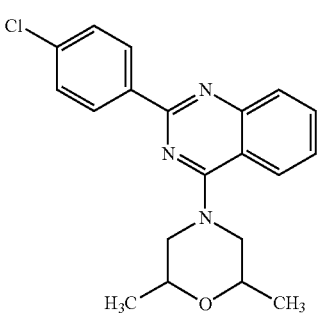 | 170 |

TABLE 2-continued
Examples of Compounds of Formula I:
| Compound | Cmpd # |
|---|---|
| 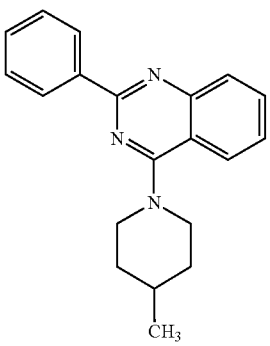 | 171 |
| 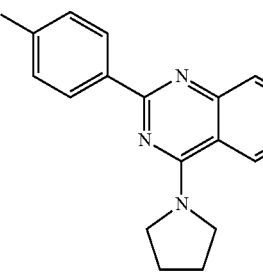 | 172 |
| 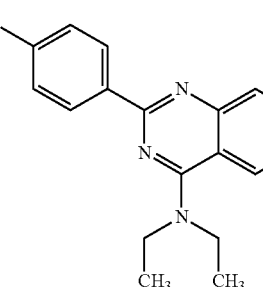 | 173 |
| 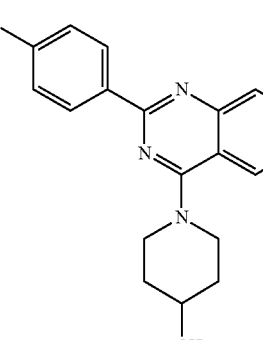 | 174 |

TABLE 2-continued

Examples of Compounds of Formula I:

| Compound | Cmpd # |
|---|---|
| | 175 |
| | 176 |
| | 177 |
| | 178 |

TABLE 2-continued

Examples of Compounds of Formula I:

| Compound | Cmpd # |
|---|---|
| 2-(2-chlorophenyl)-N,N-diethylquinazolin-4-amine | 179 |
| 2-(4-(azocan-1-yl)quinazolin-2-yl)phenol | 180 |
| 2-(4-(4-(2-methoxyphenyl)piperazin-1-yl)quinazolin-2-yl)phenol | 181 |
| 2-(4-(2-methylpiperidin-1-yl)quinazolin-2-yl)phenol | 182 |

TABLE 2-continued
Examples of Compounds of Formula I:
| Compound | Cmpd # |
|---|---|
| 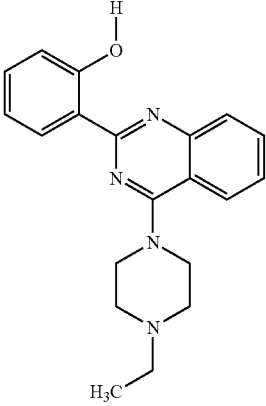 | 183 |
| 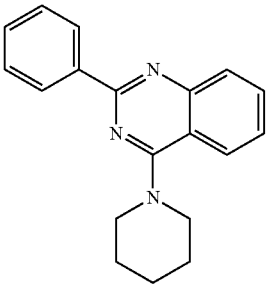 | 184 |
| 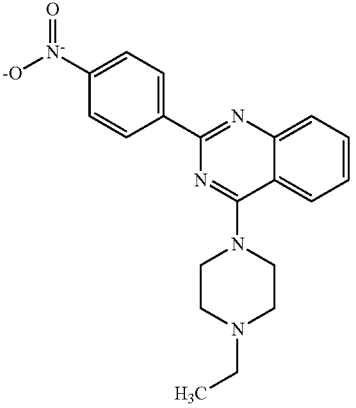 | 185 |
| 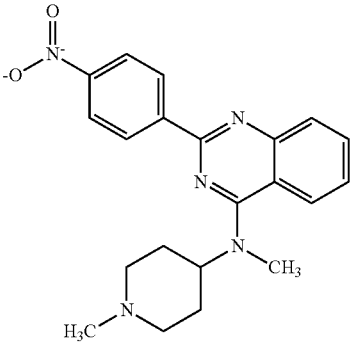 | 186 |

TABLE 2-continued

Examples of Compounds of Formula I:

| Compound | Cmpd # |
|---|---|
| | 187 |
| | 188 |
| | 189 |
| | 190 |

TABLE 2-continued

Examples of Compounds of Formula I:

| Compound | Cmpd # |
|---|---|
| | 191 |
| | 192 |
| | 193 |
| | 194 |

TABLE 2-continued

Examples of Compounds of Formula I:

| Compound | Cmpd # |
|---|---|
| (structure) | 195 |
| (structure) | 196 |
| (structure) | 197 |
| (structure) | 198 |
| (structure) | 199 |

TABLE 2-continued
Examples of Compounds of Formula I:
| Compound | Cmpd # |
|---|---|
| 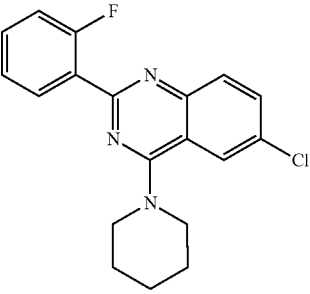 | 200 |
| 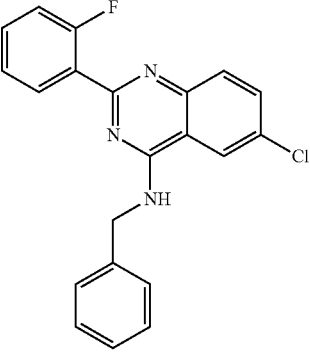 | 201 |
| 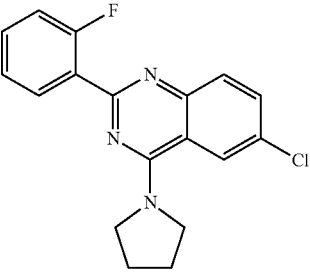 | 202 |
| 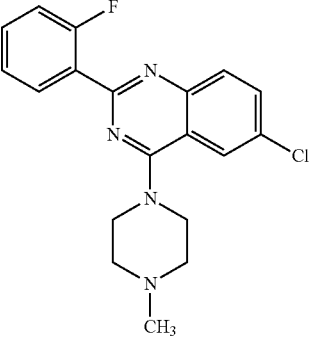 | 203 |

TABLE 2-continued
Examples of Compounds of Formula I:
| Compound | Cmpd # |
|---|---|
| 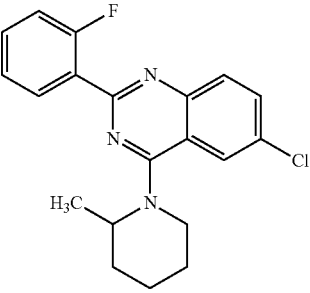 | 204 |
| 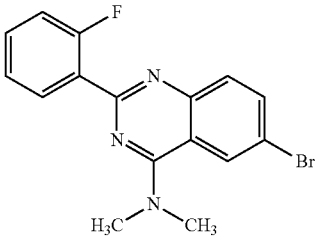 | 205 |
| 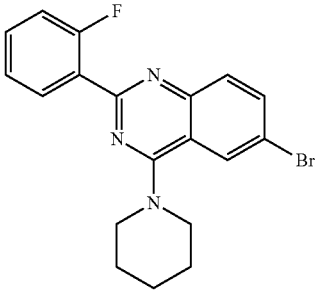 | 206 |
| 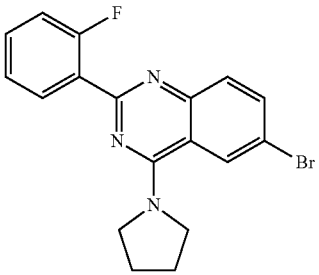 | 207 |
| 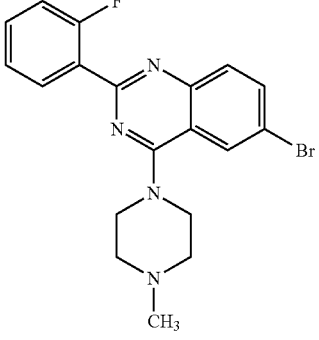 | 208 |

TABLE 2-continued
Examples of Compounds of Formula I:
| Compound | Cmpd # |
|---|---|
| 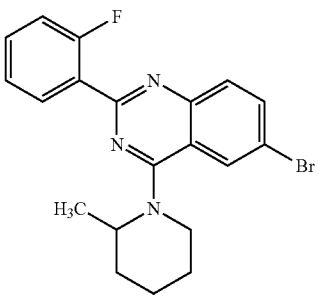 | 209 |
| 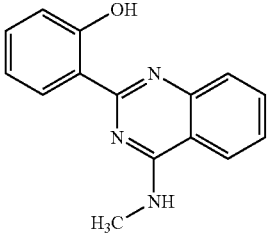 | 210 |
| 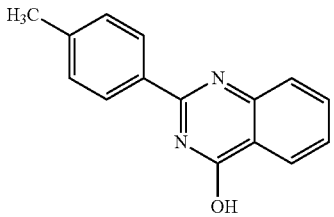 | 211 |
| 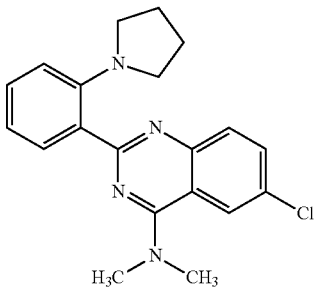 | 212 |
| 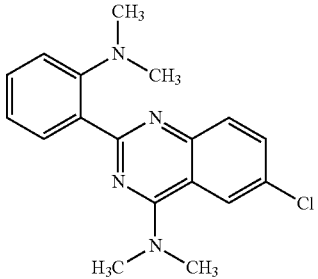 | 213 |

TABLE 2-continued

Examples of Compounds of Formula I:

| Compound | Cmpd # |
|---|---|
| 2-(2-bromophenyl)-N,N-dimethylquinazolin-4-amine | 214 |
| 2-(2-bromophenyl)-N-ethylquinazolin-4-amine | 215 |
| 2-(2-bromophenyl)-N,N-diethylquinazolin-4-amine | 216 |
| 2-(2-bromophenyl)-4-cyclopentylquinazoline | 217 |
| 2-(2-bromophenyl)-4-(piperidin-1-yl)quinazoline | 218 |

TABLE 2-continued
Examples of Compounds of Formula I:
| Compound | Cmpd # |
|---|---|
| 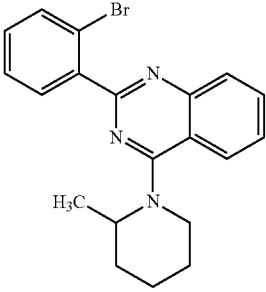 | 219 |
| 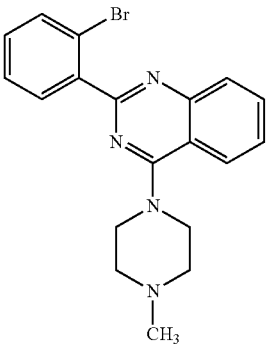 | 220 |
| 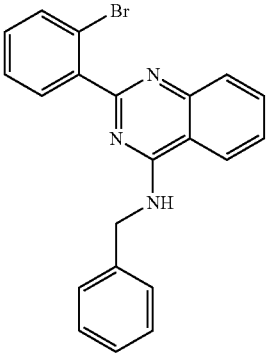 | 221 |
| 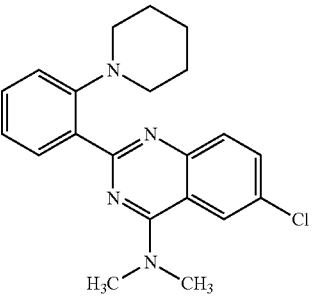 | 222 |

TABLE 2-continued
Examples of Compounds of Formula I:
| Compound | Cmpd # |
|---|---|
| 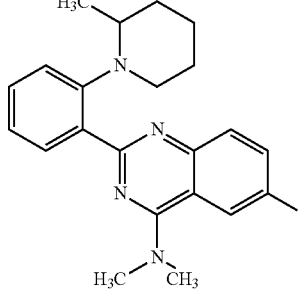 | 223 |
| 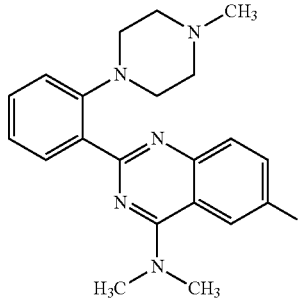 | 224 |
| 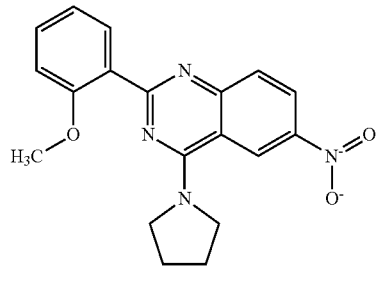 | 225 |
| 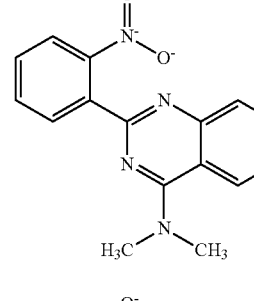 | 226 |
| 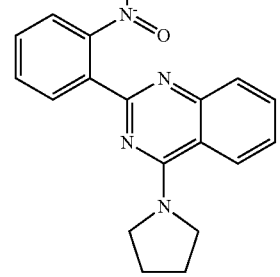 | 227 |

TABLE 2-continued

Examples of Compounds of Formula I:

| Compound | Cmpd # |
|---|---|
| | 228 |
| | 229 |
| | 230 |
| | 231 |

TABLE 2-continued

Examples of Compounds of Formula I:

| Compound | Cmpd # |
|---|---|
| 2-(2-fluorophenyl)-N-methylquinazolin-4-amine | 232 |
| 2-(2-fluorophenyl)-N,N-dimethylquinazolin-4-amine | 233 |
| N,N-diethyl-2-(2-fluorophenyl)quinazolin-4-amine | 234 |
| 2-(2-fluorophenyl)-4-(pyrrolidin-1-yl)quinazoline | 235 |
| 2-(2-fluorophenyl)-4-(piperidin-1-yl)quinazoline | 236 |

TABLE 2-continued
Examples of Compounds of Formula I:
| Compound | Cmpd # |
|---|---|
| 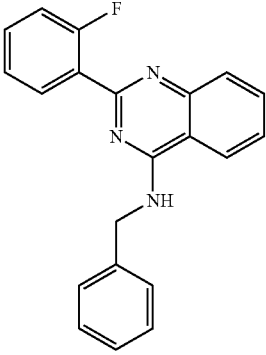 | 237 |
| 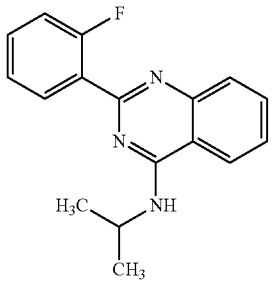 | 238 |
| 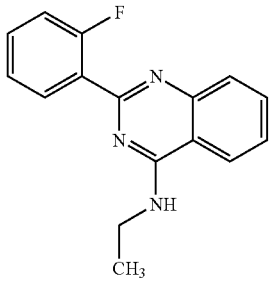 | 239 |
| 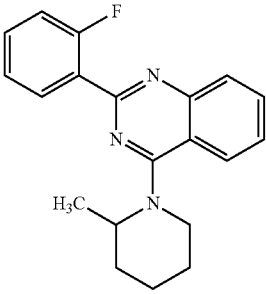 | 240 |
| 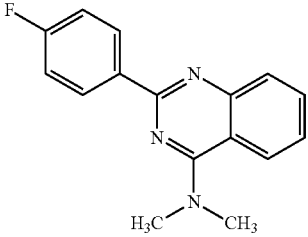 | 241 |

TABLE 2-continued

Examples of Compounds of Formula I:

| Compound | Cmpd # |
|---|---|
| 2-(4-fluorophenyl)-4-(pyrrolidin-1-yl)quinazoline | 242 |
| 2-(4-fluorophenyl)-4-(piperidin-1-yl)quinazoline | 243 |
| 2-(4-fluorophenyl)-4-(4-methylpiperazin-1-yl)quinazoline | 244 |
| N-benzyl-2-(4-fluorophenyl)quinazolin-4-amine | 245 |

TABLE 2-continued

Examples of Compounds of Formula I:

| Compound | Cmpd # |
|---|---|
| 2-(4-fluorophenyl)-N-isopropylquinazolin-4-amine | 246 |
| 2-(4-fluorophenyl)-N-ethylquinazolin-4-amine | 247 |
| 2-(2-(4-aminoquinazolin-2-yl)phenol) with 2-hydroxyethylamine | 248 |
| 2-(4-aminoquinazolin-2-yl)phenol | 249 |
| 2-(6-bromo-4-(dimethylamino)quinazolin-2-yl)phenol | 250 |

TABLE 2-continued

Examples of Compounds of Formula I:

| Compound | Cmpd # |
|---|---|
| (structure) | 251 |
| (structure) | 252 |
| (structure) | 253 |
| (structure) | 254 |
| (structure) | 255 |

TABLE 2-continued

Examples of Compounds of Formula I:

| Compound | Cmpd # |
|---|---|
| (structure) | 256 |
| (structure) | 257 |
| (structure) | 258 |
| (structure) | 259 |
| (structure) | 260 |

TABLE 2-continued

| Examples of Compounds of Formula I: | |
|---|---|
| Compound | Cmpd # |
| (structure) | 261 |
| (structure) | 262 |
| (structure) | 263 |
| (structure) | 264 |
| (structure) | 265 |

TABLE 2-continued

Examples of Compounds of Formula I:

| Compound | Cmpd # |
|---|---|
| | 266 |
| | 267 |
| | 268 |
| | 269 |
| | 270 |
| | 271 |

TABLE 2-continued
Examples of Compounds of Formula I:
| Compound | Cmpd # |
|---|---|
| 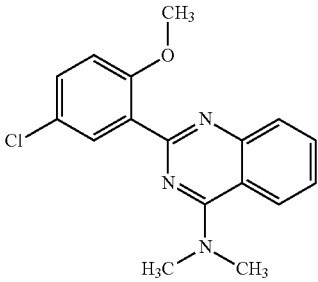 | 272 |
| 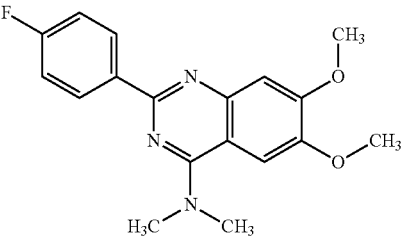 | 273 |
| 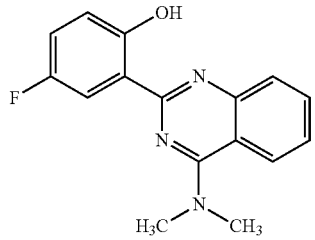 | 274 |
| 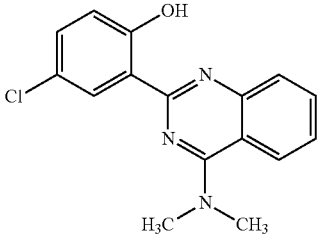 | 275 |
| 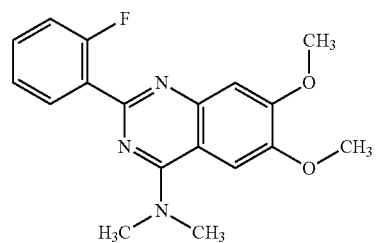 | 276 |
| 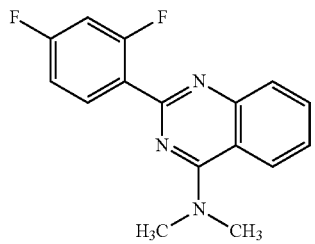 | 277 |

TABLE 2-continued
Examples of Compounds of Formula I:
| Compound | Cmpd # |
|---|---|
| 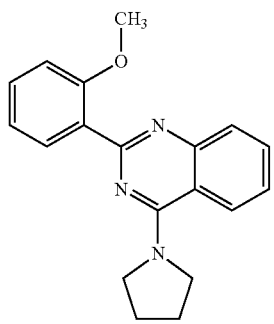 | 278 |
| 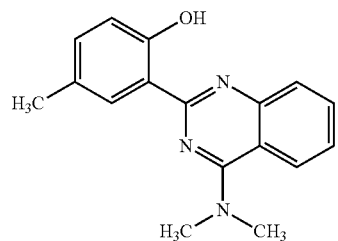 | 279 |
| 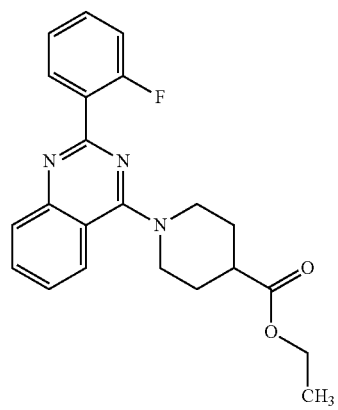 | 280 |
| 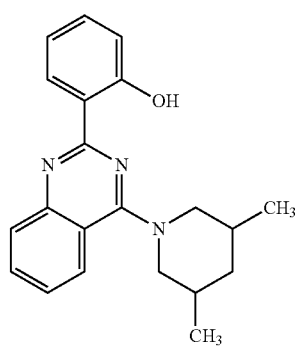 | 281 |

TABLE 2-continued
Examples of Compounds of Formula I:
| Compound | Cmpd # |
|---|---|
| 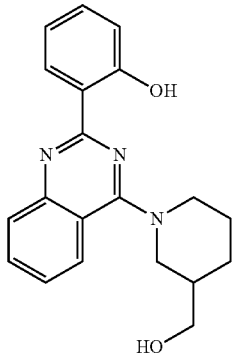 | 282 |
| 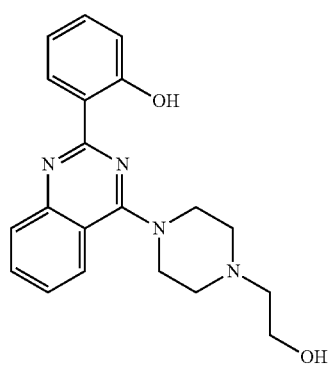 | 283 |
| 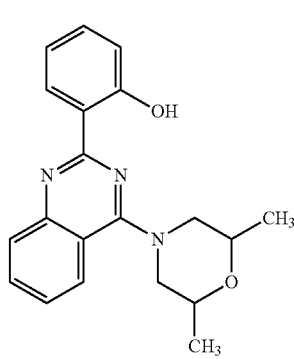 | 284 |
| 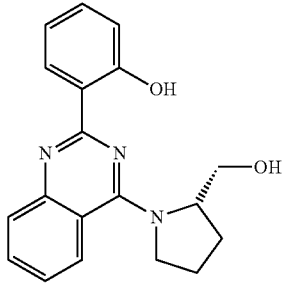 | 285 |

TABLE 2-continued

Examples of Compounds of Formula I:

| Compound | Cmpd # |
|---|---|
| | 286 |
| | 287 |
| | 288 |
| | 289 |

TABLE 2-continued

Examples of Compounds of Formula I:

| Compound | Cmpd # |
|---|---|
| | 290 |
| | 291 |
| | 292 |
| | 293 |
| | 294 |

TABLE 2-continued

Examples of Compounds of Formula I:

| Compound | Cmpd # |
|---|---|
| | 295 |
| | 296 |
| | 297 |
| | 298 |

TABLE 2-continued

Examples of Compounds of Formula I:

| Compound | Cmpd # |
|---|---|
| 3,4,5-trimethoxyphenyl-quinazoline with N(H)CH₃ | 299 |
| 2-(2-amino-4-methylphenyl)-quinazoline with N(CH₃)₂ | 300 |
| 2-(2,4-bis(trifluoromethyl)phenyl)-quinazoline with N(CH₃)₂ | 301 |
| 3-acetamidophenyl-quinazoline with N(CH₃)₂ | 302 |

TABLE 2-continued

Examples of Compounds of Formula I:

| Compound | Cmpd # |
|---|---|
| (structure) | 303 |
| (structure) | 304 |
| (structure) | 305 |
| (structure) | 306 |

TABLE 2-continued

Examples of Compounds of Formula I:

| Compound | Cmpd # |
|---|---|
| | 307 |
| | 308 |
| | 309 |
| | 310 |

TABLE 2-continued

Examples of Compounds of Formula I:

| Compound | Cmpd # |
|---|---|
| | 311 |
| | 312 |
| | 313 |
| | 314 |

TABLE 2-continued

Examples of Compounds of Formula I:

| Compound | Cmpd # |
|---|---|
| (structure) | 315 |
| (structure) | 316 |
| (structure) | 317 |
| (structure) | 318 |

TABLE 2-continued

Examples of Compounds of Formula I:

| Compound | Cmpd # |
|---|---|
| 2-(4-(pyridin-2-ylamino)quinazolin-2-yl)phenol | 319 |
| 2-(4-((pyridin-3-ylmethyl)amino)quinazolin-2-yl)phenol | 320 |
| 2-(4-((2-(pyridin-2-yl)ethyl)amino)quinazolin-2-yl)phenol | 321 |
| 2-(4-(methyl(2-(pyridin-2-yl)ethyl)amino)quinazolin-2-yl)phenol | 322 |

TABLE 2-continued

Examples of Compounds of Formula I:

| Compound | Cmpd # |
|---|---|
| | 323 |
| | 324 |
| | 325 |
| | 326 |
| | 327 |

TABLE 2-continued
Examples of Compounds of Formula I:
| Compound | Cmpd # |
|---|---|
| 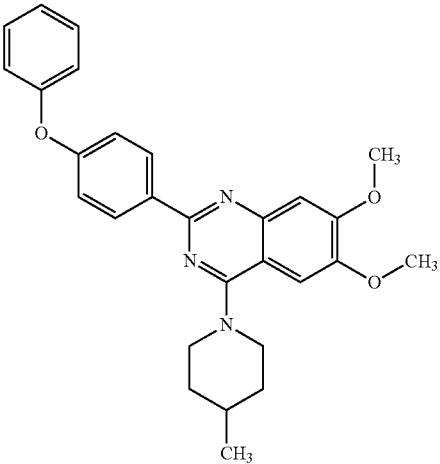 | 328 |
| 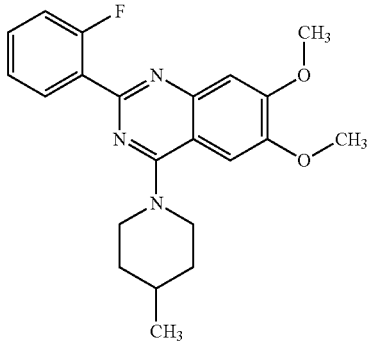 | 329 |
| 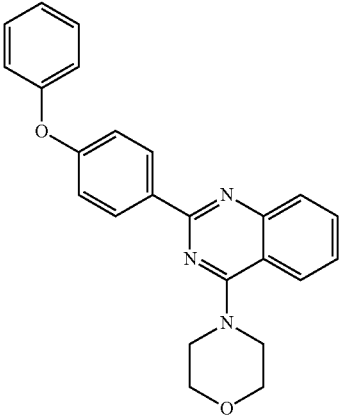 | 330 |

TABLE 2-continued
Examples of Compounds of Formula I:
| Compound | Cmpd # |
|---|---|
| 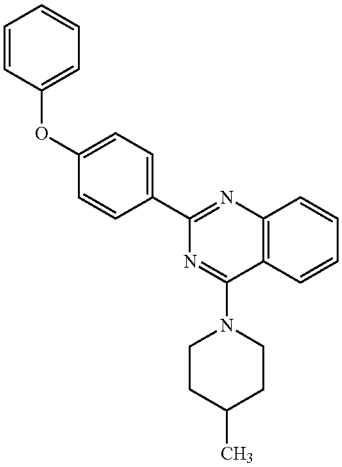 | 331 |
| 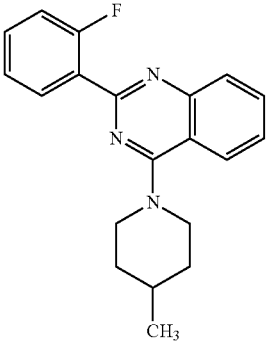 | 332 |
| 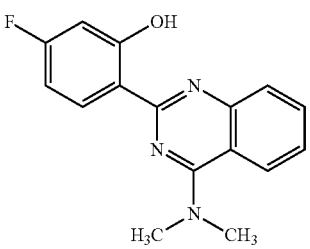 | 333 |
| 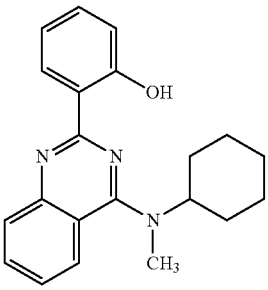 | 334 |

TABLE 2-continued

Examples of Compounds of Formula I:

| Compound | Cmpd # |
|---|---|
| | 335 |
| | 336 |
| | 337 |
| | 338 |
| | 339 |

TABLE 2-continued

Examples of Compounds of Formula I:

| Compound | Cmpd # |
|---|---|
| | 340 |
| | 341 |
| | 342 |
| | 343 |

TABLE 2-continued

Examples of Compounds of Formula I:

| Compound | Cmpd # |
|---|---|
| | 344 |
| | 345 |
| | 346 |
| | 347 |

TABLE 2-continued

Examples of Compounds of Formula I:

| Compound | Cmpd # |
|---|---|
| (structure) | 348 |
| (structure) | 349 |
| (structure) | 350 |
| (structure) | 351 |

TABLE 2-continued
Examples of Compounds of Formula I:
| Compound | Cmpd # |
|---|---|
| 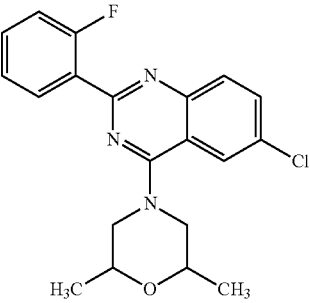 | 352 |
| 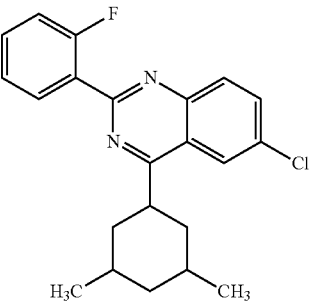 | 353 |
| 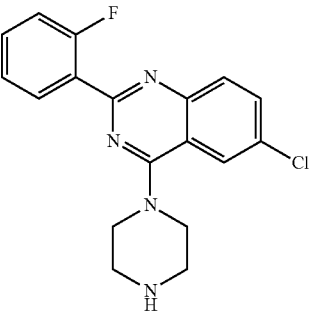 | 354 |
| 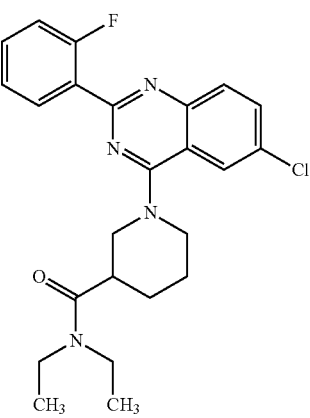 | 355 |

TABLE 2-continued

Examples of Compounds of Formula I:

| Compound | Cmpd # |
|---|---|
| | 356 |
| | 357 |
| | 358 |
| | 359 |
| | 360 |

TABLE 2-continued
Examples of Compounds of Formula I:
| Compound | Cmpd # |
|---|---|
| 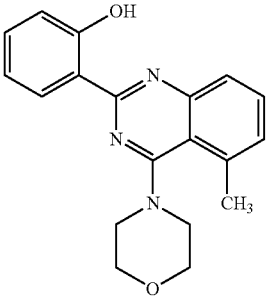 | 361 |
| 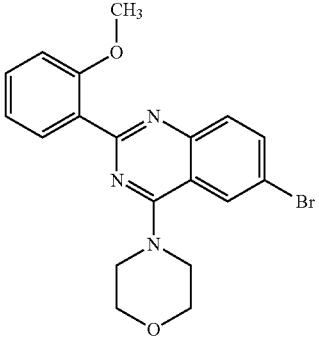 | 362 |
| 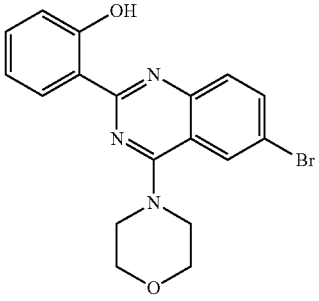 | 363 |
| 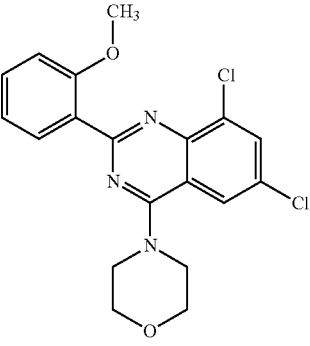 | 364 |

TABLE 2-continued

Examples of Compounds of Formula I:

| Compound | Cmpd # |
|---|---|
| | 365 |
| | 366 |
| | 367 |
| | 368 |
| | 369 |

TABLE 2-continued

Examples of Compounds of Formula I:

| Compound | Cmpd # |
|---|---|
| | 370 |
| | 371 |
| | 372 |
| | 373 |

TABLE 2-continued

Examples of Compounds of Formula I:

| Compound | Cmpd # |
|---|---|
| | 374 |
| | 375 |
| | 376 |
| | 377 |
| | 378 |

TABLE 2-continued

Examples of Compounds of Formula I:

| Compound | Cmpd # |
|---|---|
| [structure] | 379 |
| [structure] | 380 |
| [structure] | 381 |
| [structure] | 382 |

TABLE 2-continued

Examples of Compounds of Formula I:

| Compound | Cmpd # |
|---|---|
| | 383 |
| | 384 |
| | 385 |
| | 386 |

TABLE 2-continued
Examples of Compounds of Formula I:
| Compound | Cmpd # |
|---|---|
| 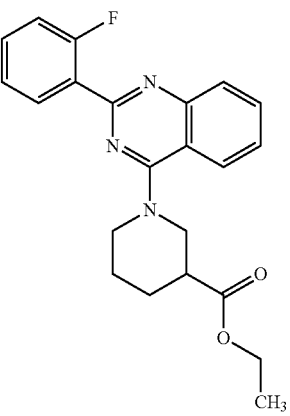 | 387 |
| 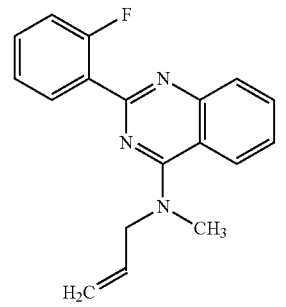 | 388 |
| 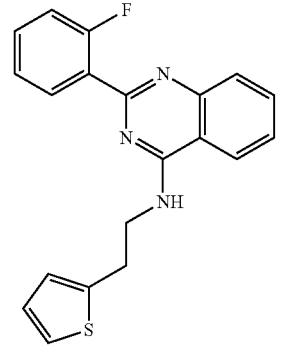 | 389 |
| 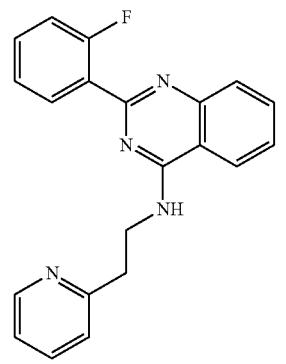 | 390 |

TABLE 2-continued

Examples of Compounds of Formula I:

| Compound | Cmpd # |
|---|---|
| | 391 |
| | 392 |
| | 393 |
| | 394 |
| | 395 |

TABLE 2-continued

Examples of Compounds of Formula I:

| Compound | Cmpd # |
|---|---|
| (structure) | 396 |
| (structure) | 397 |
| (structure) | 398 |
| (structure) | 399 |
| (structure) | 400 |

TABLE 2-continued

Examples of Compounds of Formula I:

| Compound | Cmpd # |
|---|---|
| 2-(2,6-difluorophenyl)-4-(3,5-dimethylpiperidin-1-yl)quinazoline | 401 |
| 2-(2,6-difluorophenyl)-4-(4-methylpiperidin-1-yl)quinazoline | 402 |
| 2-(2-fluoro-5-methylphenyl)-N,N-dimethylquinazolin-4-amine | 403 |
| 2-(5-fluoro-4-(dimethylamino)quinazolin-2-yl)phenol | 404 |
| 2-(2-fluorophenyl)-N4,N4-dimethylquinazoline-4,7-diamine | 405 |

TABLE 2-continued

Examples of Compounds of Formula I:

| Compound | Cmpd # |
|---|---|
| 2-(2-methoxyphenyl)-N-allyl-quinazolin-4-amine | 406 |
| 2-(2-(2-(2-methoxyphenyl)quinazolin-4-yl(methyl)amino)ethyl 4-methylbenzenesulfonate | 407 |
| 2-(2-fluorophenyl)-6-methoxy-N,N-dimethylquinazolin-4-amine | 408 |
| 6-chloro-N,N-dimethyl-2-(1H-pyrrol-1-yl)quinazolin-4-amine | 409 |

TABLE 2-continued

Examples of Compounds of Formula I:

| Compound | Cmpd # |
|---|---|
| | 410 |
| | 411 |
| | 412 |
| | 413 |
| | 414 |

TABLE 2-continued

Examples of Compounds of Formula I:

| Compound | Cmpd # |
|---|---|
| | 415 |
| | 416 |
| | 417 |
| | 418 |
| | 419 |

TABLE 2-continued

Examples of Compounds of Formula I:

| Compound | Cmpd # |
|---|---|
| (structure) | 420 |
| (structure) | 421 |
| (structure) | 422 |
| (structure) | 423 |
| (structure) | 424 |
| (structure) | 425 |

TABLE 2-continued
Examples of Compounds of Formula I:
| Compound | Cmpd # |
|---|---|
| 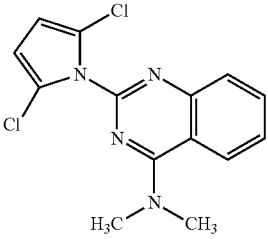 | 426 |
| 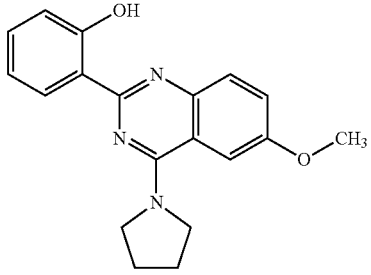 | 427 |
| 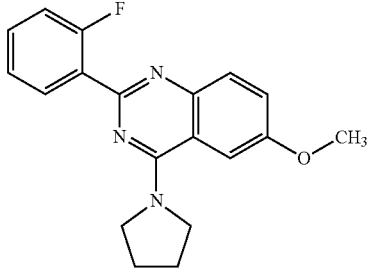 | 428 |
| 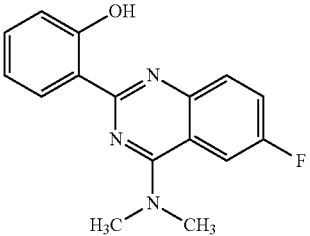 | 429 |
| 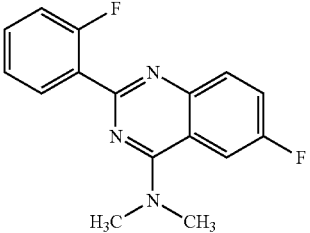 | 430 |

TABLE 2-continued
Examples of Compounds of Formula I:
| Compound | Cmpd # |
|---|---|
| 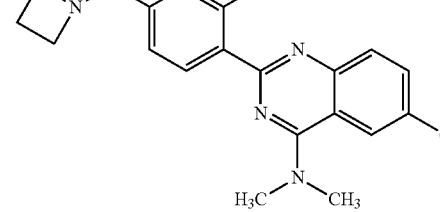 | 431 |
| 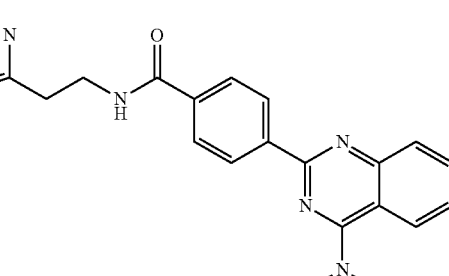 | 432 |
| 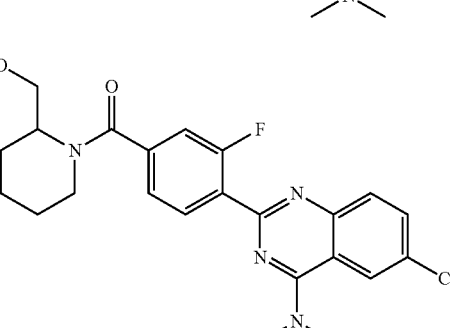 | 433 |
| 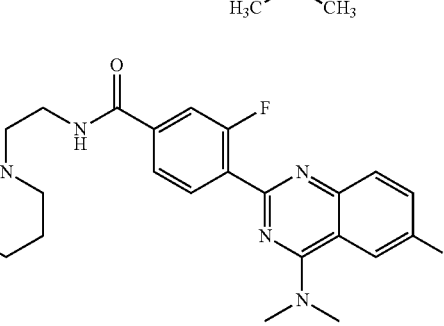 | 434 |
| 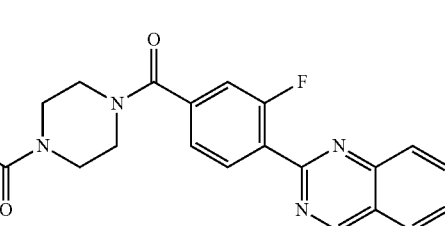 | 435 |

TABLE 2-continued

Examples of Compounds of Formula I:

| Compound | Cmpd # |
|---|---|
| | 436 |
| | 437 |
| | 438 |
| | 439 |
| | 440 |

TABLE 2-continued
Examples of Compounds of Formula I:
| Compound | Cmpd # |
|---|---|
| 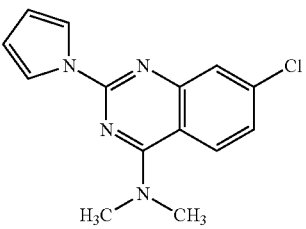 | 441 |
| 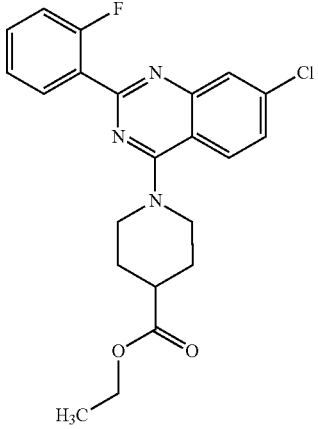 | 442 |
| 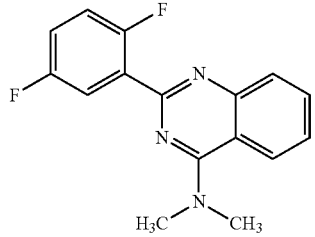 | 443 |
| 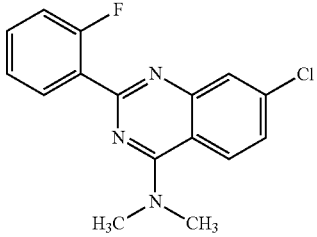 | 444 |
| 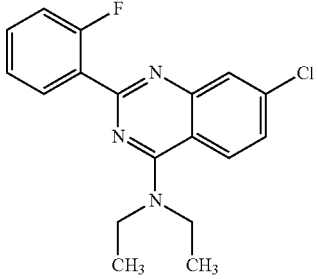 | 445 |

TABLE 2-continued

Examples of Compounds of Formula I:

| Compound | Cmpd # |
|---|---|
| | 446 |
| | 447 |
| | 448 |
| | 449 |

TABLE 2-continued

Examples of Compounds of Formula I:

| Compound | Cmpd # |
|---|---|
| | 450 |
| | 451 |
| | 452 |
| | 453 |
| | 454 |

TABLE 2-continued

Examples of Compounds of Formula I:

| Compound | Cmpd # |
|---|---|
| | 455 |
| | 456 |
| | 457 |
| | 458 |

TABLE 2-continued

Examples of Compounds of Formula I:

| Compound | Cmpd # |
|---|---|
| 7-chloro-4-(methoxyamino)-2-(2-hydroxyphenyl)quinazoline | 459 |
| 7-chloro-4-(ethoxyamino)-2-(2-hydroxyphenyl)quinazoline | 460 |
| 7-chloro-4-(tert-butoxyamino)-2-(2-hydroxyphenyl)quinazoline | 461 |
| 7-chloro-4-(allyloxyamino)-2-(2-hydroxyphenyl)quinazoline | 462 |

TABLE 2-continued

Examples of Compounds of Formula I:

| Compound | Cmpd # |
|---|---|
| | 463 |
| | 464 |
| | 465 |
| | 466 |
| | 467 |

TABLE 2-continued
Examples of Compounds of Formula I:
| Compound | Cmpd # |
|---|---|
| 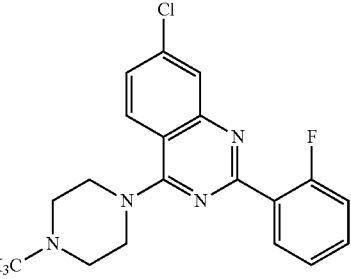 | 468 |
| 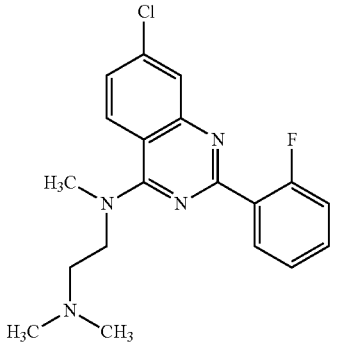 | 469 |
| 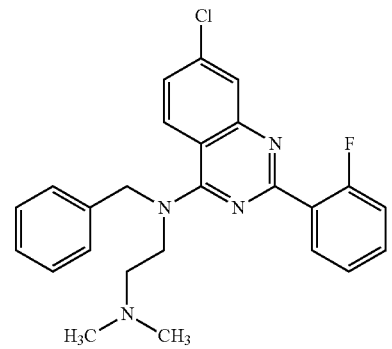 | 470 |
| 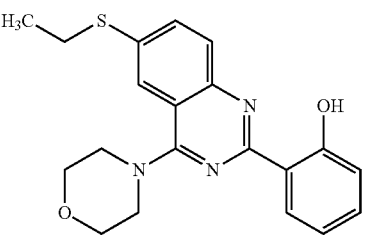 | 471 |

TABLE 2-continued

Examples of Compounds of Formula I:

| Compound | Cmpd # |
|---|---|
| | 472 |
| | 473 |
| | 474 |
| | 475 |
| | 476 |

TABLE 2-continued
Examples of Compounds of Formula I:
| Compound | Cmpd # |
|---|---|
| 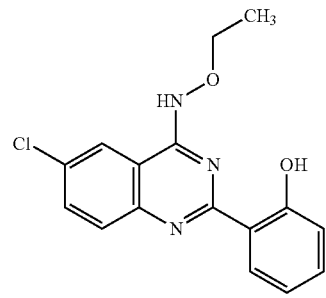 | 477 |
| 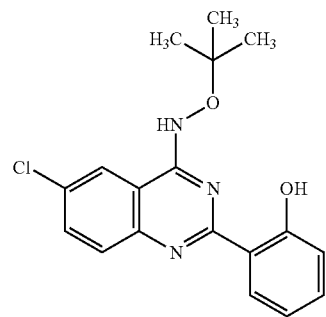 | 478 |
| 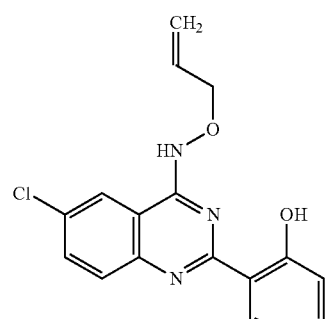 | 479 |
| 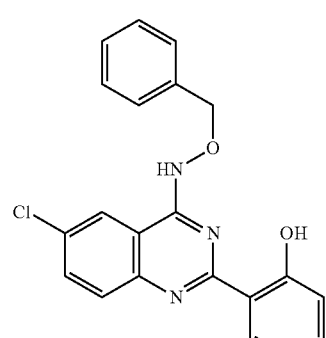 | 480 |

TABLE 2-continued

Examples of Compounds of Formula I:

| Compound | Cmpd # |
|---|---|
| (6-chloro-4-[N-methyl-N-methoxyamino]-2-(2-hydroxyphenyl)quinazoline) | 481 |
| (4-[N-ethoxyamino]-2-(2-hydroxyphenyl)quinazoline) | 482 |
| (4-(dimethylamino)-7-fluoro-2-(2-fluorophenyl)quinazoline) | 483 |
| (4-morpholino-7-fluoro-2-(2-fluorophenyl)quinazoline) | 484 |
| (4-(dimethylamino)-6-isopropoxy-2-(2-hydroxyphenyl)quinazoline) | 485 |

TABLE 2-continued

Examples of Compounds of Formula I:

| Compound | Cmpd # |
|---|---|
| | 486 |
| | 487 |
| | 488 |
| | 489 |

TABLE 2-continued

Examples of Compounds of Formula I:

| Compound | Cmpd # |
|---|---|
| | 490 |
| | 491 |
| | 492 |
| | 493 |
| | 494 |

TABLE 2-continued

Examples of Compounds of Formula I:

| Compound | Cmpd # |
|---|---|
| | 495 |
| | 496 |
| | 497 |

TABLE 2-continued

| Examples of Compounds of Formula I: | |
|---|---|
| Compound | Cmpd # |
| | 498 |
| | 499 |
| | 500 |

TABLE 2-continued
Examples of Compounds of Formula I:
| Compound | Cmpd # |
|---|---|
| 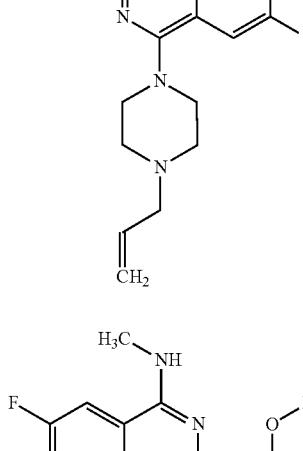 | 501 |
| 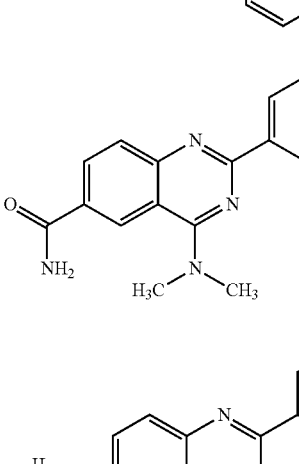 | 502 |
| 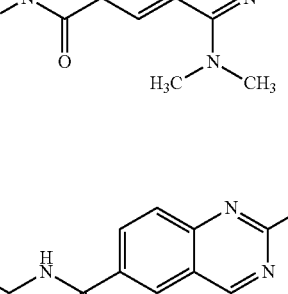 | 503 |
| 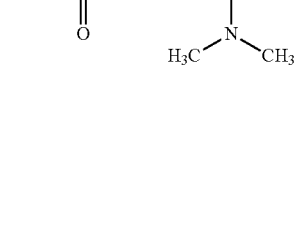 | 504 |
|  | 505 |

TABLE 2-continued

Examples of Compounds of Formula I:

| Compound | Cmpd # |
|---|---|
| | 506 |
| | 507 |
| | 508 |
| | 509 |
| | 510 |
| | 511 |

TABLE 2-continued
Examples of Compounds of Formula I:
| Compound | Cmpd # |
|---|---|
| 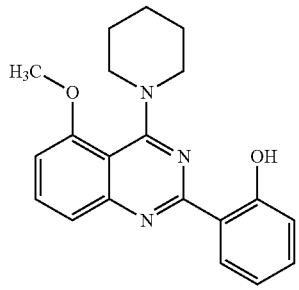 | 512 |
| 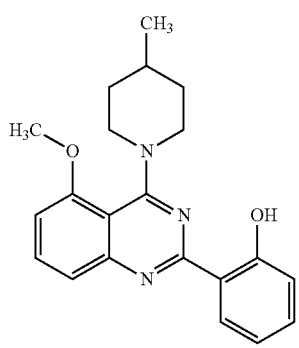 | 513 |
| 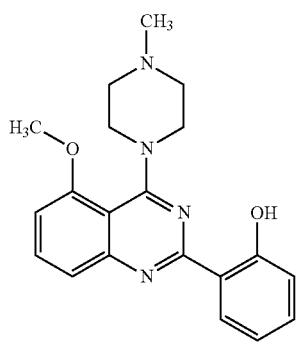 | 514 |
| 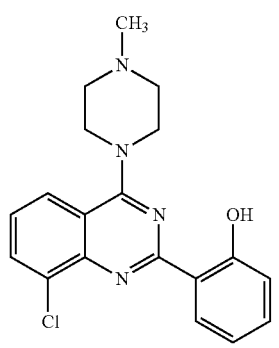 | 515 |

TABLE 2-continued

Examples of Compounds of Formula I:

| Compound | Cmpd # |
|---|---|
| | 516 |
| | 517 |
| | 518 |
| | 519 |

TABLE 2-continued

Examples of Compounds of Formula I:

| Compound | Cmpd # |
|---|---|
| | 520 |
| | 521 |
| | 522 |
| | 523 |

TABLE 2-continued

| Examples of Compounds of Formula I: | |
|---|---|
| Compound | Cmpd # |
| (structure) | 524 |
| (structure) | 525 |
| (structure) | 526 |

TABLE 2-continued

| Examples of Compounds of Formula I: | |
|---|---|
| Compound | Cmpd # |
| (structure) | 527 |
| (structure) | 528 |
| (structure) | 529 |

TABLE 2-continued

Examples of Compounds of Formula I:

| Compound | Cmpd # |
|---|---|
| | 530 |
| | 531 |
| | 532 |

TABLE 2-continued

Examples of Compounds of Formula I:

| Compound | Cmpd # |
|---|---|
| | 533 |
| | 534 |
| | 535 |

TABLE 2-continued

Examples of Compounds of Formula I:

| Compound | Cmpd # |
|---|---|
| | 536 |
| | 537 |
| | 538 |

TABLE 2-continued
Examples of Compounds of Formula I:
| Compound | Cmpd # |
|---|---|
| 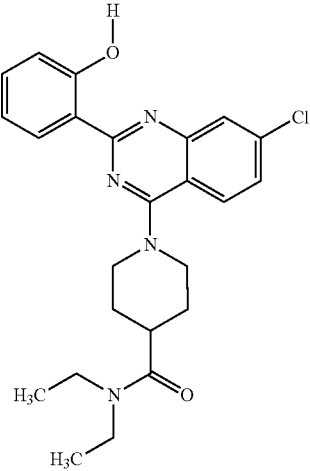 | 539 |
| 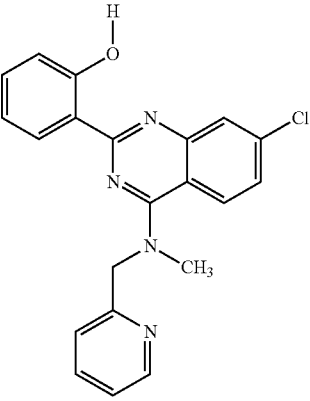 | 540 |
| 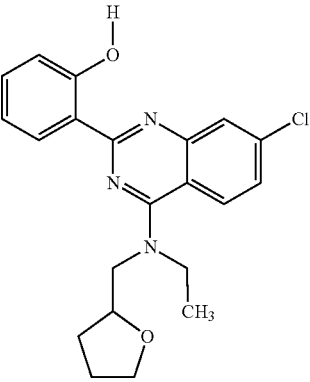 | 541 |

TABLE 2-continued
Examples of Compounds of Formula I:
| Compound | Cmpd # |
|---|---|
| 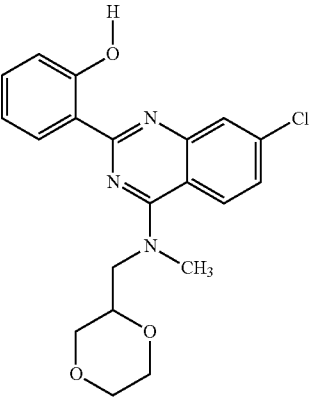 | 542 |
| 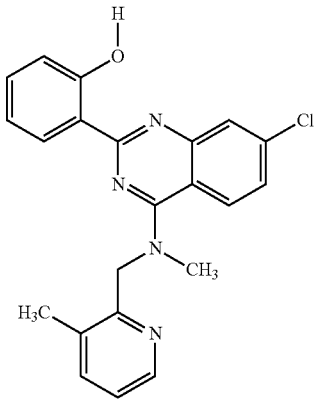 | 543 |
| 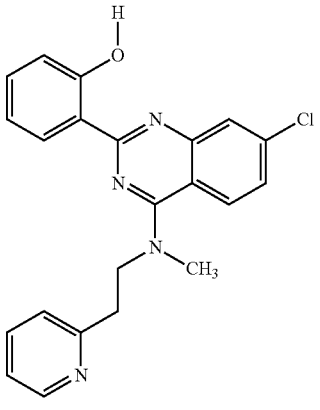 | 544 |

TABLE 2-continued

| Examples of Compounds of Formula I: | |
|---|---|
| Compound | Cmpd # |
| *[structure]* | 545 |
| *[structure]* | 546 |
| *[structure]* | 547 |

TABLE 2-continued
Examples of Compounds of Formula I:
| Compound | Cmpd # |
|---|---|
| 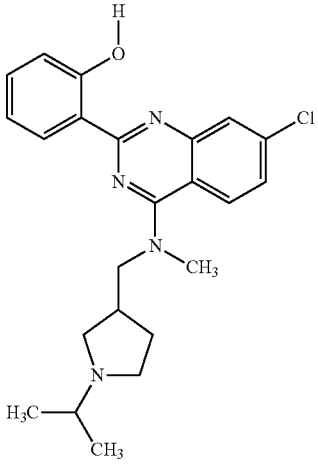 | 548 |
| 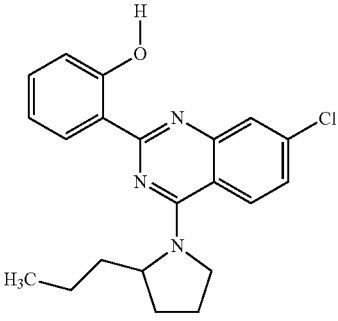 | 549 |
| 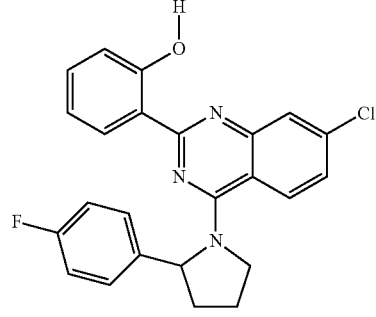 | 550 |
| 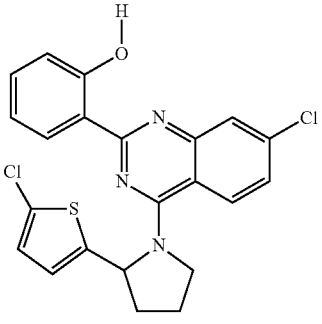 | 551 |

TABLE 2-continued

Examples of Compounds of Formula I:

| Compound | Cmpd # |
|---|---|
| (structure) | 552 |
| (structure) | 553 |
| (structure) | 554 |

TABLE 2-continued

Examples of Compounds of Formula I:

| Compound | Cmpd # |
|---|---|
| | 555 |
| | 556 |
| | 557 |
| | 558 |

TABLE 2-continued

Examples of Compounds of Formula I:

| Compound | Cmpd # |
|---|---|
| | 559 |
| | 560 |
| | 561 |
| | 562 |

TABLE 2-continued
Examples of Compounds of Formula I:
| Compound | Cmpd # |
|---|---|
| 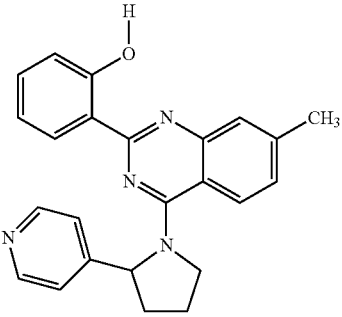 | 563 |
| 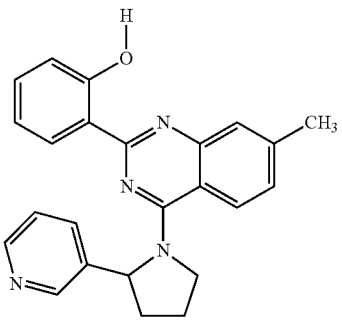 | 564 |
| 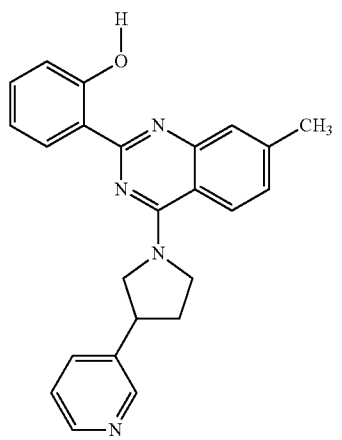 | 565 |
| 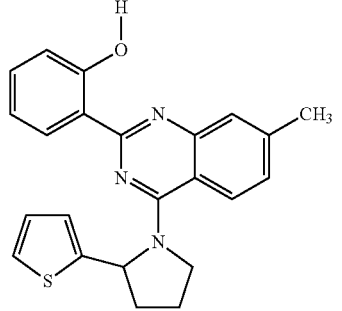 | 566 |

TABLE 2-continued
Examples of Compounds of Formula I:
| Compound | Cmpd # |
|---|---|
| 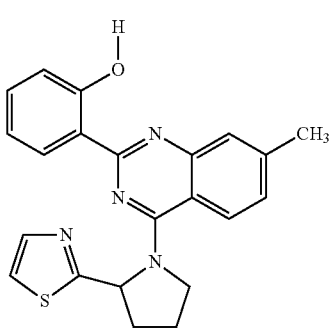 | 567 |
| 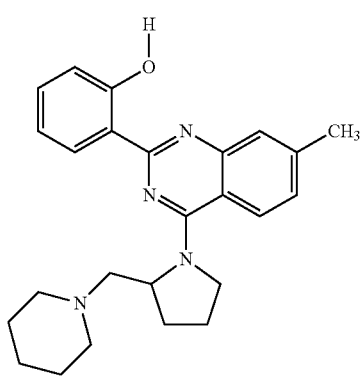 | 568 |
| 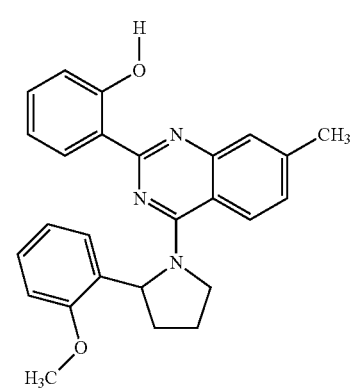 | 569 |
| 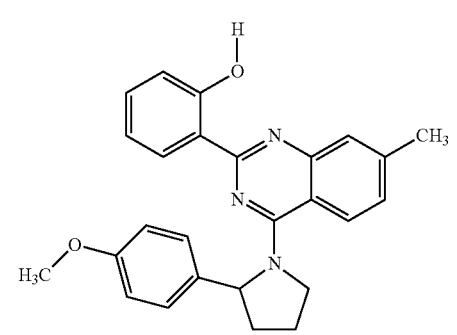 | 570 |

TABLE 2-continued

Examples of Compounds of Formula I:

| Compound | Cmpd # |
|---|---|
| | 571 |
| | 572 |
| | 573 |
| | 574 |

TABLE 2-continued
Examples of Compounds of Formula I:
| Compound | Cmpd # |
|---|---|
| 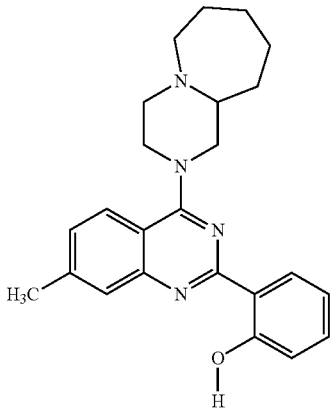 | 575 |
| 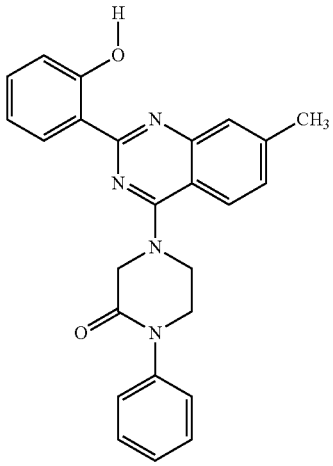 | 576 |
| 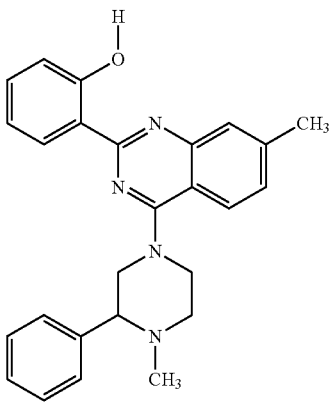 | 577 |
| 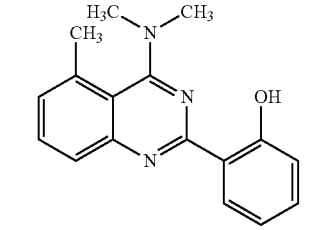 | 578 |

TABLE 2-continued

Examples of Compounds of Formula I:

| Compound | Cmpd # |
|---|---|
| (structure) | 579 |
| (structure) | 580 |
| (structure) | 581 |
| (structure) | 582 |
| (structure) | 583 |

TABLE 2-continued

Examples of Compounds of Formula I:

| Compound | Cmpd # |
|---|---|
| | 584 |
| | 585 |
| | 586 |
| | 587 |

TABLE 2-continued

Examples of Compounds of Formula I:

| Compound | Cmpd # |
|---|---|
| | 588 |
| | 589 |
| | 590 |
| | 591 |

TABLE 2-continued
Examples of Compounds of Formula I:
| Compound | Cmpd # |
|---|---|
| 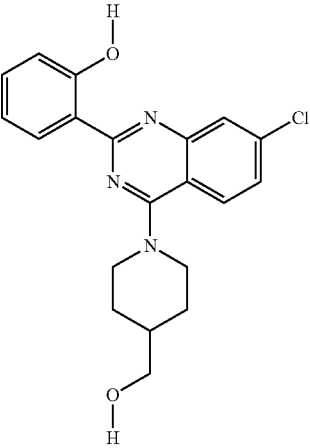 | 592 |
| 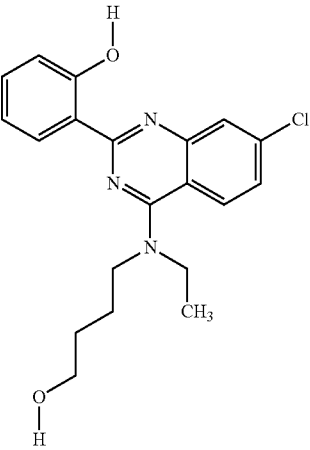 | 593 |
| 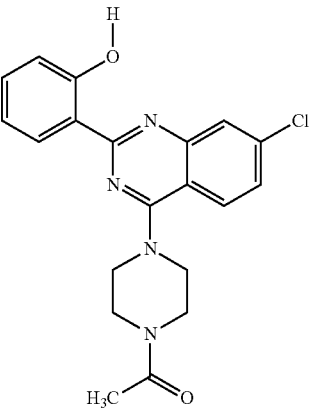 | 594 |

TABLE 2-continued

| Examples of Compounds of Formula I: | |
|---|---|
| Compound | Cmpd # |
| *[structure: 7-chloro-2-(2-hydroxyphenyl)quinazolin-4-yl connected to 4-(2-hydroxyethyl)piperidin-1-yl]* | 595 |
| *[structure: 7-chloro-2-(2-hydroxyphenyl)quinazolin-4-yl with N-ethyl-N-(pyridin-4-ylmethyl)amino substituent]* | 596 |
| *[structure: 7-chloro-2-(2-hydroxyphenyl)quinazolin-4-yl with 3-(N-methylacetamido)pyrrolidin-1-yl substituent]* | 597 |

TABLE 2-continued
Examples of Compounds of Formula I:
| Compound | Cmpd # |
|---|---|
| 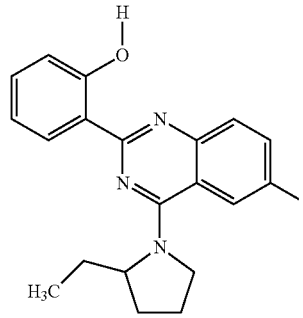 | 598 |
| 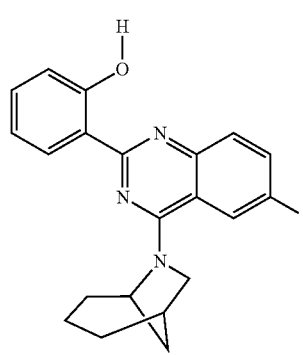 | 599 |
| 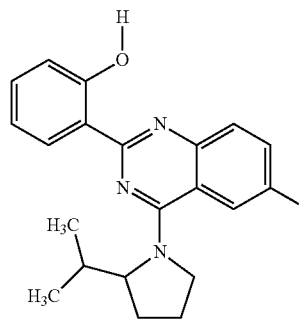 | 600 |
| 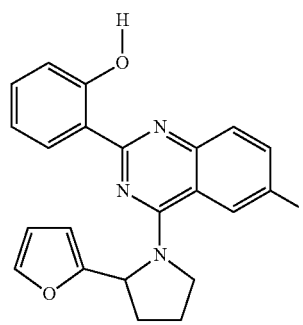 | 601 |

TABLE 2-continued

Examples of Compounds of Formula I:

| Compound | Cmpd # |
|---|---|
| | 602 |
| | 603 |
| | 604 |
| | 605 |

TABLE 2-continued

Examples of Compounds of Formula I:

| Compound | Cmpd # |
|---|---|
| | 606 |
| | 607 |
| | 608 |
| | 609 |

TABLE 2-continued
Examples of Compounds of Formula I:
| Compound | Cmpd # |
|---|---|
| 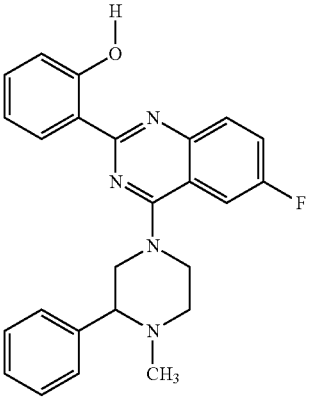 | 610 |
| 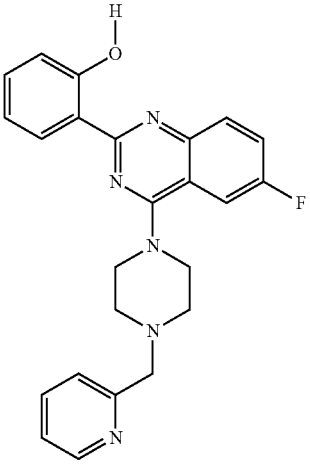 | 611 |
| 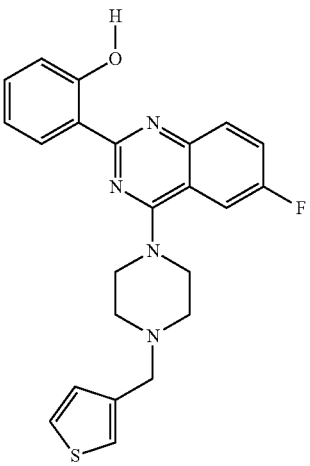 | 612 |

TABLE 2-continued

Examples of Compounds of Formula I:

| Compound | Cmpd # |
|---|---|
| | 613 |
| | 614 |
| | 615 |

TABLE 2-continued

Examples of Compounds of Formula I:

| Compound | Cmpd # |
|---|---|
| | 616 |
| | 617 |
| | 618 |

TABLE 2-continued

| Examples of Compounds of Formula I: | |
|---|---|
| Compound | Cmpd # |
| *[structure: 2-(6-fluoroquinazolin-2-yl)phenol with 3-methoxypiperidin-1-yl at 4-position]* | 619 |
| *[structure: 2-(6-fluoroquinazolin-2-yl)phenol with 4-methoxypiperidin-1-yl at 4-position]* | 620 |
| *[structure: 2-(6-fluoroquinazolin-2-yl)phenol with 3-acetylpiperidin-1-yl at 4-position]* | 621 |
| *[structure: 2-(6-fluoroquinazolin-2-yl)phenol with 2-(methoxymethyl)piperidin-1-yl at 4-position]* | 622 |

TABLE 2-continued

Examples of Compounds of Formula I:

| Compound | Cmpd # |
|---|---|
| | 623 |
| | 624 |
| | 625 |

TABLE 2-continued

Examples of Compounds of Formula I:

| Compound | Cmpd # |
|---|---|
| | 626 |
| | 627 |
| | 628 |

TABLE 2-continued

| Examples of Compounds of Formula I: | |
|---|---|
| Compound | Cmpd # |
| | 629 |
| | 630 |
| | 631 |

TABLE 2-continued

| Examples of Compounds of Formula I: | |
|---|---|
| Compound | Cmpd # |
| | 632 |
| | 633 |
| | 634 |

TABLE 2-continued
Examples of Compounds of Formula I:
| Compound | Cmpd # |
|---|---|
| 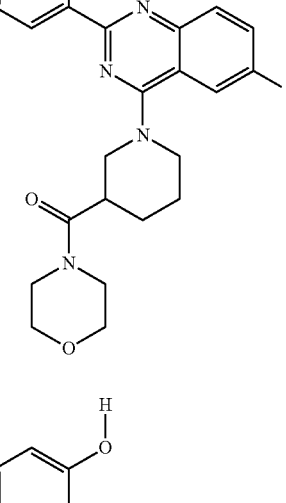 | 635 |
| 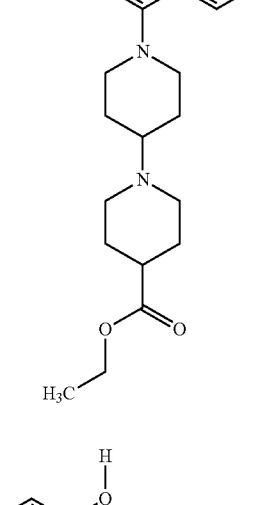 | 636 |
| 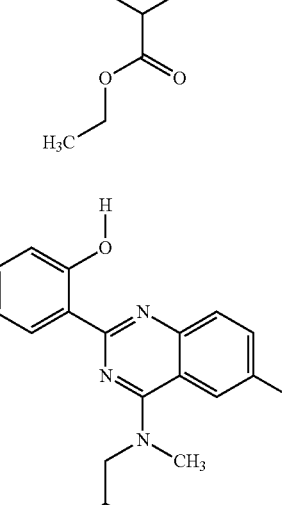 | 637 |

TABLE 2-continued
Examples of Compounds of Formula I:
| Compound | Cmpd # |
|---|---|
| 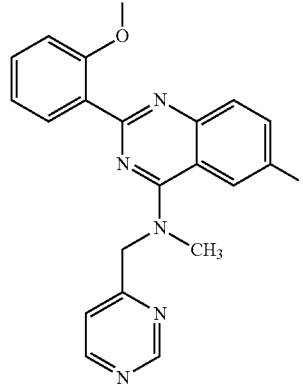 | 638 |
| 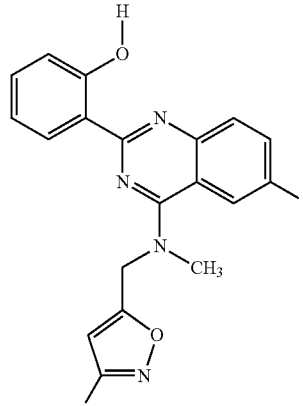 | 639 |
| 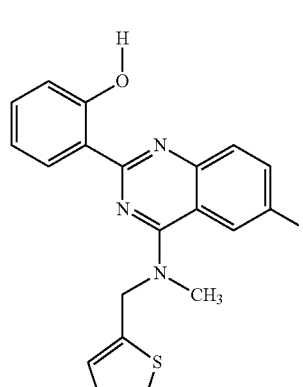 | 640 |

TABLE 2-continued
Examples of Compounds of Formula I:
| Compound | Cmpd # |
|---|---|
|  | 641 |
|  | 642 |
| 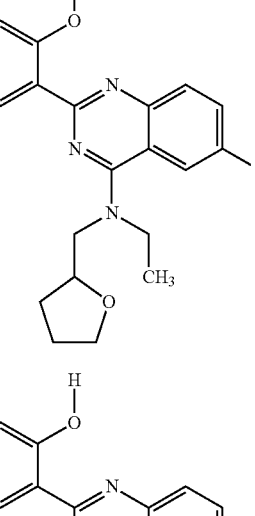 | 643 |
| 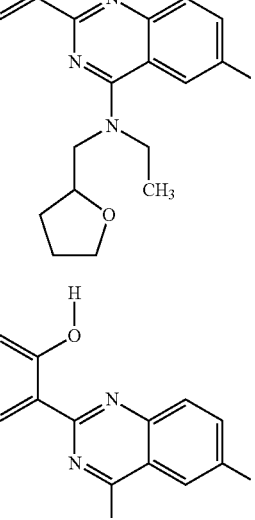 | 644 |

TABLE 2-continued
| Examples of Compounds of Formula I: | |
|---|---|
| Compound | Cmpd # |
| 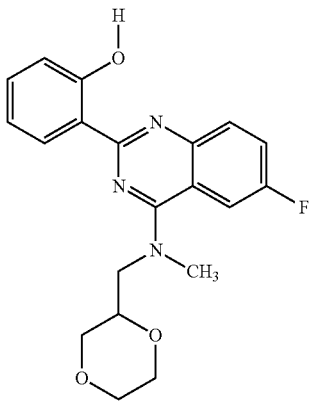 | 645 |
| 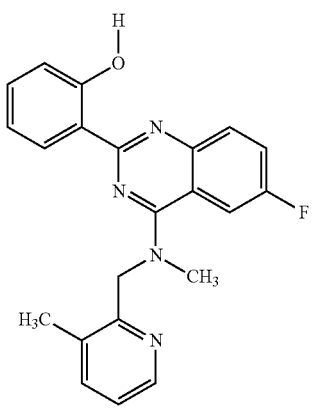 | 646 |
| 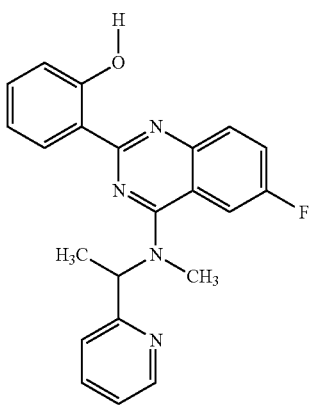 | 647 |

TABLE 2-continued
Examples of Compounds of Formula I:
| Compound | Cmpd # |
|---|---|
| 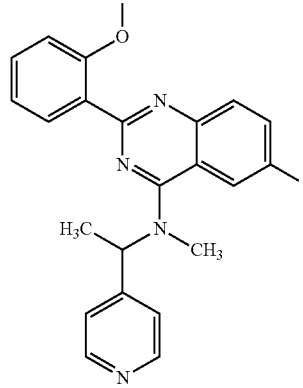 | 648 |
| 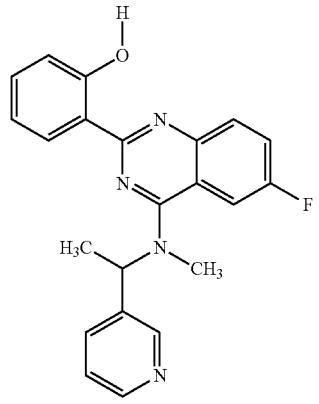 | 649 |
| 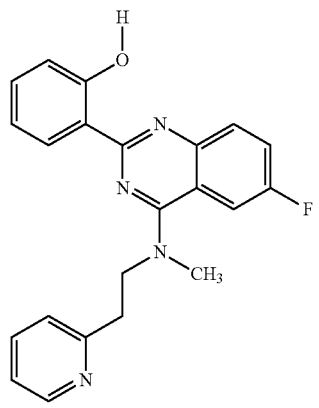 | 650 |

TABLE 2-continued
Examples of Compounds of Formula I:
| Compound | Cmpd # |
|---|---|
| 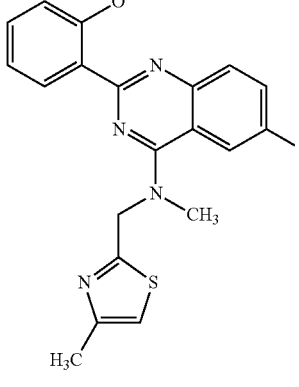 | 651 |
| 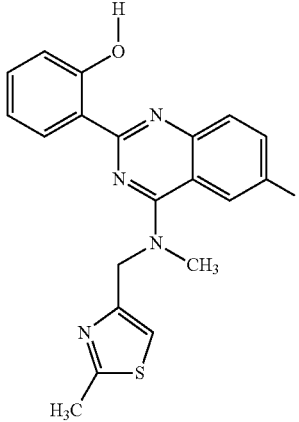 | 652 |
| 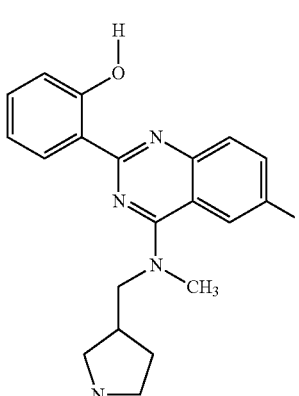 | 653 |

TABLE 2-continued

Examples of Compounds of Formula I:

| Compound | Cmpd # |
|---|---|
| | 654 |
| | 655 |
| | 656 |
| | 657 |

TABLE 2-continued

Examples of Compounds of Formula I:

| Compound | Cmpd # |
|---|---|
| | 658 |
| | 659 |
| | 660 |
| | 661 |

TABLE 2-continued
Examples of Compounds of Formula I:
| Compound | Cmpd # |
|---|---|
| 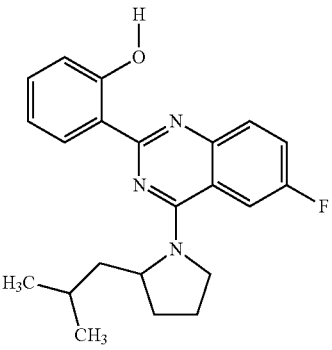 | 662 |
| 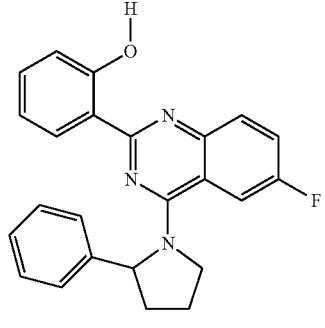 | 663 |
| 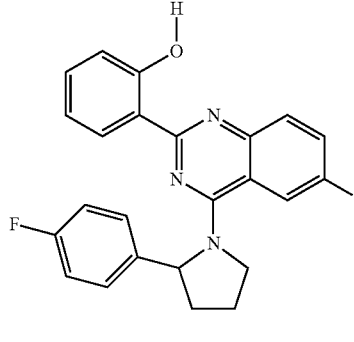 | 664 |
| 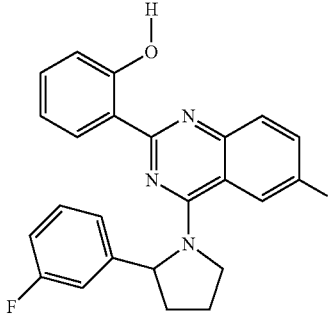 | 665 |

TABLE 2-continued
Examples of Compounds of Formula I:
| Compound | Cmpd # |
|---|---|
| 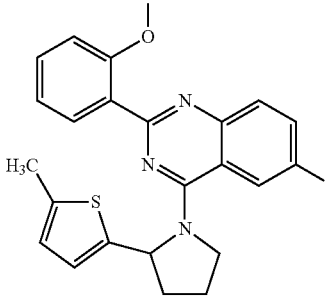 | 666 |
| 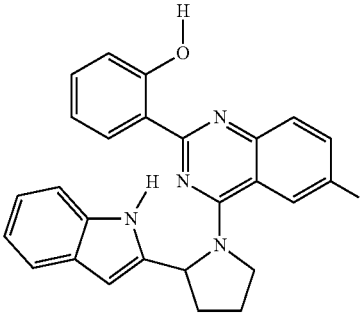 | 667 |
| 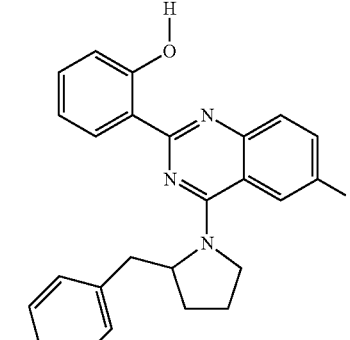 | 668 |
| 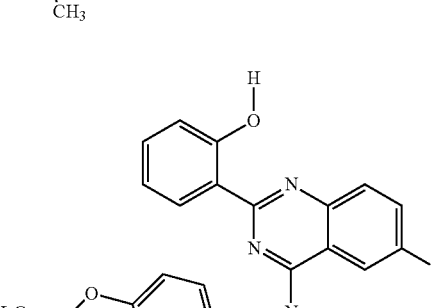 | 669 |

TABLE 2-continued

Examples of Compounds of Formula I:

| Compound | Cmpd # |
|---|---|
| | 670 |
| | 671 |
| | 672 |

TABLE 2-continued
Examples of Compounds of Formula I:
| Compound | Cmpd # |
|---|---|
| 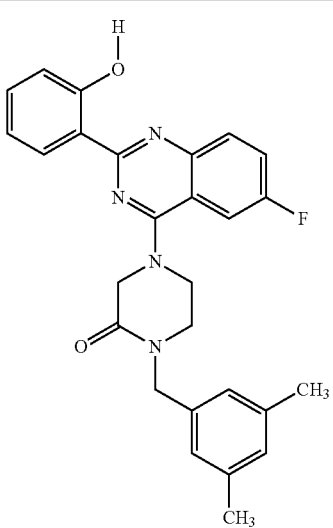 | 673 |
| 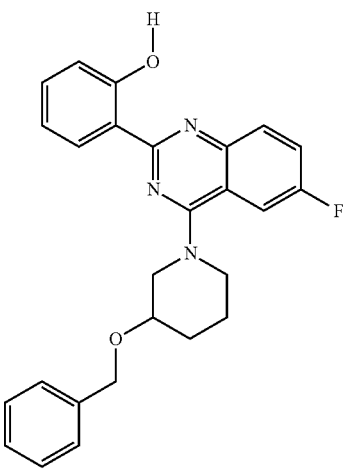 | 674 |
| 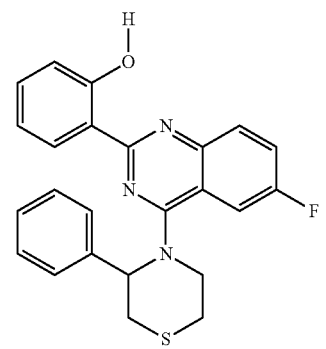 | 675 |

TABLE 2-continued

| Examples of Compounds of Formula I: | |
|---|---|
| Compound | Cmpd # |
| | 676 |
| | 677 |
| | 678 |

TABLE 2-continued

Examples of Compounds of Formula I:

| Compound | Cmpd # |
|---|---|
| | 679 |
| | 680 |
| | 681 |

TABLE 2-continued

| Examples of Compounds of Formula I: | |
|---|---|
| Compound | Cmpd # |
| (structure) | 682 |
| (structure) | 683 |
| (structure) | 684 |
| (structure) | 685 |

TABLE 2-continued
Examples of Compounds of Formula I:
| Compound | Cmpd # |
|---|---|
| 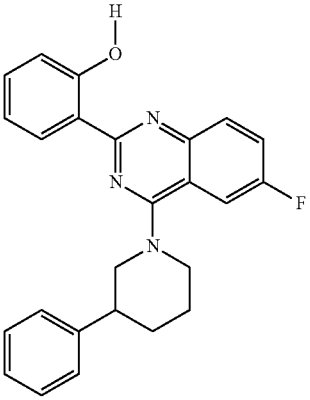 | 686 |
| 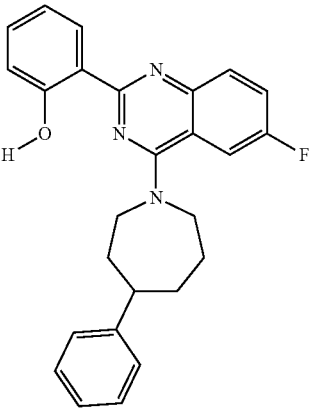 | 687 |
| 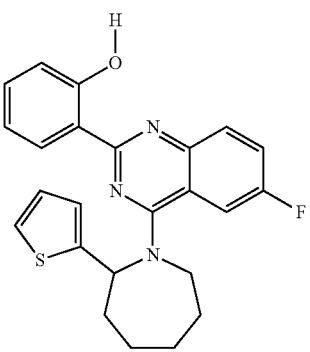 | 688 |
| 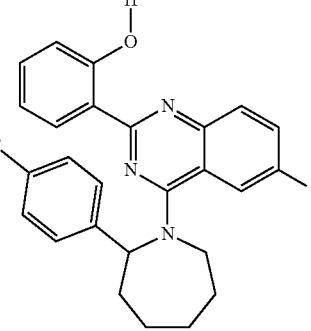 | 689 |

TABLE 2-continued

| Examples of Compounds of Formula I: | |
|---|---|
| Compound | Cmpd # |
| *(structure)* | 690 |
| *(structure)* | 691 |
| *(structure)* | 692 |
| *(structure)* | 693 |

TABLE 2-continued

Examples of Compounds of Formula I:

| Compound | Cmpd # |
|---|---|
| | 694 |
| | 695 |
| | 696 |
| | 697 |

TABLE 2-continued

Examples of Compounds of Formula I:

| Compound | Cmpd # |
|---|---|
| | 698 |
| | 699 |
| | 700 |
| | 701 |

TABLE 2-continued

Examples of Compounds of Formula I:

| Compound | Cmpd # |
|---|---|
|  | 702 |
|  | 703 |
|  | 704 |
|  | 705 |

TABLE 2-continued

Examples of Compounds of Formula I:

| Compound | Cmpd # |
|---|---|
| (structure) | 706 |
| (structure) | 707 |
| (structure) | 708 |
| (structure) | 709 |

TABLE 2-continued
Examples of Compounds of Formula I:
| Compound | Cmpd # |
|---|---|
| 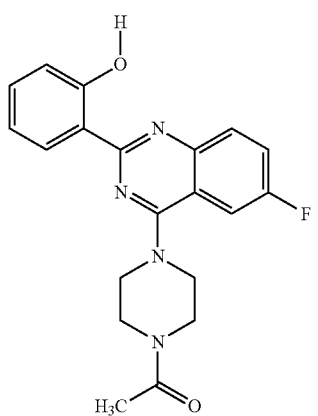 | 710 |
| 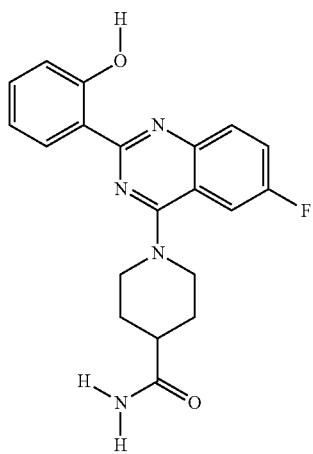 | 711 |
| | 712 |

TABLE 2-continued

| Examples of Compounds of Formula I: | |
|---|---|
| Compound | Cmpd # |
| | 713 |
| | 714 |
| | 715 |

TABLE 2-continued

Examples of Compounds of Formula I:

| Compound | Cmpd # |
|---|---|
| | 716 |
| | 717 |
| | 718 |

TABLE 2-continued
Examples of Compounds of Formula I:
| Compound | Cmpd # |
|---|---|
| 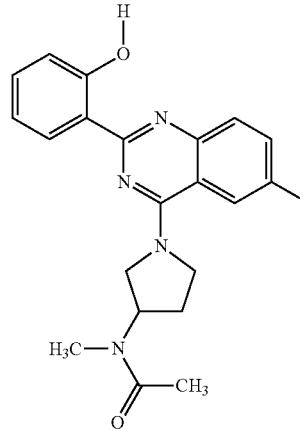 | 719 |
| 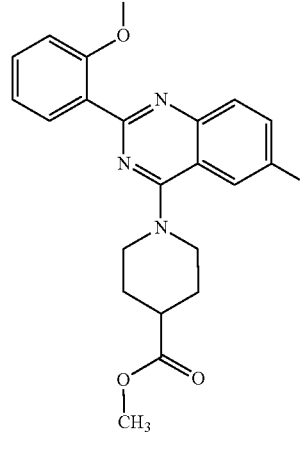 | 720 |
| 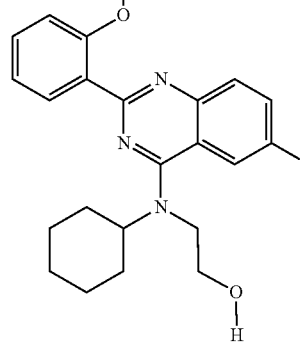 | 721 |

TABLE 2-continued

Examples of Compounds of Formula I:

| Compound | Cmpd # |
|---|---|
| | 722 |
| | 723 |
| | 724 |
| | 725 |

TABLE 2-continued
Examples of Compounds of Formula I:
| Compound | Cmpd # |
|---|---|
| 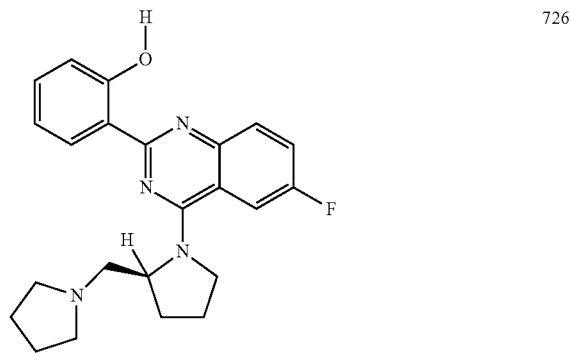 | 726 |
| 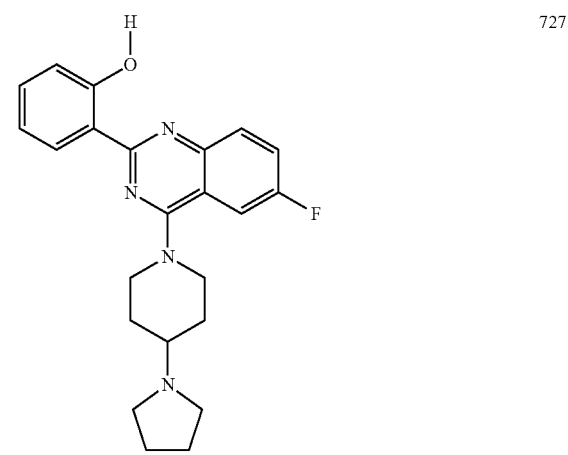 | 727 |
| 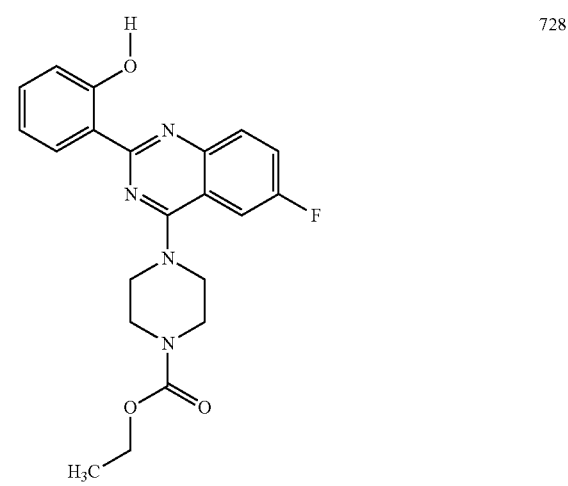 | 728 |

TABLE 2-continued
Examples of Compounds of Formula I:
| Compound | Cmpd # |
|---|---|
| 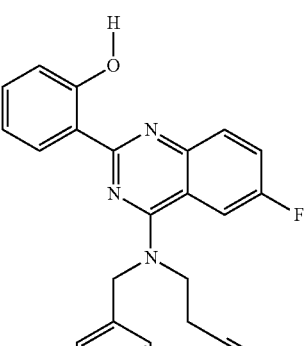 | 729 |
| | 730 |
| | 731 |

TABLE 2-continued

Examples of Compounds of Formula I:

| Compound | Cmpd # |
|---|---|
| (structure) | 732 |
| (structure) | 733 |
| (structure) | 734 |

TABLE 2-continued
Examples of Compounds of Formula I:
| Compound | Cmpd # |
|---|---|
| 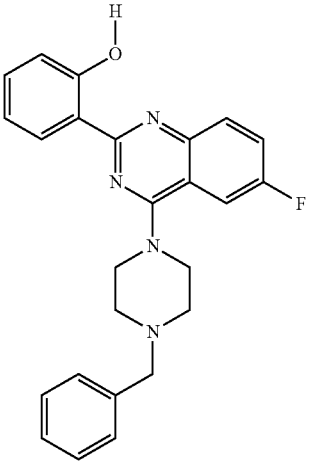 | 735 |
| 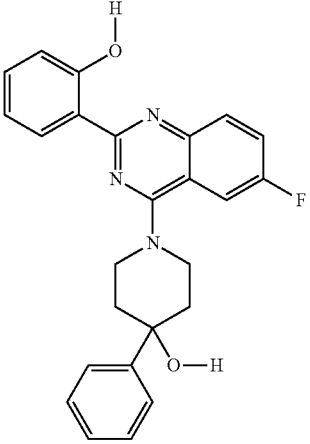 | 736 |
| 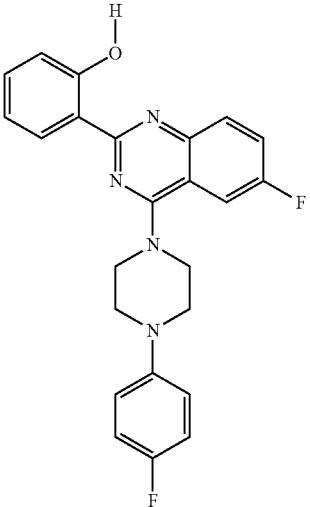 | 737 |

TABLE 2-continued

Examples of Compounds of Formula I:

| Compound | Cmpd # |
|---|---|
| | 738 |
| | 739 |
| | 740 |

TABLE 2-continued

Examples of Compounds of Formula I:

| Compound | Cmpd # |
|---|---|
|  | 741 |
|  | 742 |
|  | 743 |

TABLE 2-continued

Examples of Compounds of Formula I:

| Compound | Cmpd # |
|----------|--------|
| | 744 |
| | 745 |
| | 746 |

TABLE 2-continued
Examples of Compounds of Formula I:
| Compound | Cmpd # |
|---|---|
| 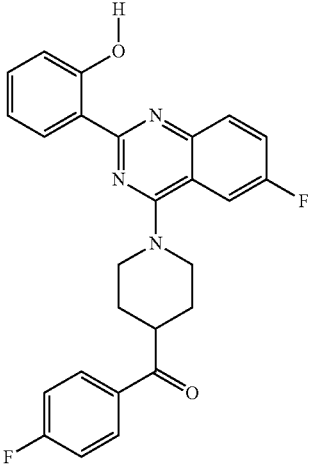 | 747 |
| 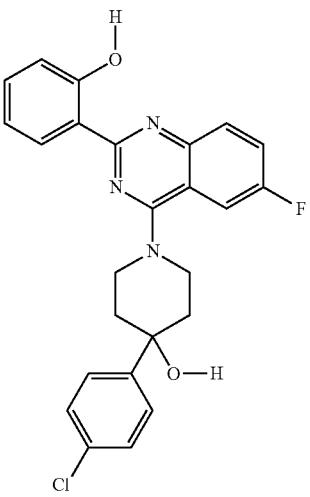 | 748 |
| 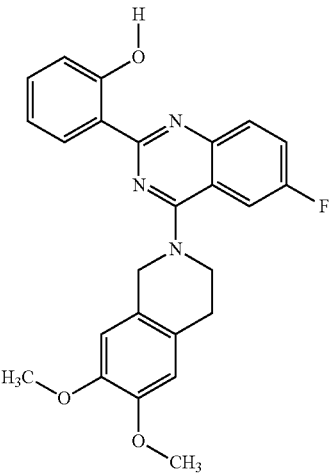 | 749 |

TABLE 2-continued
| Examples of Compounds of Formula I: | |
|---|---|
| Compound | Cmpd # |
| 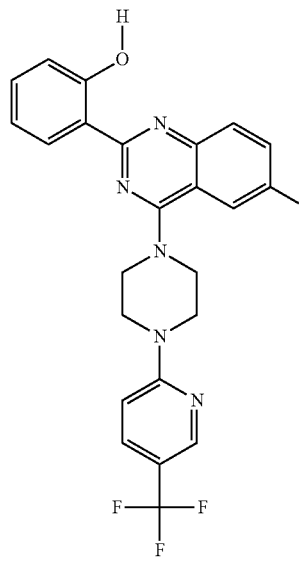 | 750 |
| 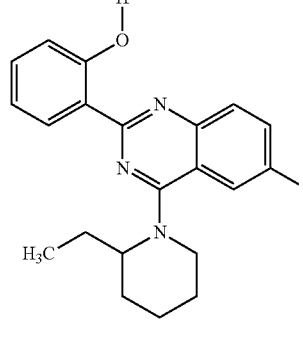 | 751 |
| 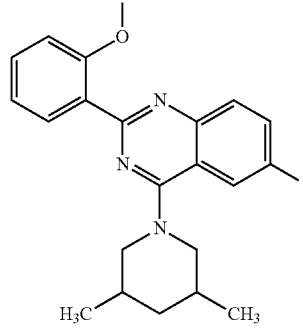 | 752 |

TABLE 2-continued
Examples of Compounds of Formula I:
| Compound | Cmpd # |
|---|---|
| 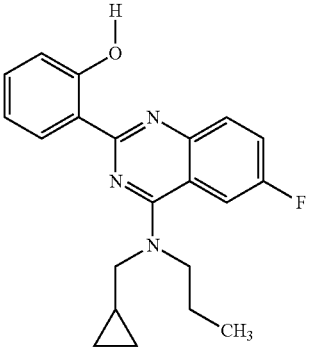 | 753 |
| 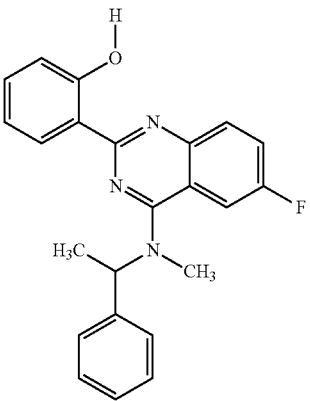 | 754 |
| 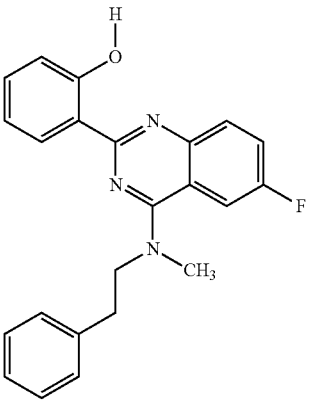 | 755 |
| 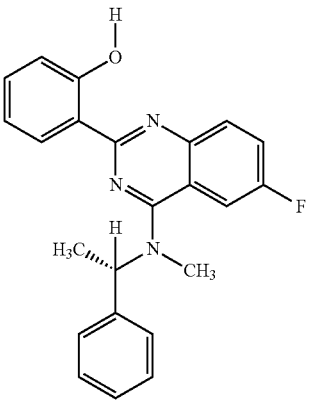 | 756 |

TABLE 2-continued
| Examples of Compounds of Formula I: | |
|---|---|
| Compound | Cmpd # |
| 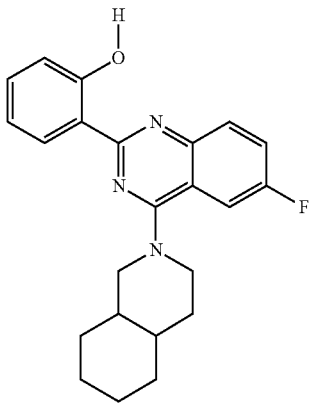 | 757 |
| 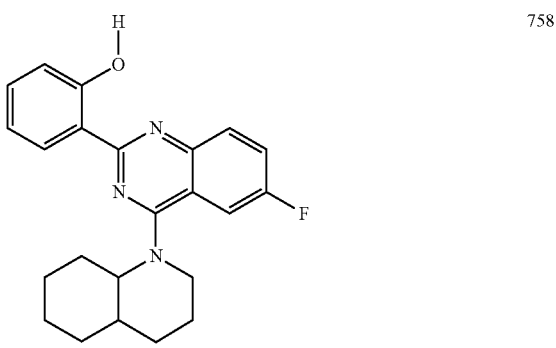 | 758 |
| 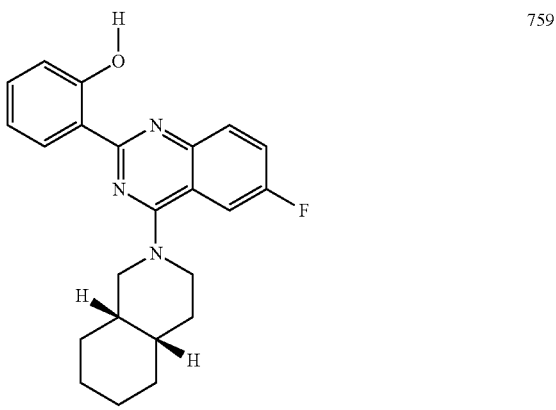 | 759 |

TABLE 2-continued
Examples of Compounds of Formula I:
| Compound | Cmpd # |
|---|---|
| 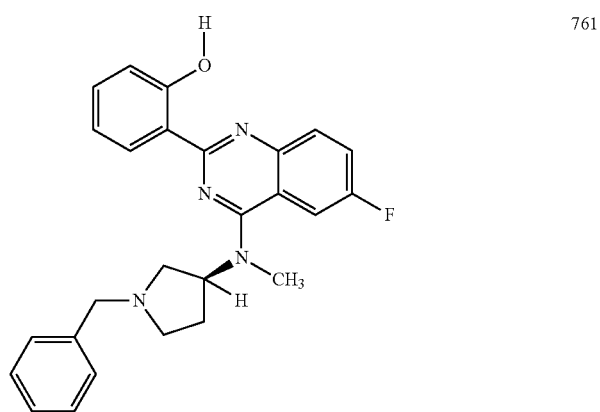 | 760 |
| 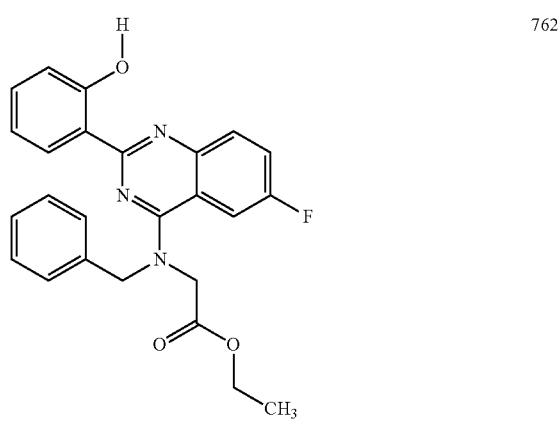 | 761 |
|  | 762 |

TABLE 2-continued

Examples of Compounds of Formula I:

| Compound | Cmpd # |
|---|---|
| | 763 |
| | 764 |
| | 765 |

TABLE 2-continued

| Examples of Compounds of Formula I: | |
|---|---|
| Compound | Cmpd # |
| (structure) | 766 |
| (structure) | 767 |
| (structure) | 768 |
| (structure) | 769 |

TABLE 2-continued
Examples of Compounds of Formula I:
| Compound | Cmpd # |
|---|---|
| 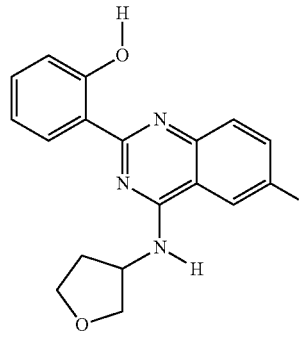 | 770 |
| 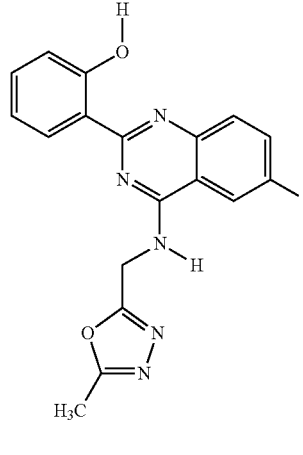 | 771 |
| 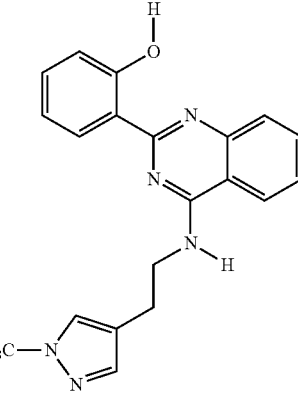 | 772 |

TABLE 2-continued

Examples of Compounds of Formula I:

| Compound | Cmpd # |
|---|---|
| | 773 |
| | 774 |
| | 775 |

TABLE 2-continued

Examples of Compounds of Formula I:

| Compound | Cmpd # |
|---|---|
| | 776 |
| | 777 |
| | 778 |

TABLE 2-continued

Examples of Compounds of Formula I:

| Compound | Cmpd # |
|---|---|
| | 779 |
| | 780 |
| | 781 |

TABLE 2-continued

| Examples of Compounds of Formula I: | |
|---|---|
| Compound | Cmpd # |
| [structure] | 782 |
| [structure] | 783 |
| [structure] | 784 |
| [structure] | 785 |

TABLE 2-continued

| Examples of Compounds of Formula I: | |
|---|---|
| Compound | Cmpd # |
| (structure) | 786 |
| (structure) | 787 |
| (structure) | 788 |
| (structure) | 789 |

TABLE 2-continued

| Examples of Compounds of Formula I: | |
|---|---|
| Compound | Cmpd # |
| | 790 |
| | 791 |
| | 792 |
| | 793 |

TABLE 2-continued
Examples of Compounds of Formula I:
| Compound | Cmpd # |
|---|---|
| 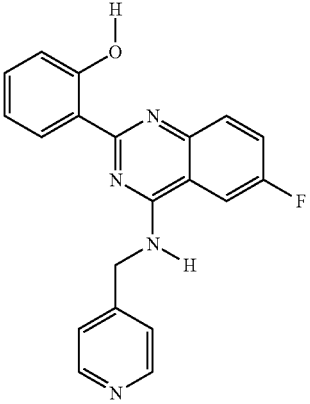 | 794 |
| 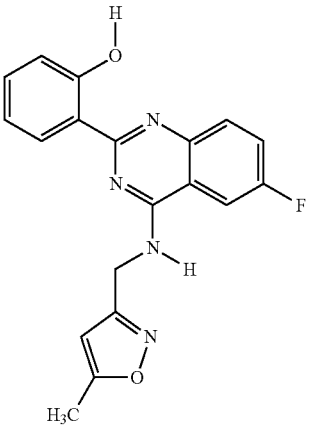 | 795 |
| 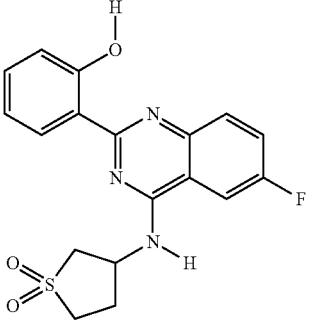 | 796 |
| 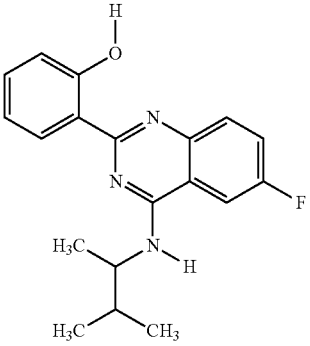 | 797 |

TABLE 2-continued

Examples of Compounds of Formula I:

| Compound | Cmpd # |
|---|---|
| | 798 |
| | 799 |
| | 800 |
| | 801 |

TABLE 2-continued
Examples of Compounds of Formula I:
| Compound | Cmpd # |
|---|---|
| 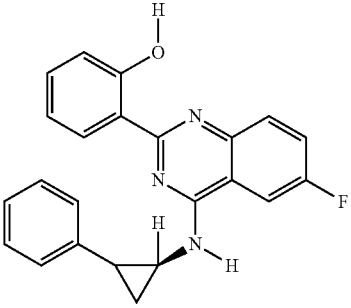 | 802 |
| 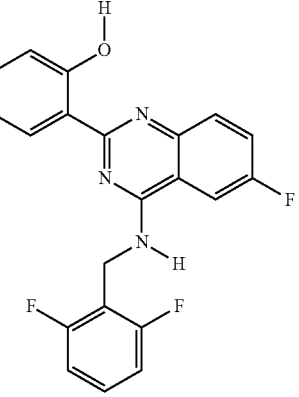 | 803 |
| 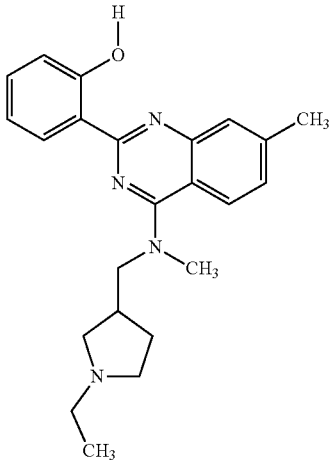 | 804 |

TABLE 2-continued

Examples of Compounds of Formula I:

| Compound | Cmpd # |
|---|---|
| (structure) | 805 |
| (structure) | 806 |
| (structure) | 807 |
| (structure) | 808 |

TABLE 2-continued

Examples of Compounds of Formula I:

| Compound | Cmpd # |
|---|---|
| | 809 |
| | 810 |
| | 811 |
| | 812 |

TABLE 2-continued

Examples of Compounds of Formula I:

| Compound | Cmpd # |
|---|---|
| | 813 |
| | 814 |
| | 815 |
| | 816 |

TABLE 2-continued

Examples of Compounds of Formula I:

| Compound | Cmpd # |
|---|---|
| | 817 |
| | 818 |
| | 819 |
| | 820 |

TABLE 2-continued

Examples of Compounds of Formula I:

| Compound | Cmpd # |
|---|---|
| | 821 |
| | 822 |
| | 823 |

TABLE 2-continued

| Examples of Compounds of Formula I: | |
|---|---|
| Compound | Cmpd # |
| | 824 |
| | 825 |
| | 826 |

TABLE 2-continued

Examples of Compounds of Formula I:

| Compound | Cmpd # |
|---|---|
| | 827 |
| | 828 |
| | 829 |

TABLE 2-continued

Examples of Compounds of Formula I:

| Compound | Cmpd # |
|---|---|
| | 830 |
| | 831 |
| | 832 |
| | 833 |

TABLE 2-continued

Examples of Compounds of Formula I:

| Compound | Cmpd # |
|---|---|
| | 834 |
| | 835 |
| | 836 |
| | 837 |

TABLE 2-continued
Examples of Compounds of Formula I:
| Compound | Cmpd # |
|---|---|
| 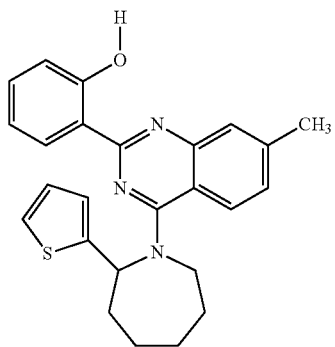 | 838 |
| 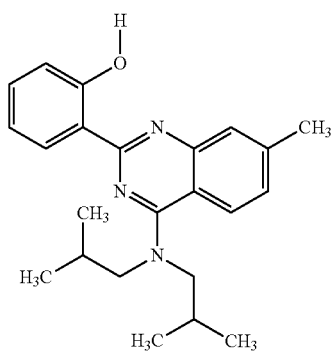 | 839 |
| 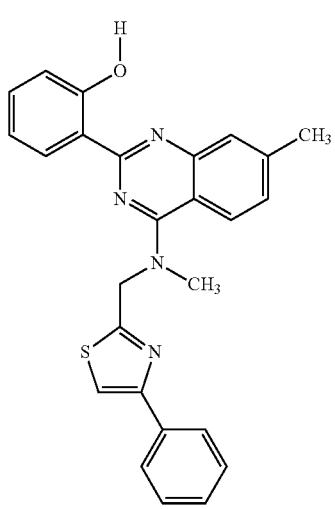 | 840 |

TABLE 2-continued

Examples of Compounds of Formula I:

| Compound | Cmpd # |
|---|---|
| | 841 |
| | 842 |
| | 843 |
| | 844 |

TABLE 2-continued
Examples of Compounds of Formula I:
| Compound | Cmpd # |
|---|---|
| 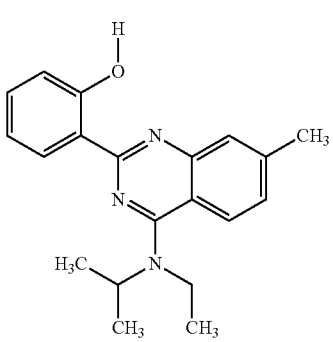 | 845 |
| 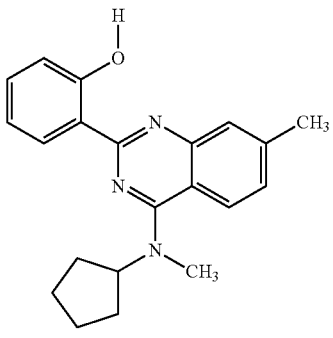 | 846 |
| 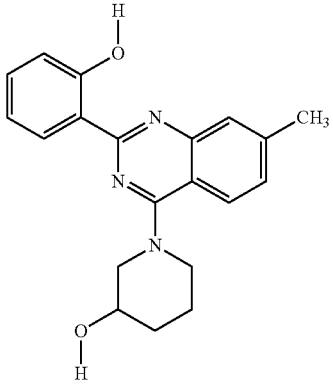 | 847 |
| 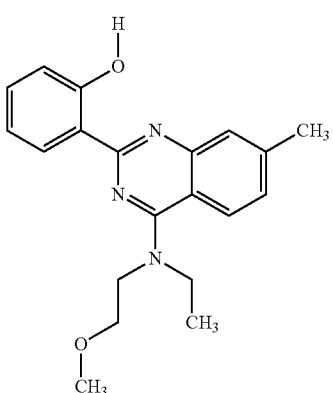 | 848 |

TABLE 2-continued
Examples of Compounds of Formula I:
| Compound | Cmpd # |
|---|---|
| 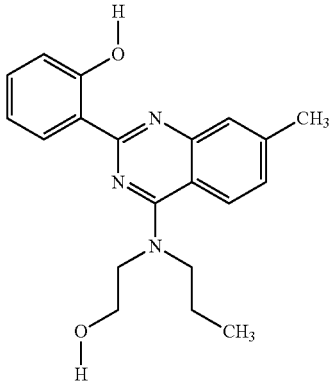 | 849 |
| 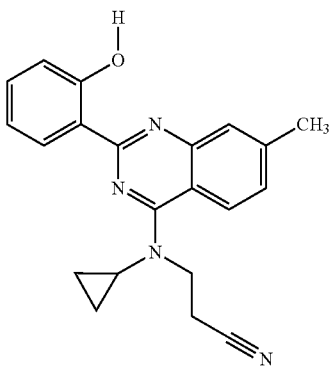 | 850 |
| 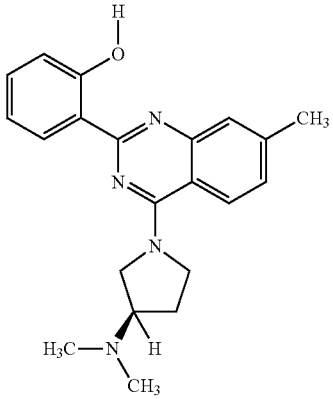 | 851 |
| 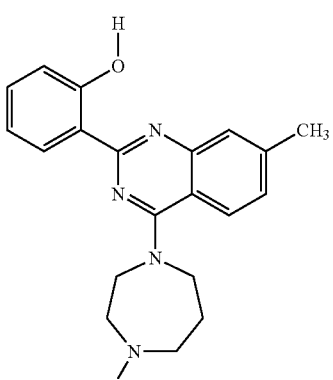 | 852 |

TABLE 2-continued

Examples of Compounds of Formula I:

| Compound | Cmpd # |
|---|---|
| | 853 |
| | 854 |
| | 855 |
| | 856 |

TABLE 2-continued
Examples of Compounds of Formula I:
| Compound | Cmpd # |
|---|---|
| 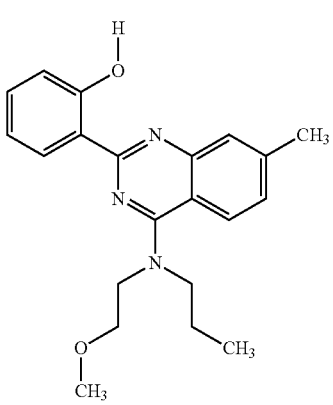 | 857 |
| 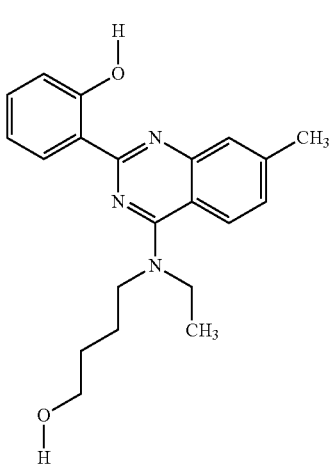 | 858 |
| 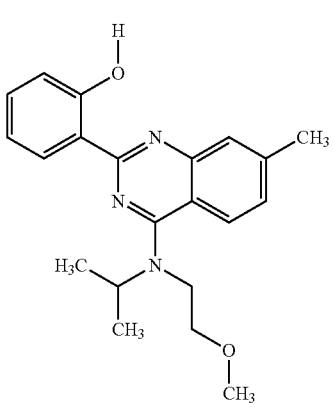 | 859 |

TABLE 2-continued

Examples of Compounds of Formula I:

| Compound | Cmpd # |
|---|---|
| | 860 |
| | 861 |
| | 862 |

TABLE 2-continued

Examples of Compounds of Formula I:

| Compound | Cmpd # |
|---|---|
| | 863 |
| | 864 |
| | 865 |
| | 866 |

TABLE 2-continued

Examples of Compounds of Formula I:

| Compound | Cmpd # |
|---|---|
| | 867 |
| | 868 |
| | 869 |

TABLE 2-continued

| Examples of Compounds of Formula I: | |
|---|---|
| Compound | Cmpd # |
| (structure) | 870 |
| (structure) | 871 |
| (structure) | 872 |

TABLE 2-continued

Examples of Compounds of Formula I:

| Compound | Cmpd # |
|---|---|
| | 873 |
| | 874 |
| | 875 |

TABLE 2-continued
Examples of Compounds of Formula I:
| Compound | Cmpd # |
|---|---|
| 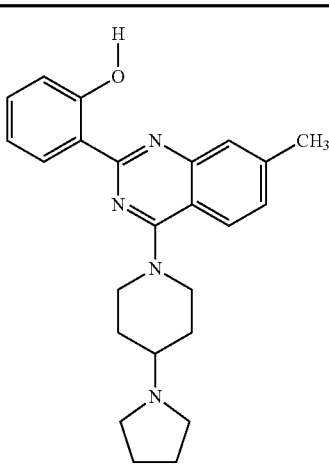 | 876 |
| 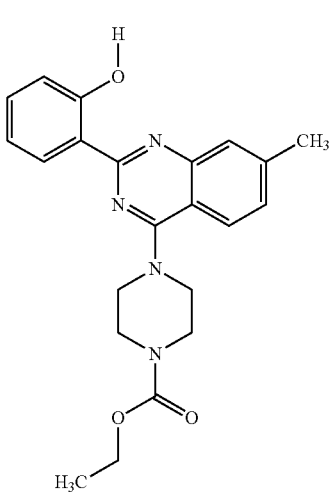 | 877 |
| 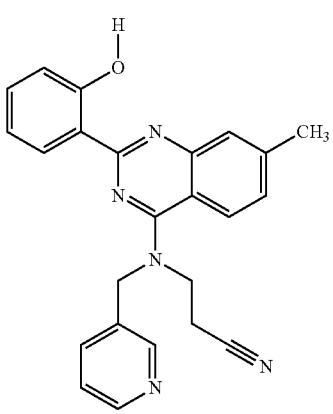 | 878 |

TABLE 2-continued
Examples of Compounds of Formula I:
| Compound | Cmpd # |
|---|---|
| 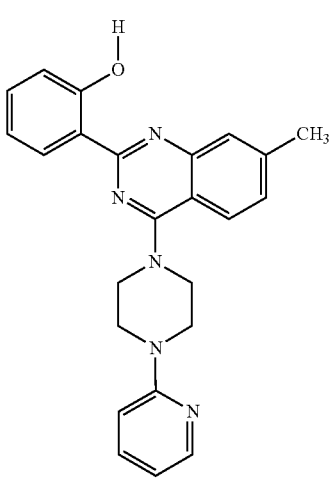 | 879 |
| 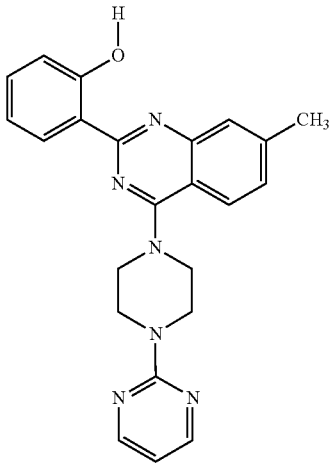 | 880 |
| 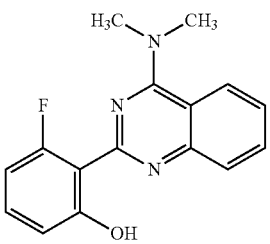 | 881 |

TABLE 2-continued
Examples of Compounds of Formula I:
| Compound | Cmpd # |
|---|---|
| 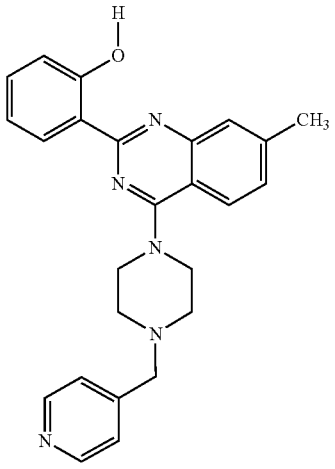 | 882 |
| 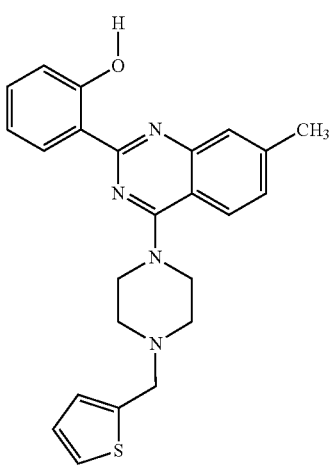 | 883 |
| 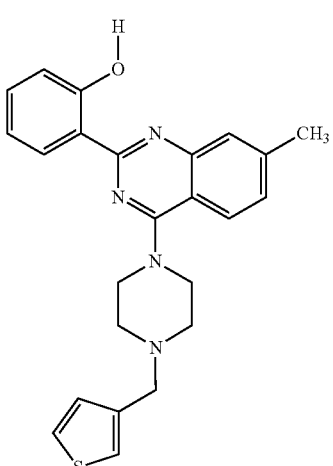 | 884 |

TABLE 2-continued

Examples of Compounds of Formula I:

| Compound | Cmpd # |
|---|---|
| | 885 |
| | 886 |
| | 887 |

TABLE 2-continued

Examples of Compounds of Formula I:

| Compound | Cmpd # |
|---|---|
| | 888 |
| | 889 |
| | 890 |

TABLE 2-continued

Examples of Compounds of Formula I:

| Compound | Cmpd # |
|---|---|
| | 891 |
| | 892 |
| | 893 |

TABLE 2-continued

Examples of Compounds of Formula I:

| Compound | Cmpd # |
|---|---|
| | 894 |
| | 895 |
| | 896 |

TABLE 2-continued
Examples of Compounds of Formula I:
| Compound | Cmpd # |
|---|---|
| 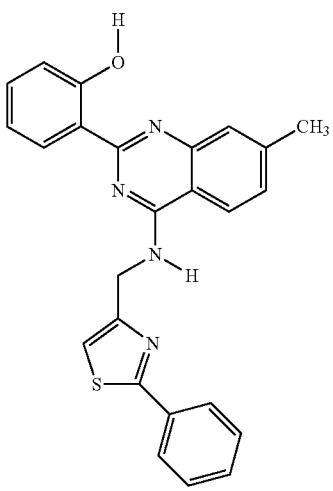 | 897 |
| 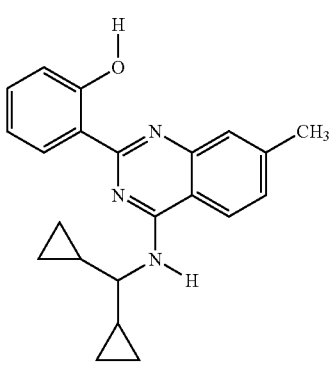 | 898 |
| 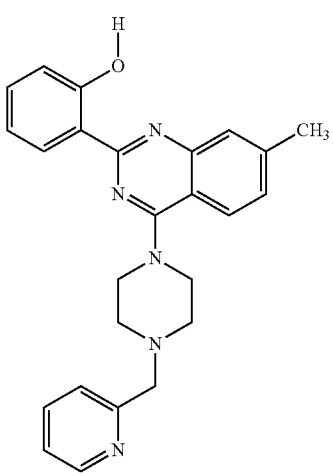 | 899 |

TABLE 2-continued
Examples of Compounds of Formula I:
| Compound | Cmpd # |
|---|---|
| 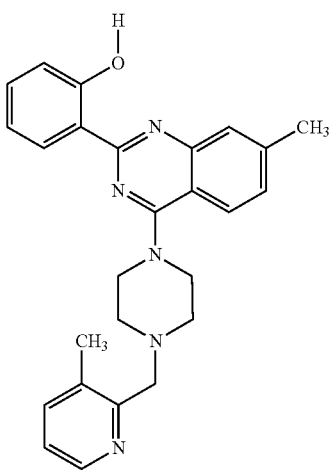 | 900 |
| 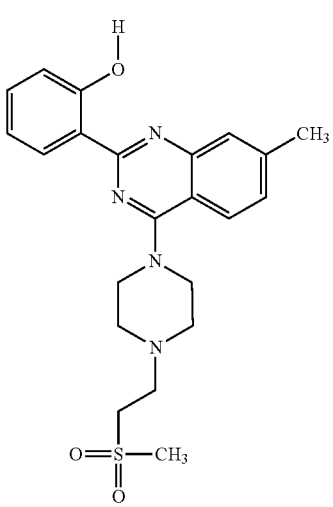 | 901 |
| 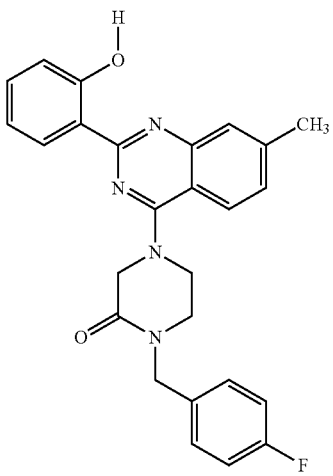 | 902 |

TABLE 2-continued

Examples of Compounds of Formula I:

| Compound | Cmpd # |
|---|---|
| (structure) | 903 |
| (structure) | 904 |
| (structure) | 905 |

TABLE 2-continued
Examples of Compounds of Formula I:
| Compound | Cmpd # |
|---|---|
| 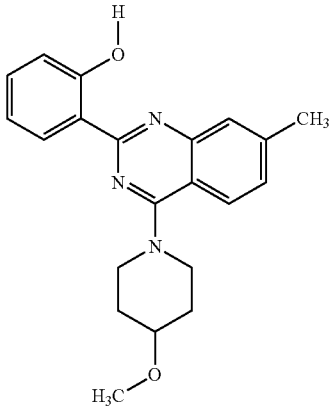 | 906 |
| 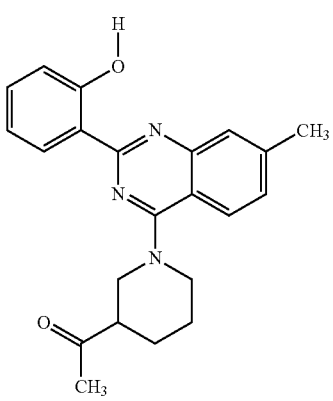 | 907 |
| 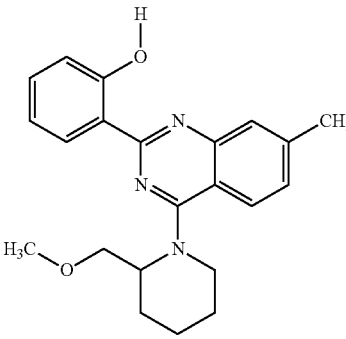 | 908 |
| 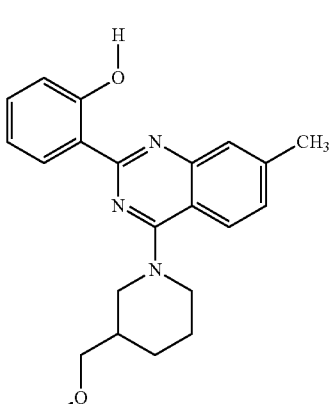 | 909 |

TABLE 2-continued
Examples of Compounds of Formula I:
| Compound | Cmpd # |
|---|---|
| 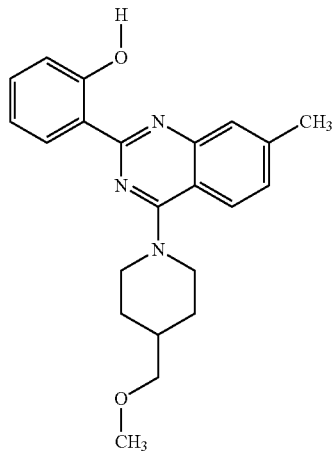 | 910 |
| 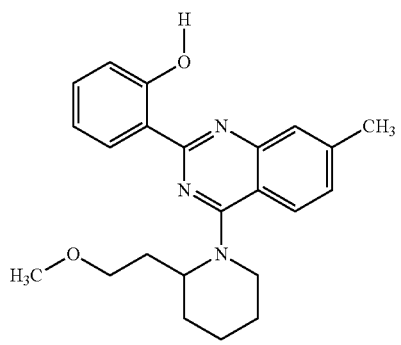 | 911 |
| 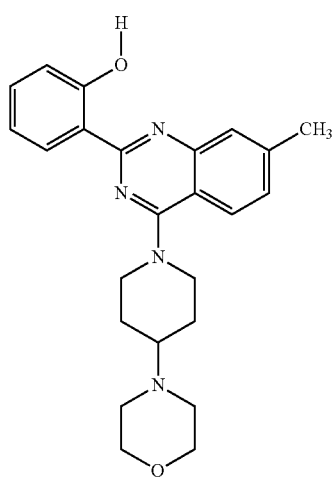 | 912 |

TABLE 2-continued

Examples of Compounds of Formula I:

| Compound | Cmpd # |
|---|---|
| (structure) | 913 |
| (structure) | 914 |
| (structure) | 915 |

TABLE 2-continued

Examples of Compounds of Formula I:

| Compound | Cmpd # |
|---|---|
| | 916 |
| | 917 |
| | 918 |

TABLE 2-continued

Examples of Compounds of Formula I:

| Compound | Cmpd # |
|---|---|
| | 919 |
| | 920 |
| | 921 |

TABLE 2-continued

Examples of Compounds of Formula I:

| Compound | Cmpd # |
|---|---|
| | 922 |
| | 923 |
| | 924 |
| | 925 |

TABLE 2-continued
Examples of Compounds of Formula I:
| Compound | Cmpd # |
|---|---|
| 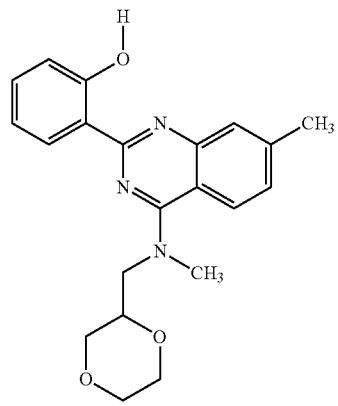 | 926 |
| 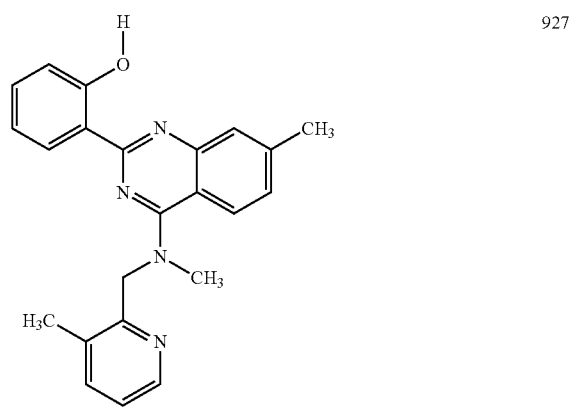 | 927 |
| 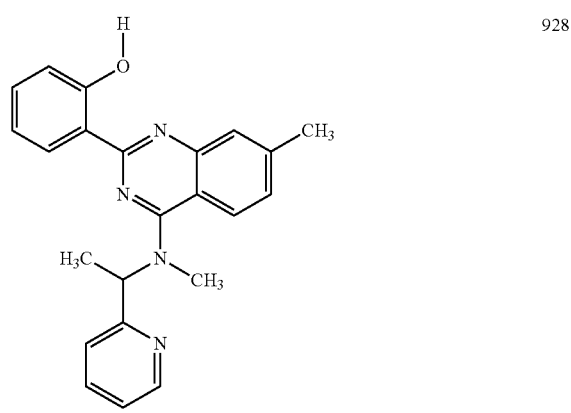 | 928 |

TABLE 2-continued

Examples of Compounds of Formula I:

| Compound | Cmpd # |
|---|---|
| | 929 |
| | 930 |
| | 931 |

TABLE 2-continued

Examples of Compounds of Formula I:

| Compound | Cmpd # |
|---|---|
| | 932 |
| | 933 |
| | 934 |

TABLE 2-continued

| Examples of Compounds of Formula I: | |
|---|---|
| Compound | Cmpd # |
| | 935 |
| | 936 |
| | 937 |

TABLE 2-continued

Examples of Compounds of Formula I:

| Compound | Cmpd # |
|---|---|
| (structure) | 938 |
| (structure) | 939 |
| (structure) | 940 |

TABLE 2-continued

Examples of Compounds of Formula I:

| Compound | Cmpd # |
|---|---|
| | 941 |
| | 942 |
| | 943 |

TABLE 2-continued

Examples of Compounds of Formula I:

| Compound | Cmpd # |
|---|---|
| | 944 |
| | 945 |
| | 946 |

TABLE 2-continued
Examples of Compounds of Formula I:
| Compound | Cmpd # |
|---|---|
| 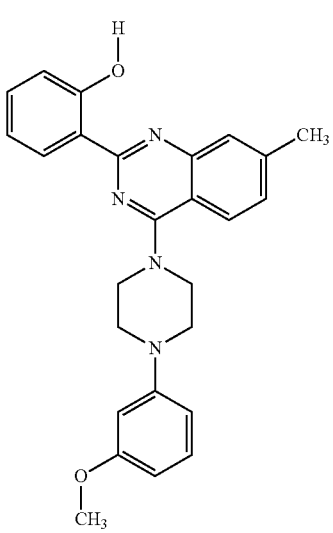 | 947 |
| 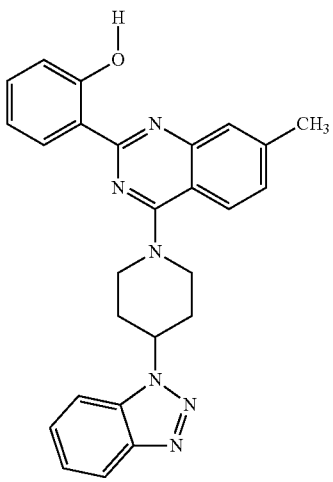 | 948 |
| 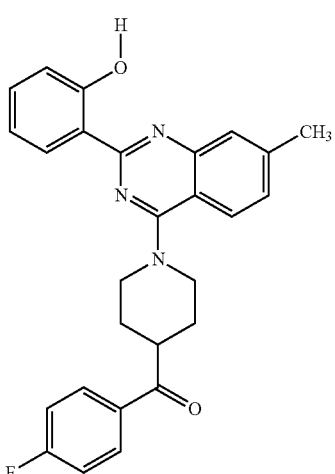 | 949 |

TABLE 2-continued

Examples of Compounds of Formula I:

| Compound | Cmpd # |
|---|---|
| (structure) | 950 |
| (structure) | 951 |
| (structure) | 952 |
| (structure) | 953 |

TABLE 2-continued

Examples of Compounds of Formula I:

| Compound | Cmpd # |
|---|---|
| | 954 |
| | 955 |
| | 956 |

TABLE 2-continued
Examples of Compounds of Formula I:
| Compound | Cmpd # |
|---|---|
| 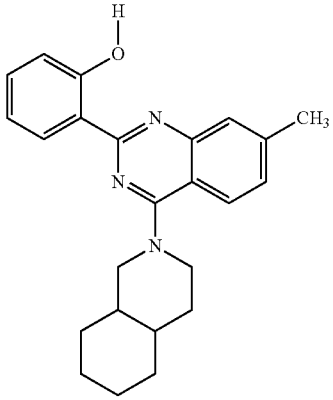 | 957 |
| 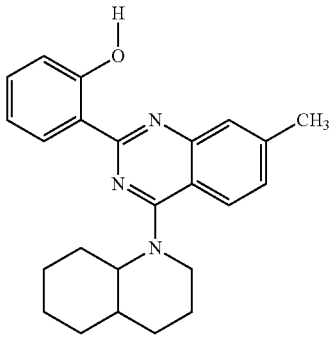 | 958 |
| 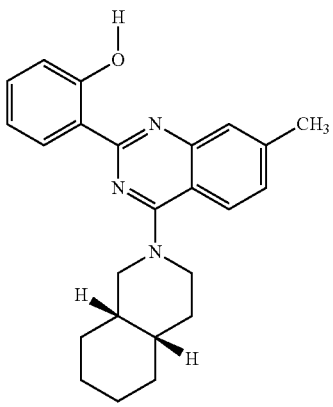 | 959 |

TABLE 2-continued

Examples of Compounds of Formula I:

| Compound | Cmpd # |
|---|---|
| 2-(7-methylquinazolin-4-yl)-4-(4-fluorophenyl)-1,2,3,6-tetrahydropyridine substituted with 2-hydroxyphenyl structure | 960 |
| (R)-1-benzyl-N-methyl-N-(2-(2-hydroxyphenyl)-7-methylquinazolin-4-yl)pyrrolidin-3-amine structure | 961 |
| N-(3,4-dimethoxyphenethyl)-N-methyl-2-(2-hydroxyphenyl)-7-methylquinazolin-4-amine structure | 962 |

TABLE 2-continued

Examples of Compounds of Formula I:

| Compound | Cmpd # |
|---|---|
| | 963 |
| | 964 |
| | 965 |

TABLE 2-continued

Examples of Compounds of Formula I:

| Compound | Cmpd # |
|---|---|
| | 966 |
| | 967 |
| | 968 |
| | 969 |

TABLE 2-continued
| Examples of Compounds of Formula I: | |
|---|---|
| Compound | Cmpd # |
| 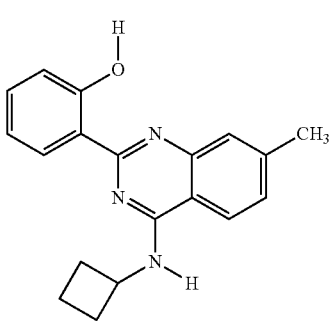 | 970 |
| 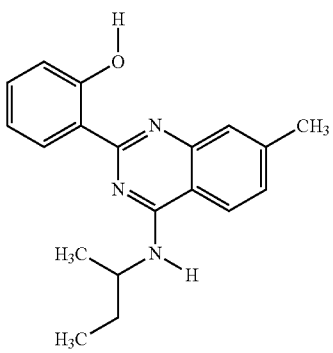 | 971 |
| 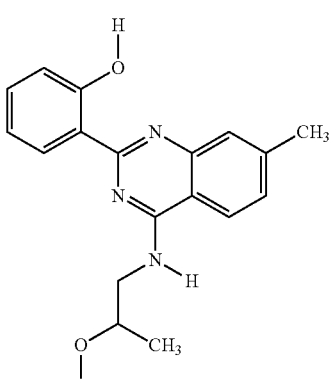 | 972 |
| 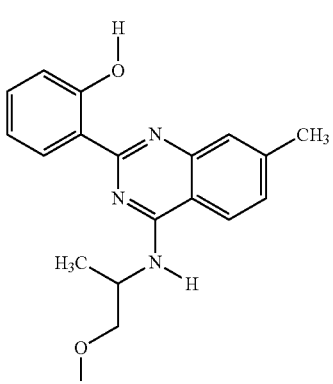 | 973 |

TABLE 2-continued

Examples of Compounds of Formula I:

| Compound | Cmpd # |
|---|---|
| | 974 |
| | 975 |
| | 976 |
| | 977 |

TABLE 2-continued
Examples of Compounds of Formula I:
| Compound | Cmpd # |
|---|---|
| 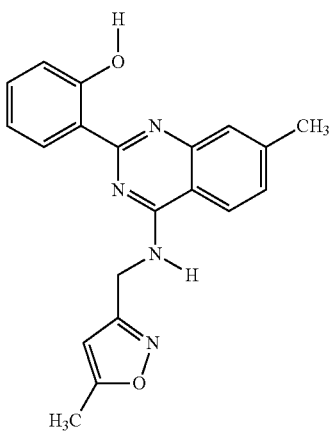 | 978 |
| 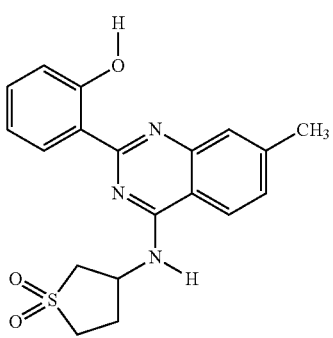 | 979 |
| 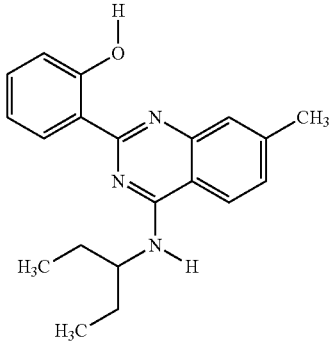 | 980 |
| 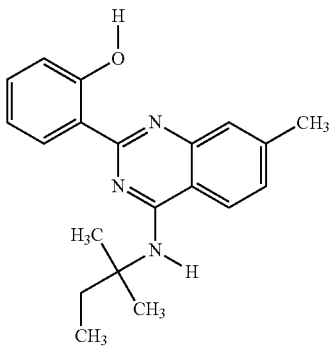 | 981 |

TABLE 2-continued

Examples of Compounds of Formula I:

| Compound | Cmpd # |
|---|---|
| | 982 |
| | 983 |
| | 984 |
| | 985 |

TABLE 2-continued
Examples of Compounds of Formula I:
| Compound | Cmpd # |
|---|---|
| 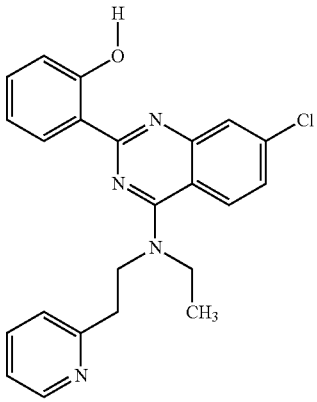 | 986 |
| 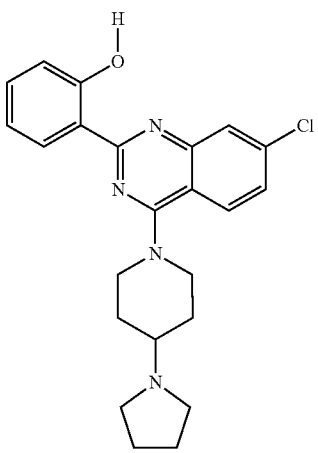 | 987 |
| 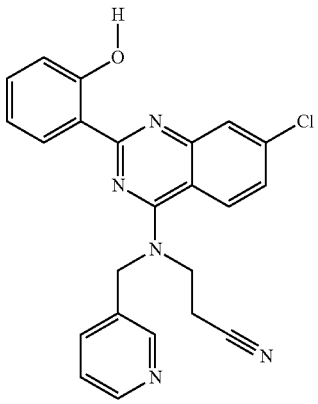 | 988 |

TABLE 2-continued
| Examples of Compounds of Formula I: | |
|---|---|
| Compound | Cmpd # |
| 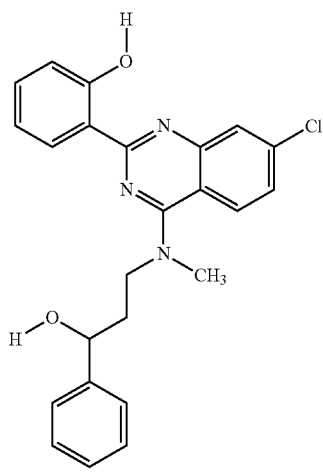 | 989 |
| 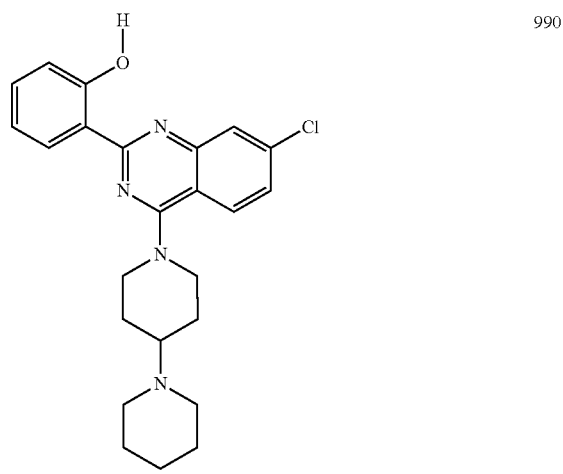 | 990 |
| 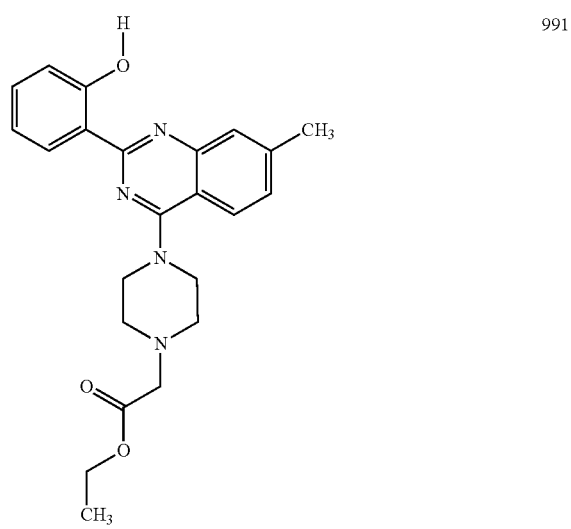 | 991 |

TABLE 2-continued

| Examples of Compounds of Formula I: | |
|---|---|
| Compound | Cmpd # |
| | 992 |
| | 993 |
| | 994 |

TABLE 2-continued

Examples of Compounds of Formula I:

| Compound | Cmpd # |
|---|---|
|  | 995 |
|  | 996 |
|  | 997 |

TABLE 2-continued

Examples of Compounds of Formula I:

| Compound | Cmpd # |
|---|---|
| | 998 |
| | 999 |
| | 1000 |

TABLE 2-continued

Examples of Compounds of Formula I:

| Compound | Cmpd # |
|---|---|
| | 1001 |
| | 1002 |
| | 1003 |

TABLE 2-continued

Examples of Compounds of Formula I:

| Compound | Cmpd # |
|---|---|
| (structure) | 1004 |
| (structure) | 1005 |
| (structure) | 1006 |

TABLE 2-continued
Examples of Compounds of Formula I:
| Compound | Cmpd # |
|---|---|
| 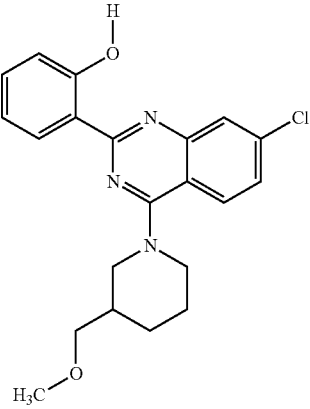 | 1007 |
| 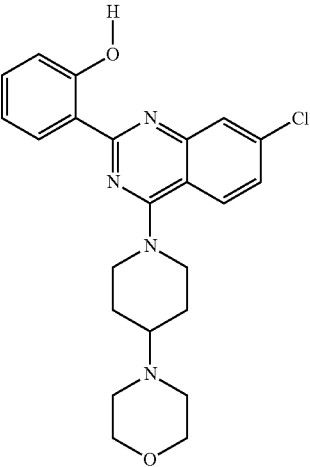 | 1008 |
| 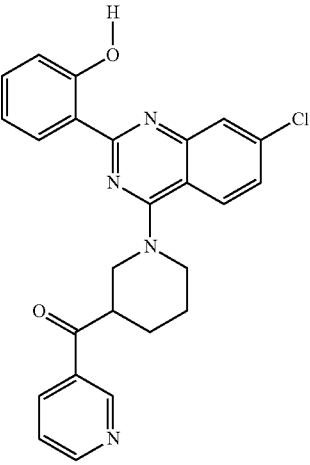 | 1009 |

TABLE 2-continued

Examples of Compounds of Formula I:

| Compound | Cmpd # |
|---|---|
| | 1010 |
| | 1011 |
| | 1012 |

TABLE 2-continued
Examples of Compounds of Formula I:
| Compound | Cmpd # |
|---|---|
| 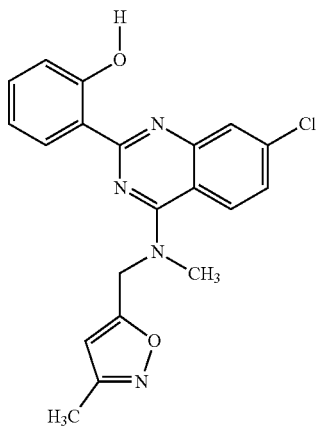 | 1013 |
| 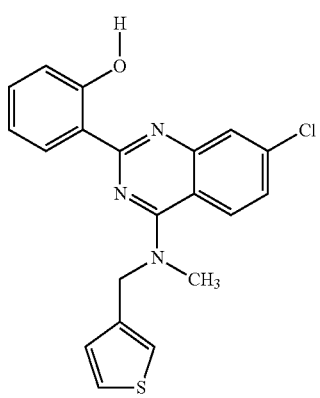 | 1014 |
| 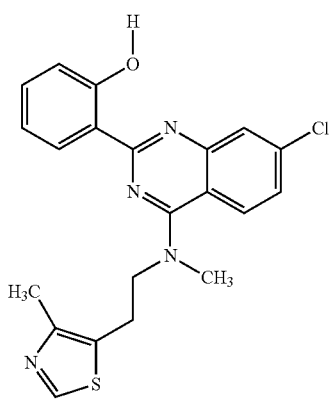 | 1015 |

TABLE 2-continued
Examples of Compounds of Formula I:
| Compound | Cmpd # |
|---|---|
| 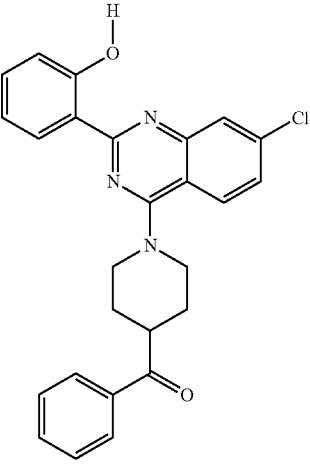 | 1016 |
| 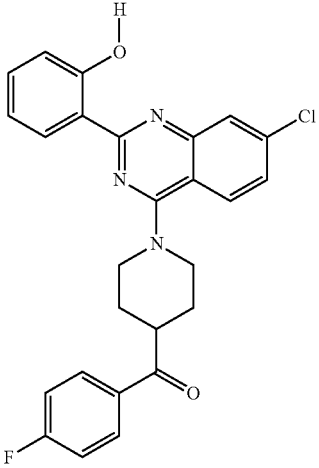 | 1017 |
| 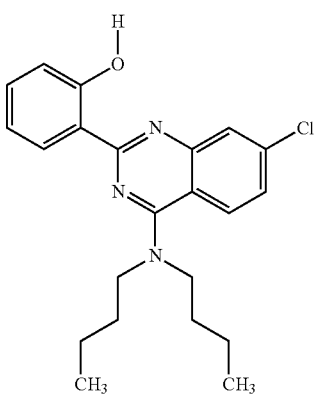 | 1018 |

TABLE 2-continued
Examples of Compounds of Formula I:
| Compound | Cmpd # |
|---|---|
| 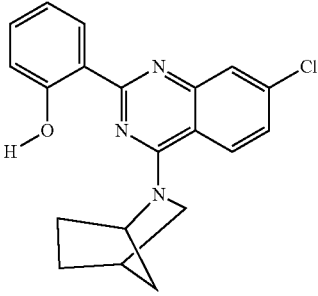 | 1019 |
| 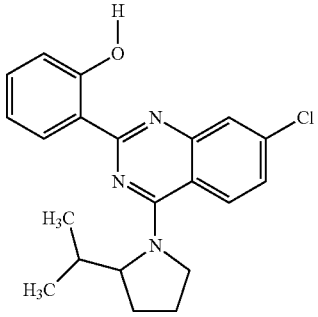 | 1020 |
| 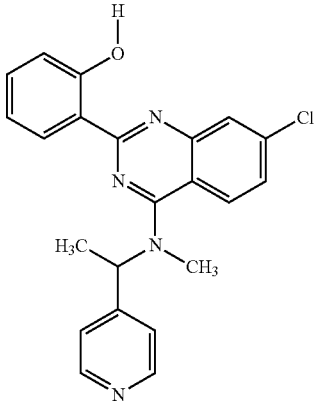 | 1021 |
| 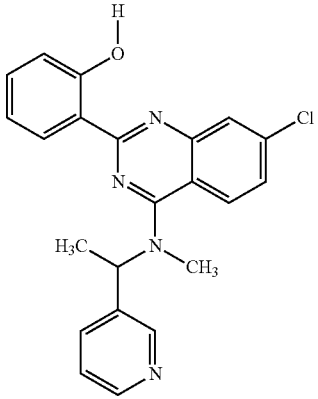 | 1022 |

TABLE 2-continued

| Examples of Compounds of Formula I: | |
|---|---|
| Compound | Cmpd # |
| *(structure)* | 1023 |
| *(structure)* | 1024 |
| *(structure)* | 1025 |
| *(structure)* | 1026 |

TABLE 2-continued

Examples of Compounds of Formula I:

| Compound | Cmpd # |
|---|---|
| | 1027 |
| | 1028 |
| | 1029 |
| | 1030 |

TABLE 2-continued

Examples of Compounds of Formula I:

| Compound | Cmpd # |
|---|---|
| (structure) | 1031 |
| (structure) | 1032 |
| (structure) | 1033 |
| (structure) | 1034 |

TABLE 2-continued

| Examples of Compounds of Formula I: | |
|---|---|
| Compound | Cmpd # |
| | 1035 |
| | 1036 |
| | 1037 |
| | 1038 |

TABLE 2-continued

Examples of Compounds of Formula I:

| Compound | Cmpd # |
|---|---|
| | 1039 |
| | 1040 |
| | 1041 |
| | 1042 |

TABLE 2-continued

Examples of Compounds of Formula I:

| Compound | Cmpd # |
|---|---|
| | 1043 |
| | 1044 |
| | 1045 |
| | 1046 |
| | 1047 |

TABLE 2-continued
Examples of Compounds of Formula I:
| Compound | Cmpd # |
|---|---|
| 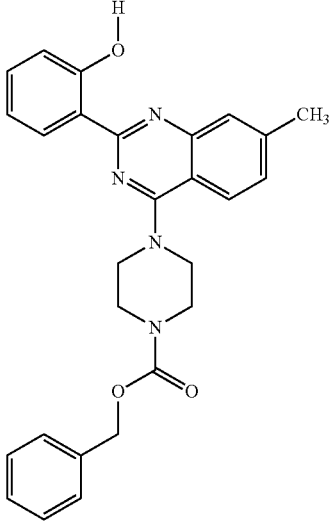 | 1048 |
| 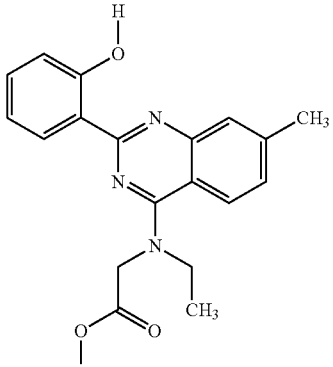 | 1049 |
| 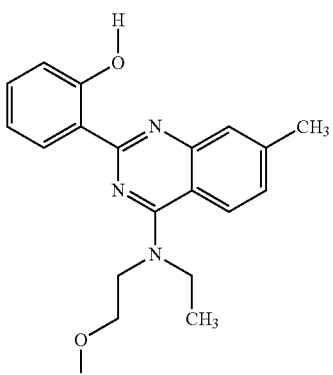 | 1050 |

TABLE 2-continued
Examples of Compounds of Formula I:
| Compound | Cmpd # |
|---|---|
| 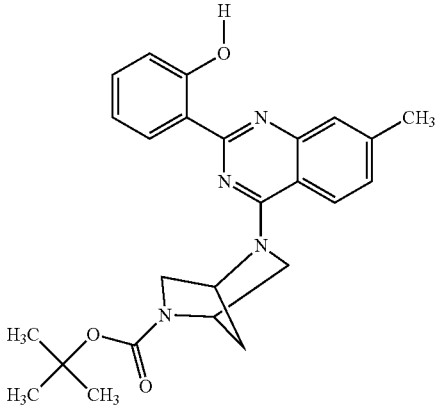 | 1051 |
| 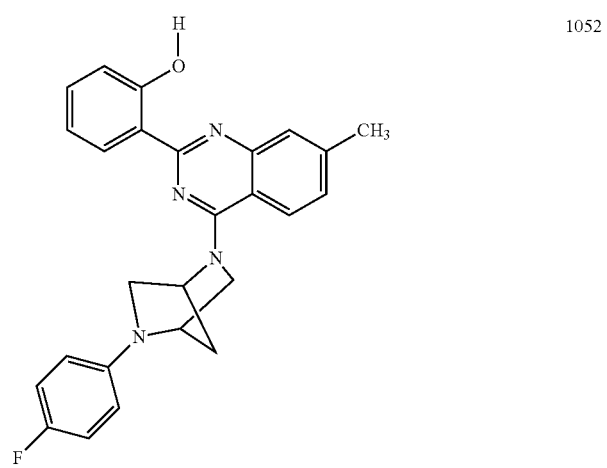 | 1052 |
| 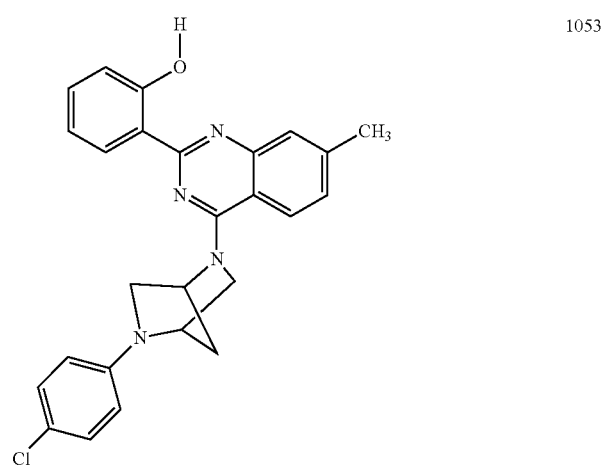 | 1053 |

TABLE 2-continued
Examples of Compounds of Formula I:
| Compound | Cmpd # |
|---|---|
| 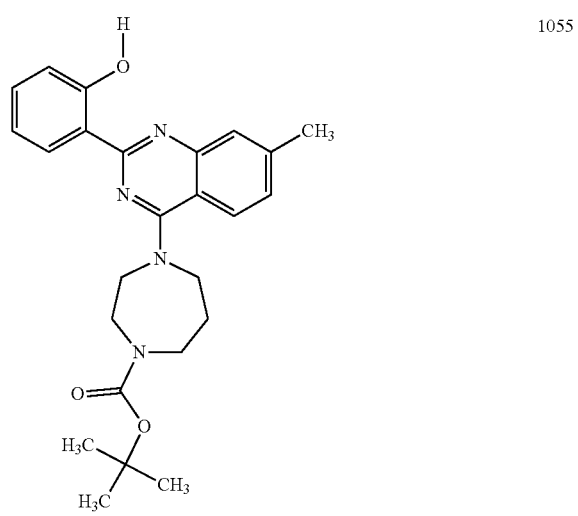 | 1054 |
| 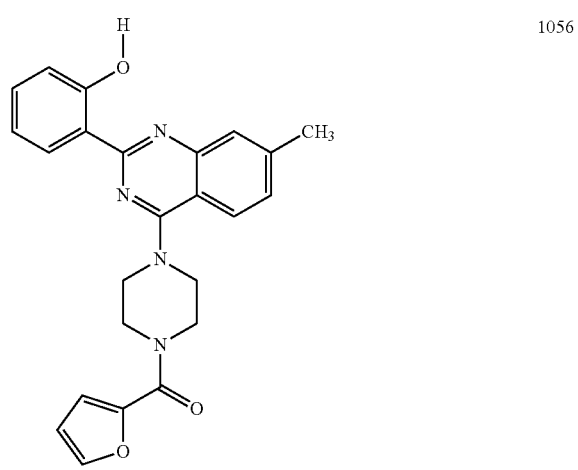 | 1055 |
| | 1056 |

TABLE 2-continued

Examples of Compounds of Formula I:

| Compound | Cmpd # |
|---|---|
| | 1057 |
| | 1058 |
| | 1059 |

TABLE 2-continued

Examples of Compounds of Formula I:

| Compound | Cmpd # |
|---|---|
| | 1060 |
| | 1061 |
| | 1062 |
| | 1063 |

TABLE 2-continued

Examples of Compounds of Formula I:

| Compound | Cmpd # |
|---|---|
| | 1064 |
| | 1065 |
| | 1066 |
| | 1067 |

TABLE 2-continued

Examples of Compounds of Formula I:

| Compound | Cmpd # |
|---|---|
| | 1068 |
| | 1069 |
| | 1070 |
| | 1071 |

TABLE 2-continued

Examples of Compounds of Formula I:

| Compound | Cmpd # |
|---|---|
| | 1072 |
| | 1073 |
| | 1074 |
| | 1075 |

TABLE 2-continued
Examples of Compounds of Formula I:
| Compound | Cmpd # |
|---|---|
| 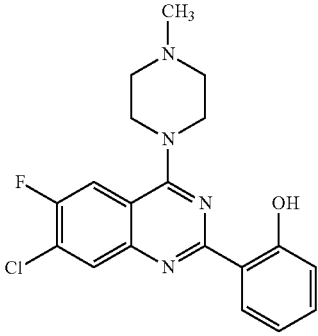 | 1076 |
| 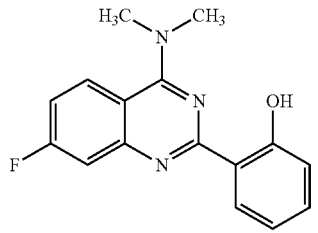 | 1077 |
| 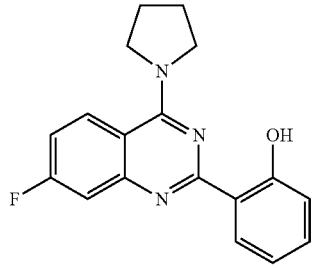 | 1078 |
| 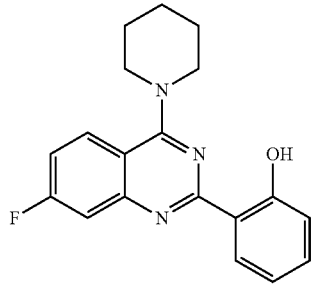 | 1079 |
| 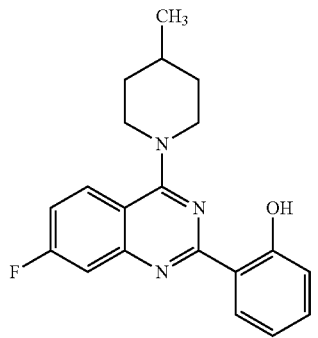 | 1080 |

TABLE 2-continued

Examples of Compounds of Formula I:

| Compound | Cmpd # |
|---|---|
| | 1081 |
| | 1082 |
| | 1083 |
| | 1084 |
| | 1085 |

TABLE 2-continued

Examples of Compounds of Formula I:

| Compound | Cmpd # |
|---|---|
| | 1086 |
| | 1087 |
| | 1088 |
| | 1089 |

TABLE 2-continued

| Examples of Compounds of Formula I: | |
|---|---|
| Compound | Cmpd # |
| | 1090 |
| | 1091 |
| | 1092 |
| | 1093 |

TABLE 2-continued
Examples of Compounds of Formula I:
| Compound | Cmpd # |
|---|---|
| 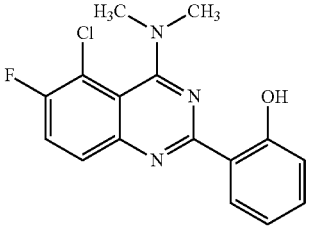 | 1094 |
| 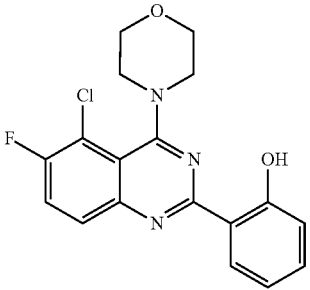 | 1095 |
| 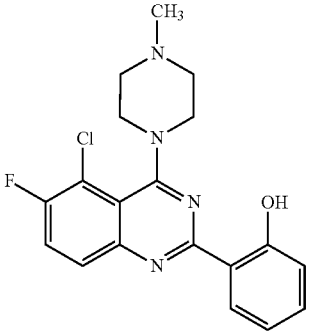 | 1096 |
| 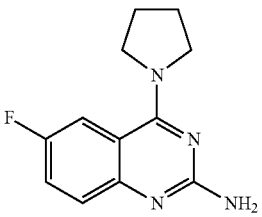 | 1097 |
| 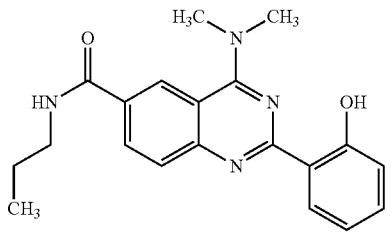 | 1098 |

TABLE 2-continued

Examples of Compounds of Formula I:

| Compound | Cmpd # |
|---|---|
| | 1099 |
| | 1100 |
| | 1101 |
| | 1102 |
| | 1103 |

TABLE 2-continued

Examples of Compounds of Formula I:

| Compound | Cmpd # |
|---|---|
| | 1104 |
| | 1105 |
| | 1106 |
| | 1107 |

TABLE 2-continued
Examples of Compounds of Formula I:
| Compound | Cmpd # |
|---|---|
| 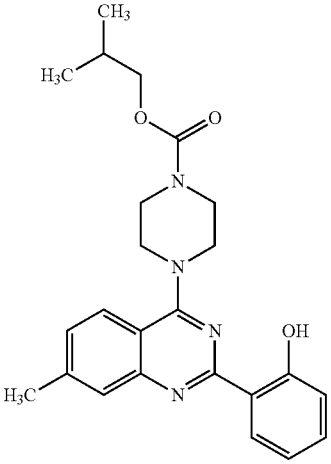 | 1108 |
| 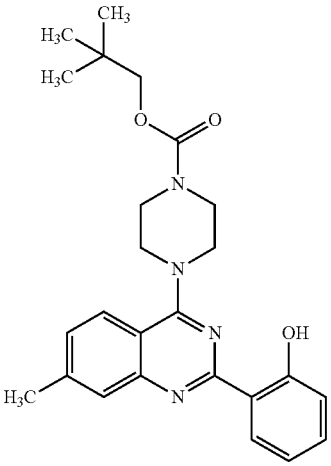 | 1109 |
| 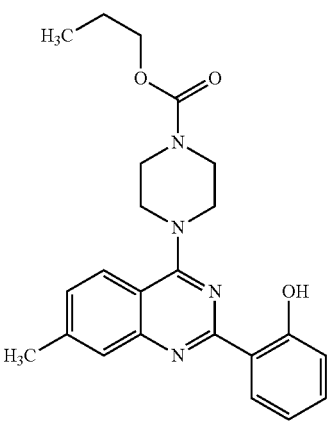 | 1110 |

TABLE 2-continued

Examples of Compounds of Formula I:

| Compound | Cmpd # |
|---|---|
| 2-(7-methyl-4-(4-(methylsulfonyl)piperazin-1-yl)quinazolin-2-yl)phenol | 1111 |
| 2-(4-(4-(ethylsulfonyl)piperazin-1-yl)-7-methylquinazolin-2-yl)phenol | 1112 |
| 2-(7-methyl-4-(4-(propylsulfonyl)piperazin-1-yl)quinazolin-2-yl)phenol | 1113 |

TABLE 2-continued

Examples of Compounds of Formula I:

| Compound | Cmpd # |
|---|---|
| | 1114 |
| | 1115 |
| | 1116 |

TABLE 2-continued
Examples of Compounds of Formula I:
| Compound | Cmpd # |
|---|---|
| 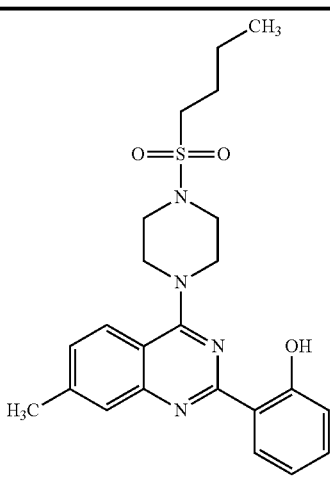 | 1117 |
| 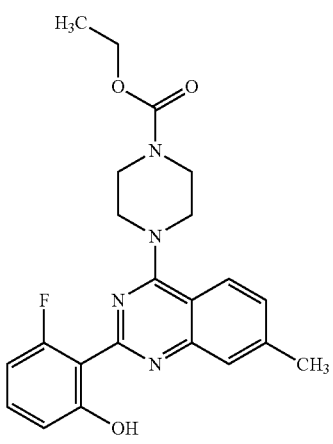 | 1118 |
| 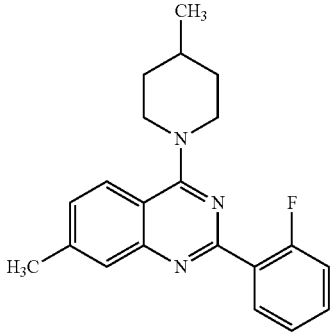 | 1119 |
| 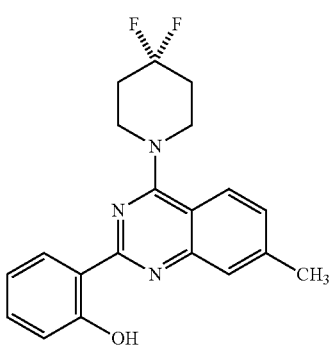 | 1120 |

TABLE 2-continued

Examples of Compounds of Formula I:

| Compound | Cmpd # |
|---|---|
| (ethyl 4-(7-methyl-2-(2-fluorophenyl)quinazolin-4-yl)piperazine-1-carboxylate) | 1121 |
| (isopropyl 4-(7-methyl-2-(2-hydroxyphenyl)quinazolin-4-yl)piperazine-1-carboxylate) | 1122 |
| (4-(3,3-difluoropyrrolidin-1-yl)-2-(2-hydroxyphenyl)-7-methylquinazoline) | 1123 |

TABLE 2-continued

Examples of Compounds of Formula I:

| Compound | Cmpd # |
|---|---|
| (structure) | 1124 |
| (structure) | 1125 |
| (structure) | 1126 |

TABLE 2-continued
Examples of Compounds of Formula I:
| Compound | Cmpd # |
|---|---|
| 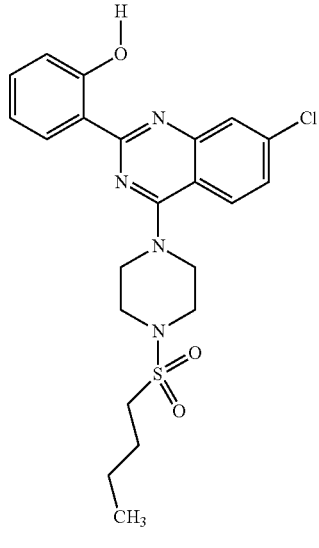 | 1127 |
| 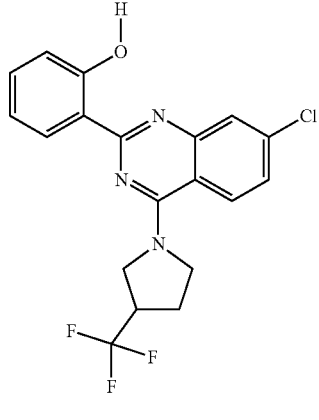 | 1128 |
| 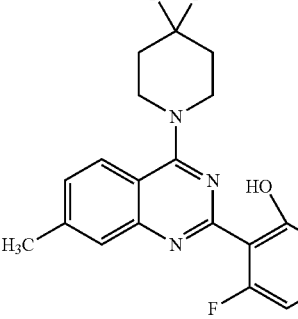 | 1129 |

TABLE 2-continued
Examples of Compounds of Formula I:
| Compound | Cmpd # |
|---|---|
| 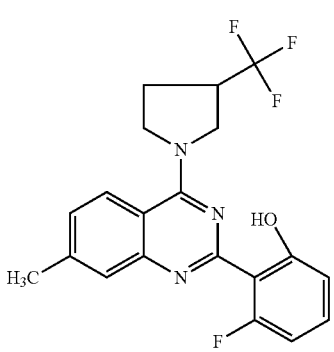 | 1130 |
| 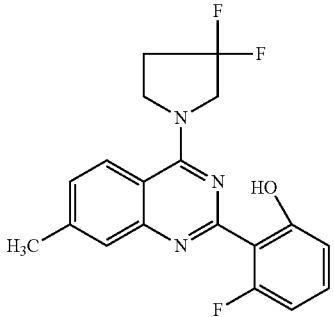 | 1131 |
| 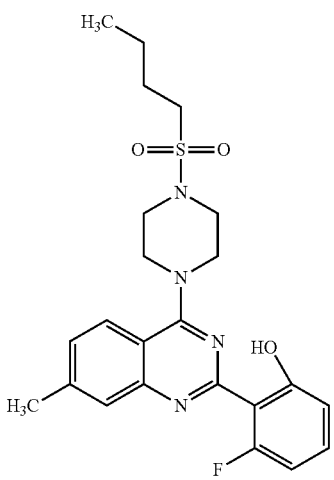 | 1132 |

TABLE 2-continued

Examples of Compounds of Formula I:

| Compound | Cmpd # |
|---|---|
| | 1133 |
| | 1134 |
| | 1135 |
| | 1136 |

TABLE 2-continued
Examples of Compounds of Formula I:
| Compound | Cmpd # |
|---|---|
| 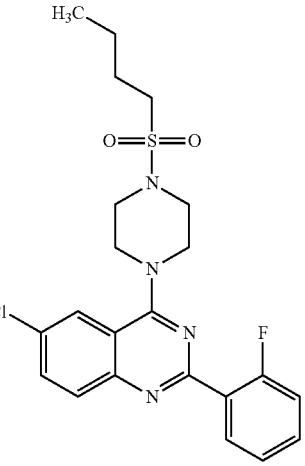 | 1137 |
| 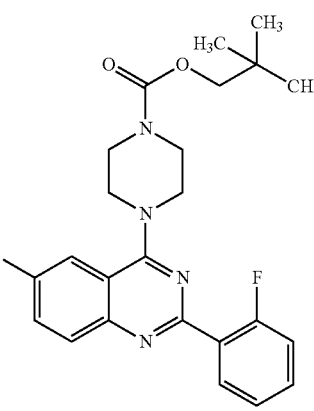 | 1138 |
| 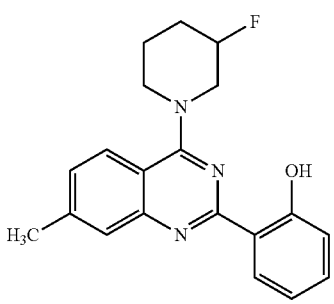 | 1139 |
| 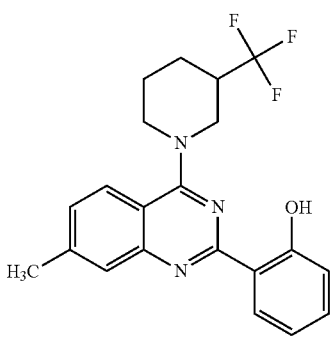 | 1140 |

TABLE 2-continued
Examples of Compounds of Formula I:
| Compound | Cmpd # |
|---|---|
| 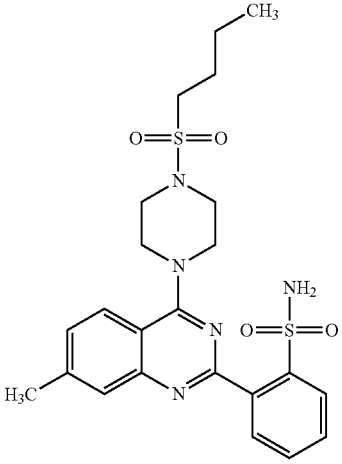 | 1141 |
| 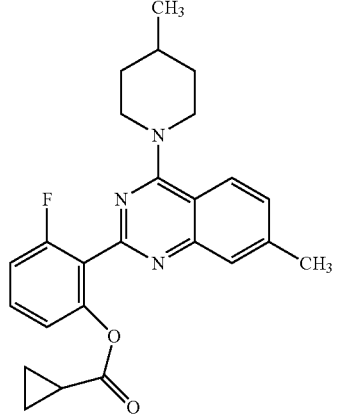 | 1142 |
| 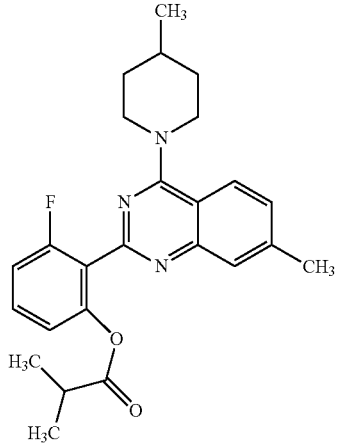 | 1143 |

TABLE 2-continued
Examples of Compounds of Formula I:
| Compound | Cmpd # |
|---|---|
| 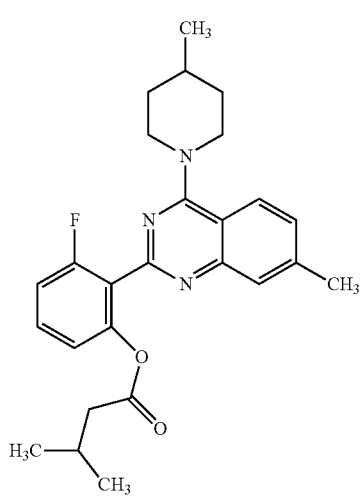 | 1144 |
| 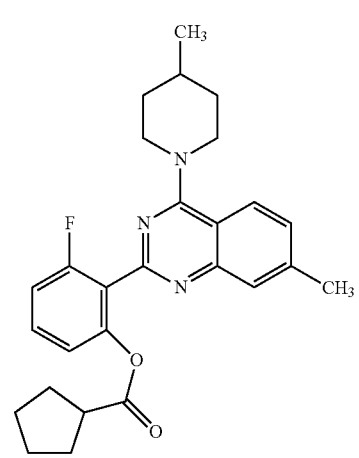 | 1145 |
| 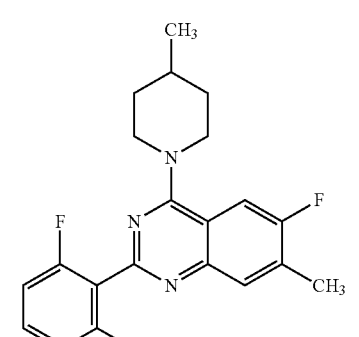 | 1146 |

TABLE 2-continued
Examples of Compounds of Formula I:
| Compound | Cmpd # |
|---|---|
| 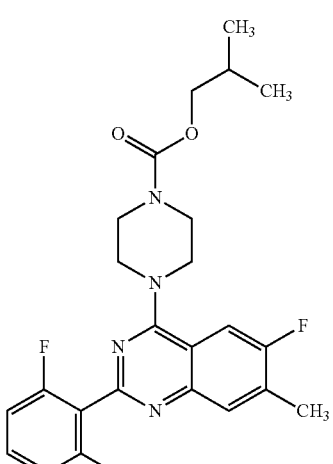 | 1147 |
| 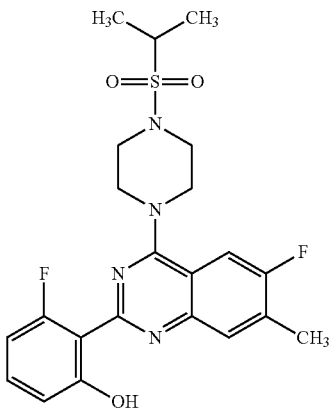 | 1148 |
| 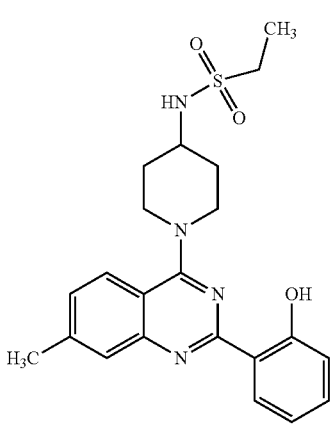 | 1149 |

TABLE 2-continued
Examples of Compounds of Formula I:
| Compound | Cmpd # |
|---|---|
| 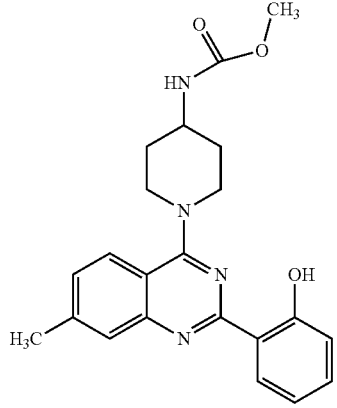 | 1150 |
| 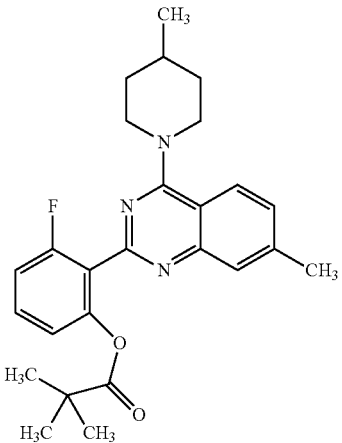 | 1151 |
| 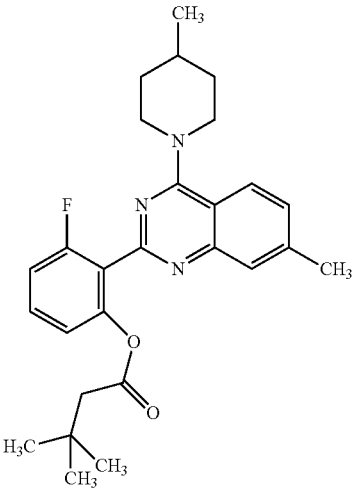 | 1152 |

TABLE 2-continued
Examples of Compounds of Formula I:
| Compound | Cmpd # |
|---|---|
| 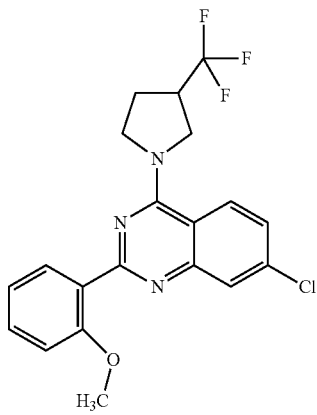 | 1153 |
| 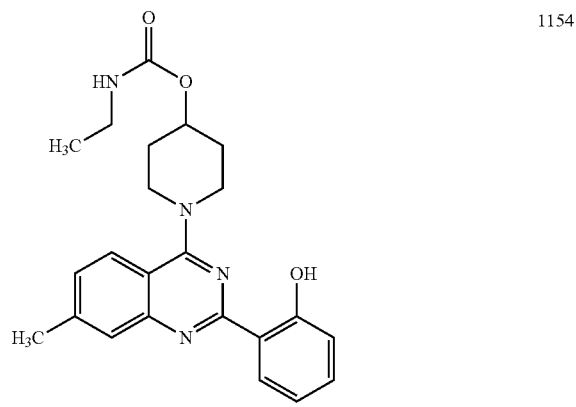 | 1154 |
| 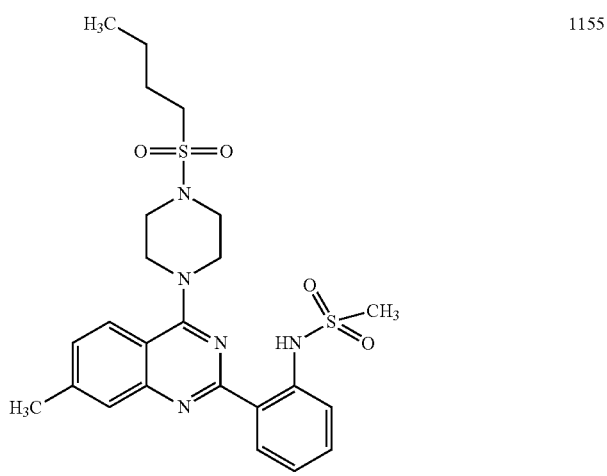 | 1155 |

TABLE 2-continued

Examples of Compounds of Formula I:

| Compound | Cmpd # |
|---|---|
| (structure) | 1156 |
| (structure) | 1157 |
| (structure) | 1158 |

TABLE 2-continued
Examples of Compounds of Formula I:
| Compound | Cmpd # |
|---|---|
| 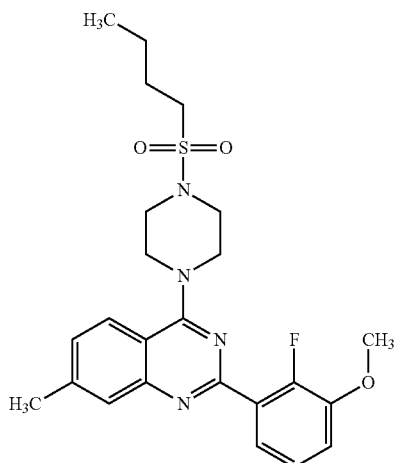 | 1159 |
| 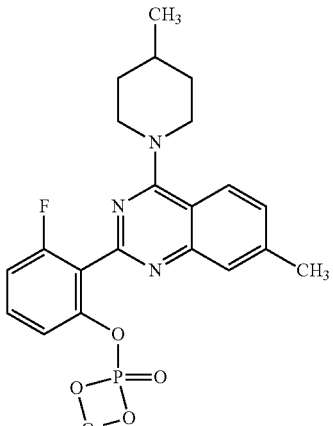 | 1160 |
| 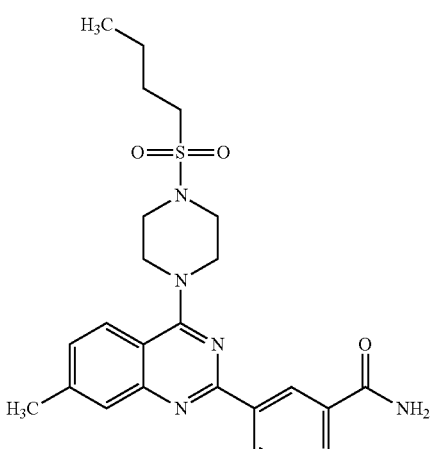 | 1161 |

TABLE 2-continued

Examples of Compounds of Formula I:

| Compound | Cmpd # |
|---|---|
| | 1162 |
| | 1163 |
| | 1164 |

TABLE 2-continued
Examples of Compounds of Formula I:
| Compound | Cmpd # |
|---|---|
| 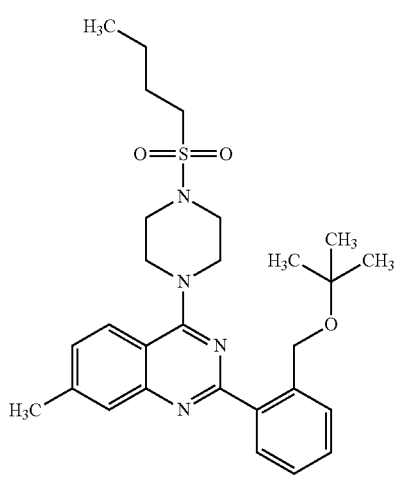 | 1165 |
| 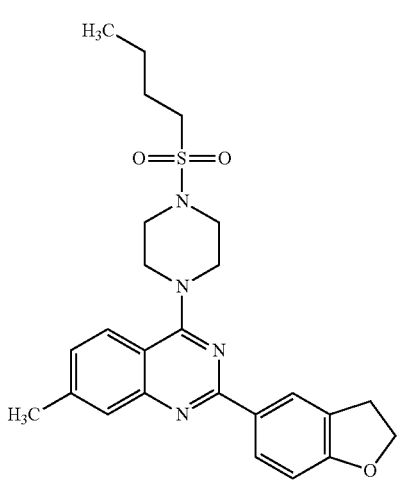 | 1166 |
| 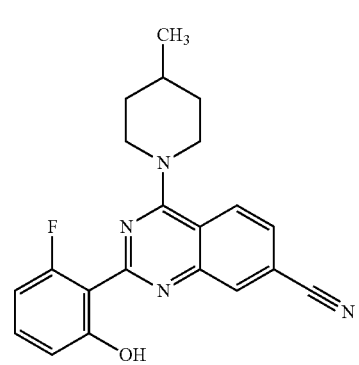 | 1167 |

TABLE 2-continued

Examples of Compounds of Formula I:

| Compound | Cmpd # |
|---|---|
| | 1168 |
| | 1169 |
| | 1170 |

TABLE 2-continued

Examples of Compounds of Formula I:

| Compound | Cmpd # |
|---|---|
| | 1171 |
| | 1172 |
| | 1173 |

TABLE 2-continued
Examples of Compounds of Formula I:
| Compound | Cmpd # |
|---|---|
| 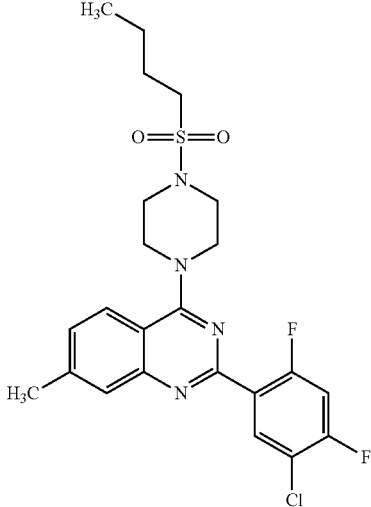 | 1174 |
| 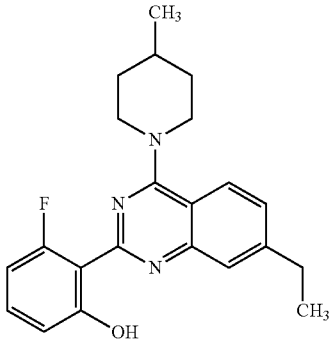 | 1175 |
| 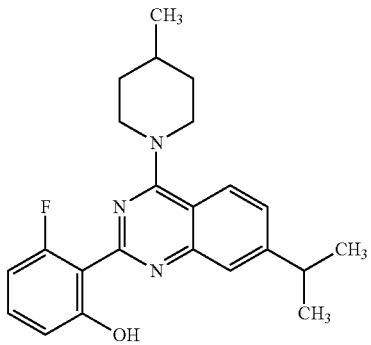 | 1176 |

TABLE 2-continued
Examples of Compounds of Formula I:
| Compound | Cmpd # |
|---|---|
| 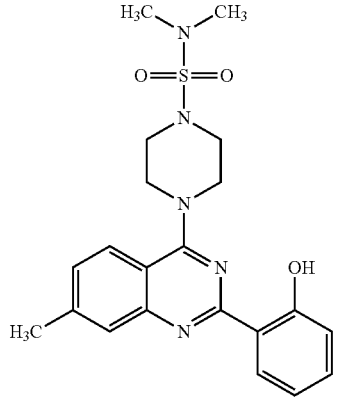 | 1177 |
| 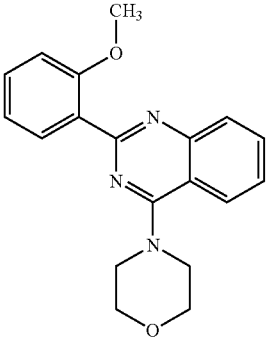 | 1178 |
| 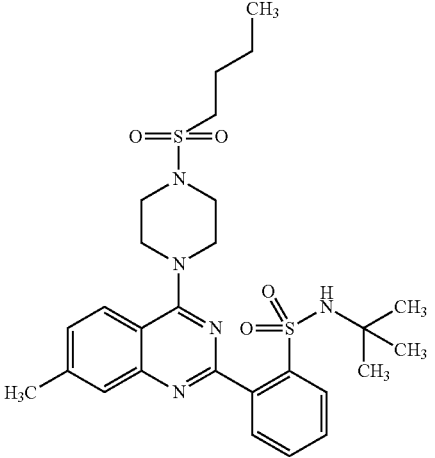 | 1179 |

TABLE 2-continued

Examples of Compounds of Formula I:

| Compound | Cmpd # |
|---|---|
| | 1180 |
| | 1181 |
| | 1182 |
| | 1183 |

TABLE 2-continued

Examples of Compounds of Formula I:

| Compound | Cmpd # |
|---|---|
| | 1184 |
| | 1185 |
| | 1186 |
| | 1187 |
| | 1188 |

TABLE 2-continued

Examples of Compounds of Formula I:

| Compound | Cmpd # |
|---|---|
| | 1189 |
| | 1190 |
| | 1191 |
| | 1192 |
| | 1193 |

TABLE 2-continued
Examples of Compounds of Formula I:
| Compound | Cmpd # |
|---|---|
| 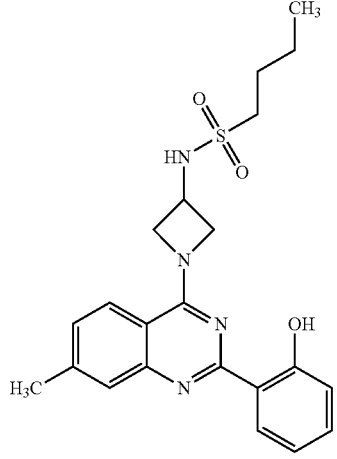 | 1194 |
| 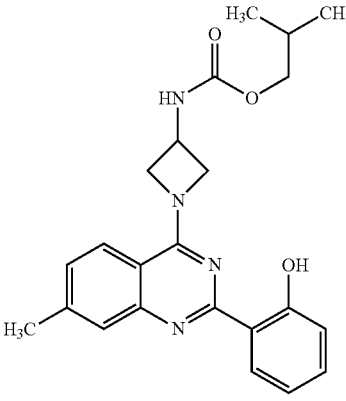 | 1195 |
| 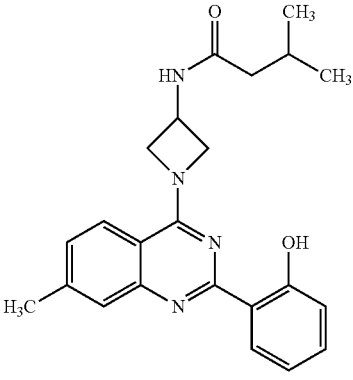 | 1196 |
| 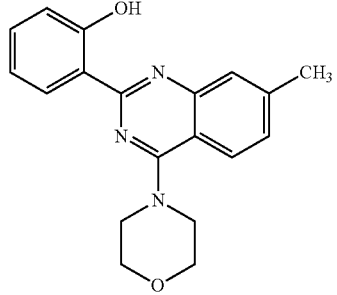 | 1197 |

TABLE 2-continued
Examples of Compounds of Formula I:
| Compound | Cmpd # |
|---|---|
| 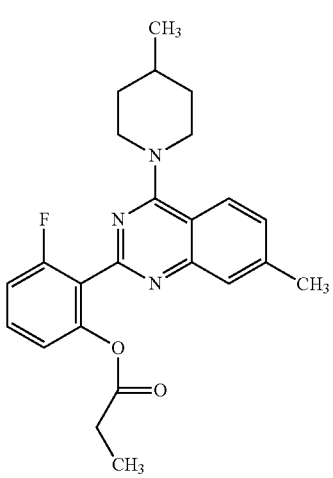 | 1198 |
| 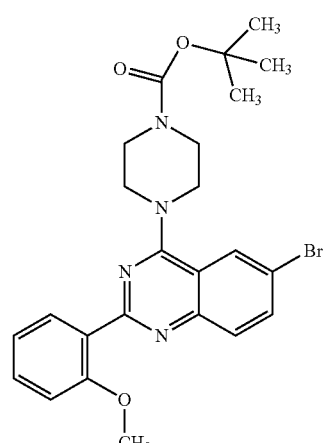 | 1199 |
| 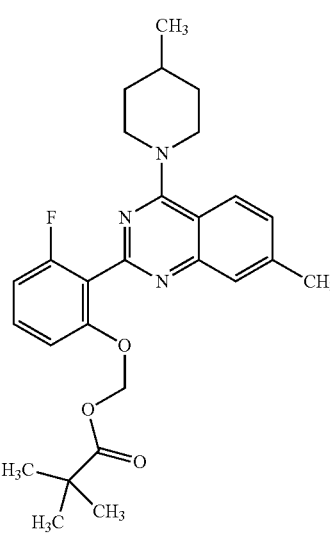 | 1200 |

TABLE 2-continued
| Examples of Compounds of Formula I: | |
|---|---|
| Compound | Cmpd # |
| 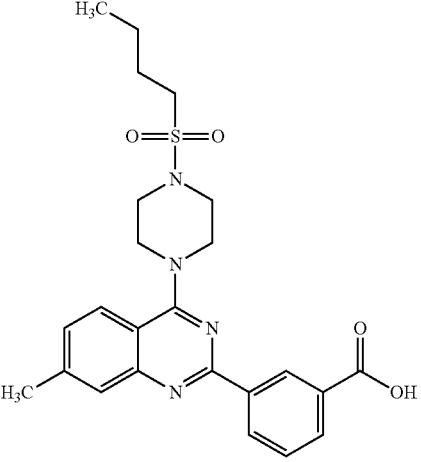 | 1201 |
| 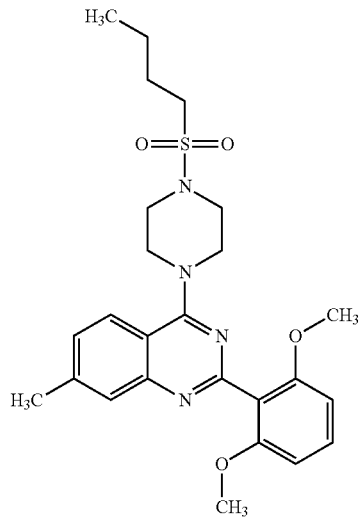 | 1202 |
| 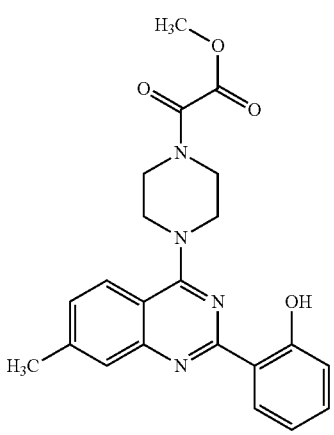 | 1203 |

TABLE 2-continued
Examples of Compounds of Formula I:
| Compound | Cmpd # |
|---|---|
| 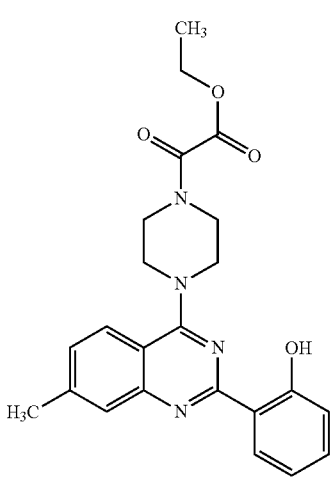 | 1204 |
| 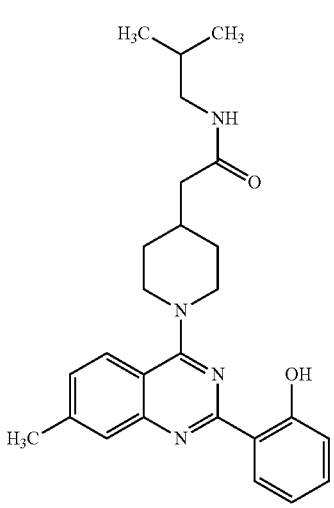 | 1205 |
| 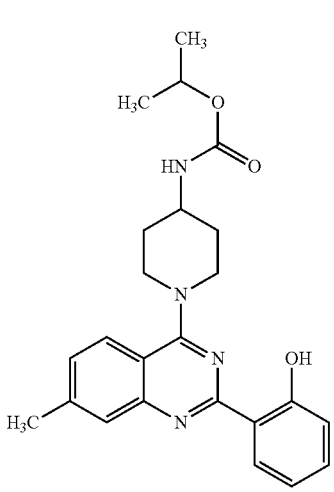 | 1206 |

TABLE 2-continued
Examples of Compounds of Formula I:
| Compound | Cmpd # |
|---|---|
| 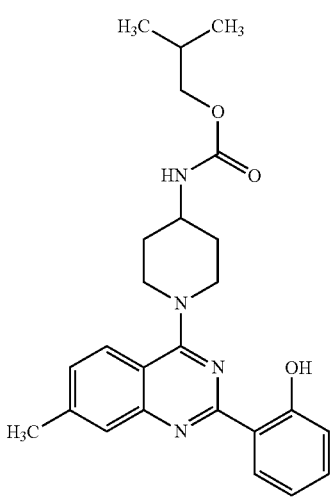 | 1207 |
| 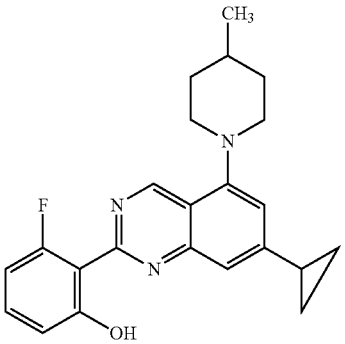 | 1208 |
| 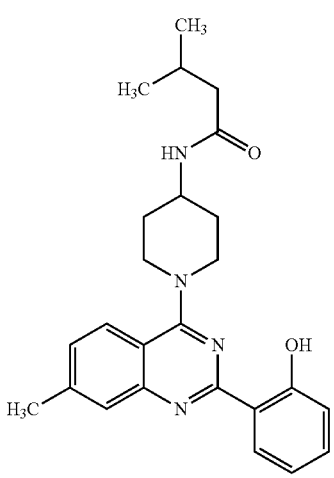 | 1209 |

TABLE 2-continued
Examples of Compounds of Formula I:
| Compound | Cmpd # |
|---|---|
| 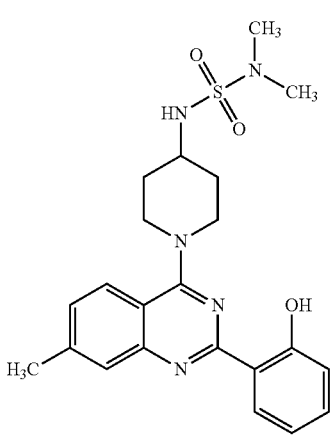 | 1210 |
| 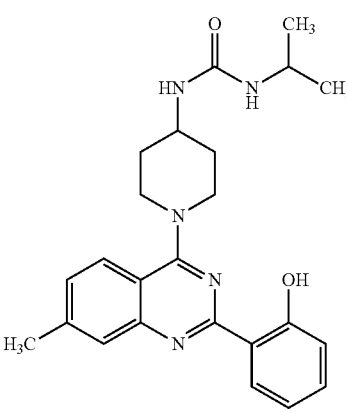 | 1211 |
| 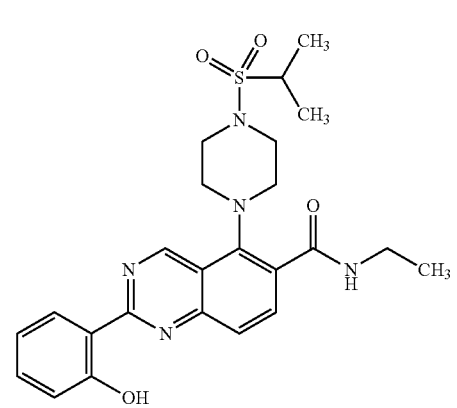 | 1212 |

TABLE 2-continued

Examples of Compounds of Formula I:

| Compound | Cmpd # |
|---|---|
| (structure) | 1213 |
| (structure) | 1214 |
| (structure) | 1215 |

TABLE 2-continued
Examples of Compounds of Formula I:
| Compound | Cmpd # |
|---|---|
| 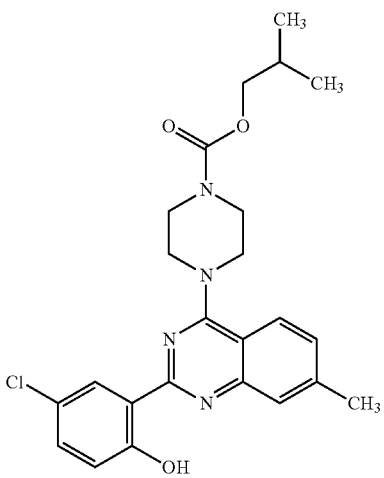 | 1216 |
| 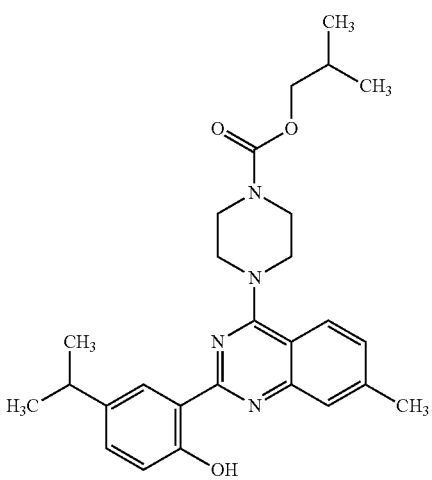 | 1217 |
| 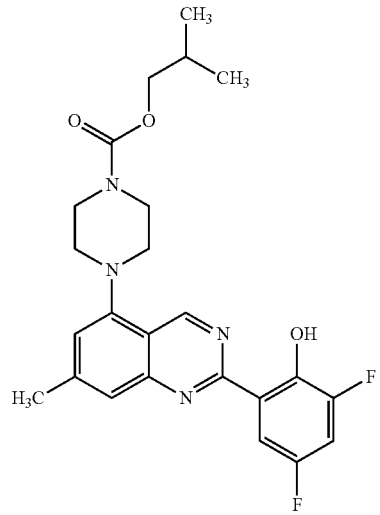 | 1218 |

TABLE 2-continued

Examples of Compounds of Formula I:

| Compound | Cmpd # |
|---|---|
| (structure) | 1219 |
| (structure) | 1220 |
| (structure) | 1221 |

TABLE 2-continued
Examples of Compounds of Formula I:
| Compound | Cmpd # |
|---|---|
| 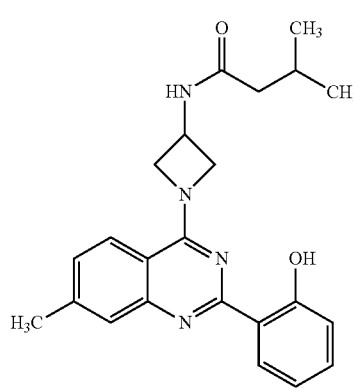 | 1222 |
| 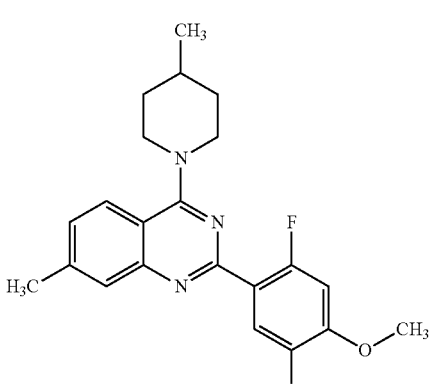 | 1223 |
| 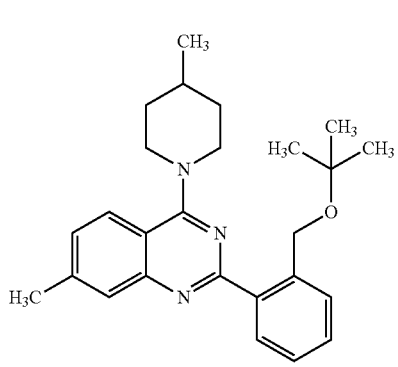 | 1224 |

TABLE 2-continued
Examples of Compounds of Formula I:
| Compound | Cmpd # |
|---|---|
| 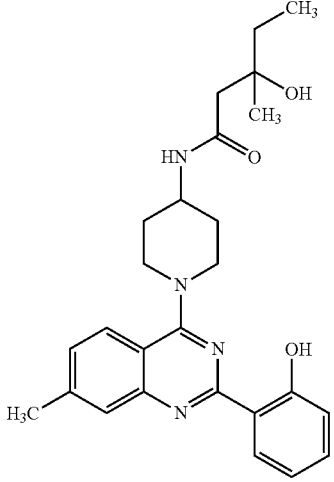 | 1225 |
| 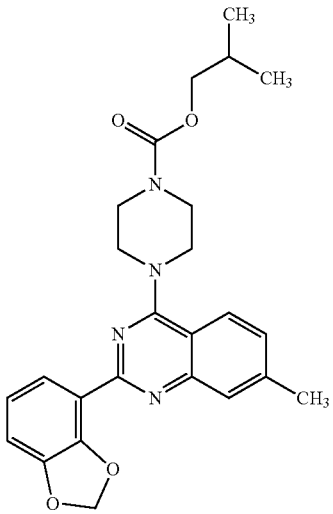 | 1226 |
| 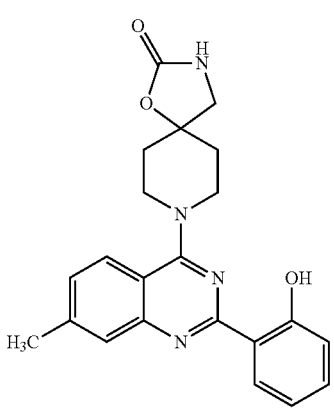 | 1227 |

TABLE 2-continued
Examples of Compounds of Formula I:
| Compound | Cmpd # |
|---|---|
| 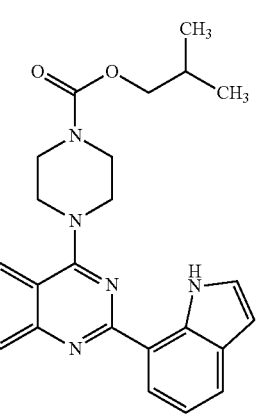 | 1228 |
| 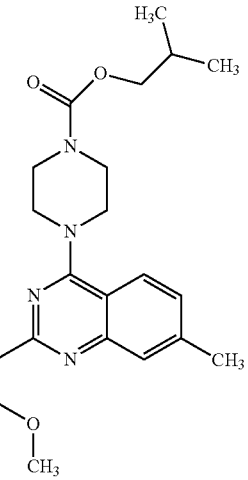 | 1229 |
| 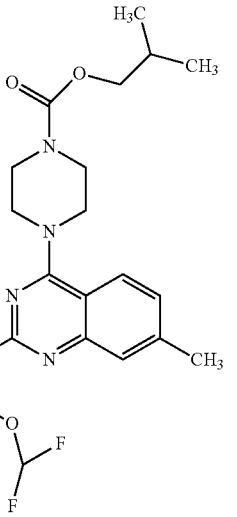 | 1230 |

TABLE 2-continued
Examples of Compounds of Formula I:
| Compound | Cmpd # |
|---|---|
| 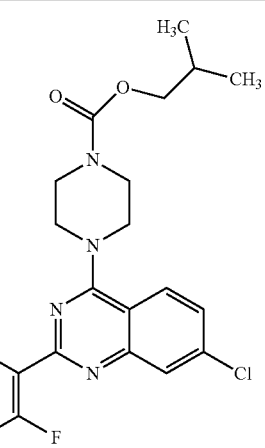 | 1231 |
| 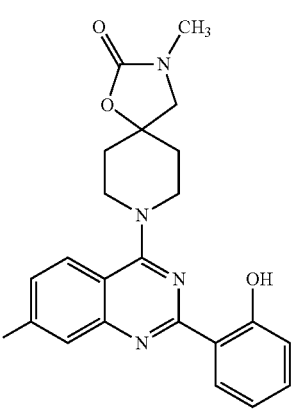 | 1232 |
| 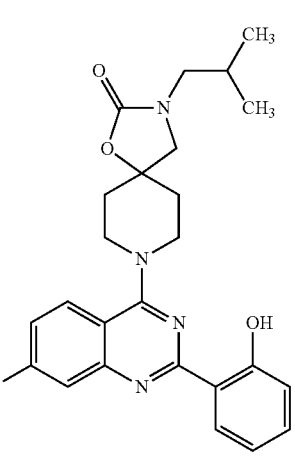 | 1233 |

TABLE 2-continued
Examples of Compounds of Formula I:
| Compound | Cmpd # |
|---|---|
| 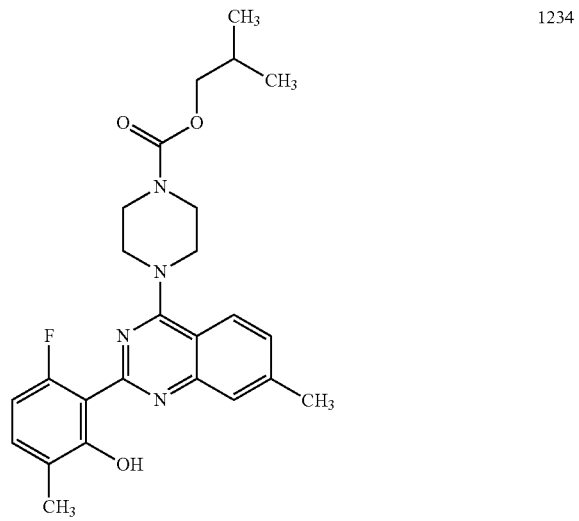 | 1234 |
| 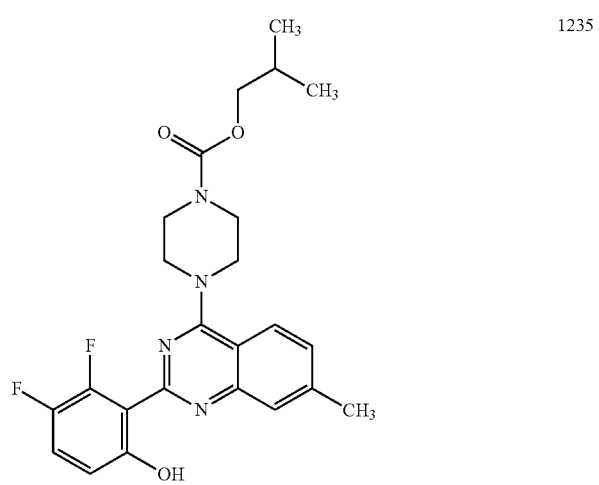 | 1235 |
| 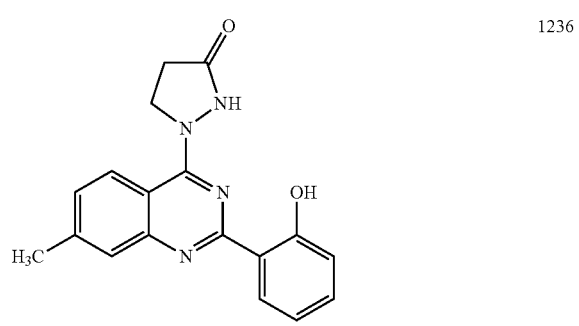 | 1236 |

TABLE 2-continued
Examples of Compounds of Formula I:
| Compound | Cmpd # |
|---|---|
| 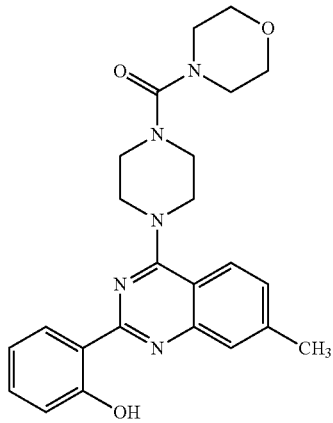 | 1237 |
| 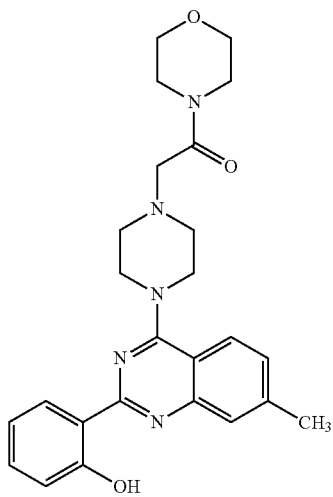 | 1238 |
| 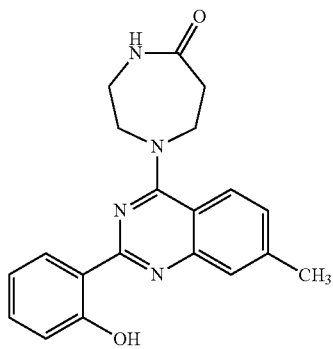 | 1239 |

TABLE 2-continued
Examples of Compounds of Formula I:
| Compound | Cmpd # |
|---|---|
| 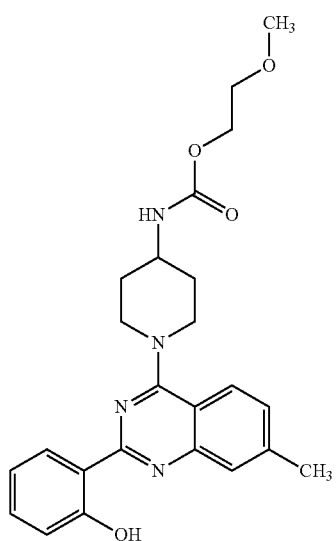 | 1240 |
| 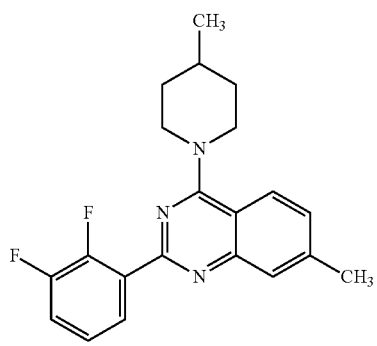 | 1241 |
| 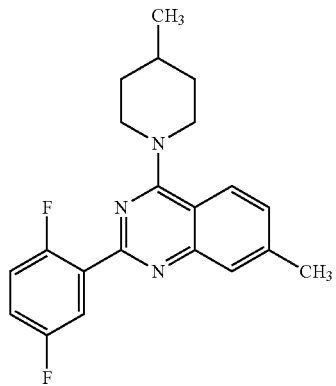 | 1242 |

TABLE 2-continued
Examples of Compounds of Formula I:
| Compound | Cmpd # |
|---|---|
| 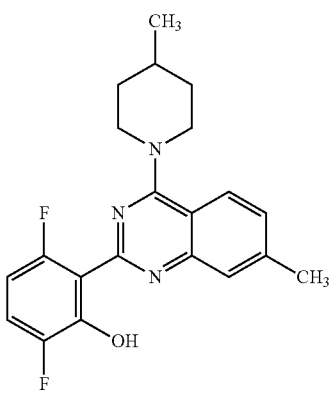 | 1243 |
| 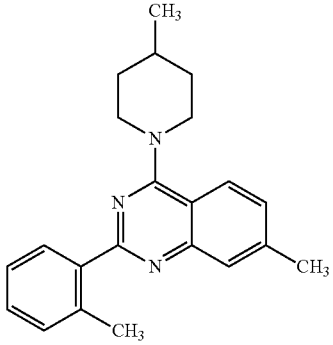 | 1244 |
| 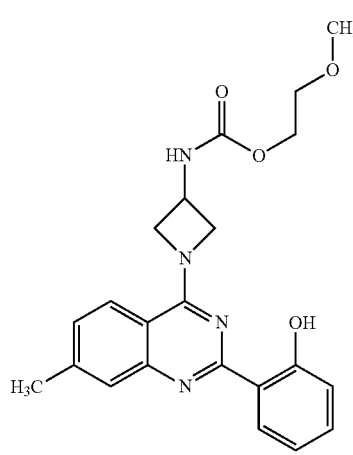 | 1245 |

TABLE 2-continued
Examples of Compounds of Formula I:
| Compound | Cmpd # |
|---|---|
| 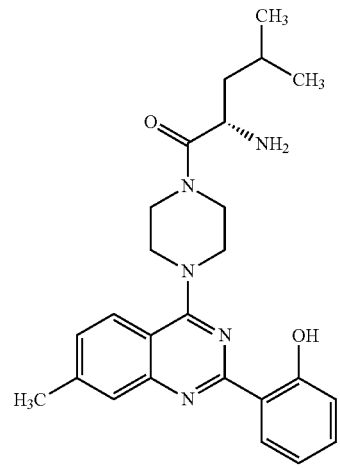 | 1246 |
| 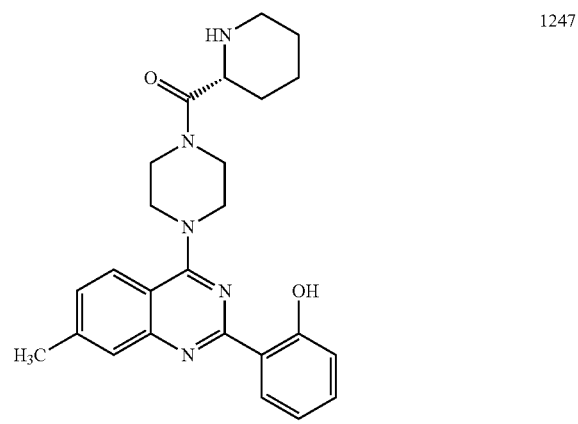 | 1247 |
| 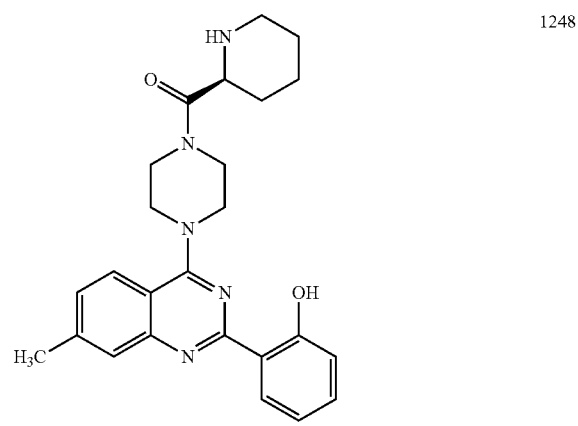 | 1248 |

TABLE 2-continued

Examples of Compounds of Formula I:

| Compound | Cmpd # |
|---|---|
| | 1249 |
| | 1250 |
| | 1251 |
| | 1252 |

TABLE 2-continued
Examples of Compounds of Formula I:
| Compound | Cmpd # |
|---|---|
| 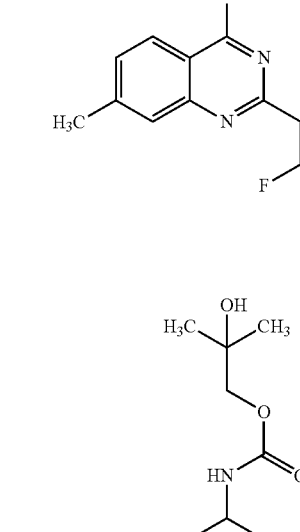 | 1253 |
| 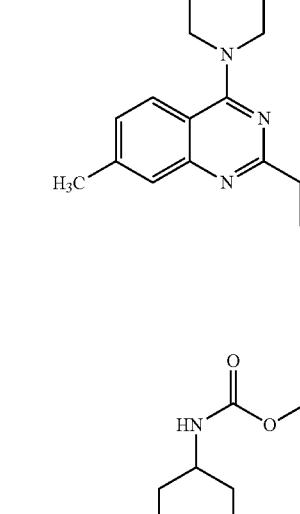 | 1254 |
| 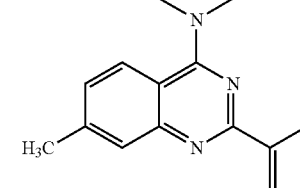 | 1255 |

TABLE 2-continued

Examples of Compounds of Formula I:

| Compound | Cmpd # |
|---|---|
| | 1256 |
| | 1257 |
| | 1258 |

TABLE 2-continued
Examples of Compounds of Formula I:
| Compound | Cmpd # |
|---|---|
| 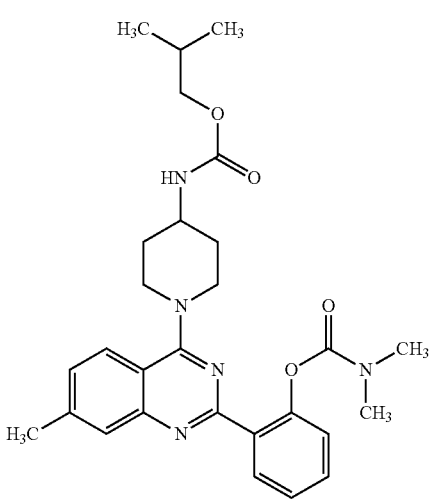 | 1259 |
| 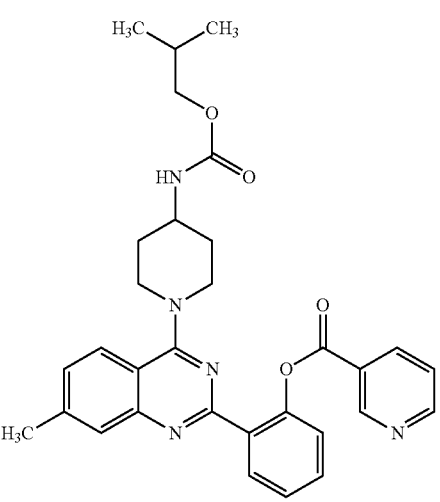 | 1260 |
| 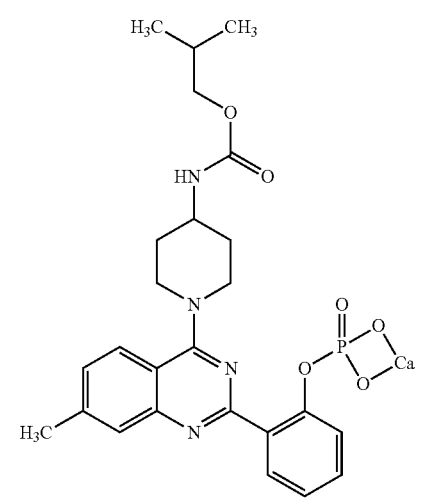 | 1261 |

TABLE 2-continued
Examples of Compounds of Formula I:
| Compound | Cmpd # |
|---|---|
| 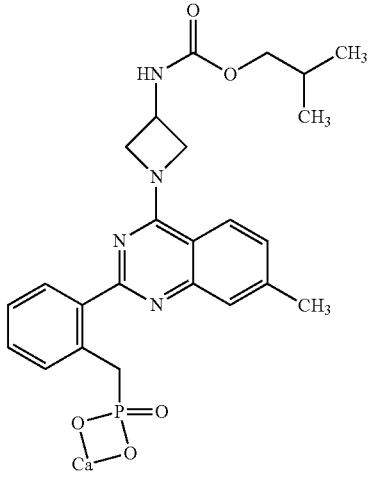 | 1262 |
| 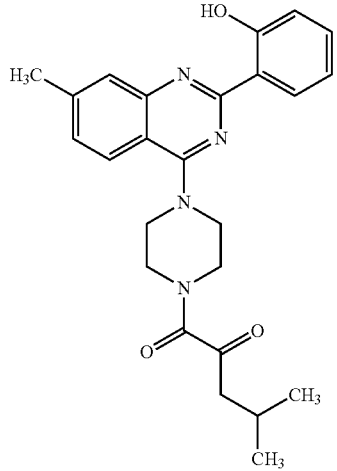 | 1263 |
| 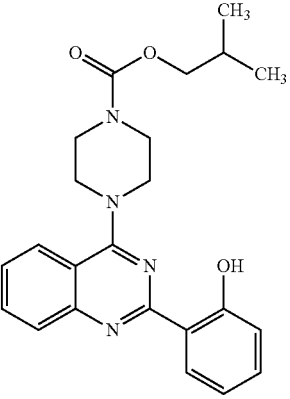 | 1264 |

TABLE 2-continued

Examples of Compounds of Formula I:

| Compound | Cmpd # |
|---|---|
| 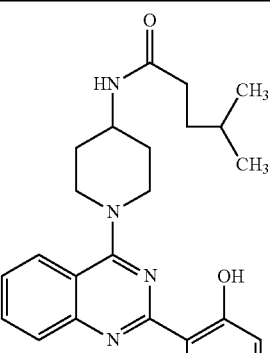 | 1265 |

4. General Synthetic Methodology

The compounds of this invention may be prepared in general by methods known to those skilled in the art for analogous compounds, as illustrated by the general scheme below, and the preparative examples that follow.

Scheme A below depicts general conditions for the synthesis of compounds of formula IA where X is $NR^2$. In general, the useful intermediate iii can be obtained by condensing a benzoylchloride with an anthranilamide.

Scheme B: Scheme B depicts an alternative synthesis for compounds of formula IA:

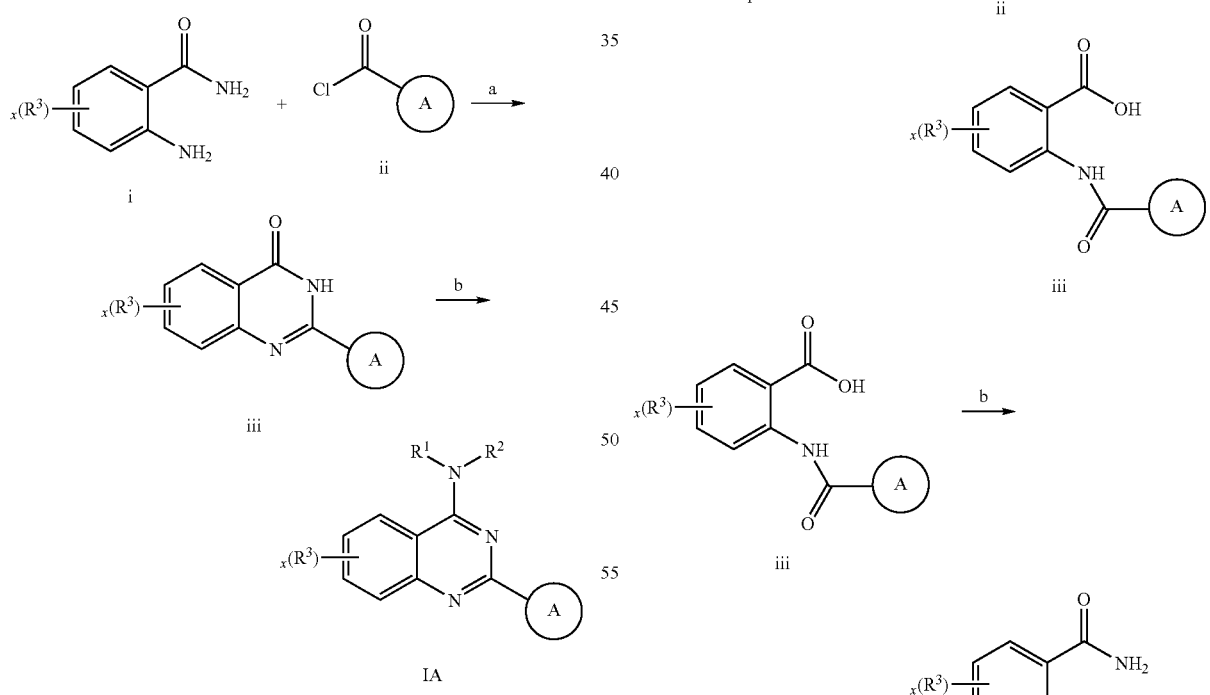

Reaction of i and ii (step a) using $K_2CO_3$ and ether under reflux conditions, and subsequent treatment with 5% aq. NaOH under reflux conditions yields intermediate iii. Reaction of intermediate iii with $POCl_3$ to generate the 4-chloro compound, and subsequent reaction with i) N,N-dimethylaniline in benzene under reflux conditions; ii) $BBr_3$, $CH_2Cl_2$, $-78°$ C.; and iii) $R^1R^2NH$, in $THF/CH_2Cl_2$ at room temperature yields the desired product IA.

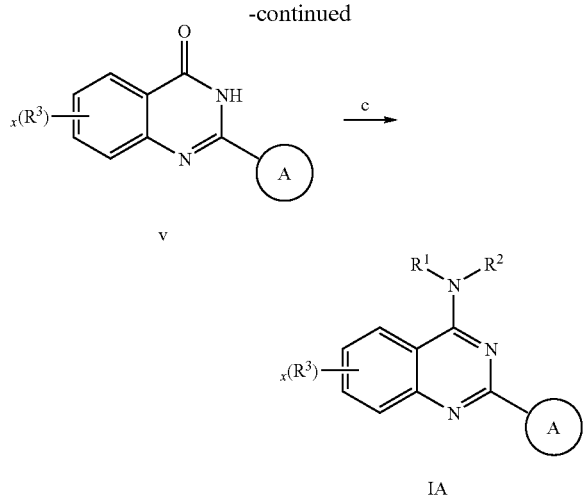

Reaction of i and ii (step a) using triethylamine and 1,4-Dioxane under ambient conditions yields intermediate iii. Reaction of intermediate iii (step b) with 0.5M solution of ammonia in 1,4-Dioxane, triethylamine and BOP reagent was stirred at ambient temperature for 16 h to yield intermediate iv. Treatment of iv with 5% aq. NaOH under reflux conditions yields intermediate v. Treatment of v with POCl$_3$ to generate the 4-chloro compound, and subsequent reaction with i) N,N-dimethylaniline in benzene under reflux conditions; ii) BBr$_3$, CH$_2$Cl$_2$, −78° C.; and iii) R$^1$R$^2$NH, in THF/CH$_2$Cl$_2$ at room temperature yields the desired product IA.

Scheme C:

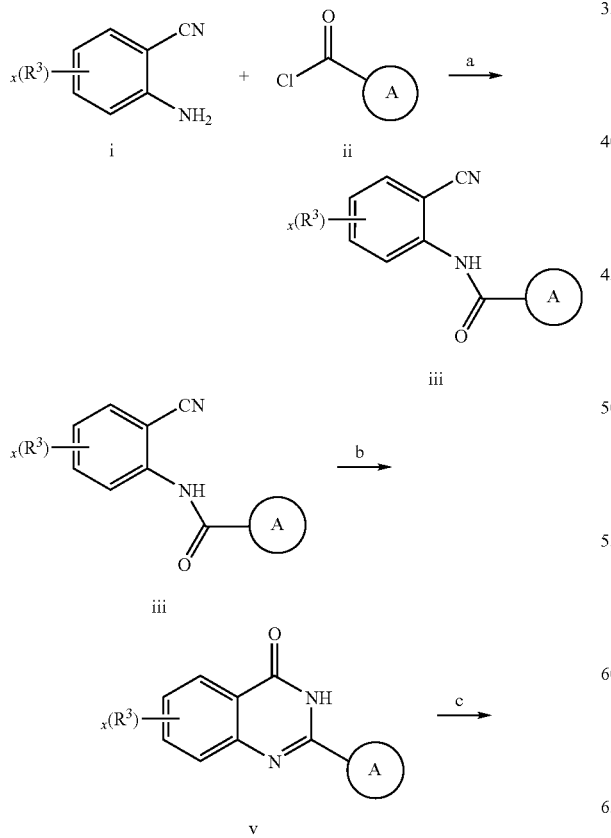

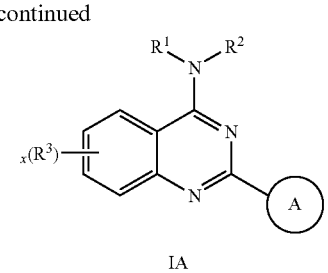

Reaction of i and ii (step a) using pyridine yields intermediate iii. Treatment of iii with 5% aq. NaOH under reflux conditions yields intermediate iv. Reaction of intermediate iv with POCl$_3$ to generate the 4-chloro compound, and subsequent reaction with i) N,N-dimethylaniline in benzene under reflux conditions; ii) BBr$_3$, CH$_2$Cl$_2$, −78° C.; and iii) R$^1$R$^2$NH, in THF/CH$_2$Cl$_2$ at room temperature yields the desired product IA.

Schemes D and E below depict the synthesis of a variety of useful anthranilimides:

Scheme D:

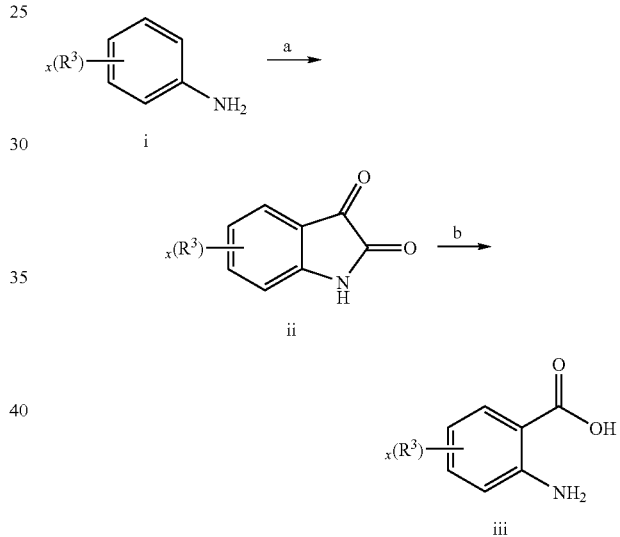

Reaction of i (step a) with chloral hydrate in the presence of hydroxylamine hydrochloride yields isatin ii. Treatment of ii with basic hydrogen peroxide gives iii (step b), useful as shown in Scheme D.

Scheme E:

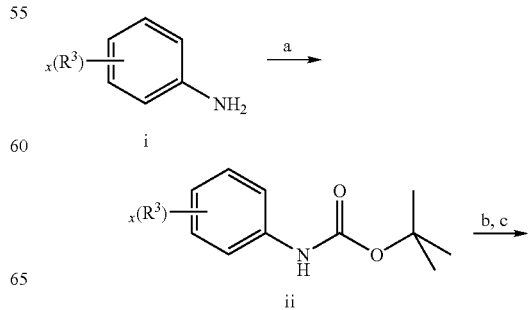

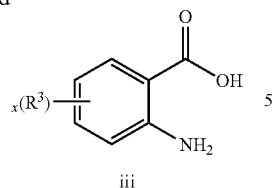

Reaction of i (step a) with Boc anhydride yields ii. Subsequent metalation of ii with butyl lithium at low temperature and reaction with $CO_2$ yields the N-protected anthranilic acid (step b). Boc removal with TFA yields the anthranilic acid iii, useful as shown in Scheme E.

Scheme F:

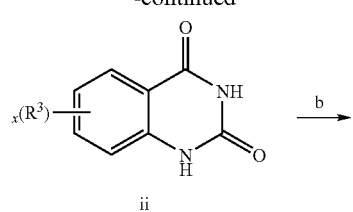

Reaction of isatoic anhydrides i (step a) with aqueous ammonium hydroxide yields ii, useful as shown in Scheme F.

Scheme G:

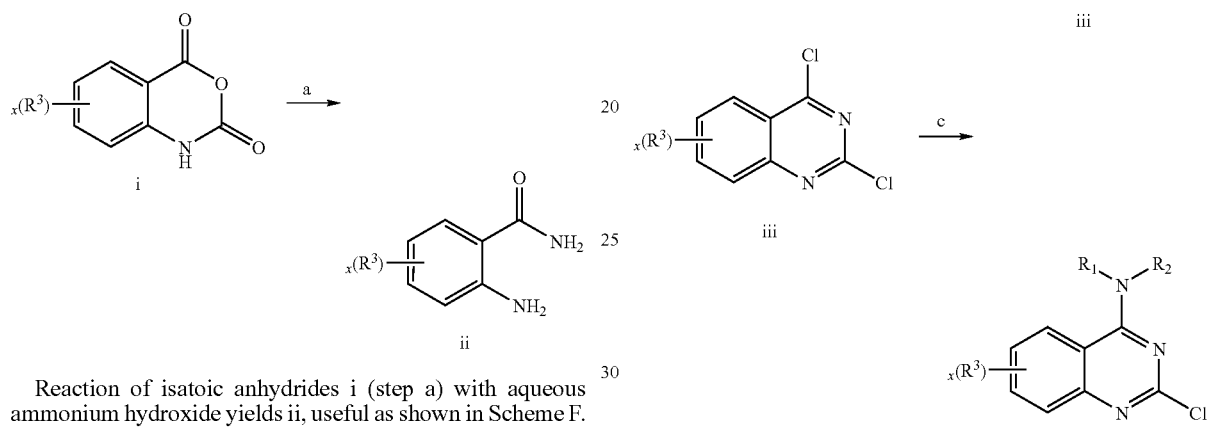

(step a) i) Treatment of i in water with AcOH and KOCN 0° C. to room temperature for 24 h, and subsequent reaction with ii) NaOH followed by acidification with HCl yields intermediate ii. (step b) Treatment of ii with $POCl_3$ and triethylamine under reflux conditions yields intermediate iii. (step c) Treatment of iii with $R^1R^2NH$, in $THF/CH_2Cl_2$ 0° C. to room temperature yields intermediate iv.

Scheme H:

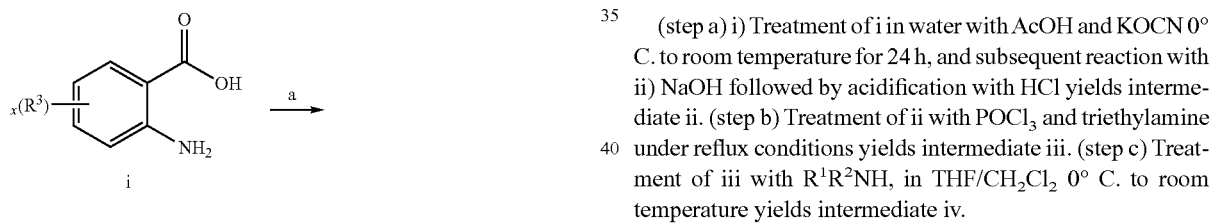

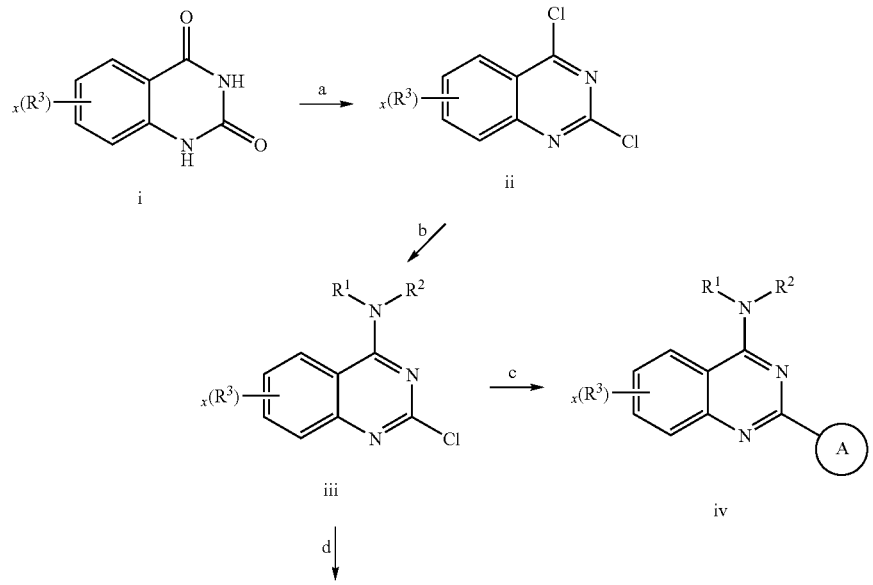

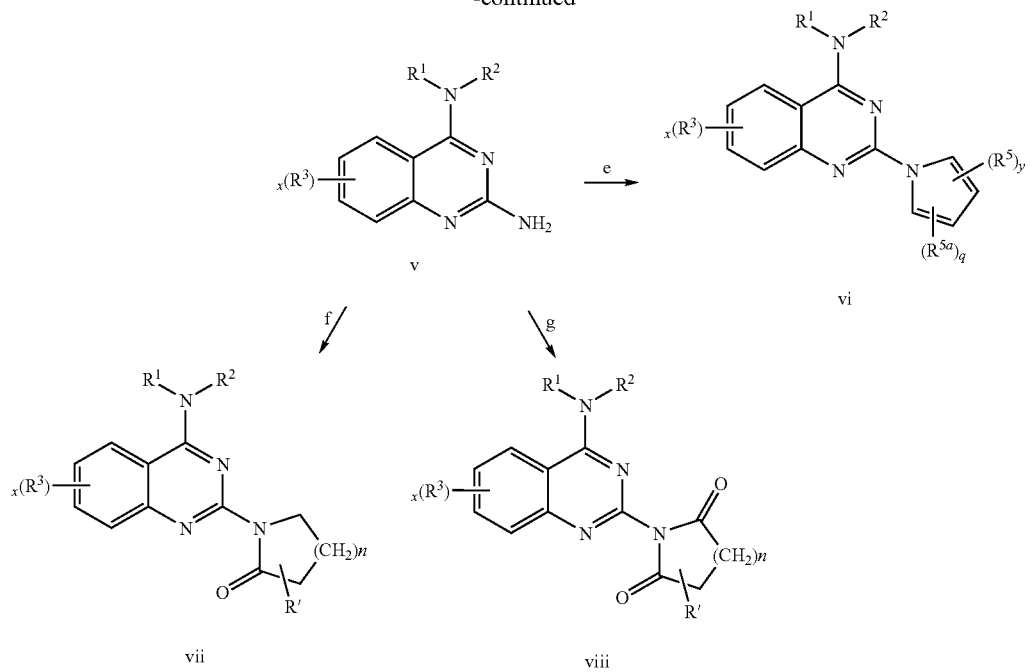

Reaction of intermediate i (step a) with POCl₃ generates the 2,4-dichloro compound ii. Reaction of intermediate ii (step b) with R₁—NH—R₂, and Et₃N, in CH₂Cl₂ yields amine iii. Reaction of intermediate iii (step c) with an NH containing heterocycle, NaH, and THF generates iv. Reaction of intermediate iii (step d) with LiHMDS, Pd₂(dba)₃, 2-(dicyclohexyl)phosphinobiphenyl, and THF yields diamine v.

Reaction of intermediate v (step e) with a substituted 2,5-dimethoxytetrahydrofuran, in AcOH generates vi. Reaction of intermediate v (step f) with ClCO—CH₂—(CH₂)ₙ—CH₂—Cl, Et₃N, and p-dioxane generates vii. Reaction of intermediate iii (step g) with a cyclic anhydride, and p-dioxane generates viii.

Scheme I:

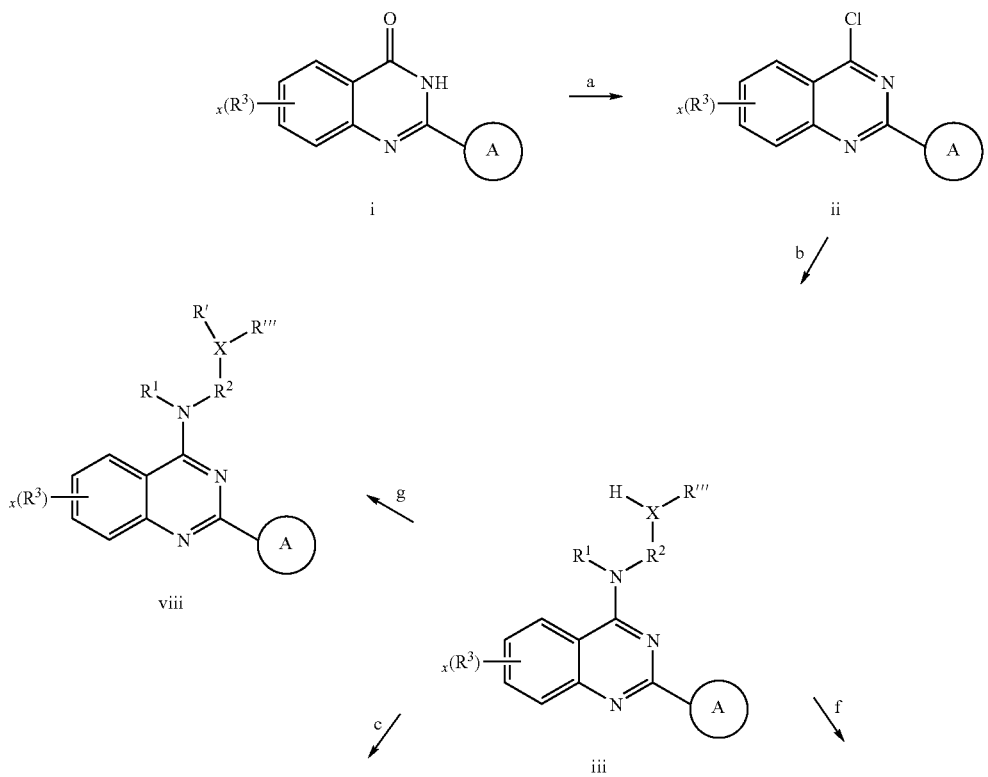

-continued

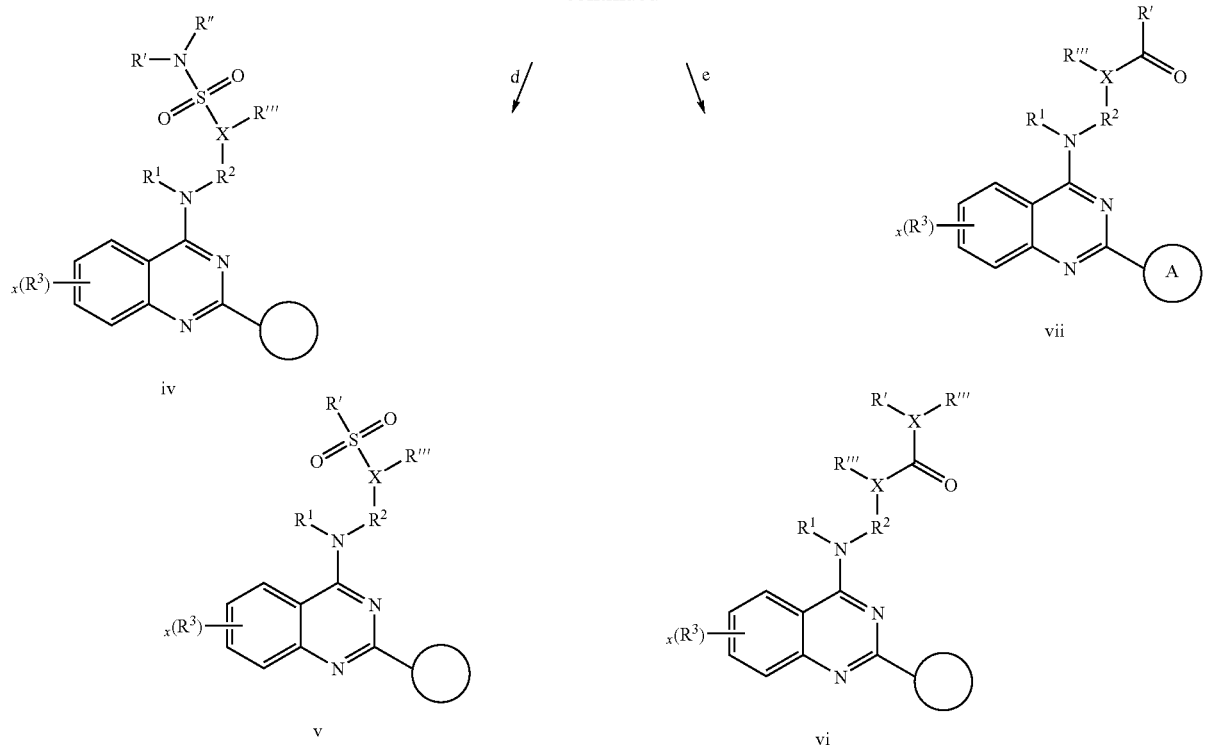

Reaction of intermediate i (step a) with POCl₃ and subsequent treatment with BBr₃, CH₂Cl₂, at −78° C. generates the 4-chloro compound II. Reaction of intermediate ii (step b) with R'—NH—R²—X(R''')H, and Et₃N, in CH₂Cl₂ yields iii. Reaction of intermediate iii (step c) with R'N(R'')X—SO₂Cl, and Et₃N, in CH₂Cl₂ generates iv. Reaction of intermediate iii (step d) with R'—SO₂Cl, and Et₃N, in CH₂Cl₂ generates v. Reaction of intermediate iii (step e) with R'—CO₂Cl, and Et₃N, in CH₂Cl₂ or with phosgene, and R'(R'')XH generates vi. Reaction of intermediate iii (step f) with R'COCl, Et₃N, in CH₂Cl₂ generates vi. Reaction of intermediate iii (step g) with electrophiles in the presence of Et₃N (organic halide electrophiles) or NaBH(OAc)₃ (aldehyde and ketone electrophiles) yields viii.

Scheme J:

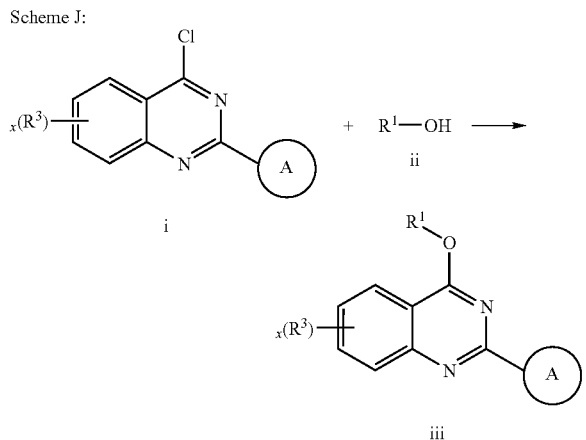

Reaction of i with ii in dichloromethane under microwave irradiation at 150° C. yields product iii.

Scheme K:

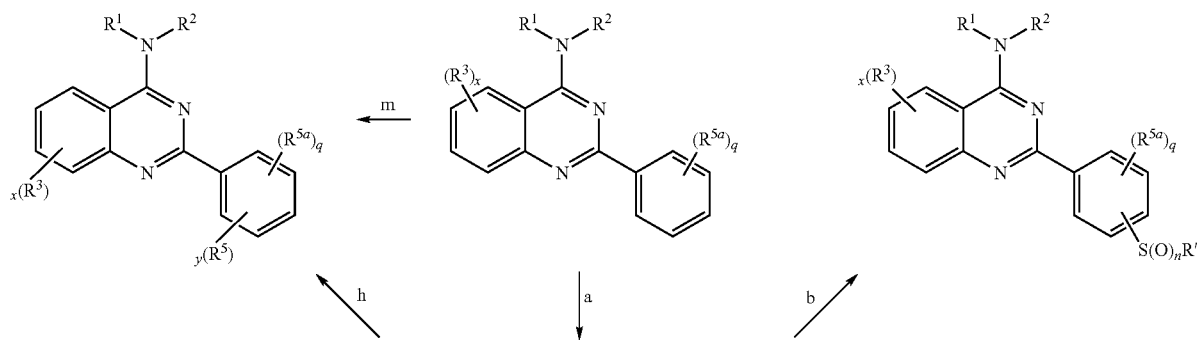

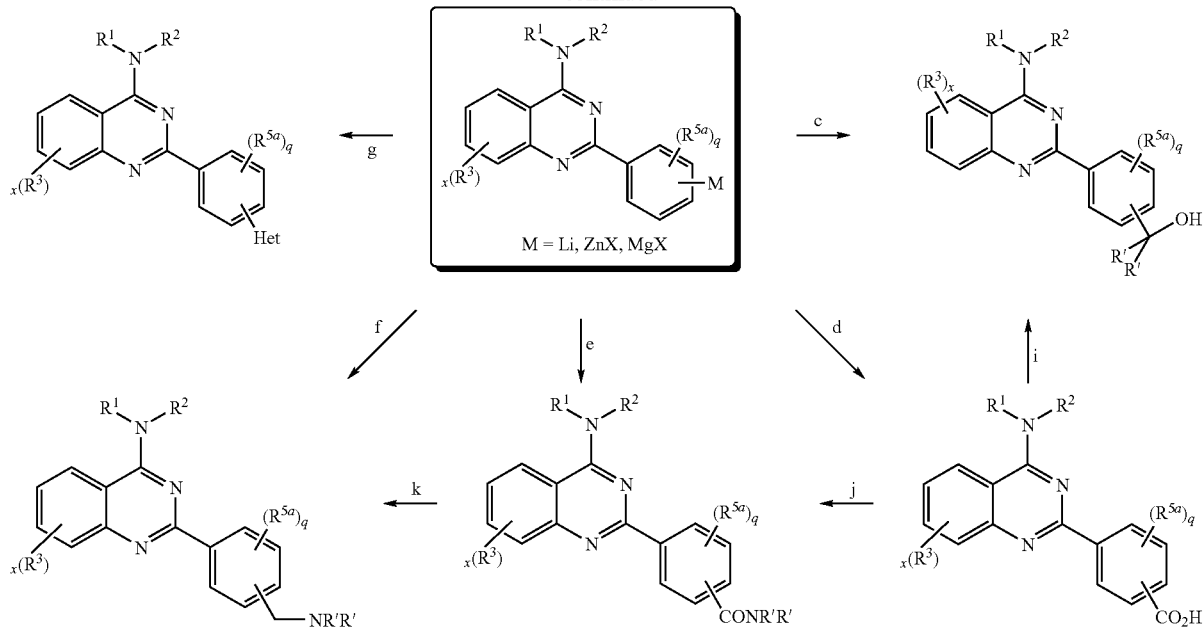

Conditions: (a) for M=Li: s-BuLi, TMEDA, THF, −78° C.; for M=ZnX: i. s-BuLi, TMEDA, THF, −78° C.; ii. ZnCl$_2$; for M=MgX: Mg, THF, reflux. (b) i. RSSR; ii. H$_2$O$_2$ (n=1) or KMnO$_4$ (n=2). (c) R$^1$R$^2$C=O, THF, −78° C. to RT. (d) CO$_2$, THF, −78° C. to RT. (e) for R$^1$=H: R$^2$NCO; others: R$^1$R$^2$COCl, THF. (f) i. H$_2$C=O; ii. PBr$_3$; iii. R$^1$R$^2$NH. (g) Het-OTf, Ni(acac)$_2$, PPh$_3$, MeMgBr, THF, RT. (h) i. B(OMe)$_3$; ii. ArX (X=halogen), Pd(PPh$_3$)$_4$, NaOEt, toluene, 80° C. (i) i. SOCl$_2$, CH$_2$Cl$_2$; ii. R$^1$Sn(R)$_3$, Pd(PPh$_3$)$_4$, toluene; iii. R$^1$MgX, THF. (j) i. SOCl$_2$, CH$_2$Cl$_2$; ii. R$^1$R$^2$NH, THF. (k) LiAlH$_4$, THF.

Scheme L:

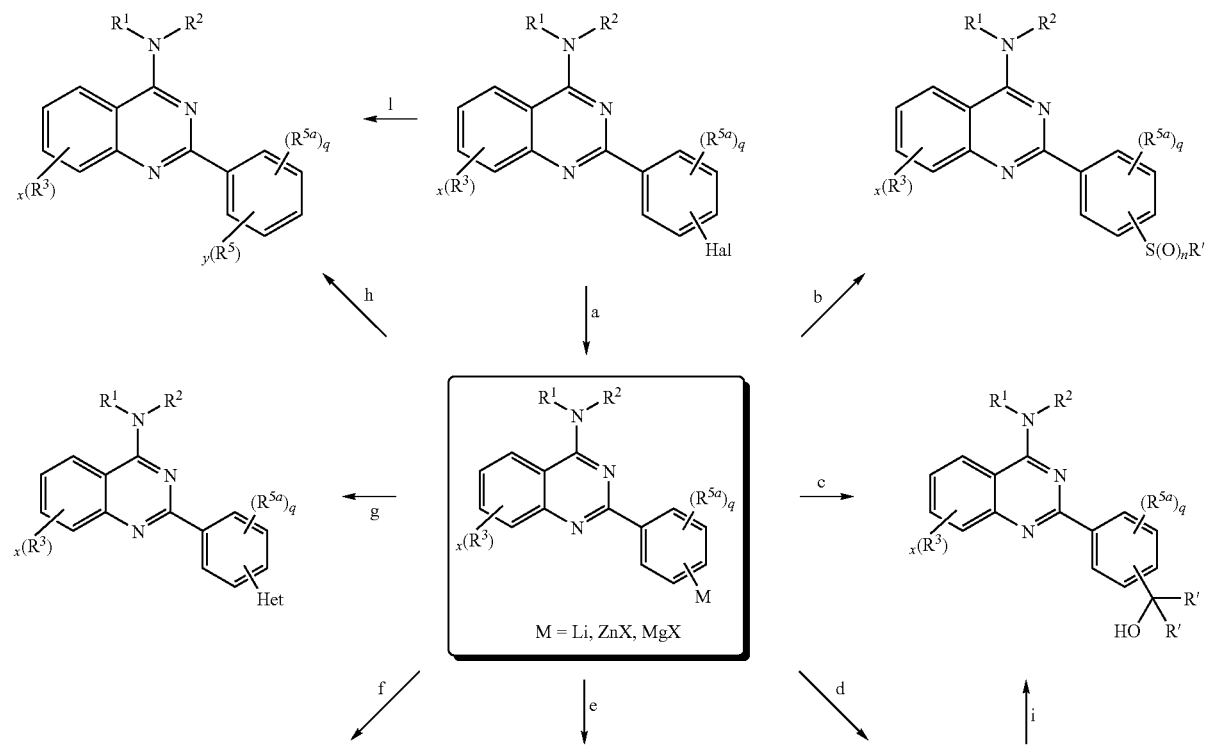

801

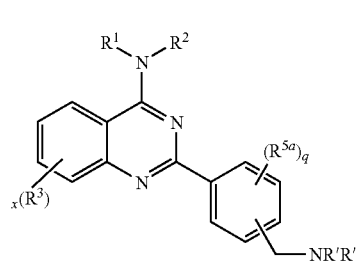

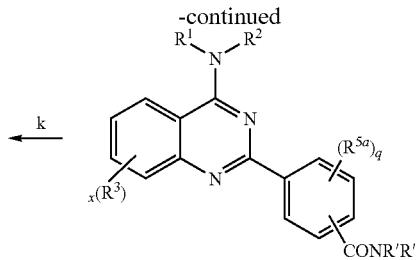

802

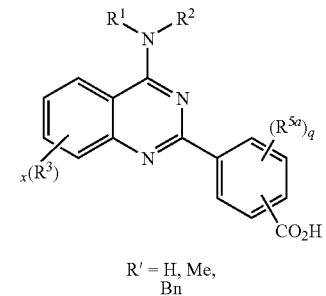

R' = H, Me, Bn

Conditions: (a) For M=Li: s-BuLi, TMEDA, THF, −78° C.; for M=ZnX: i. s-BuLi, TMEDA, THF, −78° C.; ii. ZnCl$_2$; for M=MgX: Mg, THF, reflux. (b) i. RSSR; ii. H$_2$O$_2$ (n=1) or KMnO$_4$ (n=2). (c) R$^1$R$^2$C=O, THF, −78° C. to RT. (d) CO$_2$, THF, −78° C. to RT. (e) for R$^1$=H: R$^2$NCO; others: R$^1$R$^2$COCl, THF. (f) i. H$_2$C=O; ii. PBr$_3$; iii. R$^1$R$^2$NH. (g) Het-OTf, Ni(acac)$_2$, PPh$_3$, MeMgBr, THF, RT. (h) for R$^1$=Aryl: i. B(OMe)$_3$; ii. ArX (X=halogen), Pd(PPh$_3$)$_4$, NaOEt, toluene, 80° C. for R$^1$=alkyl: R$^1$I, THF, −78° C. to RT. (i) i. SOCl$_2$, CH$_2$Cl$_2$; ii. R$^1$Sn(R)$_3$, Pd(PPh$_3$)$_4$, toluene; iii. R$^2$MgX, THF. (j) i. SOCl$_2$, CH$_2$Cl$_2$; ii. R$^1$R$^2$NH, THF. (k) LiAlH$_4$, THF. (l) ArXB(OR)$_2$, Pd(PPh$_3$)$_4$, NaOEt, toluene, 80° C.

Scheme M:

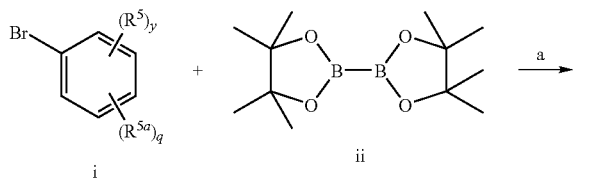

Treatment of i with ii using palladium catalyzed conditions (step a) Pd(dppf)Cl$_2$, KOAc, in DMSO or DMF at 84° C. for 2-6 hours yields intermediate iii. Reaction of intermediate iii with intermediate iv using palladium cross coupling conditions (step b) Pd(dppf)Cl2 or (Ph$_3$P)$_4$Pd, K$_2$CO$_3$, DMF:H2O (4:1) under microwave irradiation at 170° C. for 6 minutes yields compound v.

Scheme N:

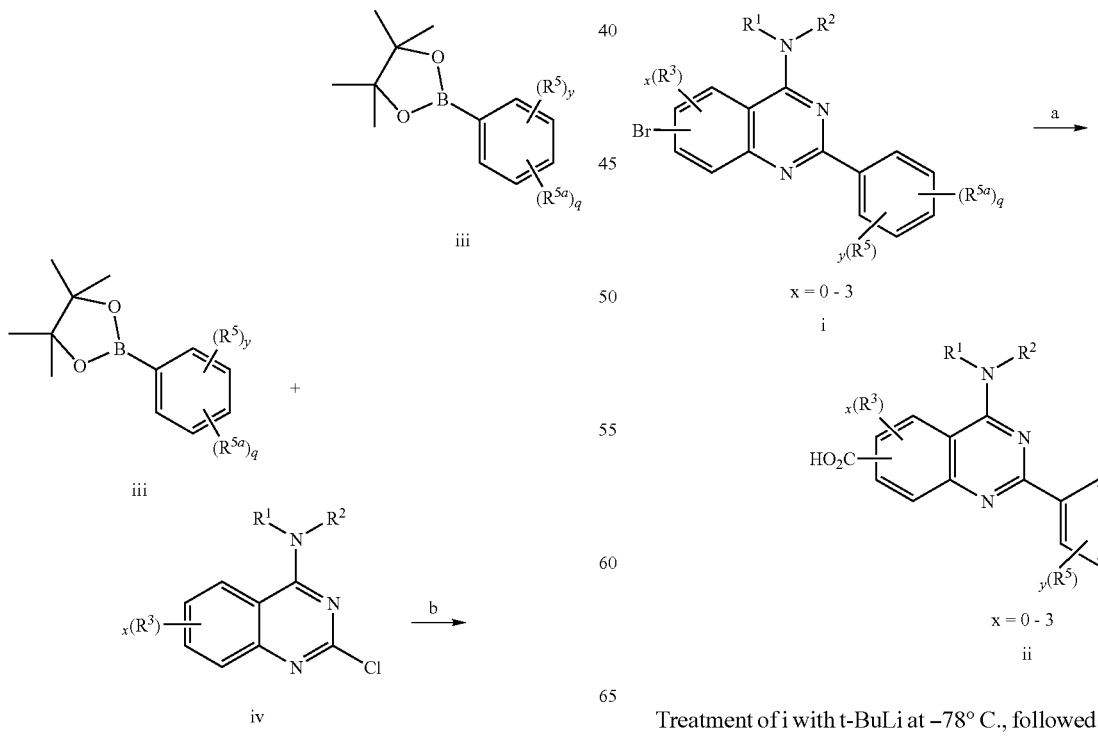

Treatment of i with t-BuLi at −78° C., followed by addition of solid CO$_2$ and warming to room temperature yield carboxylate ii. The carboxylate in ii can be retained or utilized for reactions characteristic of the functional group.

Scheme O:

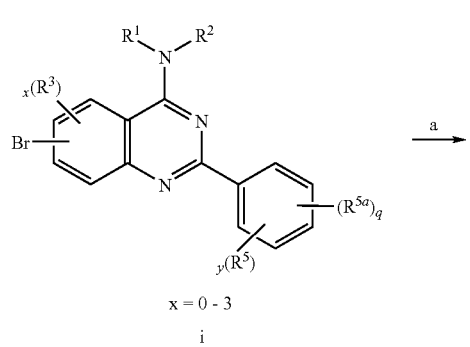

x = 0 - 3
i

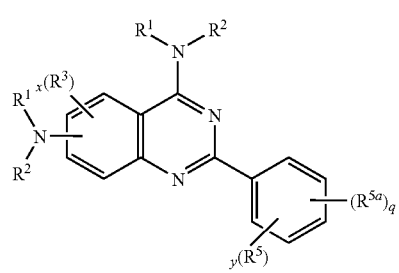

x = 0 - 3
ii

Palladium catalyzed cross coupling of i with the appropriate amine in toluene (80° C.) yields ii.

Scheme P:

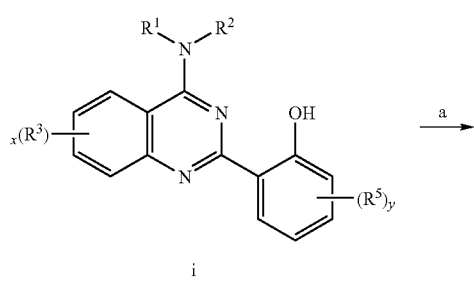

i

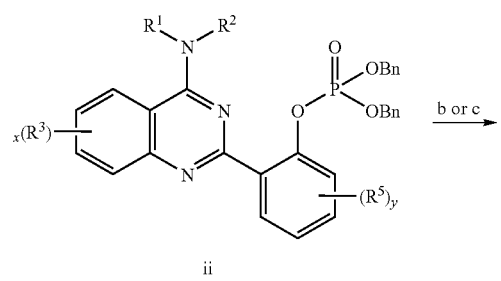

ii

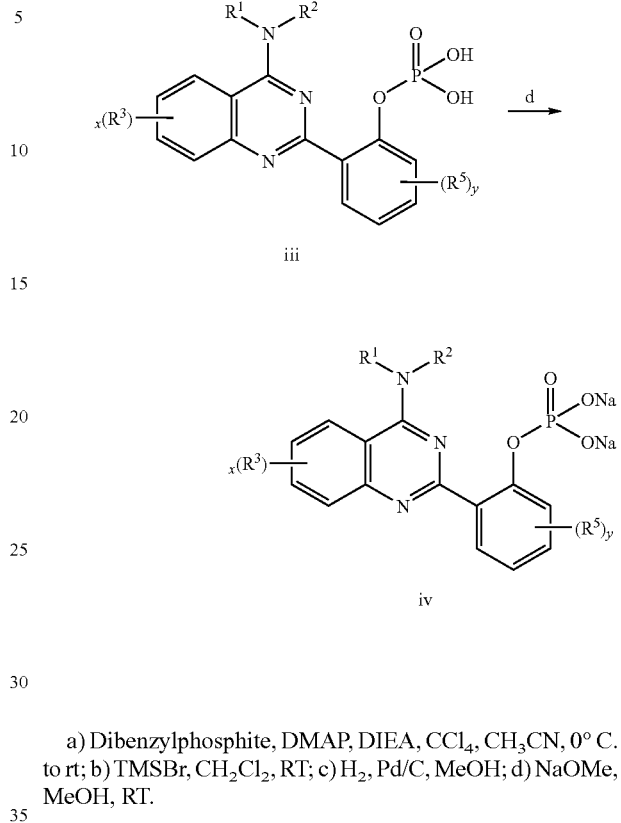

iii iv a) Dibenzylphosphite, DMAP, DIEA, $CCl_4$, $CH_3CN$, 0° C. to rt; b) TMSBr, $CH_2Cl_2$, RT; c) $H_2$, Pd/C, MeOH; d) NaOMe, MeOH, RT.

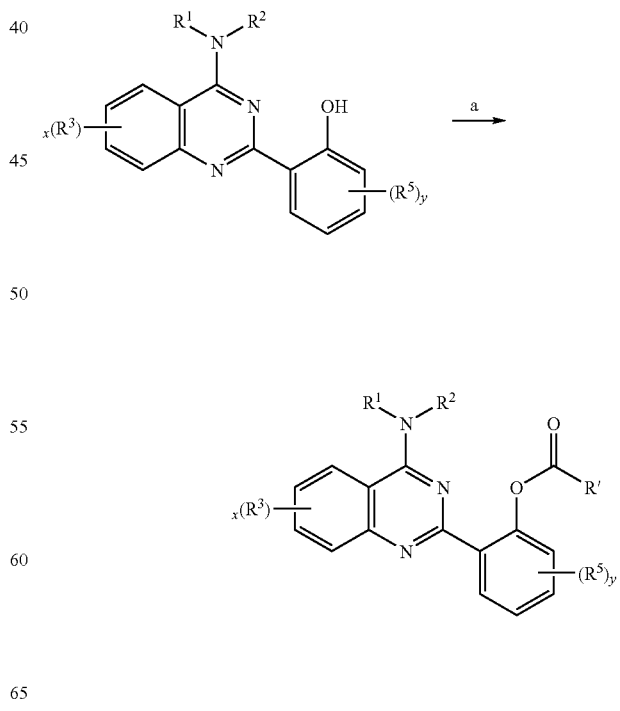

Conditions: (a) $R^4COCl$, pyridine, $CH_2Cl_2$, 0° C., then RT.

Scheme Q:

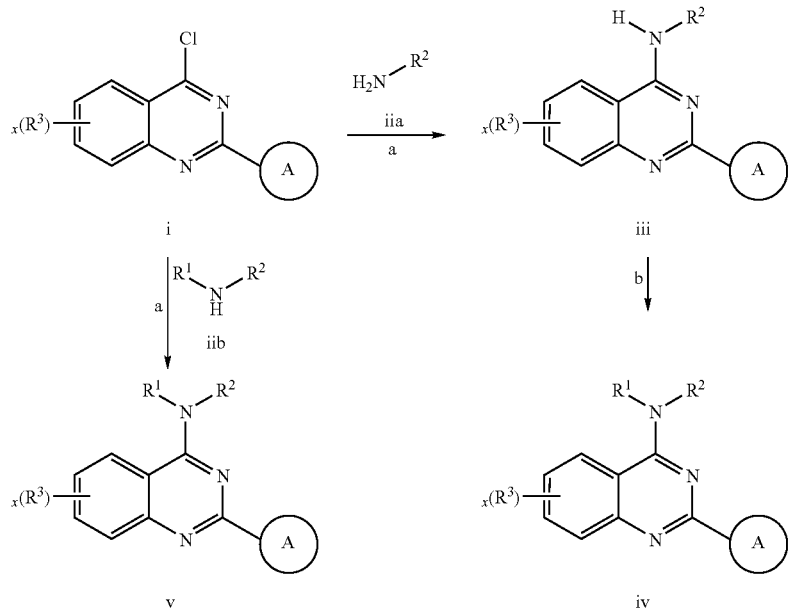

Reaction of i with iia or iib (step a), treatment with triethylamine in THF/CH$_2$Cl$_2$ at room temperature yields compounds iii and v respectively. Treatment of iii (step b) with i) NaH in THF 0° C., then reaction with electrophiles at 0° C. to room temperature yields compound iv.

Although certain exemplary embodiments are depicted and described above and herein, it will be appreciated that a compounds of the invention can be prepared according to the methods described generally above using appropriate starting materials, and according to methods known in the art. For example, in certain embodiments, compounds as described herein wherein R$^1$ is hydrogen, and R$^2$ is pyrazolyl, exemplary procedures and compounds can be found in WO02/22607, WO 02/22604, WO 02/066461, WO 02/22601, WO 02/22603, WO 02/22608, WO 02/022605, or WO 02/22602.

5. Uses, Formulation and Administration

Pharmaceutically Acceptable Compositions

As discussed above, the present invention provides compounds that are inhibitors of voltage-gated sodium ion channels and/or calcium channels, and thus the present compounds are useful for the treatment of diseases, disorders, and conditions including, but not limited to acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, and incontinence. According to one embodiment, the compounds of the present invention are useful for treating a disease selected from femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phanton pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); and prostatitis.

In another embodiment, the present invention is useful for treating lower urinary tract disorders (see, e.g., International PCT Publication No. WO 2004/066990 A2, the contents of which is incorporated herein by reference).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium ion channel or calcium channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, or cancer pain is provided comprising administering an effective amount of a compound or a pharmaceutically acceptable composition to a subject in need thereof. In yet other embodiments, a method for the treatment or lessening the severity of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phanton pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis is provided comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

In certain embodiments of the present invention an "effective amount" of the compound or pharmaceutically acceptable composition is that amount effective for treating or lessening the severity of one or more of femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phanton pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis.

The compounds and compositions, according to the method of the present invention, may be administered using any amount and any route of administration effective for treating or lessening the severity of one or more of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, cancer pain, femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phanton pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cyctitis (IC); or prostatitis. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium ion channels or calcium channels, preferably N-type calcium channels. In one embodiment, the compounds and compositions of the invention are inhibitors of one or more of NaV1.1, NaV1.2, NaV1.3, NaV1.4, NaV1.5, NaV1.6, NaV1.7, NaV1.8, NaV1.9, or CaV2.2, and thus, without wishing to be bound by any particular theory, the compounds and compositions are particularly useful for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease, condition, or disorder. When activation or hyperactivity of NaV1.1, NaV1.2, NaV1.3, NaV1.4, NaV1.5, NaV1.6, NaV1.7, NaV1.8, NaV1.9, or CaV2.2, is implicated in a particular disease, condition, or disorder, the disease, condition, or disorder may also be referred to as a "NaV1.1, NaV1.2, NaV1.3, NaV1.4, NaV1.5, NaV1.6, NaV1.7, NaV1.8 or NaV1.9-mediated disease, condition or disorder" or a "CaV2.2-mediated condition or disorder". Accordingly, in another aspect, the present invention provides a method for treating or lessening the severity of a disease, condition, or disorder where activation or hyperactivity of one or more of NaV1.1, NaV1.2, NaV1.3, NaV1.4, NaV1.5, NaV1.6, NaV1.7, NaV1.8, NaV1.9, or CaV2.2 is implicated in the disease state.

The activity of a compound utilized in this invention as an inhibitor of NaV1.1, NaV1.2, NaV1.3, NaV1.4, NaV1.5, NaV1.6, NaV1.7, NaV1.8, NaV1.9, or CaV2.2 may be assayed according to methods described generally in the Examples herein, or according to methods available to one of ordinary skill in the art.

In certain exemplary embodiments, compounds of the invention are useful as inhibitors of NaV1.8. In other embodiments, compounds of the invention are useful as inhibitors of NaV1.8 and CaV2.2. In still other embodiments, compounds of the invention are useful as inhibitors of CaV2.2. In yet other embodiments, compounds of the invention are useful as dual inhibitors of NaV1.8 and a TTX-sensitive ion channel such as NaV1.3 or NaV1.7.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting one or more of NaV1.1, NaV1.2, NaV1.3, NaV1.4, NaV1.5, NaV1.6, NaV1.7, NaV1.8, NaV1.9, or CaV2.2 activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of one or more of NaV1.1, NaV1.2, NaV1.3, NaV1.4, NaV1.5, NaV1.6, NaV1.7, NaV1.8, NaV1.9, or CaV2.2 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

In order that the invention described herein may be more fully understood, the following examples are set forth. It should be understood that these examples are for illustrative purposes only and are not to be construed as limiting this invention in any manner.

EXAMPLES

Synthesis of Exemplary Compounds of the Invention

Example 1

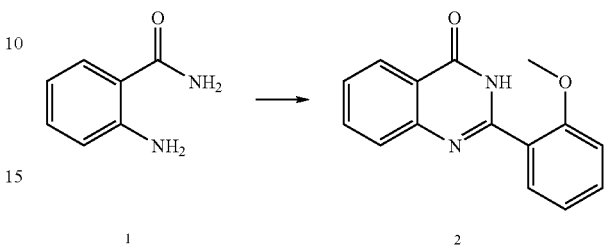

In a 2 L three-necked round-bottomed flask equipped with an overhead stirrer and reflux condenser, anthranilamide 1 (20.0 g, 147 mmol) and potassium carbonate (28.4 g, 206 mmol) was suspended in 1 L dry ether and heated to reflux. o-Anisoyl chloride (32.5 g, 191 mmol) was added slowly to the refluxing mixture. After 3 hours at reflux, the reaction mixture was allowed to cool to room temperature, the ether was removed under reduced pressure, and the resulting residue was filtered and washed with water. The resulting solid was then suspended in 600 mL of 5% aq. NaOH solution and boiled for one hour. The reaction was allowed to cool to room temperature, then neutralized with acetic acid, upon which quinazilinone 2 was precipitated. Product 2 was collected by filtration, washed with water, and dried overnight in vacuo to yield 27 g (73%) of pure 2.

LC/MS (10-99%) M/Z 253.0 retention time 3.22 min; $^1$H NMR (DMSO) δ 3.86 (s, 3H), δ 7.09 (t, 1H), δ 7.18 (d, 1H), δ 7.53 (m, 2H), δ 7.70 (m, 2H), δ 7.80 (m, 1H), δ 8.14 (d, 1H), δ 12.11 (s, 1H); $^{13}$C NMR (DMSO) δ 55.75, δ 111.86, δ 120.89, δ 120.97, δ 122.74, δ 125.75, δ 126.45, δ 127.26, δ 130.41, δ 132.13, δ 134.32, δ 148.97, δ 152.48, δ 157.12, δ 161.35

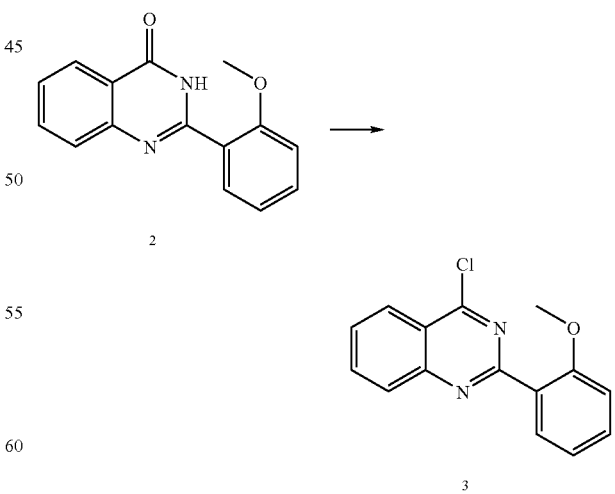

Quinazolinone 2 (20.0 g, 79.3 mmol) was suspended in 500 mL dry benzene in a 1 L round-bottomed flask equipped with a reflux condenser. N,N-Dimethylanaline (14.4 g, 119 mmol) was added and the reaction was refluxed for 30 minutes under nitrogen. Upon cooling to room temperature, phosphorus oxychloride (12.2 g, 79.3 mmol) was added and the reaction mixture was then refluxed for an additional 3 hours under nitrogen. The mixture was cooled to room temperature, poured over ice, and neutralized with saturated aqueous sodium bicarbonate. The solution was then extracted four times with toluene and the combined organic layers dried over magnesium sulfate, filtered, and concentrated in vacuo to a reddish-brown solid. The resulting 4-chloroquinazoline 3 was purified via flash chromatography (40% hexanes, 60% dichloromethane) to afford 20 g (93%) 3 as a yellow solid.

LC/MS (40-99%) M/Z 271.4 retention time 2.49 min; $^1$H NMR (CDCl$_3$) δ 3.89 (s, 3H), 67.06 (d, 1H), δ 7.09 (d, 1H), δ 7.45 (m, 1H), δ 7.71 (m, 1H), δ 7.80 (m, 1H), δ 7.95 (m, 1H), δ 8.17 (d, 1H), δ 8.30 (d, 1H); $^{13}$C NMR (CDCl$_3$) δ 56.3 (d), δ 112.15 (d), δ 121.0 (s), δ 122.29 (s), δ 125.97 (s), δ 126.76 (s), δ 127.25 (d), δ 128.71 (d), δ 132.10 (m), δ 135.26 (s), δ 151.16 (s), δ 158.19 (s), δ 161.02 (s), δ 162.58 (s).

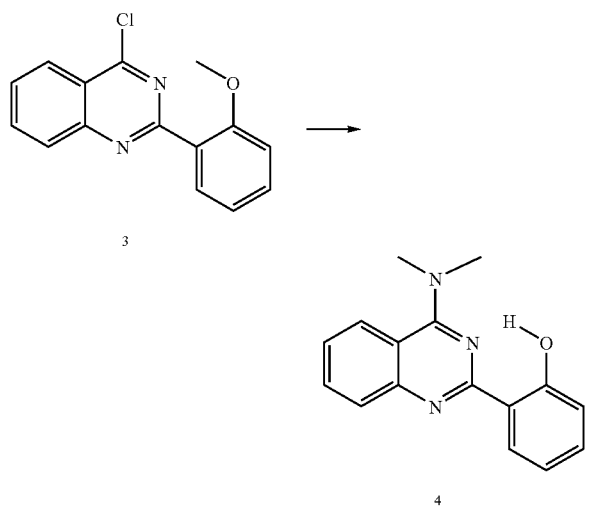

A 500 mL two-necked round-bottomed flask equipped with an addition funnel was charged with 4-Chloroquinazoline 3 (5.00 g, 18.5 mmol) and 80 mL dry dichloromethane under nitrogen. The mixture was cooled to −78° C. and 92 mL of 1M boron tribromide in dichloromethane was added dropwise via the addition funnel. The cooling bath was removed and the reaction allowed to stir for three hours at room temperature. The mixture was then cooled to 0° C. and slowly neutralized with saturated aqueous sodium bicarbonate, extracted 3 times with dichloromethane, and the combined organic solutions dried over magnesium sulfate, filtered, and concentrated in vacuo to a yellow solid. The residue was promptly dissolved in 30 mL of 2:1 dry THF/CH$_2$Cl$_2$, then treated with 2 M dimethylamine in THF (46.3 mL, 92.5 mmol). After 30 min the solvent was removed under reduced pressure, the residue partitioned between dichloromethane and water, and the aqueous solution extracted 4 times with dichloromethane. The combined organic solutions were dried over magnesium sulfate, filtered, and concentrated in vacuo to an orange solid. Recrystallization from ethanol gave 2.61 g (53%) yellow crystalline 4.

LC/MS (10-99%) M/Z 266.0 retention time 2.59 min; $^1$H NMR (DMSO) δ 3.32 (s,), δ 3.45 (s, 6H), δ 6.93 (m, 2H), δ 7.35 (m, 1H), δ 7.46 (m, 1H), δ 7.78 (m, 2H), δ 8.21 (d, 1H), δ 8.43 (d, 1H); $^{13}$C NMR (DMSO) δ 41.62, 113.77, 117.18, 118.25, 118.97, 124.75, 126.15, 126.51, 128.96, 132.36, 133.11, 149.09, 159.22, 160.74, 161.69.

HCl Salt:

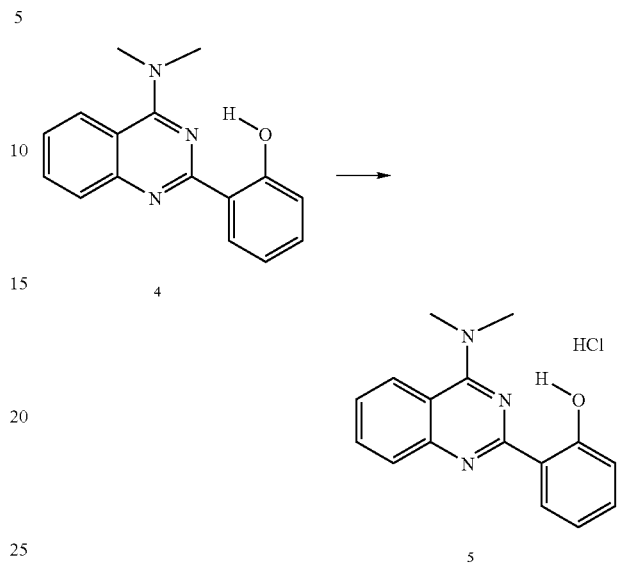

A 250 mL round-bottomed flask was charged with quinazoline 4 (1.0 g, 3.8 mmol), 100 mL dry ether, 11 mL dry methanol, then sealed with a septum and placed in a sonicator with the bath temperature at 43° C. Upon complete dissolution of 4, 2 M ethereal HCl solution was added (1.9 mL, 3.8 mmol), causing immediate precipitation of 5. The solvent was removed in vacuo, and the salt twice re-suspended in dry ether, concentrated, and dried in vacuo. After drying overnight under vacuum, 1.13 g (98%) 5 was obtained as a pale yellow solid.

M/Z 266.0 retention time 2.59 min; $^1$H NMR (DMSO) 63.59 (s, 6H), δ 7.02 (m, 1H), δ 7.19 (d, 1H), δ 7.49 (m, 1H), δ 7.64 (m, 1H), δ 7.96 (m, 1H), δ 8.05 (d, 1H), δ 8.20 (d, 1H), δ 8.35 (d, 1H); $^{13}$C NMR (DMSO) δ 42.37, 112.07, 117.19, 119.23, 121.09, 126.15, 127.48, 130.45, 134.01, 134.67, 155.37, 158.61, 160.97.

Example 2

Synthesis of 2-(2-Methoxy-phenyl)-7-trifluoromethyl-3H-quinazolin-4-one

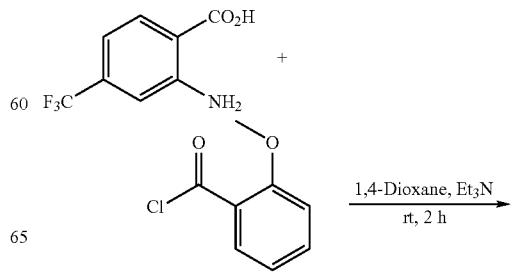

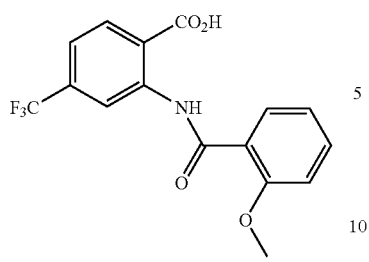

2-(2-Methoxy-benzoylamino)-4-trifluoromethyl-benzoic acid

2-Amino-4-trifluoro-benzoic acid (3.84 g, 18.73 mmol) was dissolved in 30 ml dry 1,4-Dioxane followed by the slow addition of O-Anisoyl chloride (3.3 ml, 24.35 mmol), then triethylamine (7.85 ml, 56.19 mmol) and stirred under a nitrogen atmosphere at room temperature for 2 hours. Solvent was remove under reduced pressure and organic was partitioned between water and EtOAc and the pH was adjusted to 3 with HCl. Organic layer was separated, dried over MgSO4, filtered and concentrated to an off white solid. Recovered 6.35 g 100% yield. LC/MS (10-99%) M/Z 339.9, retention time 3.58 minutes.

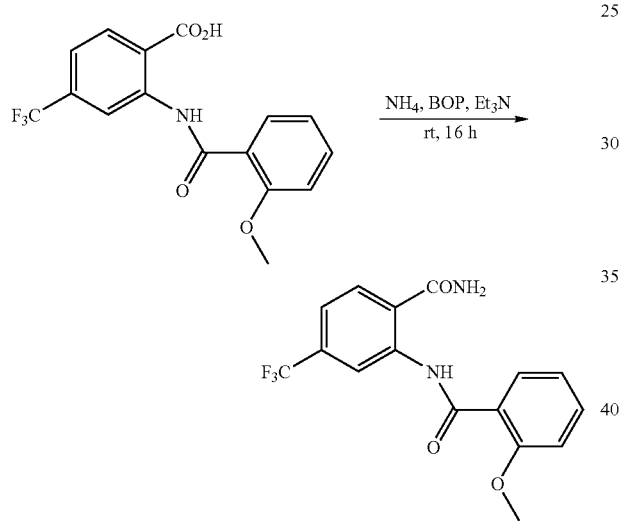

2-(2-Methoxy-benzoylamino)-4-trifluoromethyl-benzamide 2-(2-Methoxy-benzoylamino)-4-trifluoromethyl-benzoic acid (7.04 g, 20.77 mmol) was suspended in 0.5M solution of ammonia in 1,4-Dioxane (125 ml, 62.31 mmol), followed by the addition of triethylamine (5.78 ml, 41.54 mmol) then BOP reagent (12 g, 27.0 mmol) and stirred at room temperature for 16 hours. The product was collected by vacuum filtration and washed with water. The desired product was dried on the lyophilizer for 24 h. Recovered 3.8 g as a white solid. LC/MS (10-99%) M/Z 339.1, retention time 2.93 minutes.

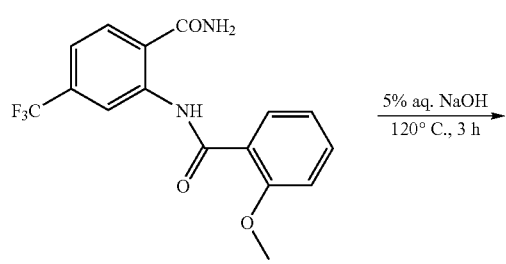

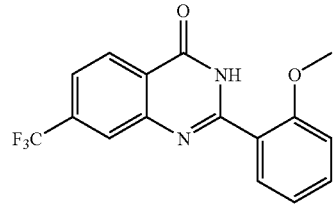

2-(2-Methoxy-phenyl)-7-trifluoromethyl-3H-quinazolin-4-one 2-(2-Methoxy-benzoylamino)-4-trifluoromethyl-benzamide (3.8 g, 11.24 mmol) was suspended in 145 ml 5% aqueous NaOH solution then refluxed fro three hours at 120° C. The reaction was cooled to room temperature and adjusted to pH 4 causing the desired product to precipitate from solution. Solid was collected by vacuum filtration as a white solid and dried on the lyophilizer for 24 h. White solid 2.7 g, 75% yield. LC/MS (10-99%) M/Z 321.1, retention time 3.25 minutes.

Synthesis of 2-(2-Methoxy-phenyl)-7-methyl-3H-quinazolin-4-one

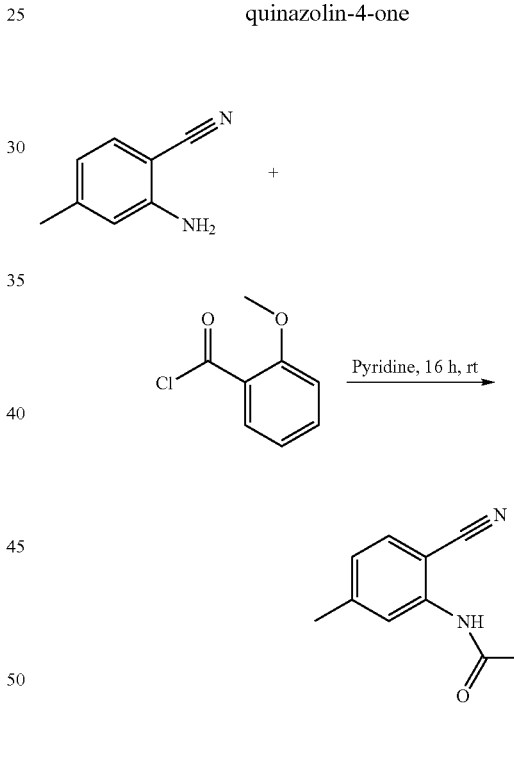

N-(2-Cyano-5-methyl-phenyl)-2-methoxy-benzamide

2-Amino-4-methyl anthronitrile (50.0 g, 378.3 mmol) was dissolved in 1 L dry pyridine and cooled to 0° C. O-Anisoyl chloride (63.0 ml, 453.96 mmol) was added dropwise over a 40 minute period and the reaction was allowed to warm to room temperature and stirred under a nitrogen atmosphere for 16 hours. The reaction was poured over 2 L of ice and the product formed a precipitate. The product was collected by vacuum filtration and dried for 3 days to produce the desired product a fluffy tan solid. Recovered 92.0 g 91% yield. LC/MS (10-99%) M/Z 267.2, retention time 3.34 minutes.

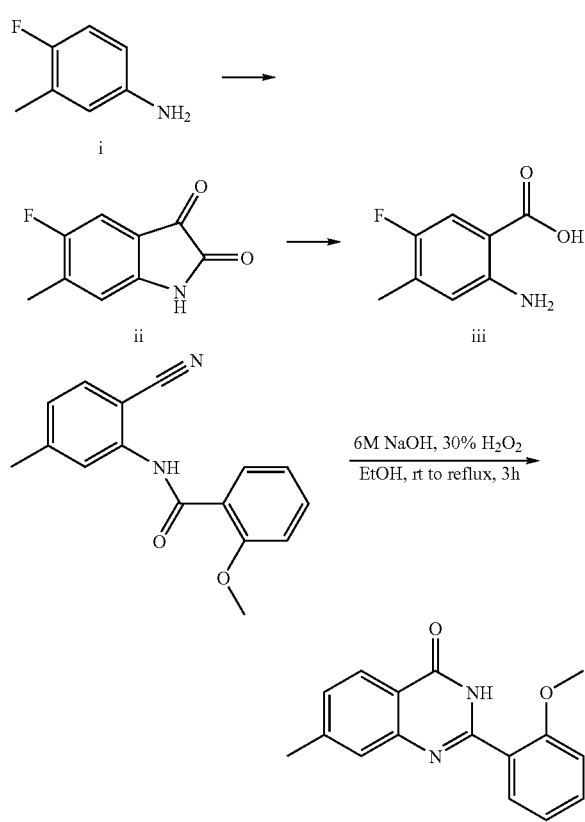

2-(2-Methoxy-phenyl)-7-methyl-3H-quinazolin-4-one

N-(2-Cyano-5-methyl-phenyl)-2-methoxy-benzamide (47.0 g, 176.5 mmol) was suspended in 1 L of ethanol followed by the addition of a 6M aqueous NaOH solution (326 ml), then a 30% solution of $H_2O_2$ (100 ml). The reaction was refluxed for 3 hours, cooled to room temperature and poured over an equal volume of ice. The solution was adjusted to pH3.5 and the product precipitated from solution. Desired product was collected by vacuum filtration and dried on the lyophilizer for 24 h. 22.4 g, 48% yield. LC/MS (10-99%) M/Z 267.0, retention time 2.54 minutes.

5-Fluoro-4-methyl-anthranilic acid

2-Amino-5-fluoro-4-methyl-benzoic acid. Chloral hydrate (76 g) was dissolved in 1 L water and subsequently 1 kg $Na_2SO_4$, 94.1 g $H_2NOH \cdot HCl$, and 51.3 g 4-fluoro-3-methyl aniline in 250 ml 5% aq. HCl were added. The suspension was heated to boiling and kept boiling for 1 minute. After cooling down to room temperature, the solid was filtered off and washed twice with warm water (40° C.). Yield after drying overnight at 60° C. under vacuum was 275 g, which was used without further purification or drying. The 275 g of crude product was slowly poured in 500 ml of concentrated $H_2SO_4$ at 50° C., such that the temperature was kept below 75° C. After completion of addition, the dark/purple solution was heated to 85° C. for 15 minutes. After cooling down to room temperature, the solution was poured in 2 L of ice water and was left standing for an half hour. The red solid was filtered and washed twice with cold water. Subsequently, the solid was dried under vacuum at 70° C. Yield: 69.9 g (quantitatively from 4-fluoro-3-methyl aniline) of a mixture of two regio isomers: 5-fluoro and 3-fluoro 3-methyl-isatin in a ratio of about 55:45. The mixture of isatins (69.4 g) was dissolved in 1 L 1N aq. NaOH and subsequently 100 ml of 30% aq. $H_2O_2$ was added drop wise, keeping the temperature below 30° C. After completion of addition, the mixture was heated to 45° C. until evolution of gas ceased. The solution was cooled to room temperature, filtered and acidified with glacial acetic acid. The precipitate formed was filtered off, washed twice with water and air-dried 45° C. Yield: 29.4 g of 5-fluoro-4-methyl-anthranilic acid iii.

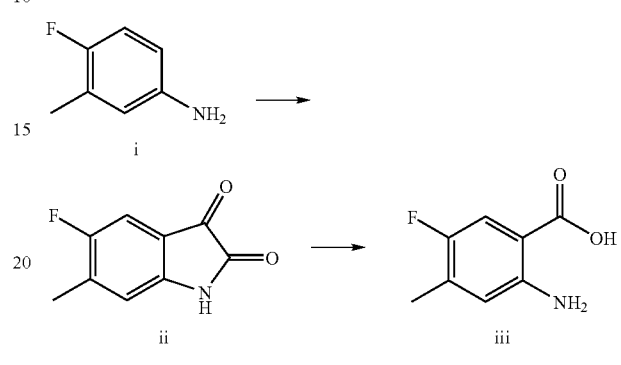

2-Amino-5-trifluoromethyl-benzoic acid. 4-(trifluoromethyl)aniline (25 g, 0.15 mol) was dissolved in THF (275 mL), then treated with Boc anhydride (41 g, 0.19 mol), $ET_3N$ (19 g, 0.19 mol), and 4-(dimethylamino)pyridine (0.1 g, 0.8 mmol). The mixture was refluxed for 3 hours, the solvents removed in vacuo, and the organic residue dissolved in EtOAc, washed with 1 M NaOH, then 1 M HCl, then dried and concentrated. The resulting product was recrystallized from heptane yielding 39 g final product as a white solid. The solid (0.15 mol) was dissolved in THF (350 mL) and cooled to −78° C. under nitrogen, then treated dropwise with BuLi (1.6 M in hexane, 282 mL, 0.45 mol). After 1 h, the solution was warmed to 0° C. and held for 1.5 h. The mixture was poured onto excess solid $CO_2$ and stirred overnight at RT. After partitioning against 1 M HCl, the THF layer was evaporated and the residue dissolved in EtOAc, washed with 1 M HCl, then dried and concentrated. The solid product was triturated with hexan to yield the final product as a white solid (15.8 g). LC/MS retention time 2.70 min, m/z (obs, M−H)= 304.1. Finally the Boc anthranilate (11.3 g) was dissolved in CH2CL2 (26 mL) and treated with TFA (21 mL). After stirring at RT for 2 h, the solution was dried in vacuo, the resulting residue dissolved in toluene (100 mL), concentrated to dryness, and the dissolution/drying process repeated twice more, yielding the desired product as a white solid (10.8 g), LC/MS retention time 1.2 min, m/z (obs, M−H)=204.0.

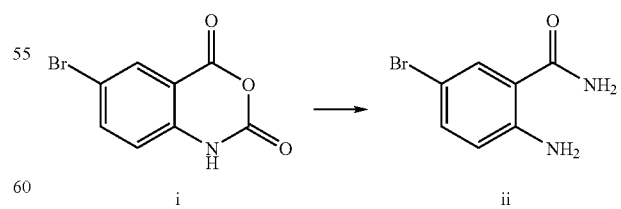

2-Amino-5-bromo-benzamide. The isatoic anhydride (15 g, 0.062 mol) was combined with 1 M aq. $NH_4OH$ (340 mL) and stirred for 2 d at RT. The solid product was collected by filtration and dried in vacuo (6.6 g). LC/MS retention time 2.47 min, m/z obs=215.2.

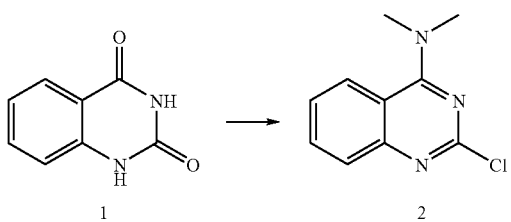

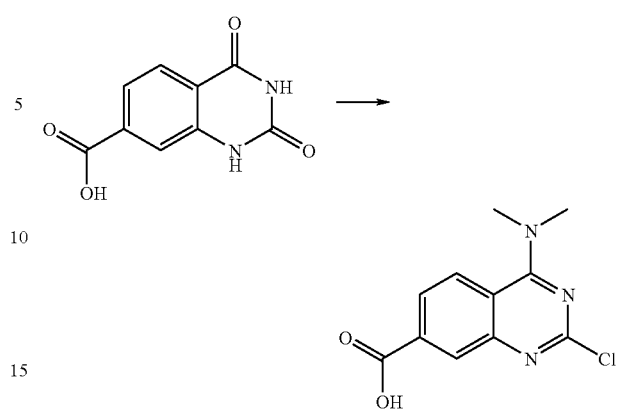

To a stirring suspension of benzoyleneurea 1 (10.0 g, 61.7 mmol) and phosphorus oxychloride (20 ml) in a 500 mL three-necked round-bottomed flask equipped with a magnetic stirrer and reflux condenser, was added N,N-dimethylaniline (7.80 ml, 61.7 mmol) in a single portion. The suspension was heated at reflux for 3 hours and slowly formed a light red solution. The solution was concentrated under reduced pressure and the residue was poured onto ice (100 g). The solution was basified to pH=9.0 using concentrated aqueous sodium bicarbonate solution. The mixture was partitioned between $CH_2Cl_2$ and $H_2O$. The organic portion was dried ($MgSO_4$) and evaporated to dryness under reduced pressure. The residue was dissolved in anhydrous THF (75 ml) and cooled to 0° C. Dimethylaniline (67.7 mL, 135 mmol, 2.0 M in THF) was added dropwise, with stirring, over a period of 30 minutes. The solution was then stirred at 0° C. for 1 hour. The solution was concentrated under reduced pressure and the residue was purified by silica gel chromatography using (70% hexanes, 30% ethyl acetate) to obtain 2 (7.90 g, 38.1 mmol, 62% yield) as a white solid.

$^1$H NMR (CDCl$_3$) δ3.43 (s, 6H), 7.40 (t, 1H), 7.69 (t, 1H), 7.78 (d, 1H), 8.02 (d, 1H); M+1 (obs)=208.0; $R_f$=2.26.

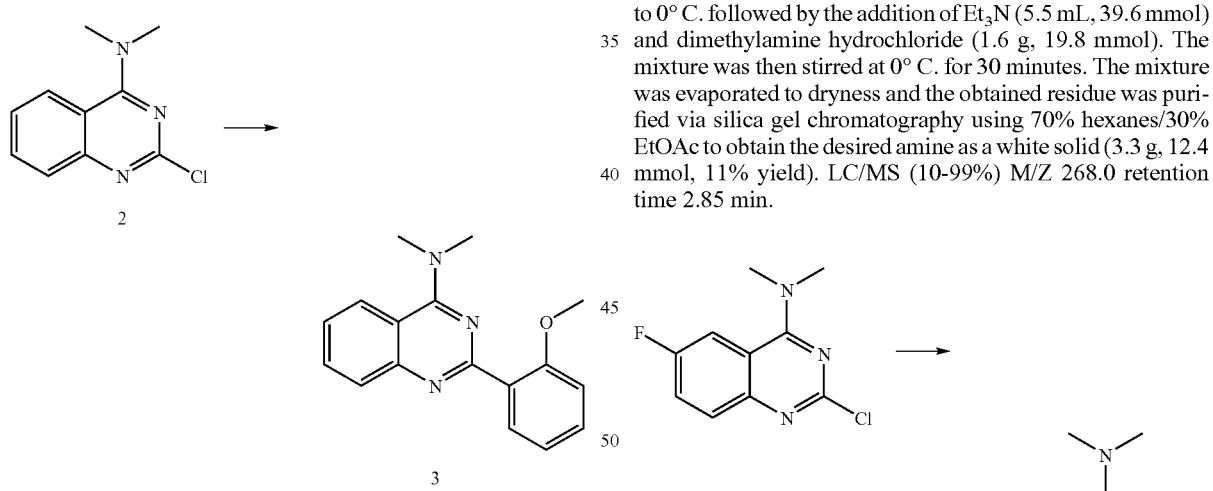

A 5 mL microwave reaction vessel was charged with a mixture of 2 (100 mg, 0.48 mmol), 2-methoxyphenylboronic acid (96 mg, 0.63 mmol), tetrakis(triphenylphosphine)palladium(0) (55 mg, 0.048 mmol), sodium carbonate (1.20 mL, 0.48 mmol, 0.40 M aqueous solution), and acetonitrile (1.20 mL). The vessel was sealed and heated, with stirring, at 170° C. for 10 minutes via microwave irradiation. The organic portion was concentrated under reduced pressure and the residue was purified by silica gel chromatography using (80% hexanes, 20% ethyl acetate) to obtain 3 (120 mg, 0.43 mmol, 89% yield) as a white solid.

$^1$H NMR (CDCl$_3$) δ3.32 (s, 6H), 3.81 (s, 3H), 6.89-7.02 (m, 2H), 7.28-7.34 (m, 2H), 7.62 (t, 1H), 7.75 (d, 1H), 7.89 (d, 1H), 7.95 (d, 1H); M+1 (obs)=280.2; $R_f$=2.46.

2-Chloro-4-dimethylaminoquinazoline-7-carboxylic acid methyl ester. A stirring suspension of 2,4-dioxo-1,2,3,4-tetrahydro-quinazoline-7-carboxylic acid methyl ester (12.2 g, 55.4 mmol), N,N-dimethylaniline (14.0 mL, 110.8 mmol), and POCl$_3$ (25 mL), under N$_2$, was heated at 100° C. for 15 minutes. The solution was evaporated to dryness under reduced pressure and the residual oil was poured into ice-water (800 mL). The mixture was made strongly basic by the addition of 50% aqueous NaOH solution at 0° C. The mixture was partitioned between CH$_2$Cl$_2$ and H$_2$O and the organic portion was evaporated to dryness under reduced pressure. The residue was purified by silica gel chromatography using 70% hexanes/30% EtOAc to obtain the intermediate chloride as a white solid (5.1 g, 19.8 mmol). The obtained intermediate was dissolved in CH$_2$Cl$_2$ (100 mL). The solution was cooled to 0° C. followed by the addition of Et$_3$N (5.5 mL, 39.6 mmol) and dimethylamine hydrochloride (1.6 g, 19.8 mmol). The mixture was then stirred at 0° C. for 30 minutes. The mixture was evaporated to dryness and the obtained residue was purified via silica gel chromatography using 70% hexanes/30% EtOAc to obtain the desired amine as a white solid (3.3 g, 12.4 mmol, 11% yield). LC/MS (10-99%) M/Z 268.0 retention time 2.85 min.

6-Fluoro-N4,N4-dimethylquinazoline-2,4-diamine. A stirring mixture of (2-chloro-6-fluoro-quinazolin-4-yl)-dimethylamine (50 mg, 0.22 mmol), lithium bis(trimethylsilyl) amide (260 µL, 0.26 mmol, 1.0 M in hexanes), Pd$_2$(dba)$_3$ (20 mg, 0.022 mmol), 2-(dicyclohexyl)phosphinobiphenyl (19 mg, 0.053 mmol), and THF (1.0 mL) was heated in a sealed tube via microwave irradiation at 65° C. for 1.5 hours. 1.0 N aqueous HCl solution (3.0 mL) was added and the mixture was stirred at room temperature for 30 minutes. The mixture was partitioned between H$_2$O and EtOAc. The organic portion was evaporated to dryness under reduced pressure. The obtained residue was purified via silica gel chromatography using 95% CH$_2$Cl$_2$/5% MeOH to obtain the desired amine as a tan solid (40 mg, 19.4 mmol, 88% yield). LC/MS (10-99%) M/Z 206.9 retention time 1.18 min.

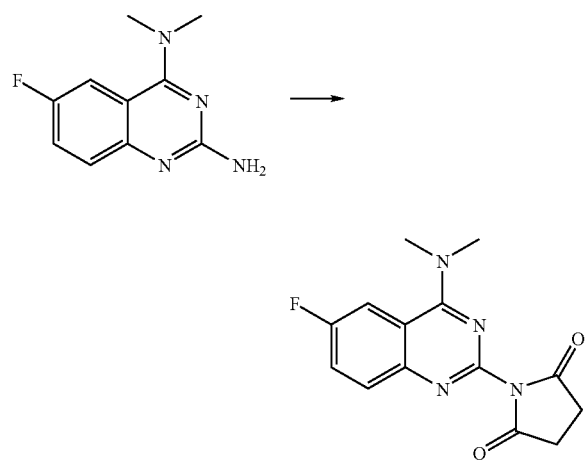

1-(4-Dimethylamino-6-fluoroquinazolin-2-yl)-pyrrolidine-2,5-dione. A stirring mixture of 6-fluoro-N4,N4-dimethylquinazoline-2,4-diamine (30.0 mg, 0.13 mmol), succinic anhydride (12 mg, 0.12 mmol), and p-dioxane (500 µL) was heated in a sealed tube via microwave irradiation at 170° C. for 20 minutes. The mixture was purified via HPLC to obtain the desired succinate as a TFA salt (40 mg, 0.10 mmol, 76% yield). LC/MS (10-99%) M/Z 289.3 retention time 2.01 min.

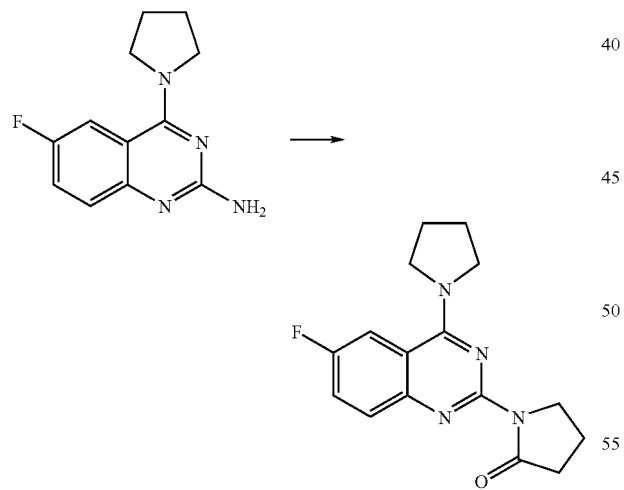

1-(6-Fluoro-4-pyrrolidin-1-yl-quinazolin-2-yl)-pyrrolidin-2-one. A stirring mixture of 6-fluoro-4-pyrrolidin-1-yl-quinazolin-2-ylamine (30.0 mg, 0.14 mmol), 4-chlorobutyryl chloride (17 µL, 0.15 mmol), Et$_3$N (42 µL, 0.30 mmol), and p-dioxane (500 µL) was heated in a sealed tube via microwave irradiation at 170° C. for 20 minutes. The mixture was purified via HPLC to obtain the desired lactam as a TFA salt (45 mg, 0.11 mmol, 81% yield). LC/MS (10-99%) M/Z 301.2 retention time 2.24 min.

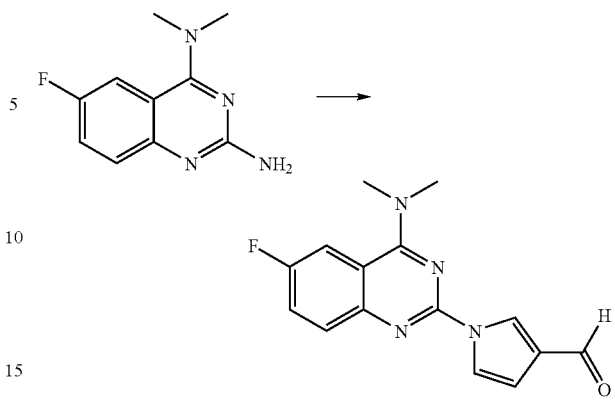

1-(4-Dimethylamino-6-fluoro-quinazolin-2-yl)-1H-pyrrole-3-carbaldehyde. A stirring mixture of 6-fluoro-N4,N4-dimethylquinazoline-2,4-diamine (20.0 mg, 0.10 mmol), 2,5-dimethyoxy-3-tetrahydrofurancarboxaldehyde (43 µL, 0.30 mmol), and AcOH (500 µL) was heated at 90° C. for 30 minutes. The mixture was evaporated to dryness and the obtained residue was purified via silica gel chromatography using 70% hexanes/30% EtOAc to obtain the desired aldehyde as a white solid (15 mg, 0.05 mmol, 50% yield). LC/MS (10-99%) M/Z 285.1 retention time 3.23 min.

(6-Methoxy-2-pyrrol-1-yl-quinazolin-4-yl)-dimethylamine. To a stirring solution pyrrole (310 mg, 4.6 mmol) and DMF (5.0 mL), under N$_2$, was added NaH (170 mg, 4.2 mmol, 60% in mineral oil). The mixture was stirred at room temperature for 10 minutes. To this solution was added (2-chloro-6-methoxyquinazolin-4-yl)dimethylamine (1.0 g, 4.2 mmol). The mixture was heated in a sealed tube via microwave irradiation at 220° C. for 20 minutes. The mixture was evaporated to dryness and the obtained residue was purified via silica gel chromatography using 70% hexanes/30% EtOAc to obtain the desired aldehyde as a white solid (15 mg, 0.05 mmol, 50% yield). LC/MS (10-99%) M/Z 269.0 retention time 2.39 min.

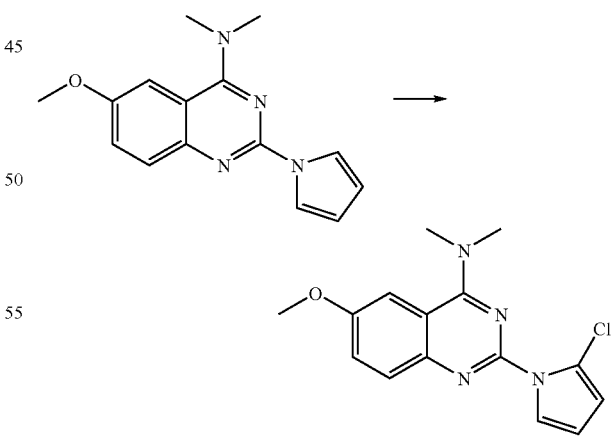

[2-(2-Chloro-pyrrol-1-yl)-6-methoxyquinazolin-4-yl]dimethyl-amine. To a stirring solution of (6-methoxy-2-pyrrol-1-yl-quinazolin-4-yl)dimethyl-amine (25 mg, 0.09 mmol) and THF (2.0 mL), under N$_2$, was added N-chlorosuccinimide (13 mg, 0.09 mmol). The solution was stirred at room temperature for 17 hours. The mixture was purified via HPLC to obtain the desired chloropyrrole as a TFA salt (23 mg, 0.06 mmol, 62% yield). LC/MS (10-99%) M/Z 303.0 retention time 2.71 min.

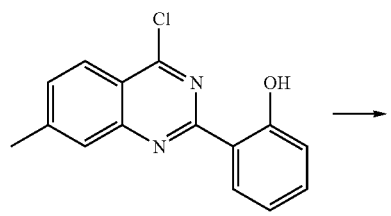

2-[4-(4-Aminopiperidin-1-yl)-7-methylquinazolin-2-yl]phenol. To a stirring solution of 2-(4-Chloro-7-methylquinazolin-2-yl)-phenol (100 mg, 0.35 mmol), Et$_3$N (72 µL, 0.52 mmol), and CH$_2$Cl$_2$ (300 µL) under N$_2$, was added 4-aminopiperidine (54 µL, 0.52 mmol). The mixture was stirred at room temperature for 2 hours. The mixture was evaporated to dryness under reduced pressure. The residue was purified by silica gel chromatography using 98% CH$_2$Cl$_2$/2% MeOH to obtain the desired amine as a white solid (11 mg, 0.31 mmol, 89% yield). LC/MS (10-99%) M/Z 349.3 retention time 2.22 min.

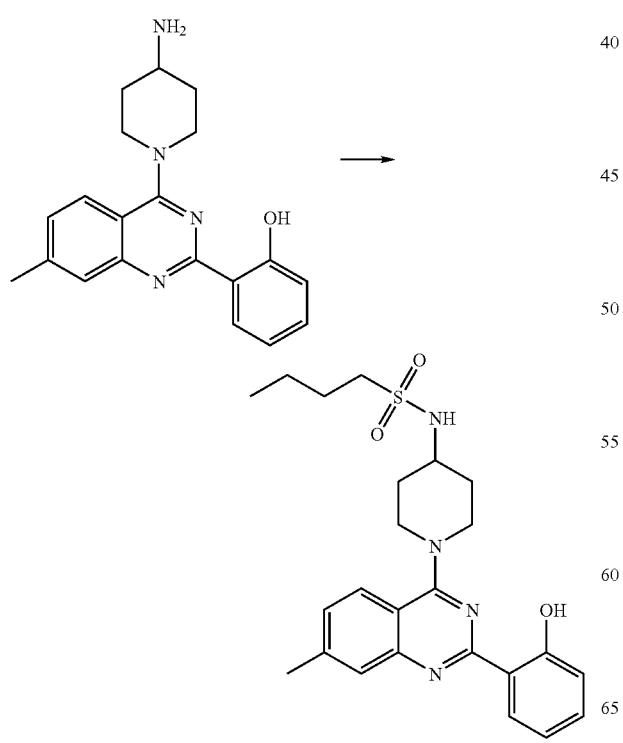

Ethanesulfonic acid {1-[2-(2-hydroxyphenyl)-7-methylquinazolin-4-yl]-piperidin-4-yl}-amide. To a stirring solution of 2-[4-(4-Aminopiperidin-1-yl)-7-methylquinazolin-2-yl]-phenol (30 mg, 0.09 mmol), Et$_3$N (25 µL, 0.18 mmol), and CH$_2$Cl$_2$ (500 mL) under N$_2$, was added ethanesulfonyl chloride (10 µL, 0.09 mmol). The mixture was stirred at room temperature for 3 hours. The mixture was purified via HPLC to obtain the desired sulfonamide as a TFA salt (33 mg, 0.06 mmol, 68% yield). LC/MS (10-99%) M/Z 427.3 retention time 2.80 min.

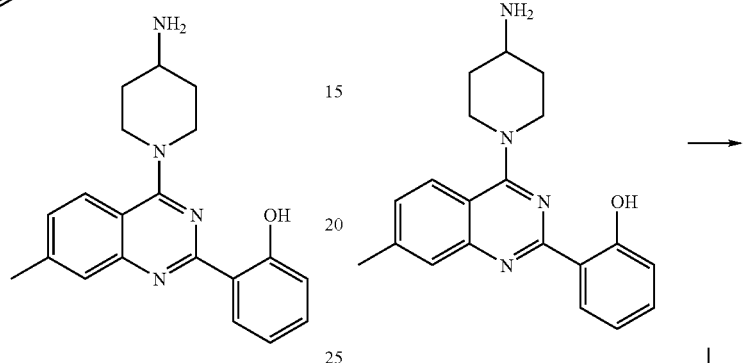

3-{1-[2-(2-Hydroxyphenyl)-7-methylquinazolin-4-yl]piperidin-4-yl}-1,1-dimethylsulfonylurea. To a stirring solution of 2-[4-(4-Aminopiperidin-1-yl)-7-methylquinazolin-2-yl]-phenol (35 mg, 0.11 mmol), Et$_3$N (30 µL, 0.22 mmol), and CH$_2$Cl$_2$ (300 mL) under N$_2$, was added dimethylsulfamoyl chloride (12 µL, 0.11 mmol). The mixture was stirred at room temperature for 17 hours. The mixture was purified via HPLC to obtain the desired sulfonylurea as a TFA salt (44 mg, 0.08 mmol, 71% yield). LC/MS (10-99%) M/Z 442.4 retention time 2.84 min.

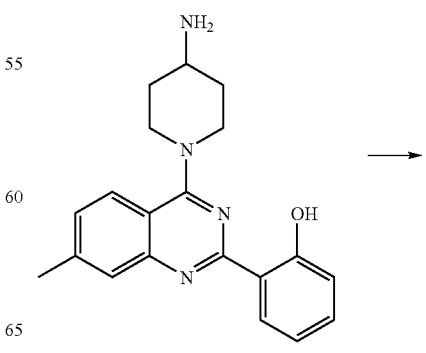

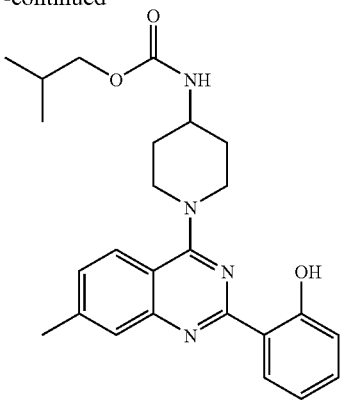

{1-[2-(2-Hydroxyphenyl)-7-methylquinazolin-4-yl]-piperidin-4-yl}-carbamic acid isobutyl ester. To a stirring solution of 2-[4-(4-Aminopiperidin-1-yl)-7-methylquinazolin-2-yl]-phenol (30 mg, 0.09 mmol), Et$_3$N (25 μL, 0.18 mmol), and CH$_2$Cl$_2$ (300 μL) under N$_2$, was added isobutylchloroformate (12 μL, 0.09 mmol). The mixture was stirred at room temperature for 1 hour. The mixture was purified via HPLC to obtain the desired carbamate as a TFA salt (27 mg, 0.05 mmol, 58% yield). LC/MS (10-99%) M/Z 435.2 retention time 3.21 min.

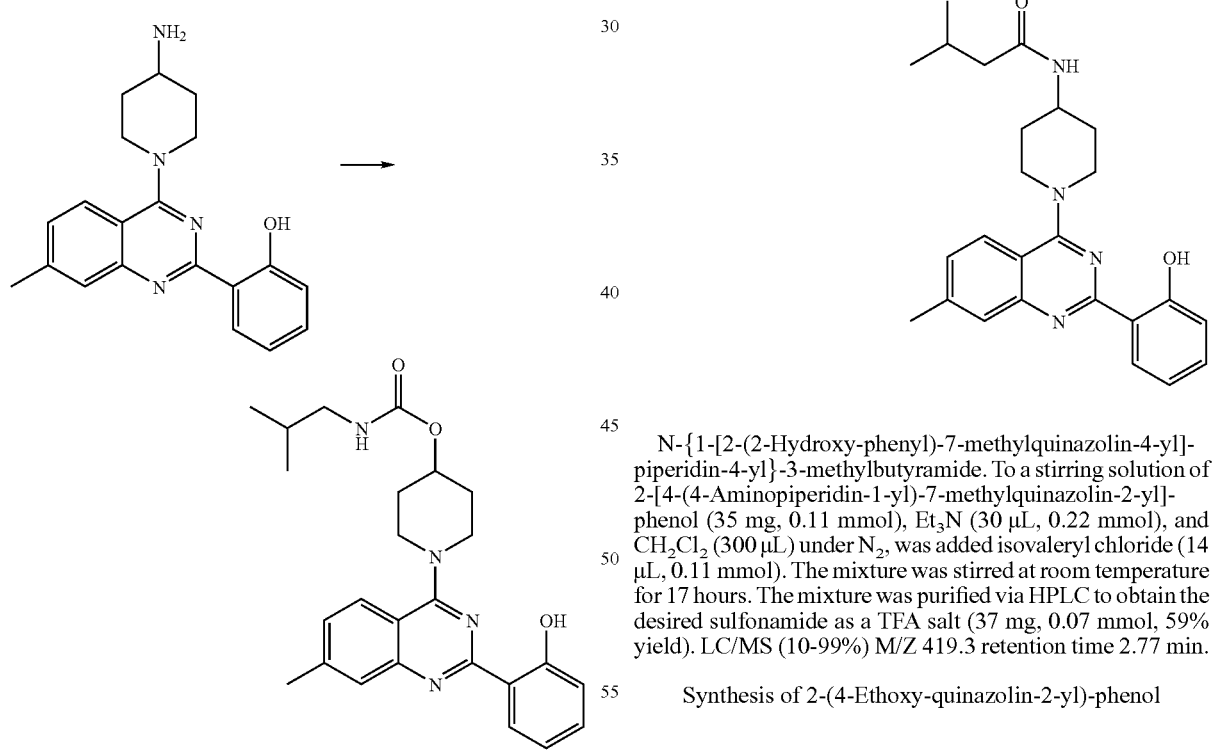

Isobutylcarbamic acid 1-[2-(2-hydroxyphenyl)-7-methylquinazolin-4-yl]-piperidin-4-yl ester. To a stirring solution of 1-[2-(2-Methoxyphenyl)-7-methylquinazolin-4-yl]-piperidin-4-ol (100 mg, 0.30 mmol) and THF (500 μL) under N$_2$, was added phosgene (317 μL, 0.60 mmol, 20% in toluene). The mixture was stirred at room temperature for 15 minutes. Isobutylamine (300 μL, 3.0 mmol) was added dropwise over a 2 minute period followed by stirring at room temperature for 1 hour. The mixture was evaporated to dryness and the obtained residue was purified via silica gel chromatography using 97% CH$_2$Cl$_2$/3% MeOH to obtain the desired carbamate intermediate as a clear oil (90 mg, 0.20 mmol). To a stirring solution of the carbamate intermediate (90 mg, 0.20 mmol) and CH$_2$Cl$_2$ (15 mL), under N$_2$, at −78° C., was added BBr$_3$ (0.60 mL, 0.60 mmol, 1.0 M in CH$_2$Cl$_2$) dropwise over a period of 2 minutes. The mixture was then allowed to warm to room temperature and was then heated at 50° C. for 15 minutes. The mixture was poured into a saturated aqueous NaHCO$_3$ solution (80 mL) and the organic portion was evaporated to dryness. The residue was purified via HPLC to obtain the desired carbamate as a TFA salt (66 mg, 0.12 mmol, 39% yield). LC/MS (10-99%) M/Z 435.3 retention time 3.08 min.

N-{1-[2-(2-Hydroxy-phenyl)-7-methylquinazolin-4-yl]-piperidin-4-yl}-3-methylbutyramide. To a stirring solution of 2-[4-(4-Aminopiperidin-1-yl)-7-methylquinazolin-2-yl]-phenol (35 mg, 0.11 mmol), Et$_3$N (30 μL, 0.22 mmol), and CH$_2$Cl$_2$ (300 μL) under N$_2$, was added isovaleryl chloride (14 μL, 0.11 mmol). The mixture was stirred at room temperature for 17 hours. The mixture was purified via HPLC to obtain the desired sulfonamide as a TFA salt (37 mg, 0.07 mmol, 59% yield). LC/MS (10-99%) M/Z 419.3 retention time 2.77 min.

Synthesis of 2-(4-Ethoxy-quinazolin-2-yl)-phenol

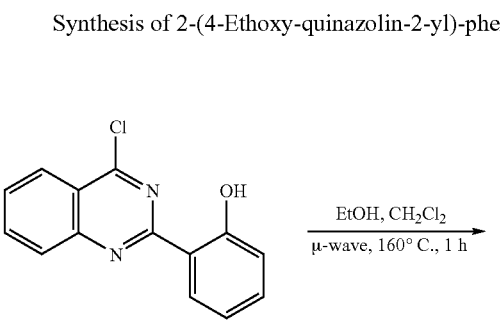

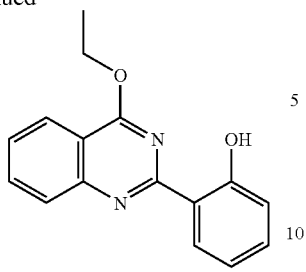

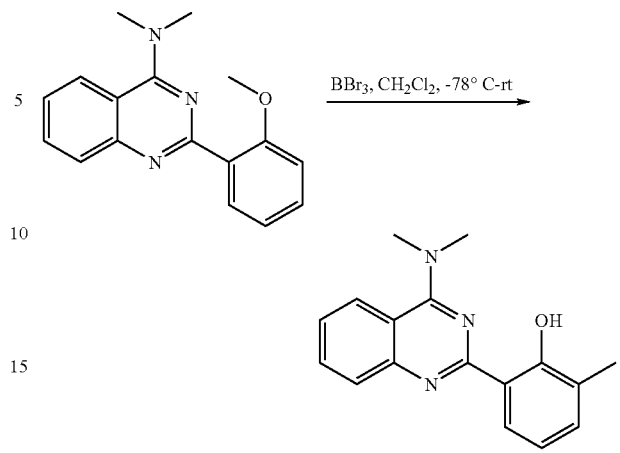

2-(4-Ethoxy-quinazolin-2-yl)-phenol. 2-(4-Chloro-quinazolin-2-yl)-phenol (50 mg, 0.196 mmol) was placed in a microwave tube charged with a stir bar and dissolved 0.5 ml dry dichloromethane, followed by the addition of 2 ml dry ethanol. Tube was sealed with a cap and heated at 160 to 200° C. for one hour in CEM microwave. Solvent was removed under reduced pressure, reconstituted organic in DMSO and purified by Gilson HPLC. The desired compound was concentrated to a white solid as the TFA salt. LC/MS (10-99%) M/Z 267.2, retention time 2.57 minutes.

Synthesis 2-(4-Dimethylamino-quinazolin-2-yl)-6-methyl-phenol

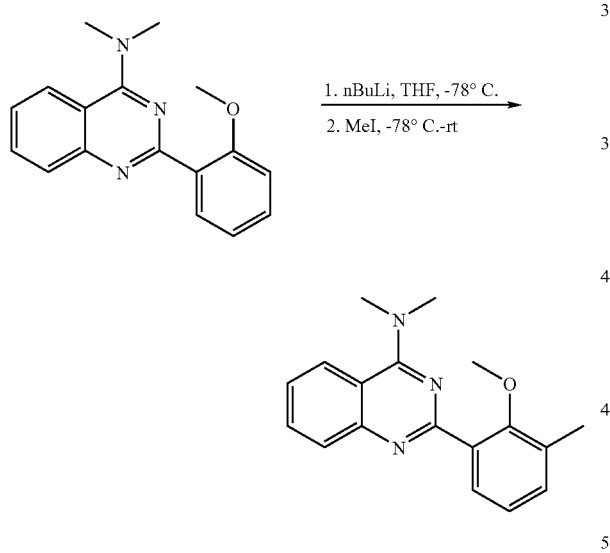

[2-(2-Methoxy-3-methyl-phenyl)-quinazolin-4-yl]-dimethyl-amine To a stirring solution of [2-(2-Methoxy-phenyl)-quinazolin-4-yl]-dimethyl-amine (200 mg, 0.72 mmol) in dry THF under an argon atmosphere at −78° C. was added dropwise a 1.6M solution of nBuLi in hexanes (0.671 ml, 1.074 mmol). After 10 minutes MeI (0.076 ml, 1.22 mmol) was added and the reaction was allowed to warm to room temperature. After 10 minutes at room temperature the reaction was quenched with a saturated aqueous solution of NH$_4$Cl and partitioned between aqueous and EtOAc. Organic phase was separated, dried over MgSO$_4$, filtered and concentrated to a yellow oil. Purified by flash chromatography 10% EtOAc/90% hexanes to afford product as a white solid. Recovered 146 mg 50% yield. LC/MS (10-99%) M/Z 294.0, retention time 3.23 minutes.

2-(4-Dimethylamino-quinazolin-2-yl)-6-methyl-phenol To a stirring solution of [2-(2-Methoxy-phenyl)-quinazolin-4-yl]-dimethyl-amine (54 mg, 0.184 mmol) in CH$_2$Cl$_2$ at −78° C. under a nitrogen atmosphere was added BBr$_3$ (0.92 ml, 0.92 mmol). The reaction was allowed to warm to room temperature and the heated at 45° C. for 4 hours. The reaction was allowed to cool to room temperature and then quenched with an aqueous solution of NaHCO$_3$ until pH8. Organic layer was separated, dried over MgSO$_4$, filtered, and concentreated to a yellow solid. Purified by Gilson HPLC and desired product was isolated as the TFA salt. LC/MS (10-99%) M/Z 280.2, retention time 2.55 minutes.

Synthesis of 2-(4-Dimethylamino-quinazolin-2-yl)-4-morpholin-4-yl-phenol

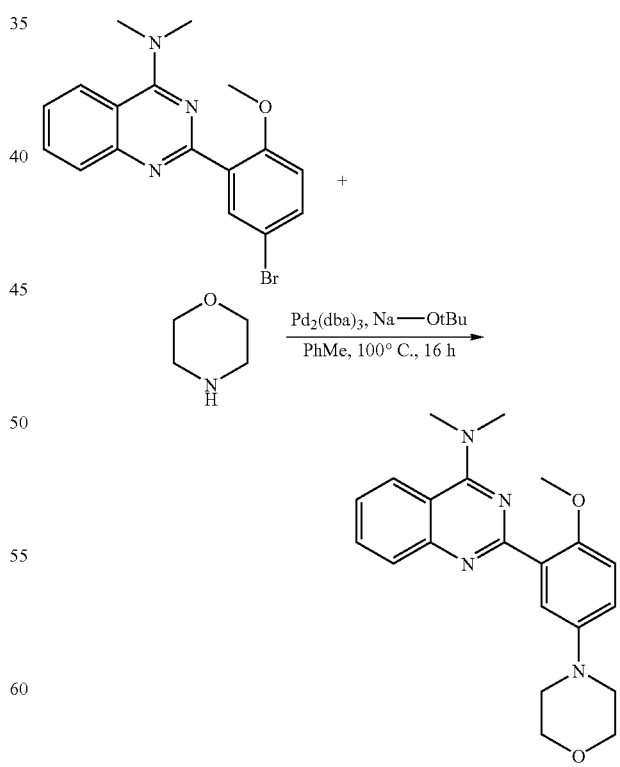

[2-(2-Methoxy-5-morpholin-4-yl-phenyl)-quinazolin-4-yl]-dimethyl-amine To a tube charged with a stirbar was added Pd$_2$(dba)$_3$ (51.1 mg, 0.0558 mmol), biphenyl-2-yl-di-tert-butyl-phosphane (67 mg, 0.223 mmol), NaOtBu (80 mg, 0.837 mmol) in 2 ml dry toluene was added 4-Bromo-2-(4-dimethylamino-quinazolin-2-yl)-phenol (200 mg, 0.558 mmol) and morpholine (0.073 ml, 0.837 mmol). The reaction was sealed with a screw cap and heated at 100° C. in an oil bath for 16 h. Purified by flash chromatography 30%-60% EtOAc/hexanes to afford product as a white solid. Recovered 100 mg 49% yield. LC/MS (10-99%) M/Z 365.0, retention time 2.07 minutes.

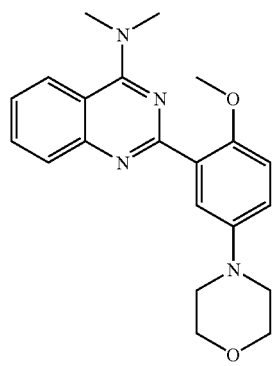

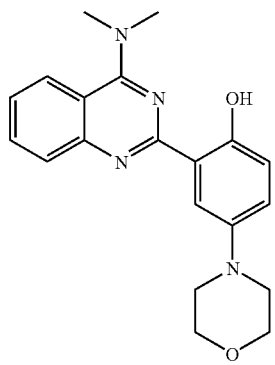

2-(4-Dimethylamino-quinazolin-2-yl)-4-morpholin-4-yl-phenol To a stirring solution of [2-(2-Methoxy-5-morpholin-4-yl-phenyl)-quinazolin-4-yl]-dimethyl-amine (109 mg, 0.299 mmol) in CH$_2$Cl$_2$ at −78° C. under a nitrogen atmosphere was added BBr$_3$ (1.5 ml, 1.5 mmol). The reaction was allowed to warm to room temperature and was heated at 40° C. for 2 hours. The reaction was quenched with an aqueous solution of NaHCO$_3$ until pH8. Organic layer was separated, dried over MgSO$_4$, filtered, and concentreated to a yellow solid. Purified by Gilson HPLC and desired product was isolated as the TFA salt. LC/MS (10-99%) M/Z 351.4, retention time 1.89 minutes.

Synthesis of 2-(4-Dimethylamino-quinazolin-2-yl)-4-methyl-phenol

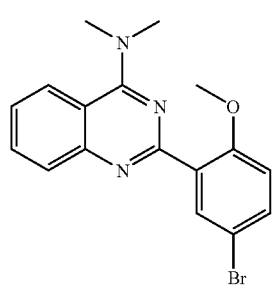

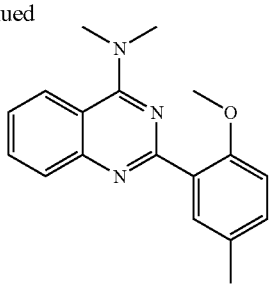

[2-(2-Methoxy-5-methyl-phenyl)-quinazolin-4-yl]-dimethyl-amine To a stirring solution of [[2-(5-Bromo-2-methoxy-phenyl)-quinazolin-4-yl]-dimethyl-amine (200 mg, 0.558 mmol) in dry THF under an argon atmosphere at −78° C. was added dropwise a 1.6M solution of nBuLi in hexanes (0.76 ml, 1.23 mmol). After 10 minutes MeI (0.054 ml, 1.23 mmol) was added and the reaction was allowed to warm to room temperature. After 10 minutes at room temperature the reaction was quenched with a saturated aqueous solution of NH$_4$Cl and partitioned between aqueous and EtOAc. Organic phase was separated, dried over MgSO$_4$, filtered and concentrated to a yellow oil. Purified by flash chromatography 30% EtOAc/70% hexanes to afford product as a white solid. Recovered 146 mg 89% yield. LC/MS (10-99%) M/Z 294.4, retention time 2.64 minutes.

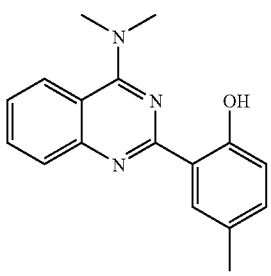

2-(4-Dimethylamino-quinazolin-2-yl)-4-methyl-phenol
To a stirring solution of [2-(2-M ethoxy-5-methyl-phenyl)-quinazolin-4-yl]-dimethyl-amine (146 mg, 0.498 mmol) in CH$_2$Cl$_2$ at −78° C. under a nitrogen atmosphere was added BBr$_3$ (2.49 ml, 2.49 mmol). The reaction was allowed to warm to room temperature and was complete after 2 hours. The reaction was quenched with an aqueous solution of NaHCO$_3$ until pH8. Organic layer was separated, dried over MgSO$_4$, filtered, and concentreated to a yellow solid. Purified by Gilson HPLC and desired product was isolated as the TFA salt. LC/MS (10-99%) M/Z 280.2, retention time 2.65 minutes.

Synthesis of 2-(2'-methylsulfonylphenyl)-4-dimethylaminoquinazoline

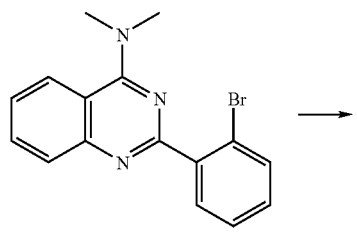

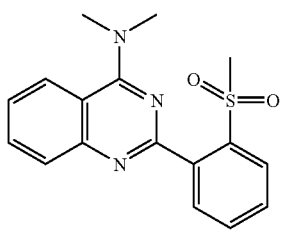

2-(2'-methylsulfonylphenyl)-4-dimethylaminoquinazoline. A 2 mL Personal Chemistry Microwave reaction vessel with a stir bar was charged with 2-(2'-bromophenyl)-4-dimethylaminoquinazoline (0.020 g, 61 mmol), copper (I) iodide (0.017 g, 91 mmol), sodium methanesulfinate (0.010 g, 97 mmol), and 0.5 mL of DMF.[1] This mixture was irradiated at 180° C. for 10 min. After cooling, water and ether were added, and an extraction was performed. The ether layer was then filtered through celite and then extracted once again, using approximately 20% $NH_4OH$ to remove additional copper. After concentrating, the product was redissolved in a 50/50 solution of DMSO/MeOH. Purification was conducted on LC/MS to provide the TFA salt. LC/MS (10-99%) M/Z 328.3, retention time 3.03 min.

Synthesis of 2-(2'-anilino)-4-dimethylaminoquinazoline

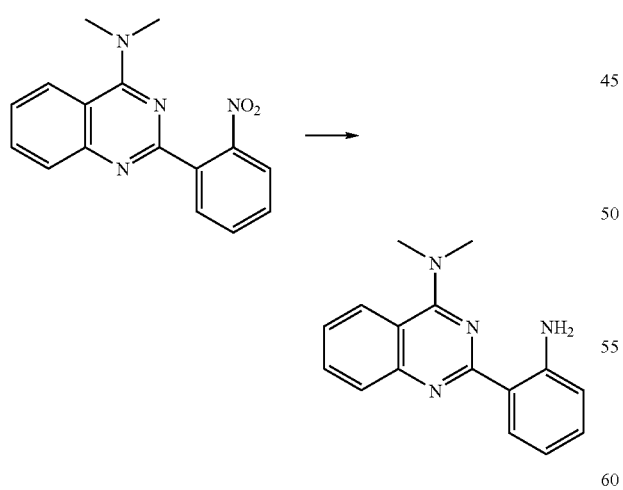

2-(2'-anilino)-4-dimethylaminoquinazoline. Zinc powder (1.18 g, 18.0 mmol) was added to a solution of 2-(2'-nitrophenyl)-4-dimethylaminoquinazoline (0.530 g, 1.80 mmol) in acetic acid (10.9 mL, 190 mmol) at 0° C. The reaction mixture solidified, but then began to stir again after the ice bath was removed.[3,4] The reaction mixture was stirred for three hours at room temperature. Deionized water (approximately 10 mL) was then added, and a solution formed, followed by formation of a precipitate. This solution was then taken slightly basic with $NaHCO_3(aq)$. The product was extracted three times with ethyl acetate, dried with $MgSO_4$, filtered, and concentrated. Approximately 20 mg of the product was redissolved in a 50/50 solution of DMSO/MeOH and purified by LC/MS to provide the bis-TFA salt. LC/MS (10-99%) M/Z 265.0, retention time 2.81 min.

Synthesis of 2-(2'-ethylsulfanylphenyl)-4-dimethylaminoquinazoline

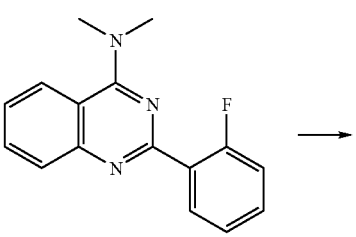

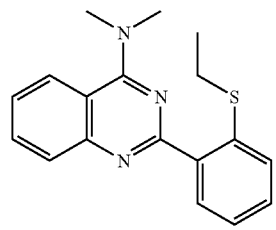

2-(2'-ethylsulfanylphenyl)-4-dimethylaminoquinazoline. Potassium carbonate (0.052 g, 0.374 mmol) and ethanethiol (0.055 mL, 0.748 mmol) were added to a solution of 2-(2'-fluorophenyl)-4-dimethylaminoquinazoline (0.020 g, 0.0748 mmol) in N,N-dimethylformamide (1 mL) in a microwave reaction vessel with a stir bar. This mixture was irradiated in the microwave at 135° C. for 1.5 hours. The resulting mixture was filtered and then purified by LC/MS to provide the TFA salt. LC/MS (10-99%) M/Z 310.2, retention time 3.27 min.

Synthesis of 2-(2'-cyanophenyl)-4-dimethylaminoquinazoline

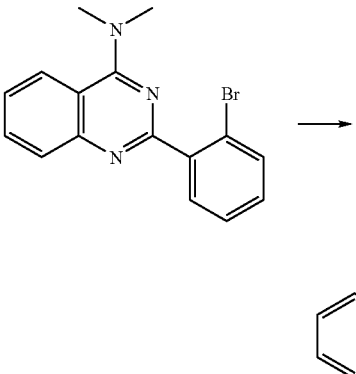

2-(2'-cyanophenyl)-4-dimethylaminoquinazoline. A round bottom flask was charged with 2-(2'-bromophenyl)-4-dimethylaminoquinazoline (0.010 g, 0.0305 mmol), potassium cyanide (0.0040 g, 0.0609 mmol), tetrakis(triphenylphosphine)palladium(0) (0.0018 g, 0.00152 mmol), copper(I) iodide (0.00058 g, 0.00305 mmol), and acetonitrile (0.50 mL) and heated to reflux overnight.[5] After cooling to room temperature, ethyl acetate was added and filtered through celite. An extraction was then performed, using ammonium hydroxide (approximately 20%) to remove additional copper. After being concentrated, the product was redissolved in a 50/50 solution of DMSO/MeOH and purified by LC/MS to provide the TFA salt. LC/MS (10-99%) M/Z 275.2, retention time 2.85 min.

Synthesis of 2-(2'-isopropenylphenyl)-4-dimethylaminoquinazoline

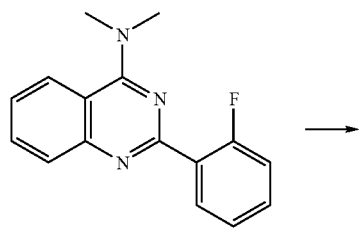

2-(2'-isopropenylphenyl)-4-dimethylaminoquinazoline. A 0.5 M solution of isopropenyl magnesium bromide (0.898 mL, 0.449 mmol) was added to a solution of 2-(2'-fluorophenyl)-4-dimethylaminoquinazoline (0.040 g, 0.150 mmol) in ethylene glycol dimethyl ether (1 mL) in a microwave vessel with a stir bar. The sample was irradiated in the microwave for 5 min at 170° C. Deionized water (approximately 2 mL) was then added. An extraction was then performed with ether. After being concentrated, the product was redissolved in a 50/50 solution of DMSO/MeOH and purified by LC/MS to provide the TFA salt. LC/MS (10-99%) M/Z 289.8, retention time 3.23 min.

Synthesis of 2-(2'-hydroxyphenyl)-4-dimethylamino-6-methoxyquinazoline

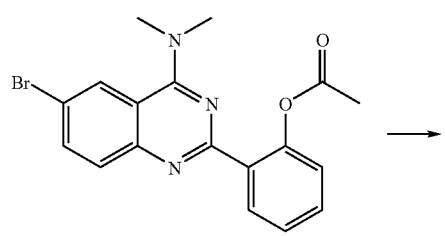

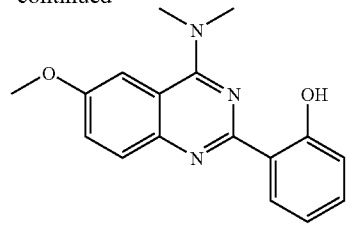

2-(2'-hydroxyphenyl)-4-dimethylamino-6-methoxyquinazoline. A microwave reaction vessel with a stir bar was charged with 2-(2'-acetoxyphenyl)-4-dimethylamino-6-bromoquinazoline (0.100 g, 0.259 mmol), copper(I) iodide (0.0245 g, 0.129 mmol), N,N-dimethylformamide (0.90 mL), and a 0.5 M solution of sodium methoxide (1.04 mL, 0.518 mmol) in methanol. The sample was irradiated in the microwave for 20 min at 150° C. After cooling, the sample was diluted with ether and then filtered through celite. Next, an extraction was performed, using ammonium hydroxide (approximately 20%) to remove additional copper. After being concentrated, the product was redissolved in a 50/50 solution of DMSO/MeOH and purified by LC/MS (20-99%) to provide the TFA salt. Approximate yield=60% (by LC/MS). LC/MS (10-99%) M/Z 296.4, retention time 2.31 min.

Synthesis of 4-Fluoro-3-(4,4,5,5-tetramethyl-[1,3,2]dioxaborolan-2-yl)-benzoic acid methyl ester

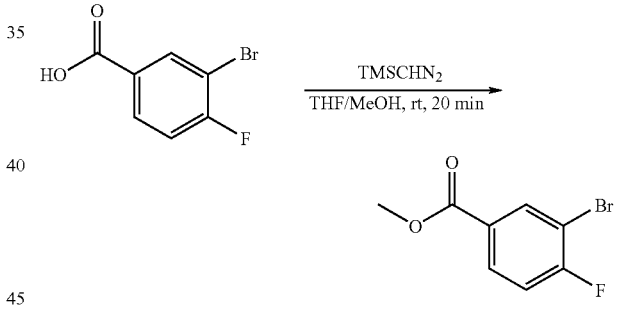

3-Bromo-4-fluoro-benzoic acid methyl ester. 3-Bromo-4-fluoro-benzoic acid (2.5 g, 11.42 mmol) was placed in a 100 ml round bottom flask charged with a stir bar, sealed with a septum and placed under a nitrogen atmosphere and dissolved in 9 ml dry THF and 3 ml dry MeOH. A 2.0M solution of TMSdiazomethane in ether (6.28 ml, 12.56 mmol) was added dropwise to the stirring solution of the acid. Conversion of the acid to the ester was complete after twenty minutes according to LC/MS analysis. The solvent was removed under reduced pressure and product was used without further purification. Recovered a light oil (2.66 g, 100% yield) LC/MS (10-99%) M/Z 234, retention time 3.09 minutes.

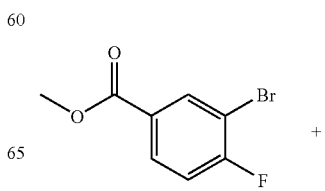 +

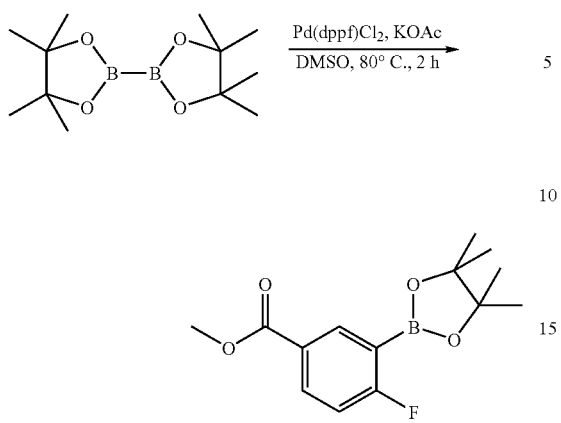

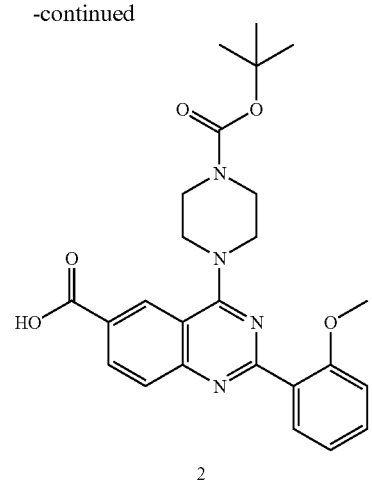

4-Fluoro-3-(4,4,5,5-tetramethyl-[1,3,2]dioxaborolan-2-yl)-benzoic acid methyl ester. To a round bottom flask charged with a stir bar was added 3-Bromo-4-fluoro-benzoic acid methyl ester (1.66 g, 7.12 mmol), Bis(pinacolato)diboron (2.2 g, 8.5 mmol), potassium acetate (2.1 g, 21.3 mmol), and (0.35 g, 0.43 mmol) [1,1'-Bis(diphenylphosphino)ferrocene]dichloropalladium (11), complex with dichloromethane (1:1). The reaction was sealed with a septum, evacuated and the placed under a nitrogen atmosphere, followed by the addition of 20 ml of dry DMSO. The reaction was heated at 80° C. in an oil bath for two hours. The reaction was allowed to cool to room temperature and partitioned between ethyl acetate and water. Organic layer was separated, and the aqueous layer was extracted two more times. All organics were combined, dried over $MgSO_4$, filtered and concentrated under reduced pressure to a black oil. The product was purified by flash chromatography using a gradient of EtOAc/Hexanes 0 to 60%, to afford the desired product as a white solid (1.48 g, 74% yield). LC/MS (10-99%) M/Z 281.4, retention time 2.73 minutes.

The quinazoline 1 (1.5 g, 3.0 mmol) was dissolved in THF (150 mL). After cooling to −78° C., t-BuLi (1.7 M in heptane, 1.76 mL) was added dropwise. After stirring for 10 min at −78° C., $CO_2$ (crushed) was added to the solution, then warmed up to RT and stirred for 30 min. Quenched the reaction with $H_2O$ (100 mL), diluted with EtOAc (100 mL), The organic layer was dried, concentrated, purified by flash chromatography (1%-10% MeOH/DCM) to obtain 2 (600 mg, 43% yield).

Synthesis of 2-(2'-hydroxyphenyl)-4-dimethylamino-6-morpholinoquinazoline

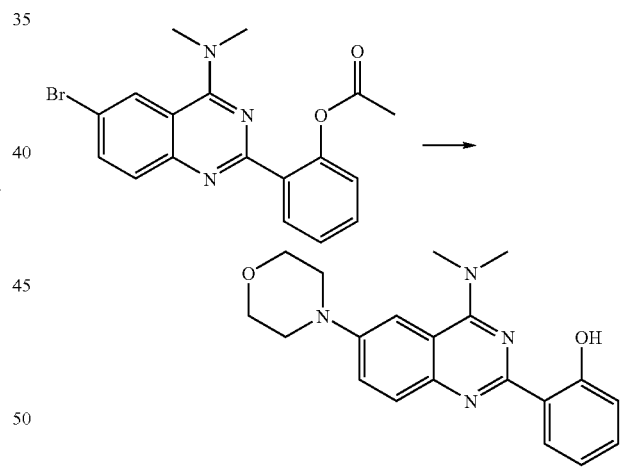

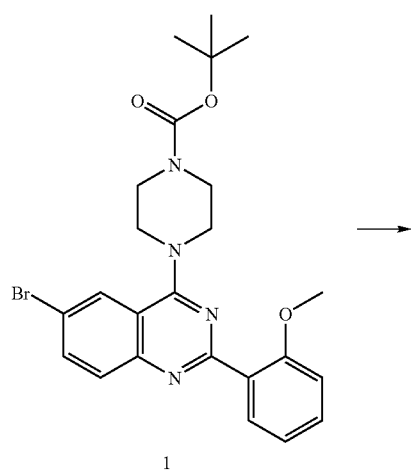

2-(2'-hydroxyphenyl)-4-dimethylamino-6-morpholinoquinazoline. A dry reaction tube with a septa screw cap under $N_2$ was charged with tris(dibenzylideneacetone)dipalladium (0) (0.012 g, 13.0 mmol), 2,2'-bis(diphenylphosphino)-1,1'-binapthyl (0.024 g, 38.8 mmol), cesium carbonate (0.097 g, 298 mmol), toluene (0.25 mL), 2-(2'-acetoxyphenyl)-4-dimethylamino-6-bromoquinazoline (0.050 g, 129 mmol), and morpholine (23 μL, 259 mmol), in that order.[2] This mixture was then heated to 80° C. for 24 hours. After cooling, the mixture was diluted with ether, filtered through celite and silica gel, and concentrated. The product was redissolved in a 50/50 solution of DMSO/MeOH and purified by LC/MS to provide the bis-TFA salt. LC/MS (10-99%) M/Z 351.0, retention time 2.75 min.

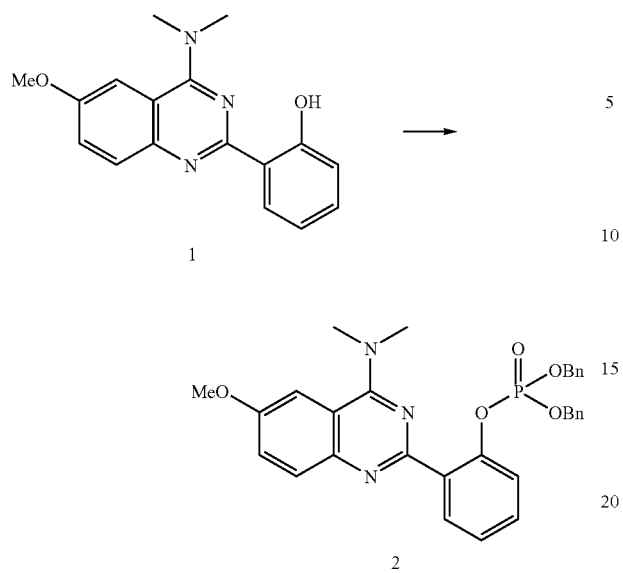

The quinazoline 1 (0.2 g, 0.62 mmol) was dissolved in CH₃CN (5 mL). After cooling to −10° C. (ice/NaCl), CCl₄, DIEA and DMAP were added. After stirring for 10 min, a solution of dibenzyl phosphite in CH₃CN (2 mL) was slowly added over 10 min. Stirring was continued at −10° C. for 2 h, then at RT for 24 h. Quenched by addition of 0.5 M K₂HPO₄, diluted with water (15 mL), extracted with DCM (30 mL), dried, concentrated, purified by flash chromatography (100% DCM) to obtain 2 (168 mg, 47% yield) as a colorless oil. LC/MS (10-99%) M/Z 586.0 retention time 2.54 min.

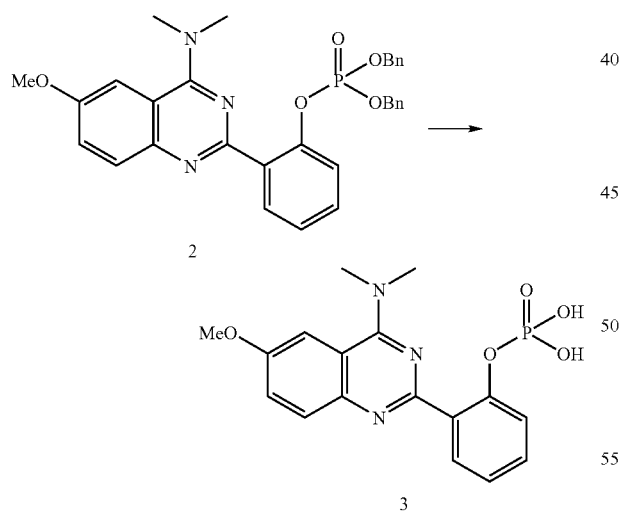

To a solution of the quinazoline 2 (0.168 g, 0.29 mmol) in DCM (1.5 mL) was added TMSBr (0.079 mL, 0.61 mmol) at 0° C. The reaction was stirred for 1 h at 0° C., then for 1 h at RT. The reaction was quenched with water (3 mL) and stirred for 15 min. The aqueous layer was washed with EtOAc (5 mL), and dried with lyophilizer overnight to give desired product 3 as white foam (0.14 g, 100% yield). LC/MS (10-99%) M/Z 406.0 retention time 3.32 min.

To a solution of the quinazoline 3 (0.14 g, 0.36 mmol) in MeOH (3 mL) was added NaOMe (1.44 mL, 0.72 mmol) at RT. The reaction was stirred overnight at RT. The reaction mixture was concentrated using rotavap (25° C.), then the residue was taken up with water (75 mL) and washed with EtOAc (3×50 mL). The aqueous phase was dried with lyophilizer to give final product 4 (0.14 g, 98% yield) as solid. LC/MS (10-99%) M/Z 406.0 retention time 3.32 min.

2-{7-Methyl-4-[methyl-(5-methyl-[1,3,4]oxadiazol-2-yl-methyl)-amino]-quinazolin-2-yl}-phenol

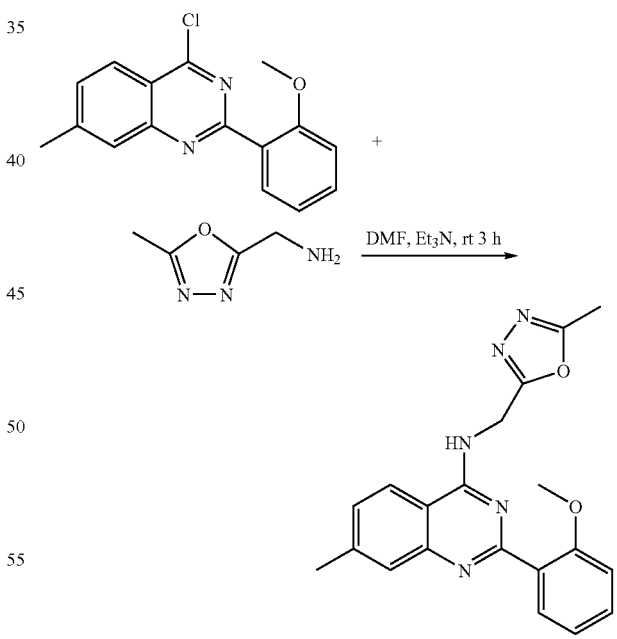

[2-(2-Methoxy-phenyl)-7-methyl-quinazolin-4-yl]-(5-methyl-[1,3,4]oxadiazol-2-ylmethyl)-amine 4-Chloro-2-(2-methoxy-phenyl)-7-methyl-quinazoline (400 mg, 1.48 mmol) was dissolved in 10 ml dry DMF followed by the addition of C-(5-Methyl-[1,3,4]oxadiazol-2-yl)-methylamine oxalate (234 mg, 1.48 mmol) then triethylamine (413 µl, 2.96 mmol). After 6 hours the reaction was complete, partitioned between EtOAc and water. The organic phase was separated, dried over MgSO$_4$, filtered and concentrated to an oil. Purified by flash chromatography 60% EtOAc/40% hexanes to afford the desired product a white solid. Recovered 290 mg 56% yield. LC/MS (10-99%) M/Z 348.4, retention time 2.17 minutes.

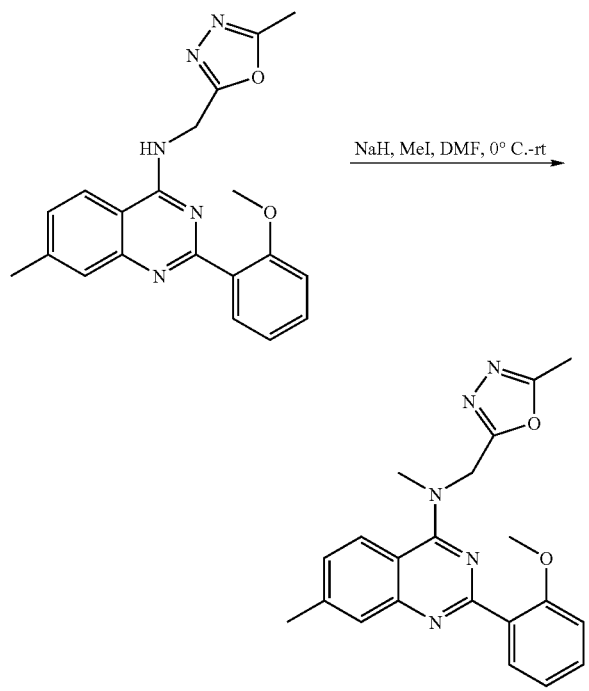

[2-(2-Methoxy-phenyl)-7-methyl-quinazolin-4-yl]-methyl-(5-methyl-[1,3,4]oxadiazol-2-ylmethyl)-amine To a stirring suspension of freshly washed sodium hydride (42 mg, 1.04 mmol) in dry DMF at 0° C. under a nitrogen atmosphere was added the [2-(2-Methoxy-phenyl)-7-methyl-quinazolin-4-yl]-(5-methyl-[1,3,4]oxadiazol-2-ylmethyl)-amine (180 mg, 0.518 mmol, in 5 ml DMF). After 30 minutes at 0° C., MeI (74 µl, 1.19 mmol) was added and the reaction was allowed to warm to room temperature. After one hour the reaction was quenched with water and extracted 3 times with EtOAc. Organics were combined, dried over MgSO$_4$, filtered and concentrated to a yellow oil. Purified by flash chromatography 50/50 EtOAc/hexanes to afford the desired product as a clear oil. 128 mg, 66% yield. LC/MS (10-99%) M/Z 376.1, retention time 2.06 minutes.

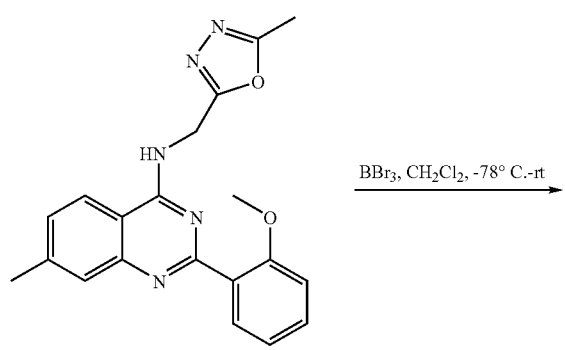

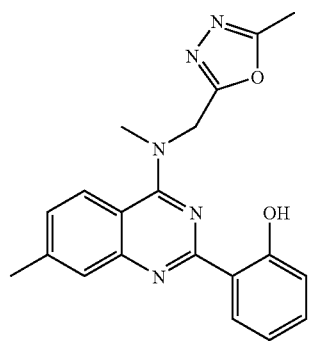

2-{7-Methyl-4-[methyl-(5-methyl-[1,3,4]oxadiazol-2-ylmethyl)-amino]-quinazolin-2-yl}-phenol To a stirring solution of [2-(2-Methoxy-phenyl)-7-methyl-quinazolin-4-yl]-methyl-(5-methyl-[1,3,4]oxadiazol-2-ylmethyl)-amine (128 mg, 0.341 mmol) in 7 ml dry CH$_2$Cl$_2$ at −78° C. under a nitrogen atmosphere was added BBr$_3$ (1.71 ml, 1.71 mmol) dropwise. The reaction was allowed to warm to room temperature and after three hours the reaction was quenched with a saturated aqueous solution of NaHCO$_3$ until pH8. The organic was separated, dried over MgSO$_4$, filtered and concentrated to a light yellow oil. Purified by Gilson HPLC and compound was isolated as the TFA salt. LC/MS (10-99%) M/Z 362.3, retention time 2.12 minutes.

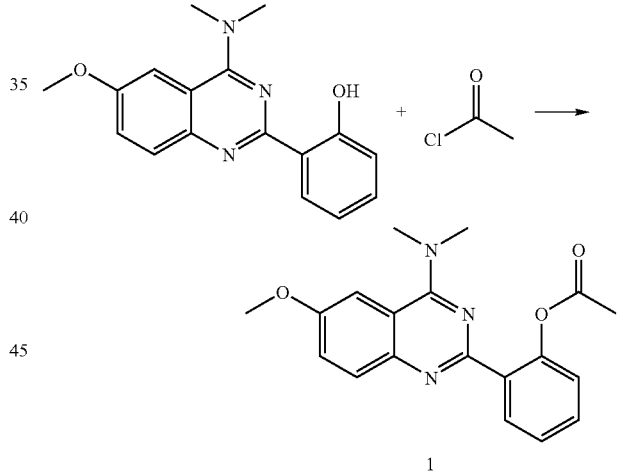

To a solution of the quinazoline (187 mg, 0.63 mmol) in CH$_2$Cl$_2$ (5 mL) was added pyridine (0.11 mL, 1.36 mmol) at RT. After cooling to 0° C. a solution of acetyl chloride (50 µL 0.70 mmol) in CH$_2$Cl$_2$ (5 mL) was added, stirring was continued for 45 Min at RT and the solvent was removed in vacuo. Chromatography over silica (hexanes/EtOAc/NEt$_3$: 2:1:0.05) afforded compound 1 as a white solid (90 mg, 42%). Compound 1: LC/MS (10-99%): m/z=338 [M+H]$^+$, R$_t$: 3.28 min.

Other compounds of general formula I have been prepared by methods substantially similar to those described above. The characterization data for these compounds is summarized in Table 3 below, and compound numbers correspond to the compounds depicted in Table 2.

TABLE 3

Exemplary Characterization Data for Compounds of Formula I

| Cmpd # | LC_MASS_PLUS |
|---|---|
| 15 | 308.40 |
| 16 | 306.00 |
| 164 | 320.00 |
| 194 | 389.20 |
| 195 | 404.20 |
| 198 | 302.00 |
| 202 | 328.20 |
| 241 | 268.30 |
| 250 | 346.00 |
| 252 | 310.00 |
| 253 | 344.00 |
| 254 | 319.00 |
| 255 | 333.00 |
| 256 | 348.00 |
| 257 | 319.00 |
| 258 | 289.80 |
| 259 | 249.80 |
| 260 | 386.20 |
| 261 | 357.00 |
| 262 | 275.20 |
| 263 | 358.00 |
| 264 | 325.00 |
| 265 | 296.40 |
| 266 | 345.20 |
| 267 | 310.00 |
| 268 | 351.00 |
| 269 | 310.00 |
| 270 | 340.10 |
| 271 | 298.10 |
| 272 | 314.00 |
| 273 | 328.20 |
| 274 | 284.00 |
| 275 | 300.10 |
| 276 | 328.10 |
| 277 | 286.90 |
| 278 | 306.00 |
| 279 | 280.20 |
| 280 | 380.00 |
| 281 | 334.00 |
| 282 | 336.00 |
| 283 | 351.00 |
| 284 | 336.00 |
| 285 | 322.00 |
| 286 | 307.00 |
| 287 | 378.00 |
| 288 | 405.00 |
| 289 | 349.00 |
| 290 | 292.00 |
| 291 | 322.00 |
| 292 | 342.00 |
| 293 | 294.00 |
| 294 | 358.20 |
| 295 | 374.00 |
| 296 | 382.40 |
| 297 | 256.80 |
| 298 | 239.00 |
| 299 | 339.80 |
| 300 | 279.00 |
| 301 | 386.00 |
| 302 | 307.20 |
| 303 | 318.00 |
| 304 | 296.20 |
| 305 | 278.00 |
| 306 | 291.80 |
| 307 | 239.00 |
| 308 | 289.00 |
| 309 | 270.00 |
| 310 | 402.20 |
| 311 | 342.00 |
| 312 | 342.00 |
| 313 | 320.20 |
| 314 | 309.00 |
| 315 | 399.00 |
| 316 | 318.00 |
| 317 | 332.00 |
| 318 | 332.00 |

TABLE 3-continued

Exemplary Characterization Data for Compounds of Formula I

| Cmpd # | LC_MASS_PLUS |
|---|---|
| 319 | 315.00 |
| 320 | 329.00 |
| 321 | 343.00 |
| 322 | 357.00 |
| 323 | 342.00 |
| 324 | 342.00 |
| 325 | 368.00 |
| 326 | 352.00 |
| 327 | 369.80 |
| 328 | 456.20 |
| 329 | 381.80 |
| 330 | 384.00 |
| 331 | 395.80 |
| 332 | 322.00 |
| 333 | 284.00 |
| 334 | 334.00 |
| 335 | 280.00 |
| 336 | 296.00 |
| 337 | 306.00 |
| 338 | 286.80 |
| 339 | 286.80 |
| 340 | 329.40 |
| 341 | 356.20 |
| 342 | 329.40 |
| 343 | 463.20 |
| 344 | 491.60 |
| 345 | 353.20 |
| 346 | 315.80 |
| 347 | 359.00 |
| 348 | 402.20 |
| 349 | 341.80 |
| 350 | 359.80 |
| 351 | 384.80 |
| 352 | 371.80 |
| 353 | 369.60 |
| 354 | 343.00 |
| 355 | 441.00 |
| 356 | 353.80 |
| 357 | 314.00 |
| 358 | 320.00 |
| 359 | 323.00 |
| 360 | 289.00 |
| 361 | 322.20 |
| 362 | 400.00 |
| 363 | 386.00 |
| 364 | 390.00 |
| 365 | 306.00 |
| 366 | 385.80 |
| 367 | 370.00 |
| 368 | 374.00 |
| 369 | 320.00 |
| 370 | 320.00 |
| 371 | 322.00 |
| 372 | 320.00 |
| 373 | 308.00 |
| 374 | 340.00 |
| 375 | 356.00 |
| 376 | 280.20 |
| 377 | 300.00 |
| 378 | 282.00 |
| 379 | 326.20 |
| 380 | 351.20 |
| 381 | 338.20 |
| 382 | 336.20 |
| 383 | 309.20 |
| 384 | 407.40 |
| 385 | 334.20 |
| 386 | 323.40 |
| 387 | 380.20 |
| 388 | 294.00 |
| 389 | 350.00 |
| 390 | 345.00 |
| 391 | 326.00 |
| 392 | 352.80 |
| 393 | 323.00 |
| 394 | 286.00 |

TABLE 3-continued

Exemplary Characterization Data for Compounds of Formula I

| Cmpd # | LC_MASS_PLUS |
|---|---|
| 395 | 344.00 |
| 396 | 340.00 |
| 397 | 326.00 |
| 398 | 314.00 |
| 399 | 312.00 |
| 400 | 343.20 |
| 401 | 354.00 |
| 402 | 340.00 |
| 403 | 282.00 |
| 404 | 285.00 |
| 405 | 283.20 |
| 406 | 292.00 |
| 407 | 464.00 |
| 408 | 298.00 |
| 409 | 273.00 |
| 410 | 326.20 |
| 411 | 326.20 |
| 412 | 356.00 |
| 413 | 359.20 |
| 414 | 355.00 |
| 415 | 338.00 |
| 416 | 370.00 |
| 417 | 328.00 |
| 418 | 298.20 |
| 419 | 279.80 |
| 420 | 281.80 |
| 421 | 340.90 |
| 422 | 269.30 |
| 423 | 303.00 |
| 424 | 372.80 |
| 425 | 272.80 |
| 426 | 307.00 |
| 427 | 322.20 |
| 428 | 324.20 |
| 429 | 284.00 |
| 430 | 286.00 |
| 431 | 429.00 |
| 432 | 439.00 |
| 433 | 443.00 |
| 434 | 456.00 |
| 435 | 486.00 |
| 436 | 326.20 |
| 437 | 328.00 |
| 438 | 253.00 |
| 439 | 257.00 |
| 440 | 299.20 |
| 441 | 273.00 |
| 442 | 414.40 |
| 443 | 286.00 |
| 444 | 302.20 |
| 445 | 330.00 |
| 446 | 328.20 |
| 447 | 355.40 |
| 448 | 412.00 |
| 449 | 286.00 |
| 450 | 338.20 |
| 451 | 352.20 |
| 452 | 267.00 |
| 453 | 326.20 |
| 454 | 284.20 |
| 455 | 309.20 |
| 456 | 399.20 |
| 457 | 312.00 |
| 458 | 340.20 |
| 459 | 302.00 |
| 460 | 316.00 |
| 461 | 344.00 |
| 462 | 328.00 |
| 463 | 378.00 |
| 464 | 316.00 |
| 465 | 327.80 |
| 466 | 371.80 |
| 467 | 355.60 |
| 468 | 356.80 |
| 469 | 359.00 |
| 470 | 435.20 |
| 471 | 368.00 |
| 472 | 344.00 |
| 473 | 282.20 |
| 474 | 281.20 |
| 475 | 355.00 |
| 476 | 302.20 |
| 477 | 316.20 |
| 478 | 344.20 |
| 479 | 328.20 |
| 480 | 378.00 |
| 481 | 316.20 |
| 482 | 282.00 |
| 483 | 286.00 |
| 484 | 328.00 |
| 485 | 324.20 |
| 486 | 353.80 |
| 487 | 377.80 |
| 488 | 365.00 |
| 489 | 339.80 |
| 490 | 267.00 |
| 491 | 281.00 |
| 492 | 310.20 |
| 493 | 352.20 |
| 494 | 342.00 |
| 495 | 328.00 |
| 496 | 402.20 |
| 497 | 439.20 |
| 498 | 421.00 |
| 499 | 367.00 |
| 500 | 397.20 |
| 501 | 365.00 |
| 502 | 270.00 |
| 508 | 290.90 |
| 516 | 403.40 |
| 517 | 403.40 |
| 518 | 403.60 |
| 519 | 403.40 |
| 520 | 408.40 |
| 521 | 409.20 |
| 522 | 432.40 |
| 523 | 432.20 |
| 524 | 431.40 |
| 525 | 432.40 |
| 526 | 432.40 |
| 527 | 437.40 |
| 528 | 437.40 |
| 529 | 446.40 |
| 530 | 452.40 |
| 531 | 463.00 |
| 532 | 370.00 |
| 533 | 382.20 |
| 534 | 384.20 |
| 535 | 398.20 |
| 536 | 437.40 |
| 537 | 439.40 |
| 538 | 439.40 |
| 539 | 439.20 |
| 540 | 377.40 |
| 541 | 384.00 |
| 542 | 386.00 |
| 543 | 391.20 |
| 544 | 391.20 |
| 545 | 397.40 |
| 546 | 397.40 |
| 547 | 397.40 |
| 548 | 411.40 |
| 549 | 368.20 |
| 550 | 420.20 |
| 551 | 441.40 |
| 552 | 446.00 |
| 553 | 449.40 |
| 554 | 394.00 |
| 555 | 450.20 |
| 556 | 330.00 |
| 557 | 332.20 |
| 558 | 334.00 |

TABLE 3-continued

Exemplary Characterization Data for Compounds of Formula I

| Cmpd # | LC_MASS_PLUS |
|---|---|
| 559 | 346.00 |
| 560 | 348.00 |
| 561 | 372.00 |
| 562 | 383.20 |
| 563 | 383.20 |
| 564 | 383.20 |
| 565 | 383.20 |
| 566 | 387.80 |
| 567 | 388.80 |
| 568 | 403.40 |
| 569 | 412.00 |
| 570 | 412.00 |
| 571 | 412.00 |
| 572 | 349.20 |
| 573 | 361.00 |
| 574 | 375.20 |
| 575 | 389.20 |
| 576 | 411.20 |
| 577 | 411.20 |
| 586 | 281.00 |
| 587 | 342.40 |
| 588 | 356.00 |
| 589 | 358.20 |
| 590 | 365.20 |
| 591 | 369.20 |
| 592 | 370.00 |
| 593 | 372.40 |
| 594 | 383.20 |
| 595 | 384.00 |
| 596 | 391.20 |
| 597 | 397.40 |
| 598 | 337.80 |
| 599 | 350.00 |
| 600 | 352.00 |
| 601 | 376.00 |
| 602 | 387.20 |
| 603 | 391.80 |
| 604 | 393.00 |
| 605 | 416.00 |
| 606 | 416.20 |
| 607 | 416.00 |
| 608 | 353.00 |
| 609 | 415.20 |
| 610 | 415.20 |
| 611 | 416.20 |
| 612 | 421.00 |
| 613 | 430.20 |
| 614 | 431.20 |
| 615 | 436.20 |
| 616 | 447.00 |
| 617 | 459.20 |
| 618 | 493.00 |
| 619 | 353.80 |
| 620 | 353.80 |
| 621 | 365.80 |
| 622 | 367.80 |
| 623 | 367.80 |
| 624 | 367.80 |
| 625 | 383.00 |
| 626 | 409.40 |
| 627 | 421.00 |
| 628 | 423.20 |
| 629 | 423.20 |
| 630 | 423.20 |
| 631 | 429.20 |
| 632 | 430.00 |
| 633 | 435.20 |
| 634 | 437.00 |
| 635 | 437.40 |
| 636 | 479.20 |
| 637 | 361.00 |
| 638 | 362.20 |
| 639 | 364.80 |
| 640 | 366.00 |
| 641 | 366.00 |
| 642 | 367.20 |
| 643 | 367.80 |
| 644 | 368.00 |
| 645 | 370.00 |
| 646 | 375.20 |
| 647 | 375.20 |
| 648 | 375.20 |
| 649 | 375.20 |
| 650 | 375.20 |
| 651 | 381.00 |
| 652 | 381.00 |
| 653 | 381.20 |
| 654 | 381.20 |
| 655 | 381.20 |
| 656 | 388.20 |
| 657 | 395.00 |
| 658 | 395.20 |
| 659 | 418.00 |
| 660 | 352.00 |
| 661 | 365.80 |
| 662 | 365.80 |
| 663 | 385.80 |
| 664 | 404.20 |
| 665 | 404.00 |
| 666 | 406.00 |
| 667 | 425.20 |
| 668 | 430.20 |
| 669 | 430.20 |
| 670 | 446.00 |
| 671 | 429.40 |
| 672 | 433.20 |
| 673 | 457.20 |
| 674 | 430.00 |
| 675 | 418.20 |
| 676 | 436.20 |
| 677 | 378.00 |
| 678 | 269.80 |
| 679 | 411.20 |
| 680 | 427.20 |
| 681 | 399.80 |
| 682 | 420.20 |
| 683 | 420.00 |
| 684 | 434.20 |
| 685 | 454.20 |
| 686 | 399.80 |
| 687 | 414.20 |
| 688 | 420.00 |
| 689 | 432.00 |
| 690 | 367.80 |
| 691 | 323.00 |
| 692 | 324.00 |
| 693 | 326.00 |
| 694 | 326.00 |
| 695 | 326.00 |
| 696 | 338.00 |
| 697 | 340.00 |
| 698 | 342.00 |
| 699 | 342.00 |
| 700 | 349.00 |
| 701 | 353.20 |
| 702 | 353.00 |
| 703 | 353.00 |
| 704 | 353.20 |
| 705 | 353.20 |
| 706 | 354.00 |
| 707 | 354.00 |
| 708 | 356.00 |
| 709 | 355.80 |
| 710 | 355.80 |
| 711 | 367.00 |
| 712 | 367.20 |
| 713 | 367.20 |
| 714 | 367.20 |
| 715 | 368.00 |
| 716 | 367.80 |
| 717 | 371.80 |
| 718 | 375.00 |

TABLE 3-continued

Exemplary Characterization Data for Compounds of Formula I

| Cmpd # | LC_MASS_PLUS |
|---|---|
| 719 | 381.00 |
| 720 | 382.00 |
| 721 | 382.20 |
| 722 | 383.20 |
| 723 | 385.00 |
| 724 | 389.20 |
| 725 | 390.00 |
| 726 | 393.20 |
| 727 | 393.20 |
| 728 | 397.20 |
| 729 | 400.20 |
| 730 | 403.40 |
| 731 | 404.20 |
| 732 | 407.40 |
| 733 | 411.20 |
| 734 | 413.20 |
| 735 | 415.40 |
| 736 | 416.20 |
| 737 | 419.00 |
| 738 | 419.20 |
| 739 | 421.00 |
| 740 | 423.20 |
| 741 | 428.20 |
| 742 | 429.40 |
| 743 | 430.20 |
| 744 | 431.40 |
| 745 | 431.20 |
| 746 | 441.40 |
| 747 | 446.00 |
| 748 | 450.20 |
| 749 | 432.00 |
| 750 | 470.20 |
| 751 | 352.00 |
| 752 | 352.00 |
| 753 | 352.00 |
| 754 | 374.00 |
| 755 | 373.80 |
| 756 | 374.00 |
| 757 | 378.00 |
| 758 | 378.00 |
| 759 | 378.00 |
| 760 | 416.20 |
| 761 | 429.20 |
| 762 | 432.00 |
| 763 | 441.40 |
| 764 | 470.20 |
| 765 | 477.00 |
| 766 | 326.00 |
| 767 | 366.00 |
| 768 | 365.80 |
| 769 | 388.20 |
| 770 | 326.00 |
| 771 | 352.20 |
| 772 | 364.20 |
| 773 | 380.80 |
| 774 | 397.20 |
| 775 | 407.40 |
| 776 | 413.20 |
| 777 | 415.20 |
| 778 | 421.00 |
| 779 | 429.20 |
| 780 | 350.00 |
| 781 | 283.80 |
| 782 | 294.00 |
| 783 | 296.00 |
| 784 | 298.00 |
| 785 | 312.00 |
| 786 | 314.00 |
| 787 | 314.00 |
| 788 | 324.00 |
| 789 | 328.00 |
| 790 | 340.00 |
| 791 | 343.80 |
| 792 | 310.00 |
| 793 | 347.00 |
| 794 | 347.00 |
| 795 | 351.00 |
| 796 | 373.80 |
| 797 | 326.00 |
| 798 | 326.00 |
| 799 | 326.20 |
| 800 | 338.00 |
| 801 | 372.00 |
| 802 | 372.00 |
| 803 | 381.80 |
| 804 | 377.20 |
| 805 | 377.20 |
| 806 | 377.20 |
| 807 | 384.00 |
| 808 | 391.00 |
| 809 | 391.20 |
| 810 | 414.40 |
| 811 | 348.00 |
| 812 | 362.00 |
| 813 | 362.00 |
| 814 | 381.80 |
| 815 | 399.80 |
| 816 | 399.80 |
| 817 | 402.00 |
| 818 | 425.80 |
| 819 | 426.00 |
| 820 | 442.00 |
| 821 | 474.20 |
| 822 | 425.20 |
| 823 | 425.20 |
| 824 | 429.20 |
| 825 | 453.00 |
| 826 | 426.00 |
| 827 | 373.80 |
| 828 | 407.40 |
| 829 | 413.00 |
| 830 | 423.20 |
| 831 | 395.80 |
| 832 | 416.00 |
| 833 | 416.00 |
| 834 | 430.00 |
| 835 | 395.80 |
| 836 | 410.00 |
| 837 | 409.80 |
| 838 | 416.00 |
| 839 | 364.00 |
| 840 | 439.20 |
| 841 | 319.00 |
| 842 | 319.80 |
| 843 | 321.80 |
| 844 | 321.80 |
| 845 | 322.00 |
| 846 | 334.00 |
| 847 | 336.20 |
| 848 | 337.80 |
| 849 | 337.80 |
| 850 | 344.80 |
| 851 | 349.20 |
| 852 | 349.20 |
| 853 | 349.20 |
| 854 | 350.00 |
| 855 | 350.00 |
| 856 | 352.20 |
| 857 | 353.00 |
| 858 | 352.00 |
| 859 | 352.00 |
| 860 | 363.00 |
| 861 | 363.00 |
| 862 | 363.00 |
| 863 | 363.20 |
| 864 | 363.80 |
| 865 | 364.00 |
| 866 | 363.80 |
| 867 | 370.80 |
| 868 | 373.20 |
| 869 | 377.00 |
| 870 | 378.00 |

TABLE 3-continued

Exemplary Characterization Data for Compounds of Formula I

| Cmpd # | LC_MASS_PLUS |
|---|---|
| 871 | 379.20 |
| 872 | 385.20 |
| 873 | 385.80 |
| 874 | 385.80 |
| 875 | 389.20 |
| 876 | 389.20 |
| 877 | 392.80 |
| 878 | 396.20 |
| 879 | 398.20 |
| 880 | 399.00 |
| 881 | 284.30 |
| 882 | 412.20 |
| 883 | 417.40 |
| 884 | 417.20 |
| 885 | 432.20 |
| 886 | 417.40 |
| 887 | 419.20 |
| 888 | 357.00 |
| 889 | 364.40 |
| 890 | 371.00 |
| 891 | 348.00 |
| 892 | 360.20 |
| 893 | 386.20 |
| 894 | 393.20 |
| 895 | 409.00 |
| 896 | 417.40 |
| 897 | 425.00 |
| 898 | 346.00 |
| 899 | 412.40 |
| 900 | 426.20 |
| 901 | 427.40 |
| 902 | 443.20 |
| 903 | 455.20 |
| 904 | 489.20 |
| 905 | 350.20 |
| 906 | 350.20 |
| 907 | 362.00 |
| 908 | 364.00 |
| 909 | 364.00 |
| 910 | 364.00 |
| 911 | 378.60 |
| 912 | 405.60 |
| 913 | 419.40 |
| 914 | 419.20 |
| 915 | 425.00 |
| 916 | 431.40 |
| 917 | 433.40 |
| 918 | 433.40 |
| 919 | 475.20 |
| 920 | 358.20 |
| 921 | 361.00 |
| 922 | 362.00 |
| 923 | 362.00 |
| 924 | 363.20 |
| 925 | 364.00 |
| 926 | 366.00 |
| 927 | 371.20 |
| 928 | 371.40 |
| 929 | 371.20 |
| 930 | 377.20 |
| 931 | 377.20 |
| 932 | 368.00 |
| 933 | 400.20 |
| 934 | 400.00 |
| 935 | 403.40 |
| 936 | 407.60 |
| 937 | 409.20 |
| 938 | 411.20 |
| 939 | 412.00 |
| 940 | 415.20 |
| 941 | 417.00 |
| 942 | 419.20 |
| 943 | 424.40 |
| 944 | 425.20 |
| 945 | 426.00 |
| 946 | 427.00 |
| 947 | 427.60 |
| 948 | 437.20 |
| 949 | 442.20 |
| 950 | 446.00 |
| 951 | 348.00 |
| 952 | 348.00 |
| 953 | 348.00 |
| 954 | 370.00 |
| 955 | 370.00 |
| 956 | 370.00 |
| 957 | 374.00 |
| 958 | 374.20 |
| 959 | 374.00 |
| 960 | 412.40 |
| 961 | 425.00 |
| 962 | 430.00 |
| 963 | 437.60 |
| 964 | 440.00 |
| 965 | 466.40 |
| 966 | 473.00 |
| 967 | 364.20 |
| 968 | 290.20 |
| 969 | 292.00 |
| 970 | 306.20 |
| 971 | 308.60 |
| 972 | 310.00 |
| 973 | 324.20 |
| 974 | 336.00 |
| 975 | 340.00 |
| 976 | 306.60 |
| 977 | 343.00 |
| 978 | 347.00 |
| 979 | 370.00 |
| 980 | 322.20 |
| 981 | 322.40 |
| 982 | 356.00 |
| 983 | 368.40 |
| 984 | 368.00 |
| 985 | 378.20 |
| 986 | 405.60 |
| 987 | 409.40 |
| 988 | 416.20 |
| 989 | 420.00 |
| 990 | 423.40 |
| 991 | 427.40 |
| 992 | 429.20 |
| 993 | 431.40 |
| 994 | 435.40 |
| 995 | 439.20 |
| 996 | 445.20 |
| 997 | 447.00 |
| 998 | 466.40 |
| 999 | 432.40 |
| 1000 | 369.00 |
| 1001 | 381.00 |
| 1002 | 409.20 |
| 1003 | 431.60 |
| 1004 | 432.40 |
| 1005 | 509.40 |
| 1006 | 384.00 |
| 1007 | 384.00 |
| 1008 | 425.40 |
| 1009 | 445.20 |
| 1010 | 451.20 |
| 1011 | 452.40 |
| 1012 | 495.40 |
| 1013 | 381.00 |
| 1014 | 382.00 |
| 1015 | 411.20 |
| 1016 | 444.40 |
| 1017 | 457.40 |
| 1018 | 384.00 |
| 1019 | 352.40 |
| 1020 | 368.00 |
| 1021 | 391.20 |
| 1022 | 391.20 |

TABLE 3-continued

Exemplary Characterization Data for Compounds of Formula I

| Cmpd # | LC_MASS_PLUS |
|---|---|
| 1023 | 328.40 |
| 1024 | 434.40 |
| 1025 | 382.00 |
| 1026 | 358.20 |
| 1027 | 369.20 |
| 1028 | 369.20 |
| 1029 | 383.20 |
| 1030 | 340.20 |
| 1031 | 409.40 |
| 1032 | 420.40 |
| 1033 | 368.00 |
| 1034 | 445.20 |
| 1035 | 330.40 |
| 1036 | 340.00 |
| 1037 | 356.00 |
| 1038 | 359.80 |
| 1039 | 363.20 |
| 1040 | 367.00 |
| 1041 | 390.00 |
| 1042 | 342.00 |
| 1043 | 342.60 |
| 1044 | 388.40 |
| 1045 | 343.80 |
| 1048 | 455.00 |
| 1049 | 338.00 |
| 1050 | 324.20 |
| 1051 | 433.60 |
| 1052 | 427.00 |
| 1053 | 443.20 |
| 1054 | 398.20 |
| 1055 | 435.20 |
| 1056 | 415.20 |
| 1057 | 417.40 |
| 1058 | 393.00 |
| 1059 | 361.00 |
| 1060 | 422.00 |
| 1065 | 385.20 |
| 1066 | 353.10 |
| 1067 | 354.10 |
| 1068 | 367.10 |
| 1069 | 380.90 |
| 1070 | 388.30 |
| 1071 | 353.10 |
| 1072 | 368.10 |
| 1073 | 410.00 |
| 1074 | 383.90 |
| 1075 | 429.10 |
| 1083 | 352.00 |
| 1084 | 350.00 |
| 1085 | 363.00 |
| 1086 | 377.00 |
| 1087 | 384.00 |
| 1088 | 380.00 |
| 1089 | 362.00 |
| 1090 | 410.00 |
| 1091 | 426.00 |
| 1092 | 370.00 |
| 1101 | 293.00 |
| 1102 | 307.00 |
| 1103 | 334.00 |
| 1106 | 374.10 |
| 1107 | 379.30 |
| 1108 | 421.10 |
| 1109 | 435.50 |
| 1110 | 407.50 |
| 1111 | 399.30 |
| 1112 | 413.30 |
| 1113 | 427.30 |
| 1114 | 391.30 |
| 1115 | 405.50 |
| 1116 | 377.30 |
| 1117 | 441.50 |
| 1118 | 410.90 |
| 1119 | 335.90 |
| 1120 | 355.80 |
| 1121 | 394.90 |
| 1122 | 407.50 |
| 1123 | 343.00 |
| 1124 | 427.10 |
| 1125 | 396.00 |
| 1127 | 461.30 |
| 1128 | 393.80 |
| 1133 | 443.00 |
| 1134 | 419.80 |
| 1135 | 453.00 |
| 1136 | 378.00 |
| 1137 | 463.00 |
| 1138 | 457.00 |
| 1141 | 504.00 |
| 1142 | 420.20 |
| 1143 | 422.20 |
| 1144 | 436.00 |
| 1145 | 448.20 |
| 1146 | 370.10 |
| 1147 | 457.50 |
| 1148 | 463.10 |
| 1151 | 435.80 |
| 1152 | 450.00 |
| 1153 | 407.60 |
| 1155 | 518.10 |
| 1156 | 482.00 |
| 1157 | 485.50 |
| 1158 | 432.20 |
| 1159 | 473.10 |
| 1160 | 432.20 |
| 1161 | 468.50 |
| 1162 | 393.80 |
| 1163 | 444.00 |
| 1164 | 450.00 |
| 1165 | 511.00 |
| 1166 | 467.00 |
| 1167 | 363.30 |
| 1168 | 463.00 |
| 1169 | 482.00 |
| 1170 | 415.00 |
| 1171 | 467.00 |
| 1172 | 511.00 |
| 1173 | 491.00 |
| 1174 | 495.00 |
| 1175 | 365.90 |
| 1176 | 380.30 |
| 1179 | 321.80 |
| 1180 | 560.00 |
| 1181 | 337.20 |
| 1182 | 280.00 |
| 1183 | 259.20 |
| 1184 | 500.20 |
| 1185 | 353.00 |
| 1186 | 526.80 |
| 1190 | 350.20 |
| 1191 | 392.00 |
| 1192 | 376.00 |
| 1193 | 404.20 |
| 1194 | 462.20 |
| 1195 | 427.20 |
| 1196 | 407.40 |
| 1197 | 322.00 |
| 1198 | 408.00 |
| 1199 | 501.10 |
| 1200 | 466.00 |
| 1201 | 469.00 |
| 1202 | 485.00 |
| 1203 | — |
| 1204 | — |
| 1205 | — |
| 1206 | — |
| 1207 | 435.10 |
| 1208 | 378.10 |
| 1209 | — |
| 1210 | — |
| 1211 | — |
| 1212 | 484.40 |

TABLE 3-continued

Exemplary Characterization Data for Compounds of Formula I

| Cmpd # | LC_MASS_PLUS |
|---|---|
| 1213 | 478.20 |
| 1214 | 477.00 |
| 1215 | 439.50 |
| 1216 | 455.30 |
| 1217 | 463.30 |
| 1218 | 457.00 |
| 1219 | 366.00 |
| 1220 | 427.20 |
| 1221 | 407.40 |
| 1222 | 391.10 |
| 1223 | 384.00 |
| 1224 | 404.00 |
| 1225 | 449.10 |
| 1226 | 449.50 |
| 1227 | 391.10 |
| 1228 | 444.50 |
| 1229 | 471.20 |
| 1230 | 471.40 |
| 1231 | 443.20 |
| 1232 | 405.20 |
| 1233 | 447.30 |
| 1234 | 453.50 |
| 1235 | 457.40 |
| 1236 | 321.10 |
| 1237 | 434.40 |
| 1238 | 448.20 |
| 1239 | 349.20 |
| 1240 | 437.20 |
| 1241 | 354.10 |
| 1242 | 354.10 |
| 1243 | 369.80 |
| 1244 | 332.20 |
| 1245 | 409.40 |
| 1246 | 434.30 |
| 1247 | 432.40 |
| 1248 | 432.40 |
| 1249 | 423.10 |
| 1250 | 359.90 |
| 1251 | 362.10 |
| 1252 | 410.00 |
| 1253 | 425.20 |
| 1254 | 451.20 |
| 1255 | 453.10 |
| 1256 | 492.40 |
| 1257 | 424.00 |
| 1258 | 449.00 |
| 1259 | 506.00 |
| 1260 | 540.00 |
| 1261 | 515.00 |
| 1262 | 487.30 |
| 1263 | 433.50 |
| 1264 | 407.00 |
| 1265 | 421.00 |

Methods:

(A) Micromass MUX LCT 4 channel LC/MS, Waters 60F pump, Gilson 215 4 probe autosampler, Gilson 849 injection module, 1.5 mL/min/column flow rate, 10-99% $CH_3CN$ (0.035% TFA)/$H_2O$ (0.05% TFA) gradient, Phenomenex Luna 5u C18 columns (50×4.60 mm), Waters MUX UV-2488 UV detector, Cedex 75 ELSD detectors.

(B) PESciex API-150-EX LC/MS, Shimadzu LC-8A pumps, Gilson 215 autosampler, Gilson 819 injection module, 3.0 mL/min flow rate, 10-99% $CH_3CN$ (0.035% TFA)/$H_2O$ (0.05% TFA) gradient, Phenomenex Luna 5u C18 column (50×4.60 mm), Shimadzu SPD-10A UV/Vis detector, Cedex 75 ELSD detector.

(C) PESciex API-150-EX LC/MS, Shimadzu LC-8A pumps, Gilson 215 autosampler, Gilson 819 injection module, 3.0 mL/min flow rate, 40-99% $CH_3CN$ (0.035% TFA)/$H_2O$ (0.05% TFA) gradient, Phenomenex Luna 5u C18 column (50×4.60 mm), Shimadzu SPD-10A UV/Vis detector, Cedex 75 ELSD detector.

Assays for Detecting and Measuring NaV Inhibition Properties of Compounds

A) Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See Gonzalez, J. E., K. Oades, et al. (1999) "Cell-based assays and instrumentation for screening ion-channel targets" *Drug Discov Today* 4(9): 431-439).

B) VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 μL of Bath Solution #2 (BS#2).
2) A 15 uM CC2-DMPE solution is prepared by mixing 5 mM coumarin stock solution with 10% Pluronic 127 1:1 and then dissolving the mix in the appropriate volume of BS#2.
3) After bath solution is removed from the 96-well plates, the cells are loaded with 80 μL of the CC2-DMPE solution. Plates are incubated in the dark for 30 minutes at room temperature.
4) While the cells are being stained with coumarin, a 15 μL oxonol solution in BS#2 is prepared. In addition to DiS-$BAC_2(3)$, this solution should contain 0.75 mM ABSC1 and 30 μL veratridine (prepared from 10 mM EtOH stock, Sigma #V-5754).
5) After 30 minutes, CC2-DMPE is removed and the cells are washed twice with 225 μL of BS#2. As before, the residual volume should be 40 μL.
6) Upon removing the bath, the cells are loaded with 80 μL of the $DiSBAC_2(3)$ solution, after which test compound, dissolved in DMSO, is added to achieve the desired test concentration to each well from the drug addition plate and mixed thoroughly. The volume in the well should be roughly 121 μL. The cells are then incubated for 20-30 minutes.
7) Once the incubation is complete, the cells are ready to be assayed on VIP® with a sodium addback protocol. 120 μL of Bath solution #1 is added to stimulate the NaV dependent depolarization. 200 μL tetracaine was used as an antagonist positive control for block of the NaV channel.

Analysis of VIPR® Data:

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\,nm} - Background_{460\,nm})}{(intensity_{580\,nm} - Background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the $Na^+$ addback analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-P} * 100.$$

where R is the ratio response of the test compound

Solutions [mM]

Bath Solution #1: NaCl 160, KCl 4.5, $CaCl_2$ 2, $MgCl_2$ 1, HEPES 10, pH 7.4 with NaOH Bath Solution #2 TMA-Cl 160, $CaCl_2$ 0.1, $MgCl_2$ 1, HEPES 10, pH 7.4 with KOH (final K concentration ~5 mM)

CC2-DMPE: prepared as a 5 mM stock solution in DMSO and stored at −20° C.

DiSBAC$_2$(3): prepared as a 12 mM stock in DMSO and stored at −20° C.

ABSC1: prepared as a 200 mM stock in distilled $H_2O$ and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% $CO_2$, to 100% confluence. They are usually split by trypsinization 1:10 or 1:20, depending on scheduling needs, and grown for 2-3 days before the next split.

C) VIPR® Optical Membrane Potential Assay Method with Electrical Stimulation

The following is an example of how NaV1.3 inhibition activity is measured using the optical membrane potential method #2. Other subtypes are performed in an analogous mode in a cell line expressing the NaV of interest.

HEK293 cells stably expressing NaV1.3 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO 10 mM DiSBAC$_2$(3) (Aurora #00-100-010) in dry DMSO 10 mM CC2-DMPE (Aurora #00-100-008) in dry DMSO 200 mM ABSC1 in $H_2O$ Hank's Balanced Salt Solution (Hyclone #SH30268.02) supplemented with 10 mM HEPES (Gibco #15630-080)

Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is to wells containing washed cells, resulting in a 10 µM final staining concentration. The cells are stained for 30 minutes in the dark at RT.

2× DISBAC$_2$(3) with ABSC1=6 µM DISBAC$_2$(3) and 1 mM ABSC1: The required amount of 10 mM DISBAC$_2$(3) is added to a 50 ml conical tube and mixed with 1 µL 10% pluronic for each mL of solution to be made and vortexed together. Then HBSS/HEPES is added to make up 2× solution. Finally, the ABSC1 is added.

The 2× DiSBAC$_2$(3) solution can be used to solvate compound plates. Note that compound plates are made at 2× drug concentration. Wash stained plate again, leaving residual volume of 50 µL. Add 50 uL/well of the 2× DiSBAC$_2$(3) w/ABSC1. Stain for 30 minutes in the dark at RT.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Reagents

Assay Buffer #1

140 mM NaCl, 4.5 mM KCl, 2 mM $CaCl_2$, 1 mM $MgCl_2$, 10 mM HEPES, 10 mM glucose, pH 7.40, 330 mOsm Pluronic stock (1000×): 100 mg/mL pluronic 127 in dry DMSO Oxonol stock (3333×): 10 mM DiSBAC$_2$(3) in dry DMSO Coumarin stock (1000×): 10 mM CC2-DMPE in dry DMSO ABSC1 stock (400×): 200 mM ABSC1 in water Assay Protocol 1. Insert or use electrodes into each well to be assayed.
2. Use the current-controlled amplifier to deliver stimulation wave pulses for 3 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\,nm} - background_{460\,nm})}{(intensity_{580\,nm} - background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A is defined as:

$$A = \frac{R-P}{N-p} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 μm in diameter) have been visually identified and probed with fine tip glass electrodes connected to an amplifier (Axon Instruments). The "voltage clamp" mode has been used to assess the compound's IC50 holding the cells at −60 mV. In addition, the "current clamp" mode has been employed to test the efficacy of the compounds in blocking action potential generation in response to current injections. The results of these experiments have contributed to the definition of the efficacy profile of the compounds.

Voltage-Clamp Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), CdCl2 (0.4), NiCl2 (0.1), TTX ($0.25\times10^{-3}$).

Current-Clamp Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM):150 K-gluconate, 10 NaCl, 0.1 EGTA, 10 Hepes, 2 $MgCl_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

Following these procedures, representative compounds of the present invention were found to possess desired voltage gated sodium channel activity and selectivity.

Assays for Detecting and Measuring CaV Inhibition Properties of Compounds

A) Optical Methods for Assaying CaV Inhibition Properties of Compounds:

Compounds of the invention are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® Optical Membrane Potential Assay Method with Electrical Stimulation

The following is an example of how CaV2.2 inhibition activity is measured using the optical membrane potential method. Other subtypes are performed in an analogous mode in a cell line expressing the CaV of interest.

HEK293 cells stably expressing CaV2.2 are plated into 96-well microtiter plates. After an appropriate incubation period, the cells are stained with the voltage sensitive dyes CC2-DMPE/DiSBAC2(3) as follows.

Reagents:

100 mg/mL Pluronic F-127 (Sigma #P2443), in dry DMSO
10 mM $DiSBAC_6(3)$ (Aurora #00-100-010) in dry DMSO
10 mM CC2-DMPE (Aurora #00-100-008) in dry DMSO
200 mM Acid Yellow 17 (Aurora #VABSC) in $H_2O$
370 mM Barium Chloride (Sigma Cat# B6394) in $H_2O$ Bath X
160 mM NaCl (Sigma Cat# S-9888)
4.5 mM KCl (Sigma Cat# P-5405)
1 mM MgCl2 (Fluka Cat#63064)
10 mM HEPES (Sigma Cat# H-4034)
pH 7.4 using NaOH Loading Protocol:

2×CC2-DMPE=20 µM CC2-DMPE: 10 mM CC2-DMPE is vortexed with an equivalent volume of 10% pluronic, followed by vortexing in required amount of HBSS containing 10 mM HEPES. Each cell plate will require 5 mL of 2×CC2-DMPE. 50 µL of 2×CC2-DMPE is added to wells containing washed cells, resulting in a 10 µM final staining concentration. The cells are stained for 30 minutes in the dark at RT.

2×CC2DMPE & DISBAC$_6$(3)=8 µM CC2DMPE & 2.5 µM DISBAC$_6$(3): Vortex together both dyes with an equivalent volume of 10% pluronic (in DMSO). Vortex in required amount of Bath X with beta-cyclodextrin. Each 96 well cell plate will require 5 ml of 2×CC2DMPE. Wash plate with ELx405 with Bath X, leaving a residual volume of 50 µL/well. Add 50 µL of 2×CC2DMPE & DISBAC$_6$(3) to each well. Stain for 30 minutes in the dark at RT.

1.5× AY17=750 µM AY17 with 15 mM BaCl$_2$: Add Acid Yellow 17 to vessel containing Bath X. Mix well. Allow solution to sit for 10 minutes. Slowly mix in 370 mM BaCl$_2$. This solution can be used to solvate compound plates. Note that compound plates are made at 1.5× drug concentration and not the usual 2×. Wash CC2 stained plate, again, leaving residual volume of 50 µL. Add 100 uL/well of the AY17 solution. Stain for 15 minutes in the dark at RT. Run plate on the optical reader.

The electrical stimulation instrument and methods of use are described in ION Channel Assay Methods PCT/US01/21652, herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate.

Assay Protocol

Insert or use electrodes into each well to be assayed.

Use the current-controlled amplifier to deliver stimulation wave pulses for 3-5 s. Two seconds of pre-stimulus recording are performed to obtain the un-stimulated intensities. Five seconds of post-stimulation recording are performed to examine the relaxation to the resting state.

Data Analysis

Data are analyzed and reported as normalized ratios of background-subtracted emission intensities measured in the 460 nm and 580 nm channels. Background intensities are then subtracted from each assay channel. Background intensities are obtained by measuring the emission intensities during the same time periods from identically treated assay wells in which there are no cells. The response as a function of time is then reported as the ratios obtained using the following formula:

$$R(t) = \frac{(intensity_{460\ nm} - background_{460\ nm})}{(intensity_{580\ nm} - background_{580\ nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated.

Control responses are obtained by performing assays in the presence of a compound with the desired properties (positive control), such as mibefradil, and in the absence of pharmacological agents (negative control). Responses to the negative (N) and positive (P) controls are calculated as above. The compound antagonist activity A is defined as:

$$A = \frac{R - P}{N - p} * 100.$$

where R is the ratio response of the test compound.

Electrophysiology Assays for CaV Activity and Inhibition of Test Compounds

Patch clamp electrophysiology was used to assess the efficacy of calcium channel blockers expressed in HEK293 cells. HEK293 cells expressing CaV2.2 have been visually identified and probed with fine tip glass electrodes connected to an amplifier (Axon Instruments). The "voltage clamp" mode has been used to assess the compound's IC50 holding the cells at −100 mV. The results of these experiments have contributed to the definition of the efficacy profile of the compounds.

Voltage-Clamp Assay in HEK293 Cells Expressing CaV2.2

CaV2.2 calcium currents were recorded from HEK293 cells using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes were allowed for the pipette solution to equilibrate within the cell before beginning recording. Currents were lowpass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +20 mV for 50 ms at frequencies of 0.1, 1, 5, 10, 15, and 20 Hz. Blocking effects were allowed to plateau before proceeding to the next test concentration.

Solutions

Intracellular solution (in mM): Cs—F (130), NaCl (10), MgCl$_2$ (1), EGTA (1.5), CaCl$_2$ (0.1), HEPES (10), glucose (2), pH=7.42, 290 mOsm.

Extracellular solution (in mM): NaCl (138), BaCl$_2$ (10), KCl (5.33), KH$_2$PO$_4$ (0.44), MgCl$_2$ (0.5), MgSO$_4$ (0.41), NaHCO$_3$ (4), Na$_2$HPO$_4$ (0.3), glucose (5.6), HEPES (10).

Following these procedures, representative compounds of the present invention were found to possess desired N-type calcium channel modulation activity and selectivity.

The invention claimed is:

1. A method of treating or lessening the severity of a disease, disorder, or condition selected from arthritis, migraine, cluster headaches, epilepsy or epilepsy conditions, osteoarthritis pain, or head pain, comprising the step of administering to said patient an effective amount of a compound of formula IA-ii:

IA-ii

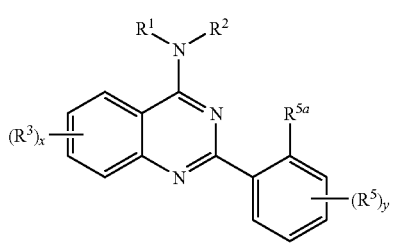

wherein R¹ and R² are each independently selected from optionally substituted methyl, ethyl, cyclopropyl, n-propyl, propenyl, cyclobutyl, CH(CH₃)CH₂CH₃, or n-butyl;
x is 0-1;
y is 0;
R³, when present, is selected from halogen, CN, NO₂, —N(R')₂, —CH₂N(R')₂, —OR', —CH₂OR', —SR', —CH₂SR', —COOR', —NRCOR', —CON(R')₂, —OCON(R')₂, COR', —NHCOOR', —SO₂R', —SO₂N(R')₂, or an optionally substituted group selected from $C_1$-$C_6$aliphatic, aryl, heteroaryl, cycloaliphatic, heterocycloaliphatic, arylC₁-C₆alkyl, heteroarylC₁-C₆alkyl, cycloaliphaticC₁-C₆alkyl, or heterocycloaliphaticC₁-C₆alkyl;
$R^{5a}$ is an optionally substituted C₁-C₆aliphatic group, halogen, —OR', —SR', —N(R')₂, —NR'COR', —NR'CON(R')₂, —NR'CO₂R', —COR', —CO₂R', —OCOR', —CON(R')₂, —OCON(R')₂, —SOR', —SO₂R', —SO₂N(R')₂, —NR'SO₂R', —NR'SO₂N(R')₂, —COCOR', —COCH₂COR', —OP(O)(OR')₂, —P(O)(OR')₂, —OP(O)₂OR', —P(O)₂OR', —PO(R')₂, or —OPO(R')₂; and
each occurrence of R is independently hydrogen or an optionally substituted C₁₋₆aliphatic group; and each occurrence of R' is independently hydrogen or an optionally substituted C₁₋₆ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur; provided that:
when x is 0, and $R^{5a}$ is Cl, Me, NO₂, or OH, then R¹ and R² are not simultaneously Et or Me; and
provided that the following additional compounds are excluded:
2-(o-hydroxyphenyl)-4-dimethylamino-7-chloroquinazoline; and
2-(o-hydroxyphenyl)-4-dimethylamino-7-nitroquinazoline.

2. The method of claim 1, wherein the disease, condition, or disorder is head pain.

3. The method of claim 1, wherein the disease, condition, or disorder is rheumatoid arthritis, osteoarthritis, chronic headache pain, migraine, or tension headache, including cluster headaches.

4. The method of claim 1 or 3, comprising administering a compound selected from:

| Compound | Cmpd # |
|---|---|
| [structure: 2-(2-hydroxyphenyl)-4-dimethylamino quinazoline] | 3 |
| [structure: 2-(2-hydroxyphenyl)-4-diethylamino quinazoline] | 158 |
| [structure: 2-(2-chlorophenyl)-4-diethylamino quinazoline] | 179 |
| [structure: 2-(2-methoxyphenyl)-4-dimethylamino quinazoline] | 197 |
| [structure: 2-(2-fluorophenyl)-4-dimethylamino-6-chloro quinazoline] | 198 |

| Compound | Cmpd # |
|---|---|
| (structure: 2-(2-fluorophenyl)-6-chloro-4-(N,N-diethylamino)quinazoline) | 199 |
| (structure: 2-(2-fluorophenyl)-6-bromo-4-(N,N-dimethylamino)quinazoline) | 205 |
| (structure: 2-(2-(N,N-dimethylamino)phenyl)-6-chloro-4-(N,N-dimethylamino)quinazoline) | 213 |
| (structure: 2-(2-bromophenyl)-4-(N,N-dimethylamino)quinazoline) | 214 |
| (structure: 2-(2-bromophenyl)-4-(N,N-diethylamino)quinazoline) | 216 |

| Compound | Cmpd # |
|---|---|
| (structure: cyclohexanecarboxamide of 2-(2-aminophenyl)-4-(N,N-dimethylamino)quinazoline) | 228 |
| (structure: ethyl ester heptanoyl amide of 2-(2-aminophenyl)-4-(N,N-dimethylamino)quinazoline) | 229 |
| (structure: 2-(2-aminophenyl)-4-(N,N-dimethylamino)quinazoline) | 230 |
| (structure: 2-(2-(N-benzylamino)phenyl)-6-chloro-4-(N,N-dimethylamino)quinazoline) | 231 |

| Compound | Cmpd # |
|---|---|
| (structure: 2-(2-fluorophenyl)-N,N-dimethylquinazolin-4-amine) | 233 |
| (structure: 2-(2-fluorophenyl)-N,N-diethylquinazolin-4-amine) | 234 |
| (structure: 6-bromo-2-(2-hydroxyphenyl)-N,N-dimethylquinazolin-4-amine) | 250 |
| (structure: 6-bromo-2-(2-hydroxyphenyl)-N,N-diethylquinazolin-4-amine) | 251 |
| (structure: 6-chloro-2-(2-(ethylthio)phenyl)-N,N-dimethylquinazolin-4-amine) | 253 |

| Compound | Cmpd # |
|---|---|
| (structure: 2-(2-(prop-1-en-2-yl)phenyl)-N,N-dimethylquinazolin-4-amine) | 258 |
| (structure: 6-bromo-2-(2-acetoxyphenyl)-N,N-dimethylquinazolin-4-amine) | 260 |
| (structure: 6-chloro-2-(2-((2-methoxyethyl)amino)phenyl)-N,N-dimethylquinazolin-4-amine) | 261 |
| (structure: 2-(2-hydroxyphenyl)-6-methoxy-N,N-dimethylquinazolin-4-amine) | 265 |
| (structure: 6-ethoxy-2-(2-hydroxyphenyl)-N,N-dimethylquinazolin-4-amine) | 267 |

-continued
| Compound | Cmpd # |
|---|---|
| 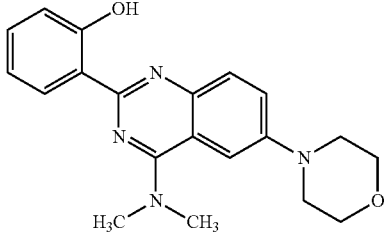 | 268 |
| 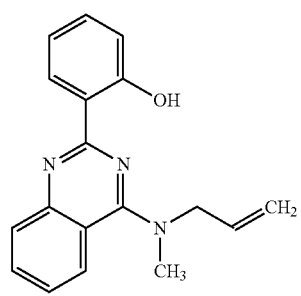 | 290 |
| 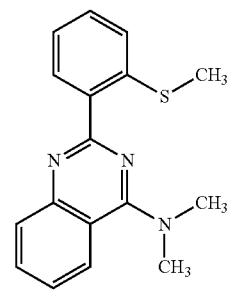 | 304 |
| 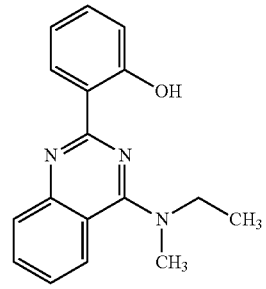 | 335 |
| 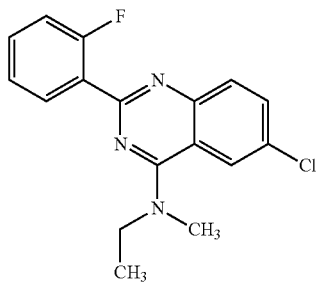 | 346 |
-continued
| Compound | Cmpd # |
|---|---|
| 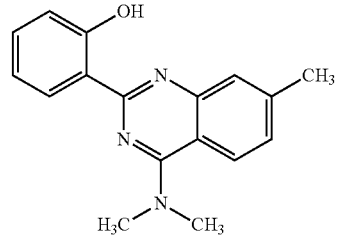 | 376 |
| 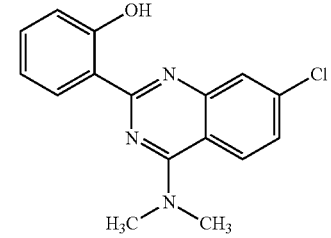 | 377 |
| 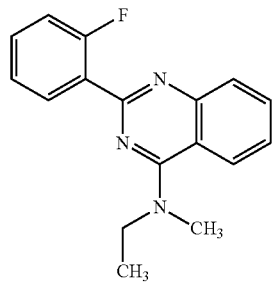 | 378 |
| 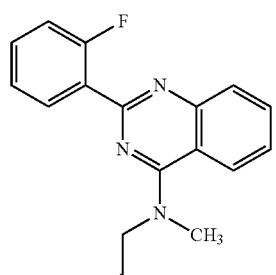 | 388 |
| 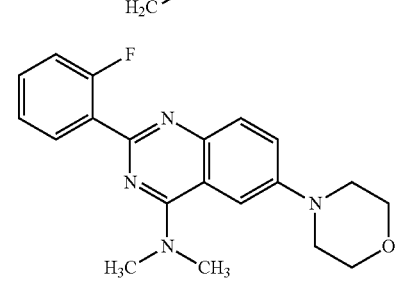 | 392 |
| 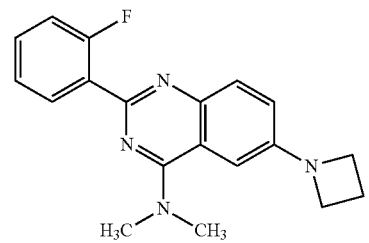 | 393 |

| Compound | Cmpd # |
|---|---|
| (structure: 5-fluoro-2-(2-hydroxyphenyl)-N,N-dimethylquinazolin-4-amine) | 404 |
| (structure: 2-(2-fluorophenyl)-N,N-dimethyl-7-aminoquinazolin-4-amine) | 405 |
| (structure: 2-(2-fluorophenyl)-6-methoxy-N,N-dimethylquinazolin-4-amine) | 408 |
| (structure: 2-(2-hydroxyphenyl)-8-methyl-N,N-dimethylquinazolin-4-amine) | 419 |
| (structure: 2-(2-fluorophenyl)-8-methyl-N,N-dimethylquinazolin-4-amine) | 420 |
| (structure: 6-fluoro-2-(2-hydroxyphenyl)-N,N-dimethylquinazolin-4-amine) | 429 |

| Compound | Cmpd # |
|---|---|
| (structure: 2-(2-fluorophenyl)-6-fluoro-N,N-dimethylquinazolin-4-amine) | 430 |
| (structure: 7-chloro-2-(2-fluorophenyl)-N,N-dimethylquinazolin-4-amine) | 444 |
| (structure: 7-chloro-2-(2-fluorophenyl)-N,N-diethylquinazolin-4-amine) | 445 |
| (structure: 7-chloro-2-(2-hydroxyphenyl)-N,N-diethylquinazolin-4-amine) | 446 |
| (structure: 2-(4-(dimethylamino)-6-methoxyquinazolin-2-yl)phenyl acetate) | 450 |

| Compound | Cmpd # |
|---|---|
| (structure: 2-(2-fluorophenyl)-4-(dimethylamino)-6-(trifluoromethoxy)quinazoline) | 451 |
| (structure: 2-(2-hydroxyphenyl)-4-(dimethylamino)-6-(ethylthio)quinazoline) | 453 |
| (structure: 2-(2-chlorophenyl)-4-(dimethylamino)quinazoline) | 454 |
| (structure: 2-(2-hydroxyphenyl)-4-(dimethylamino)-7-carbamoylquinazoline) | 455 |
| (structure: 2-(2-hydroxyphenyl)-4-(dimethylamino)-7-(N-benzylcarbamoyl)quinazoline) | 456 |

| Compound | Cmpd # |
|---|---|
| (structure: 2-(2-fluorophenyl)-4-(dimethylamino)-7-fluoroquinazoline) | 483 |
| (structure: 2-(2-hydroxyphenyl)-4-(dimethylamino)-6-isopropoxyquinazoline) | 485 |
| (structure: 2-(2-hydroxyphenyl)-4-(dimethylamino)-6-carboxyquinazoline) | 492 |
| (structure: 2-(2-methoxyphenyl)-4-(dimethylamino)-6-(1-hydroxybutyl)quinazoline) | 493 |
| (structure: 2-(2-hydroxyphenyl)-4-(dimethylamino)-6-carbamoylquinazoline) | 503 |

| Compound | Cmpd # |
|---|---|
| (chemical structure) | 504 |
| (chemical structure) | 505 |
| (chemical structure) | 506 |
| (chemical structure) | 507 |
| (chemical structure) | 508 |
| (chemical structure) | 509 |

| Compound | Cmpd # |
|---|---|
| (chemical structure) | 578 |
| (chemical structure) | 580 |
| (chemical structure) | 583 |
| (chemical structure) | 586 |
| (chemical structure) | 693 |

-continued
| Compound | Cmpd # |
|---|---|
| 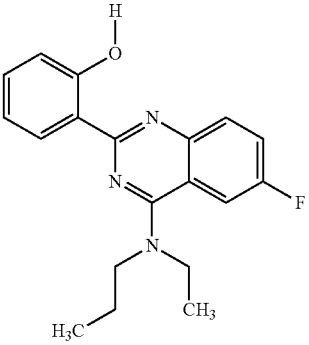 | 766 |
| 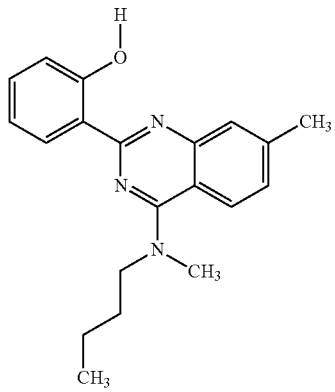 | 843 |
| 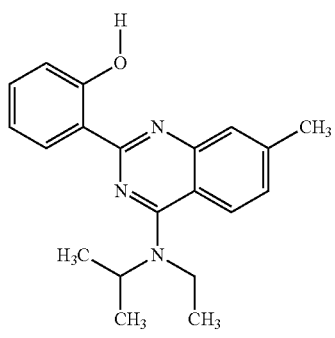 | 845 |
| 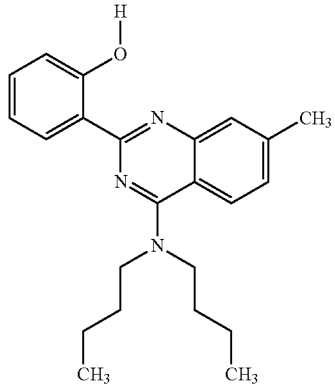 | 967 |
-continued
| Compound | Cmpd # |
|---|---|
| 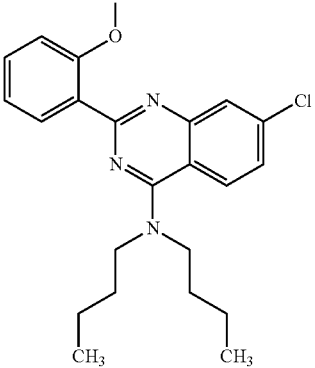 | 1018 |
| 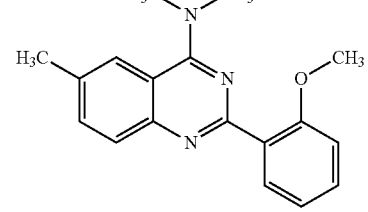 | 1046 |
| 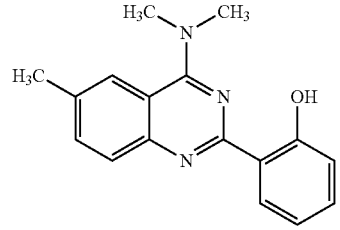 | 1047 |
| 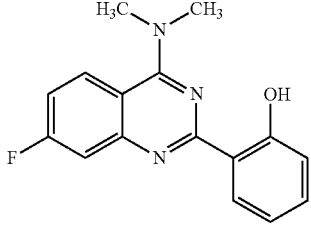 | 1077 |
| 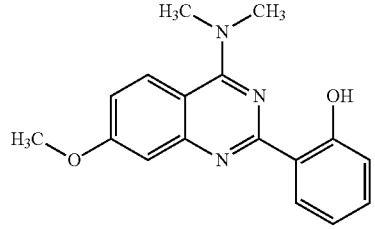 | 1082 |
| 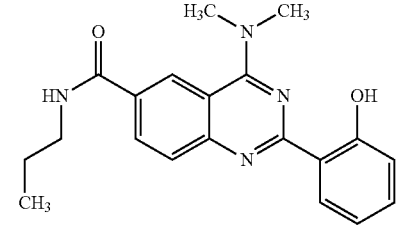 | 1098 |

| Compound | Cmpd # |
|---|---|
| (structure) | 1099 |
| (structure) | 1104 |
| (structure) | 1180 |

| Compound | Cmpd # |
|---|---|
| (structure) | 1184 |
| (structure) | 1186 |
| (structure) | 1189 |

* * * * *